United States Patent [19]
Blackburn et al.

[11] Patent Number: 5,807,688
[45] Date of Patent: Sep. 15, 1998

[54] CATALYTIC ANTIBODIES FOR CARBAMATE ACTIVATION BY A NON-SPONTANEOUS REACTION MECHANISM

[75] Inventors: George Michael Blackburn, Sheffield, United Kingdom; Paul Wentworth, San Diego, Calif.

[73] Assignee: Zeneca Limited, London, United Kingdom

[21] Appl. No.: 653,060

[22] Filed: May 24, 1996

[30] Foreign Application Priority Data

May 27, 1995 [GB] United Kingdom .................. 9510830

[51] Int. Cl.$^6$ ............................... C12N 9/00; C12Q 1/25
[52] U.S. Cl. ...................... 435/7.6; 435/188.5; 424/94.1; 424/175.1
[58] Field of Search ................... 435/188.5, 7.6; 424/171.1, 141.1, 175.1, 94.1

[56] References Cited

U.S. PATENT DOCUMENTS 5,460,960  10/1995  Kim et al. ............................ 435/188.5

OTHER PUBLICATIONS

Queen, C., et al. (1989) Proc. Natl. Acad. Sci., USA 86, 10029–10033.
Verhoeyen, M., et. al. (1988) Science 239, 1534–1536.
Neuberger, M.S., et. al. (1985) Nature 314, 268–270.
Van Vranken et al., "Catalysis of Carbamate Hydrolysis by an Antibody", *Tetrahedron Letters*, vol. 35, No. 23, 1994, pp. 3873–3876.
Pollack et al., "Design of Catalytic Antibodies", *Methods in Enzymology*, vol. 178, 1989, pp. 551–568.
Miyashita et al., "Prodrug activation via catalytic antibodies", *Proc. Natl. Acad. Sci. USA*, vol. 90, Jun. 1993, pp. 5337–5340.
Campbell et al., "Antibody–Catalyzed Prodrug Activation", *J. Am. Chem. Soc.*, vol. 116, 1994, pp. 2165–2166.
Jacobs, "New Perspectives on Catalytic Antibodies", *Biotechnology*, vol. 9, Mar. 1991, pp. 258–262.
Lerner et al., "At the Crossroads of Chemistry and Immunology: Catalytic Antibodies", *Science*, vol. 252, May 3, 1991, pp. 659–667.
Tawfik et al, "Simple Method for Selecting Catalytic Monoclona Antibodies That Exhibit Turnover and Specificity", *Biochemistry*, vol. 29, 1990, pp. 9916–9921.
Tramontano et al., "Production of Antibodies That Mimic Enzyme Catalytic Activity", *Methods in Enzymology*, vol. 178, 1989, pp. 531–550.

*Primary Examiner*—Charles L. Patterson, Jr.
*Attorney, Agent, or Firm*—Cushman Darby & Cushman IP Group of Pillsbury Madison & Sutro LLP

[57] ABSTRACT

Catalytic antibodies capable of catalysing activation of a carbamate (—O—CO—NH—) containing prodrug suitable for Antibody Directed Abzyme Prodrug Therapy (ADAPT) by catalysing breakdown of the prodrug at the carbamate position by a non-spontaneous reaction mechanism. The non-spontaneous reaction preferably has a $B_{Ac}2$ mechanism and the prodrug is a preferably a nitrogen mustard aryl carbamate. The invention also includes relevant immunogens, screens for catalytic activity using short transition state analogues and ADAPT systems.

23 Claims, 108 Drawing Sheets

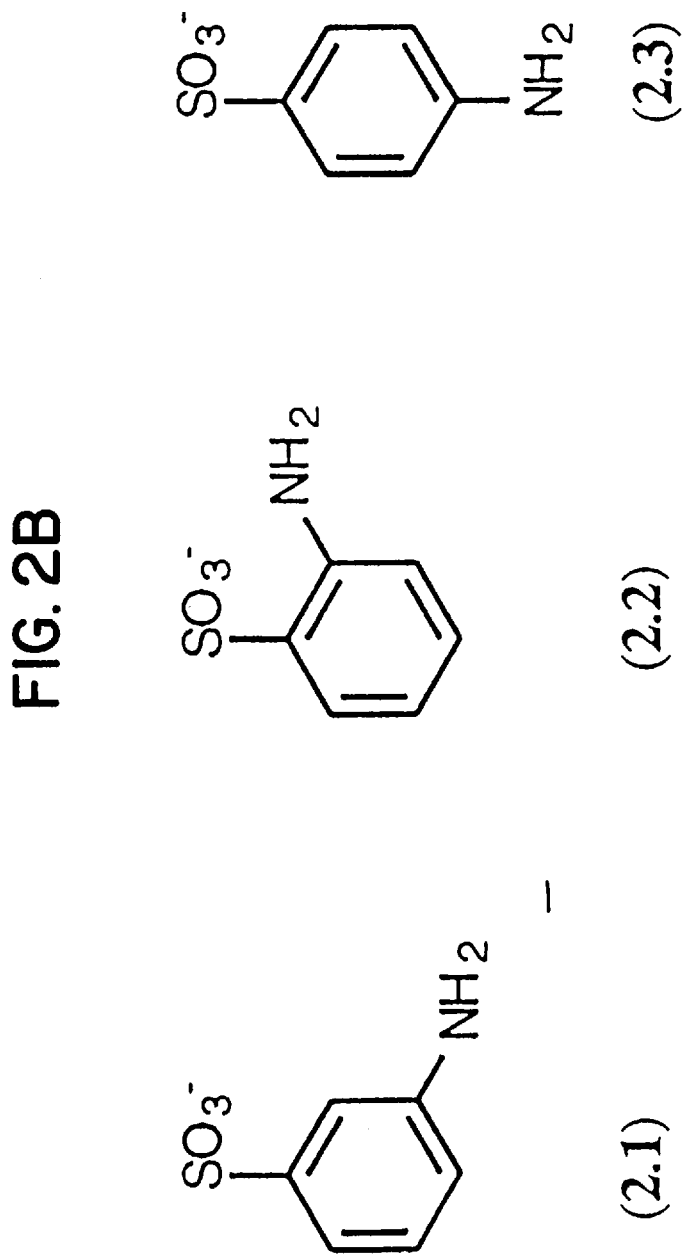

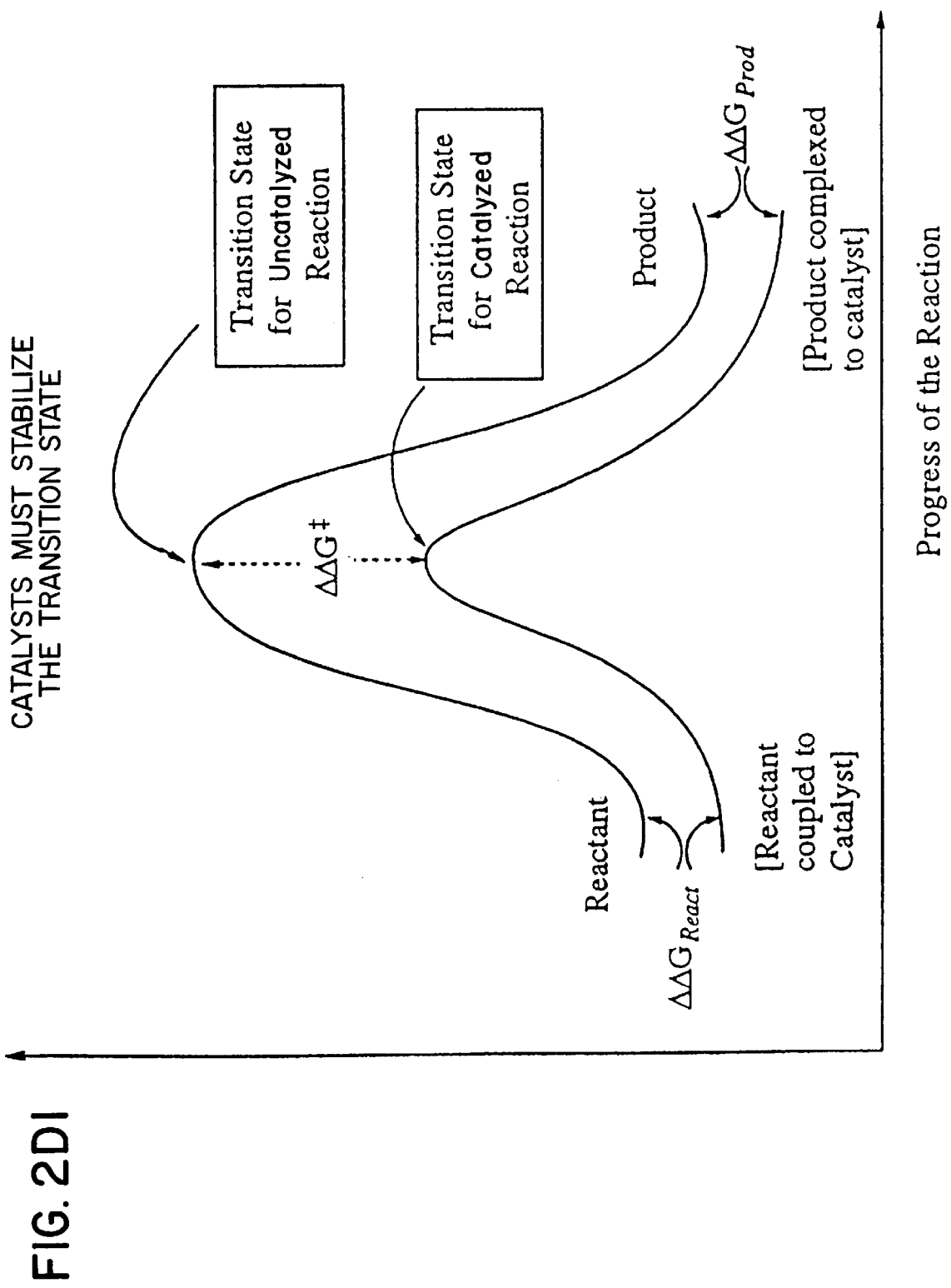
FIG. 2D1

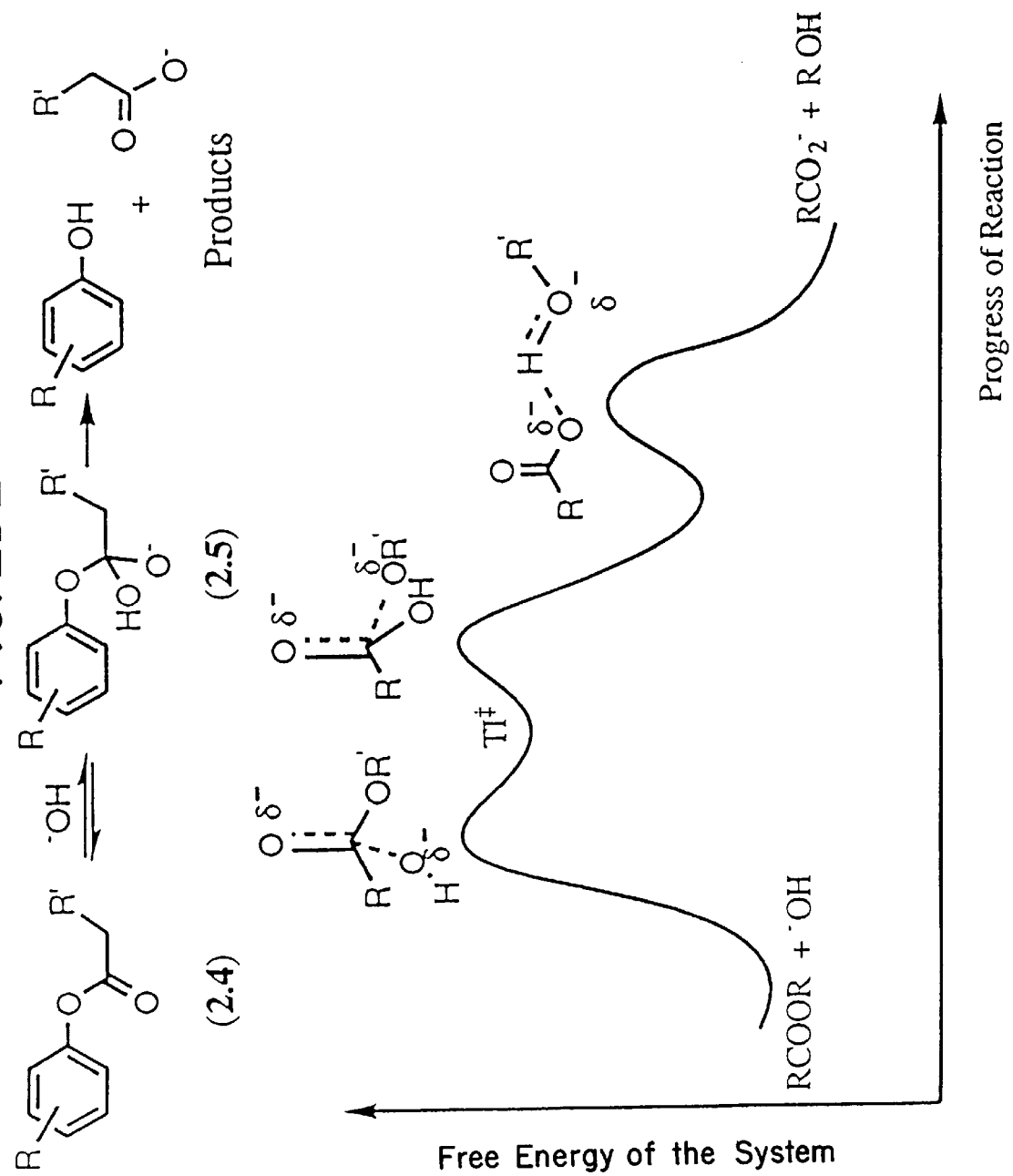
FIG. 2D2

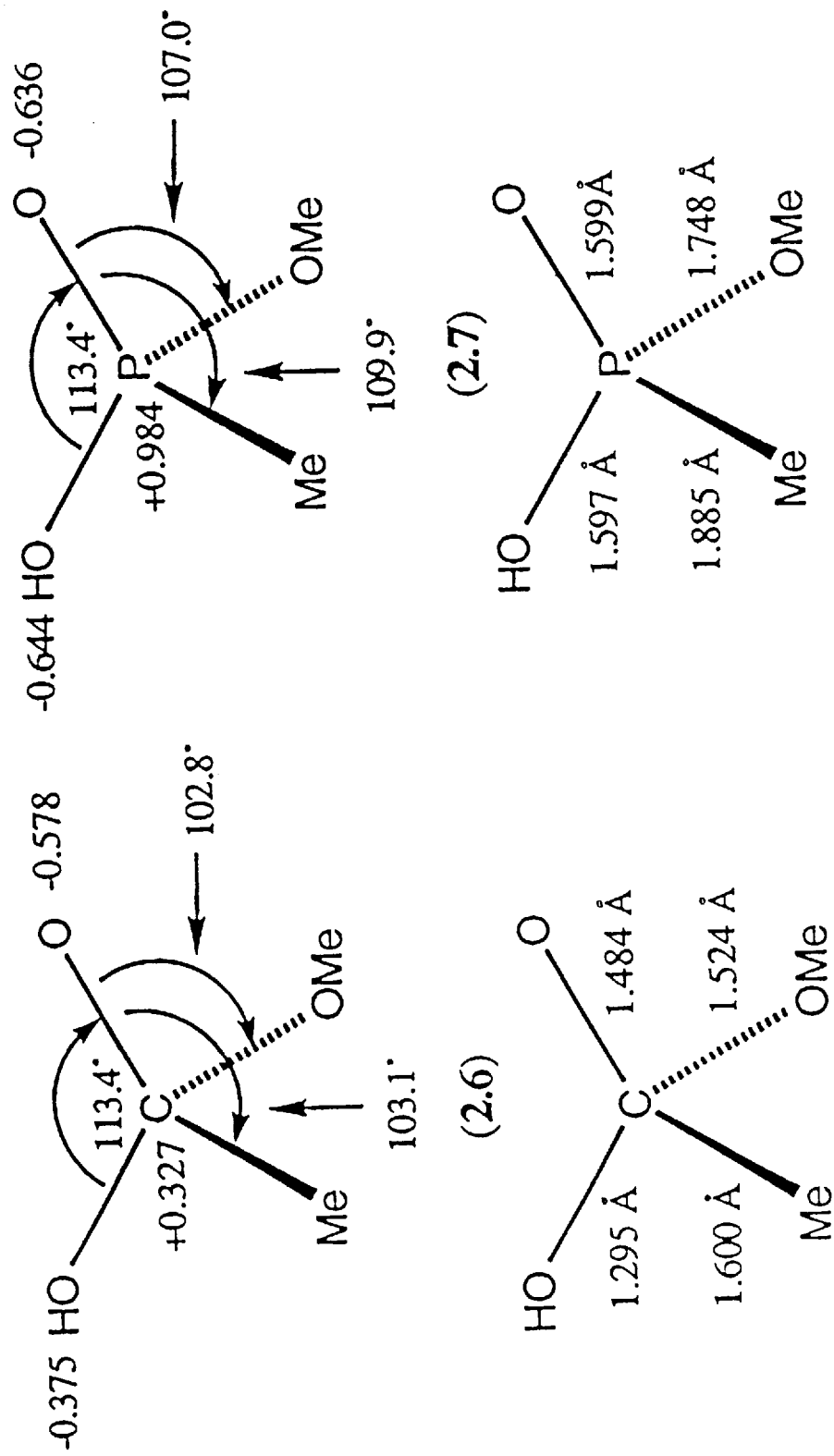
FIG. 2D3

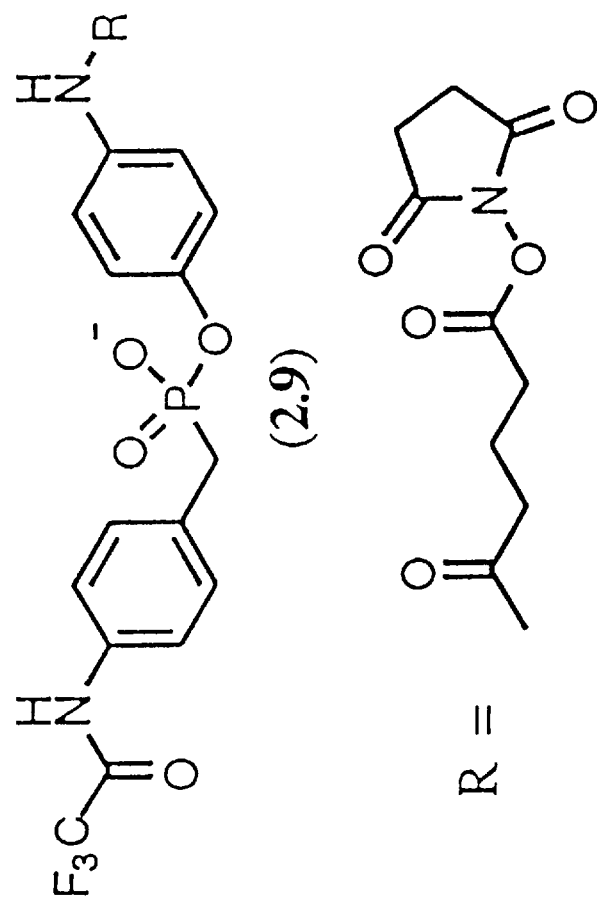
FIG. 2D4

FIG. 2D5
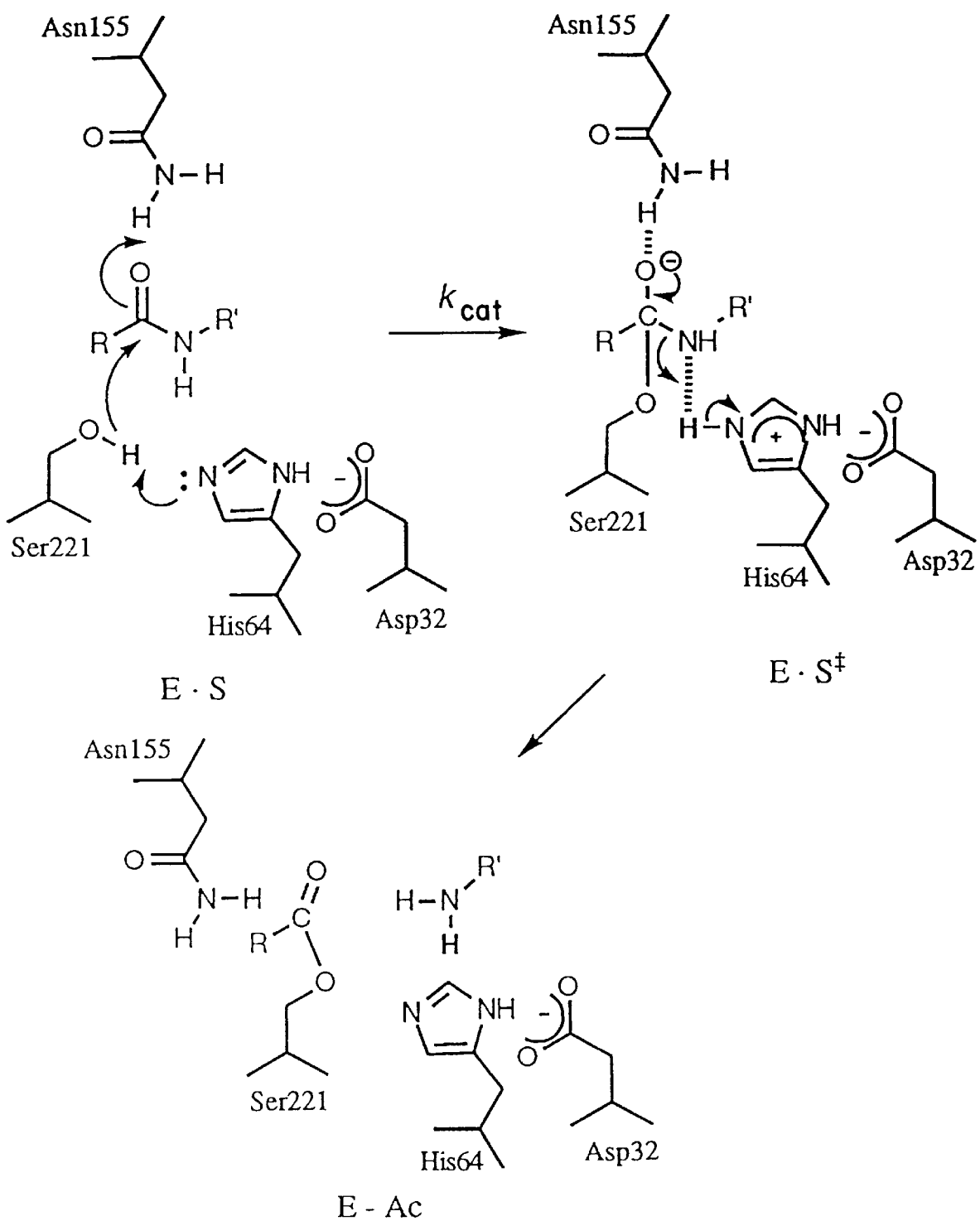

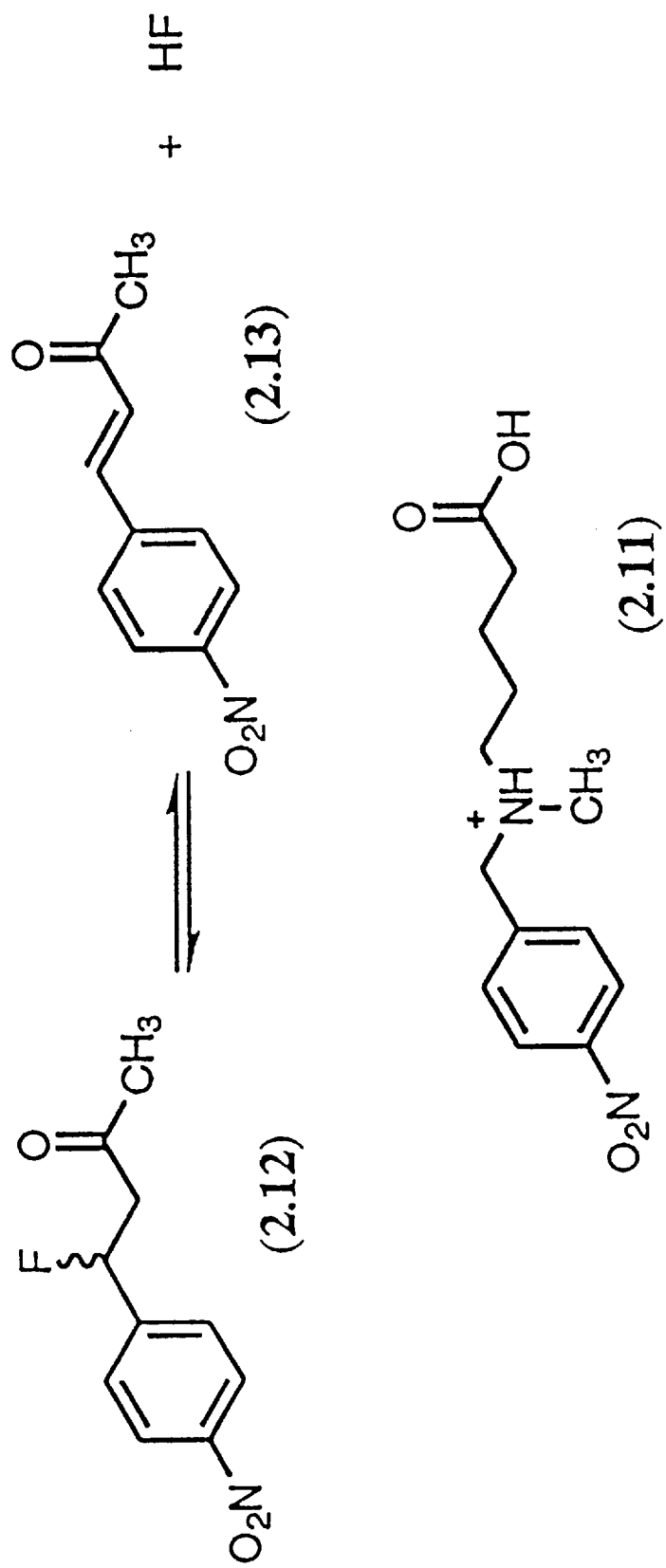
FIG. 2D6

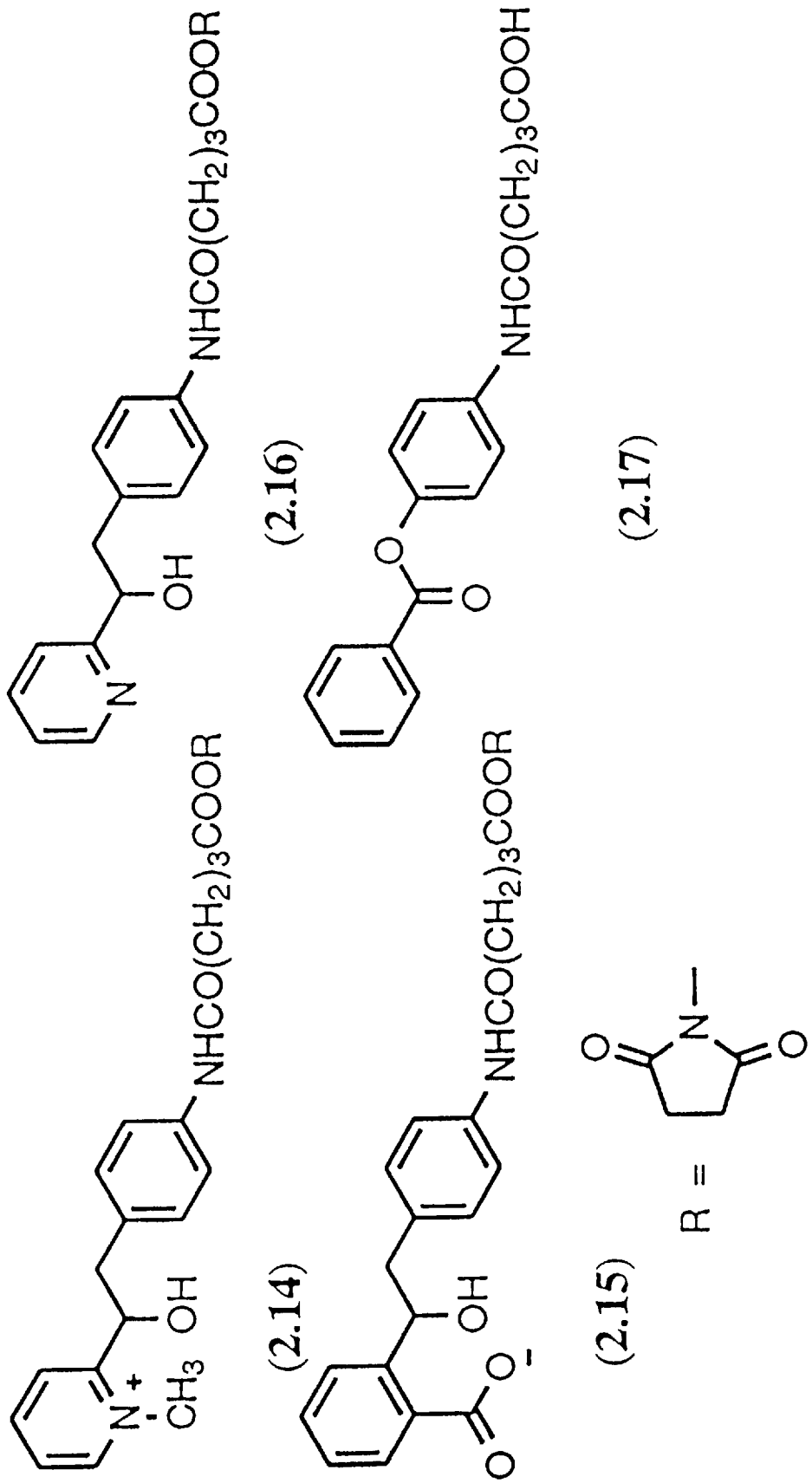
FIG. 2D7

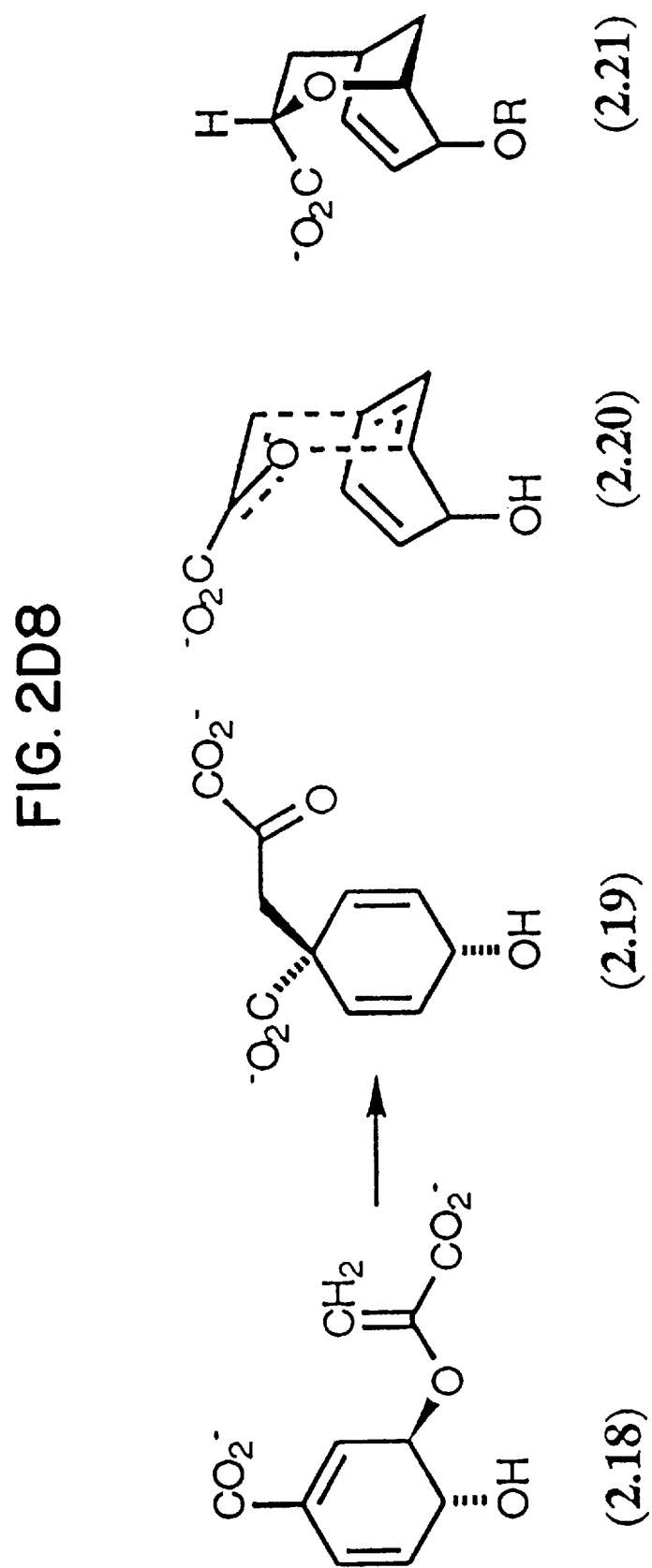
FIG. 2D8

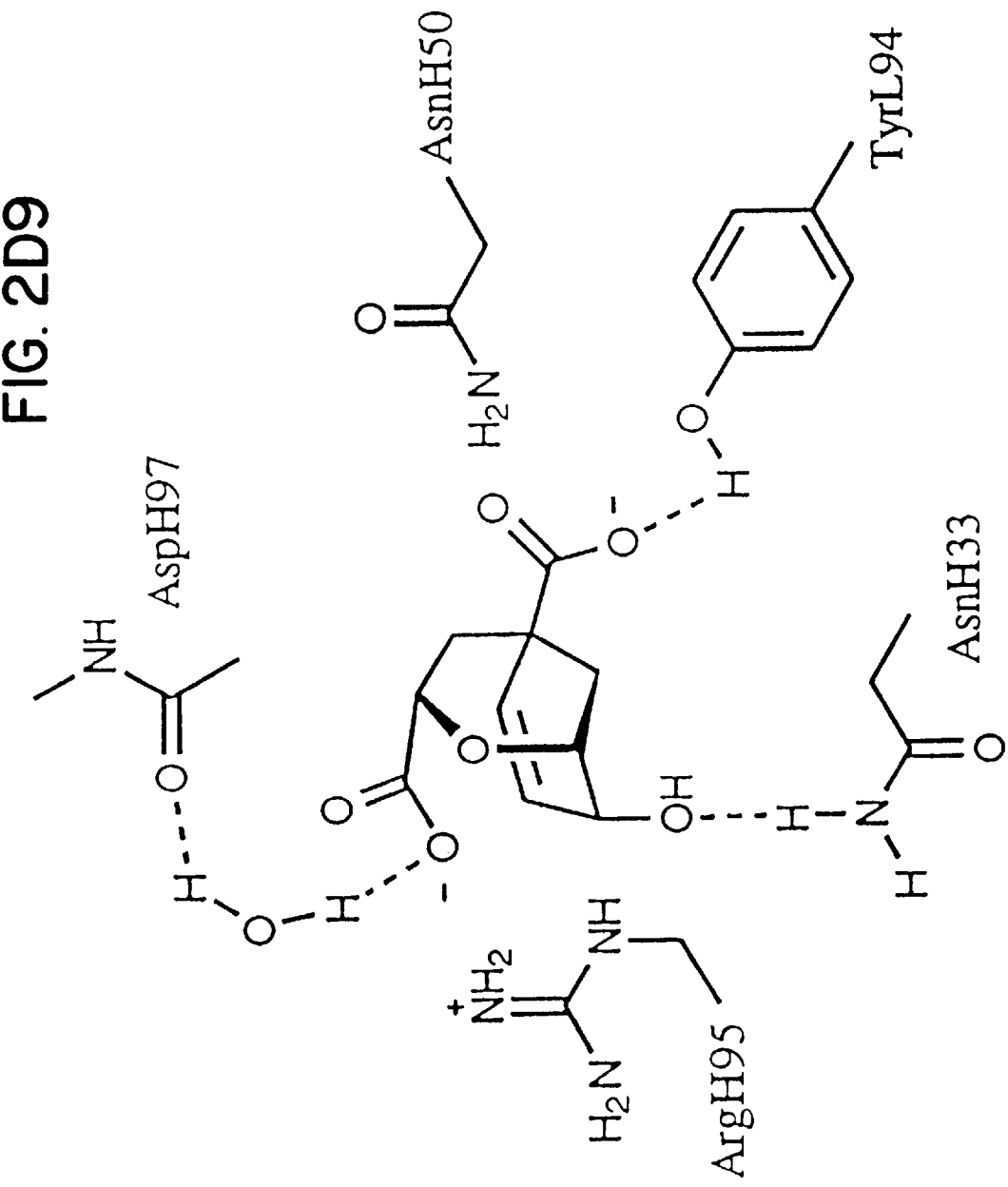
FIG. 2D9

FIG. 2D10
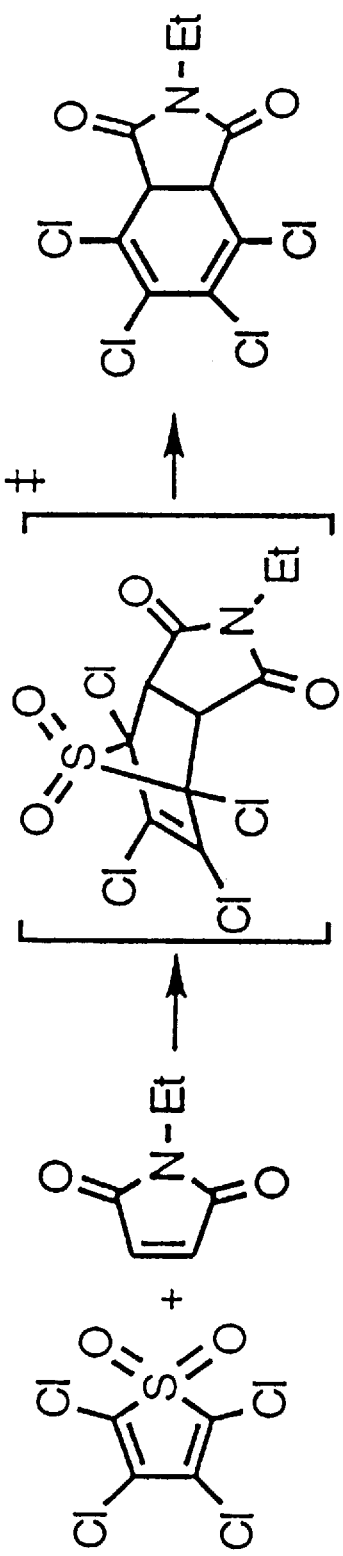
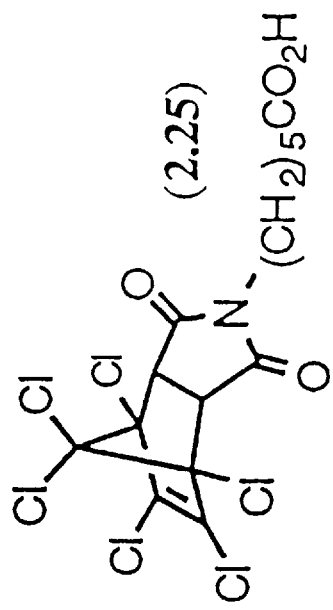

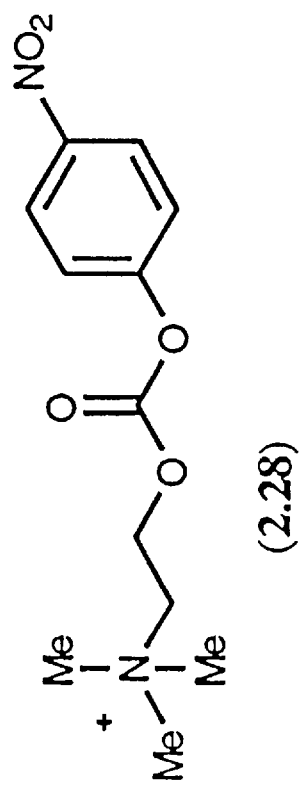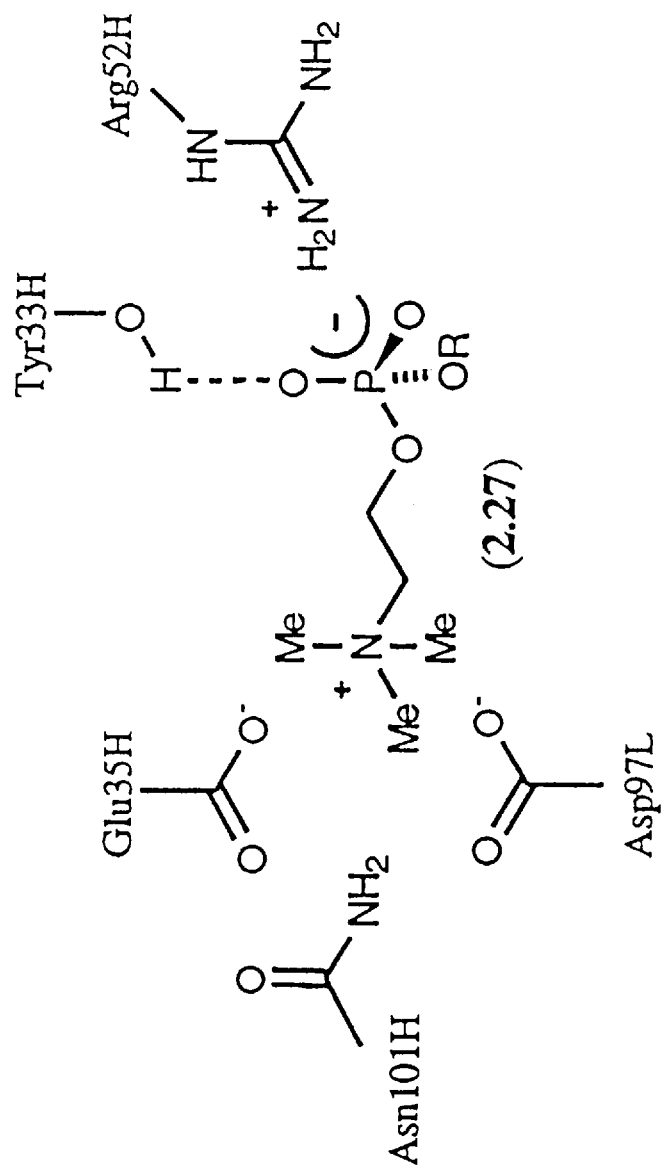
FIG. 2DII

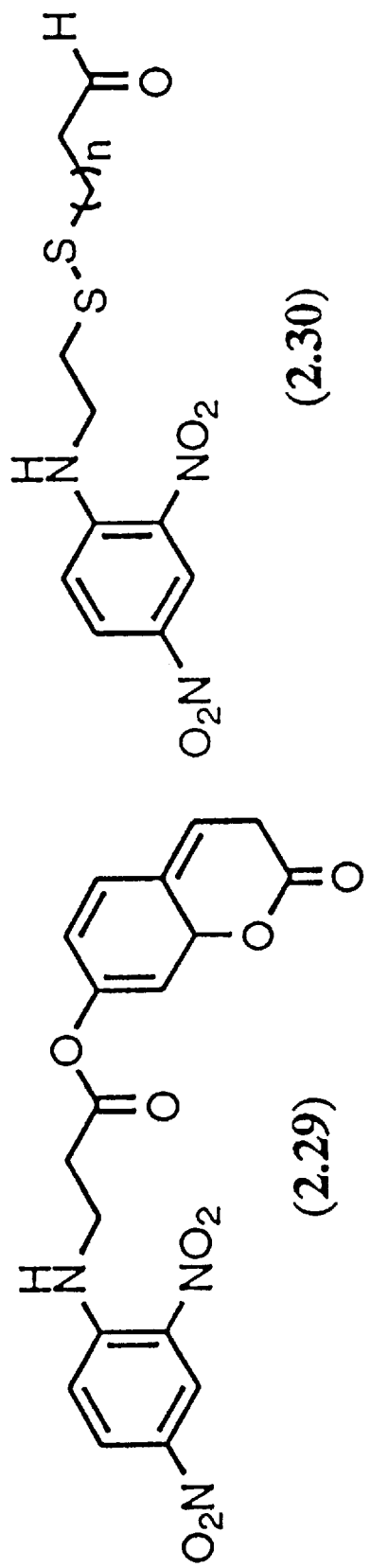
FIG. 2DI2

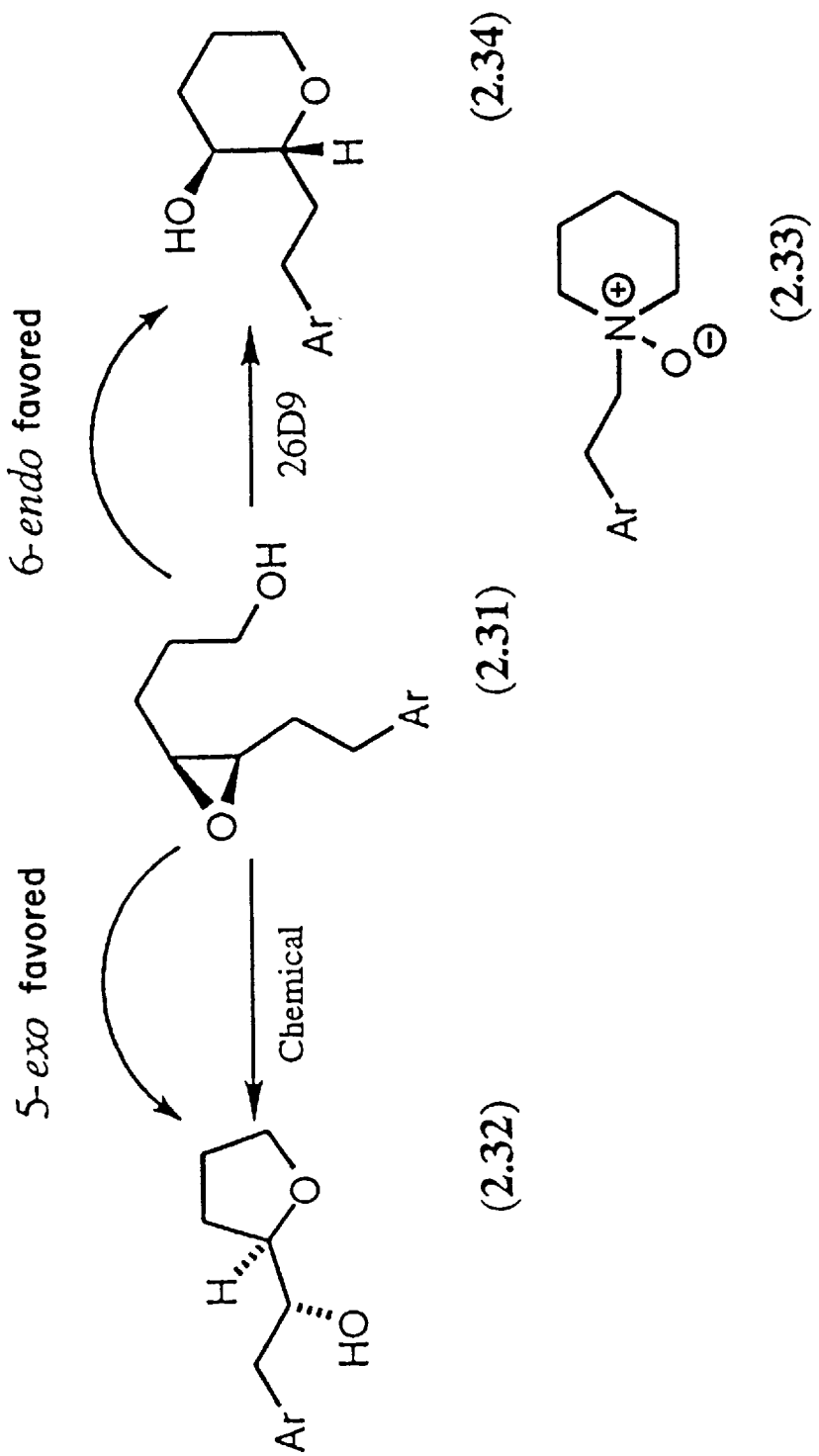
FIG. 2D13

FIG. 2D14
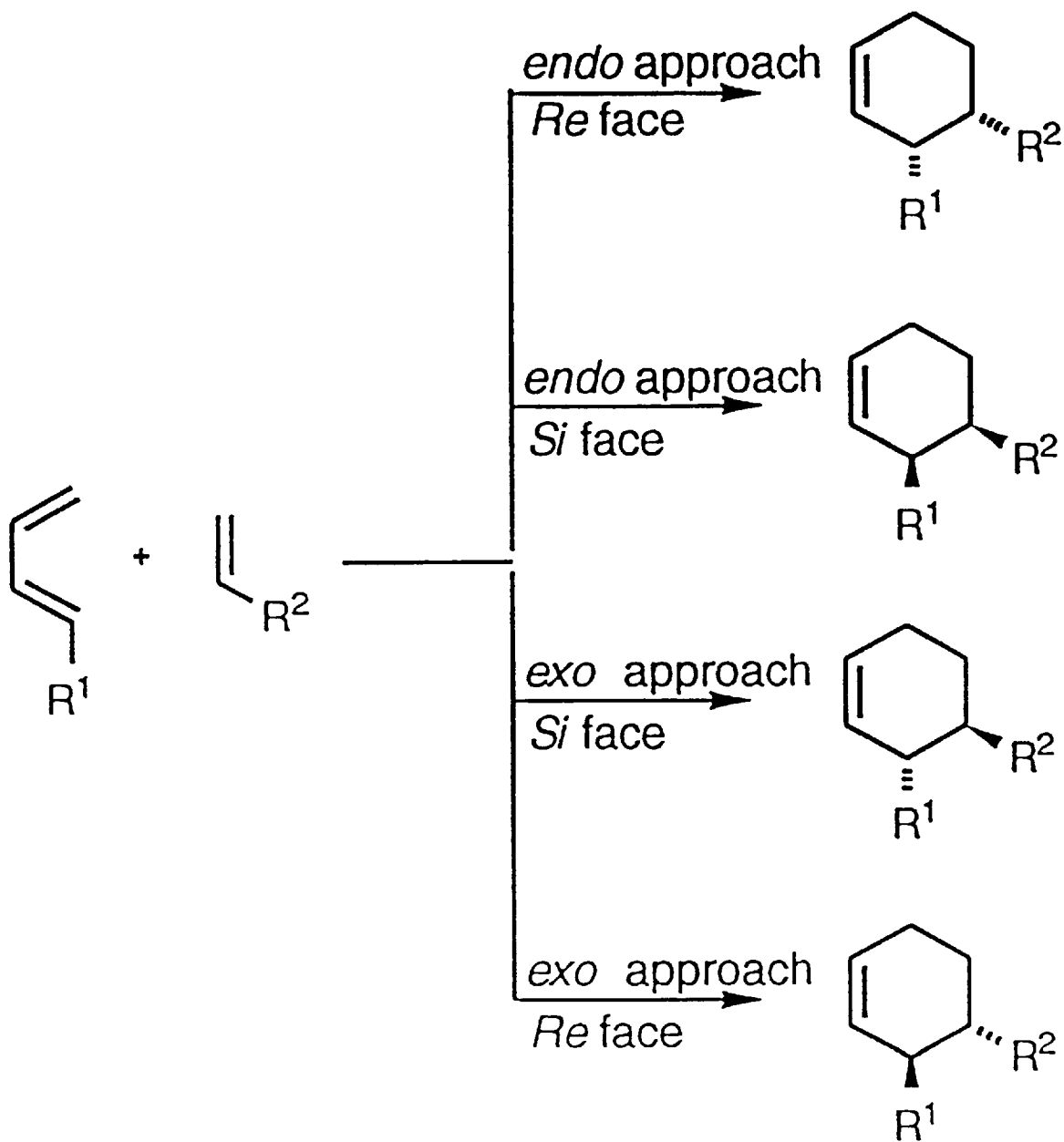

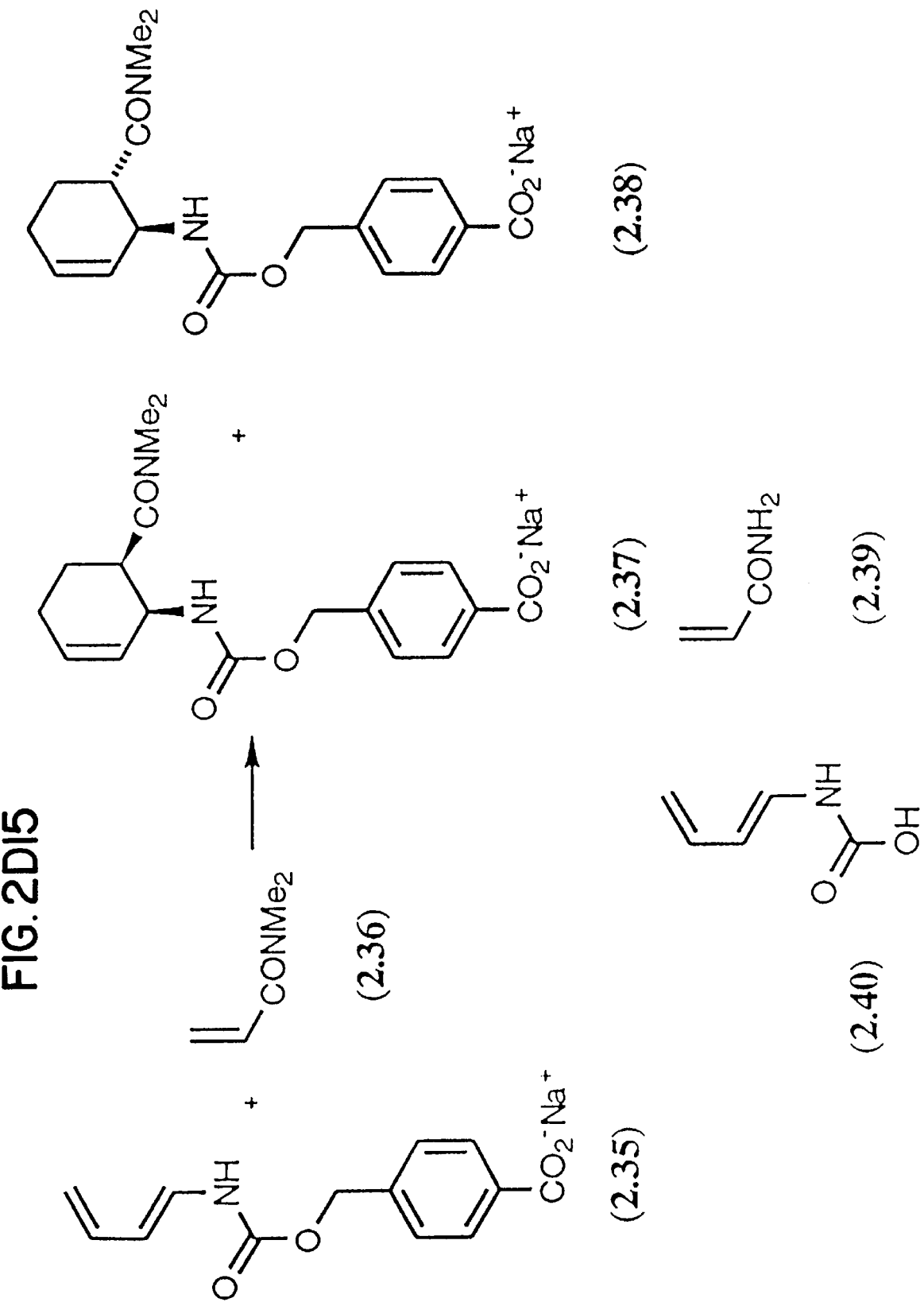
FIG. 2DI5

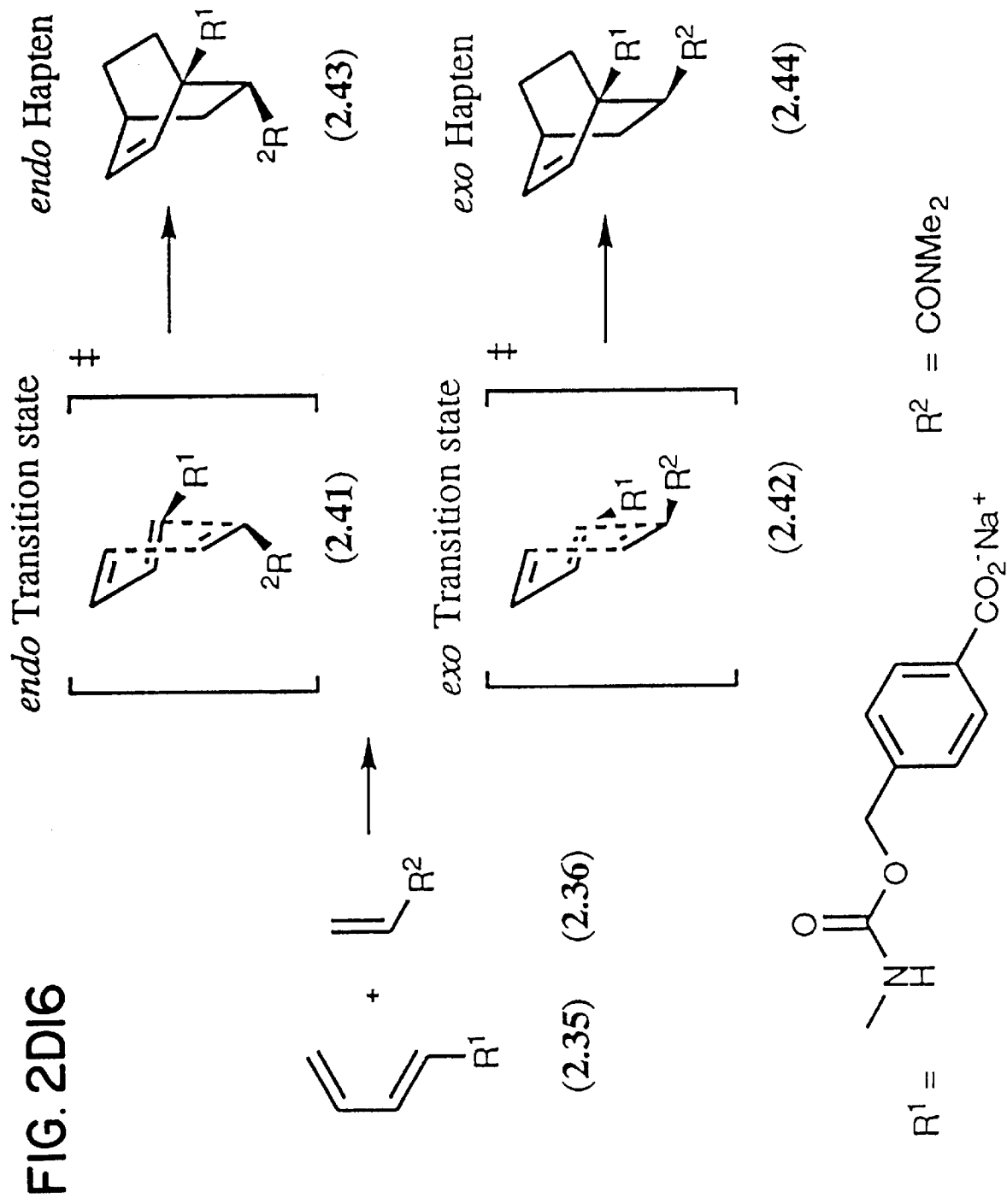
FIG. 2D16

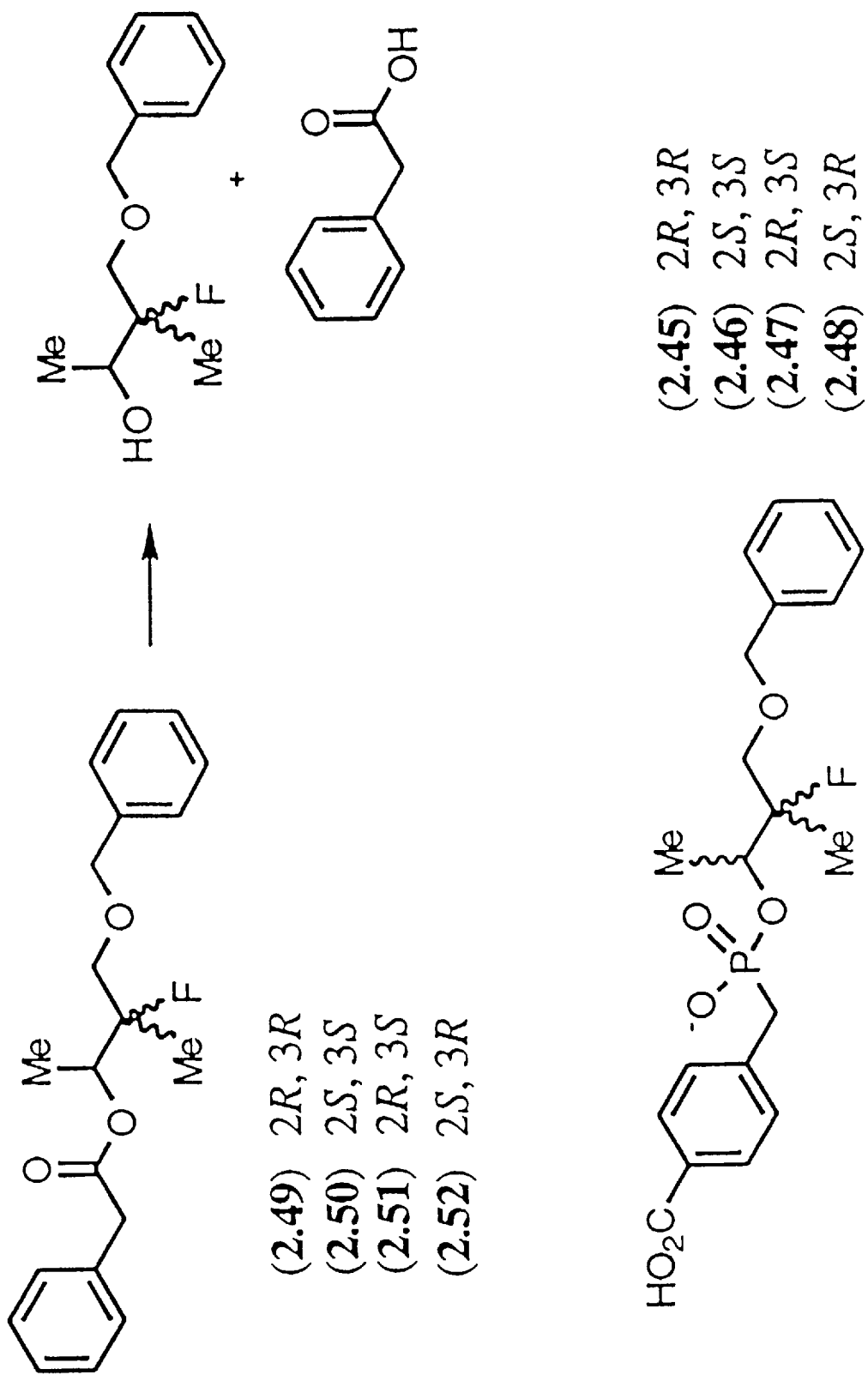
FIG. 2DI7

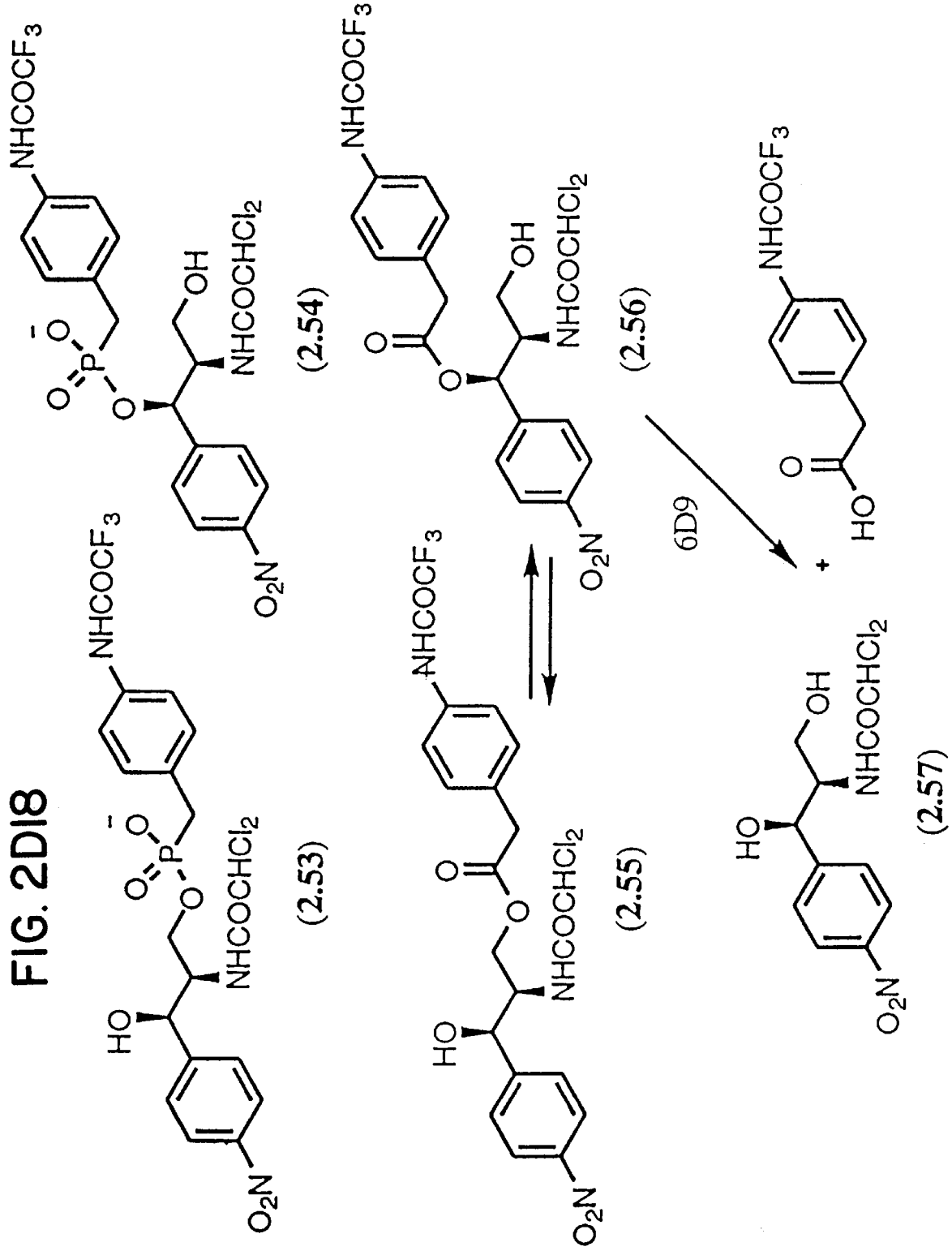
FIG. 2D18

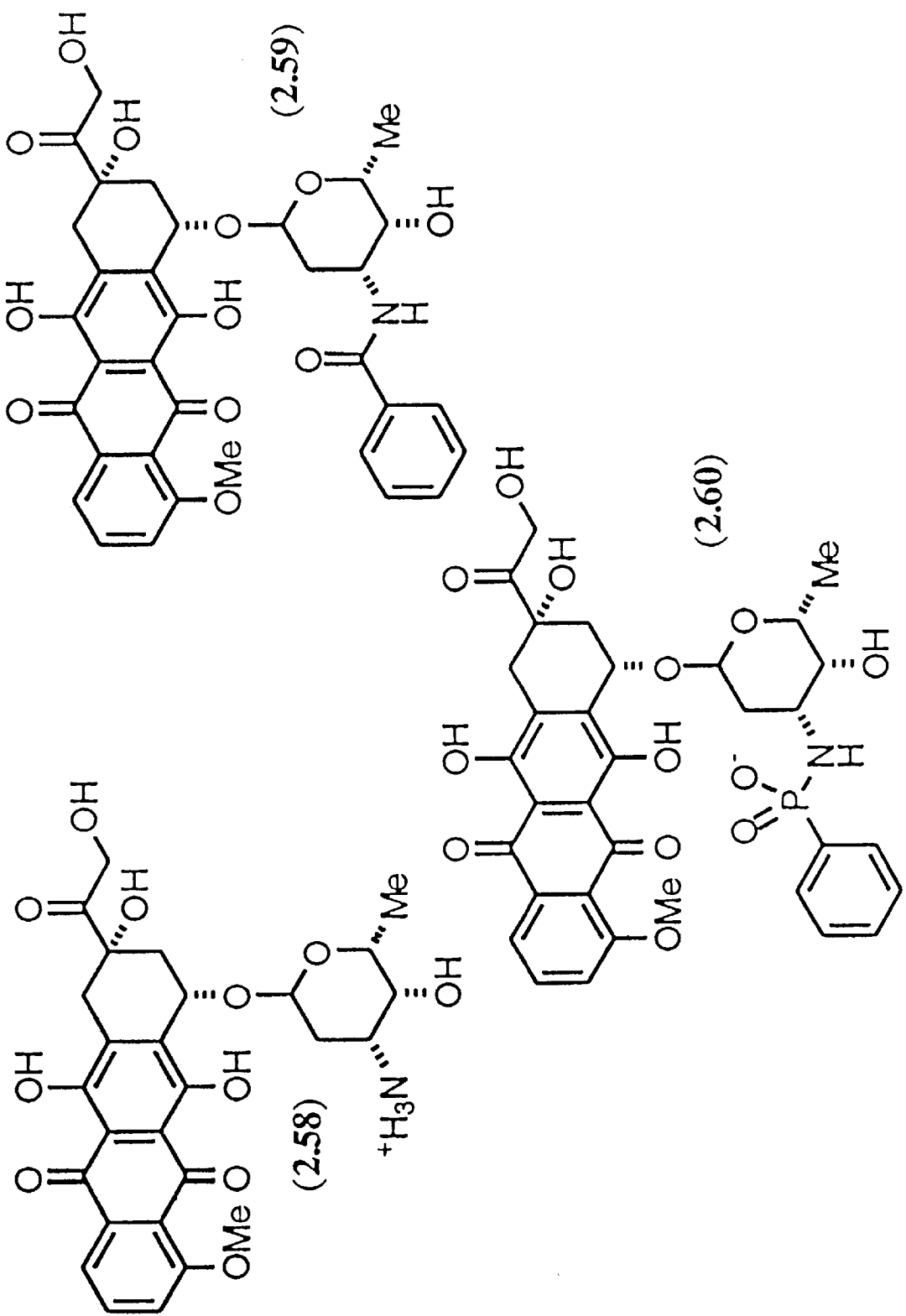
FIG. 2D19

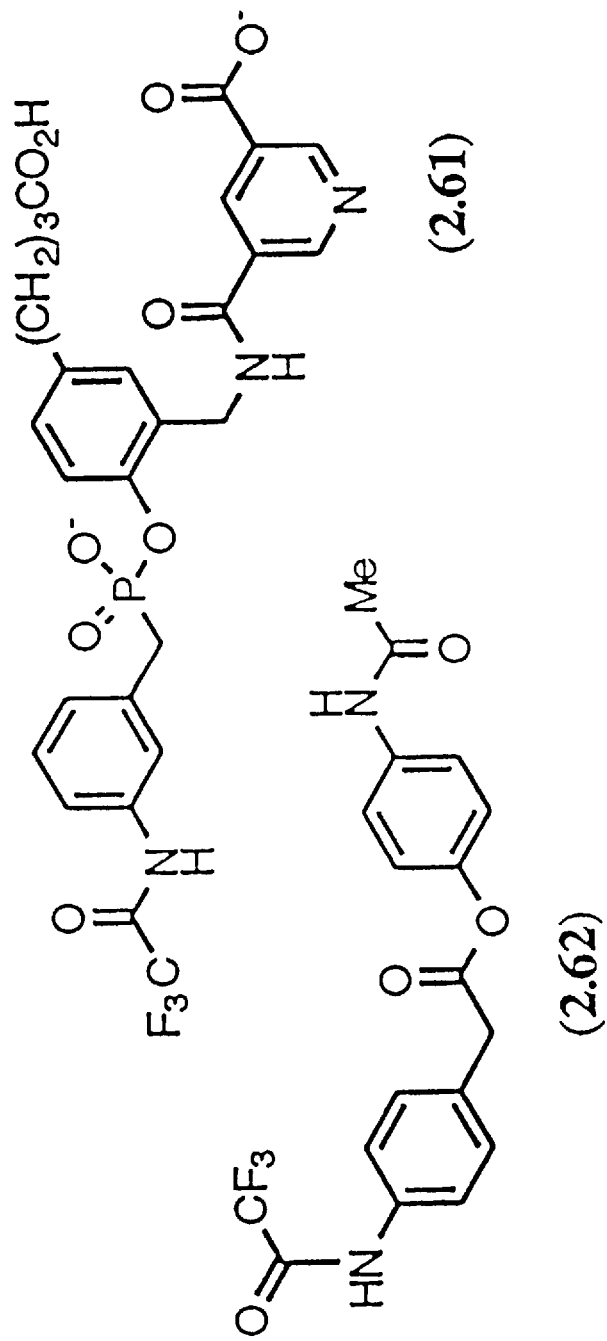
FIG. 2D20

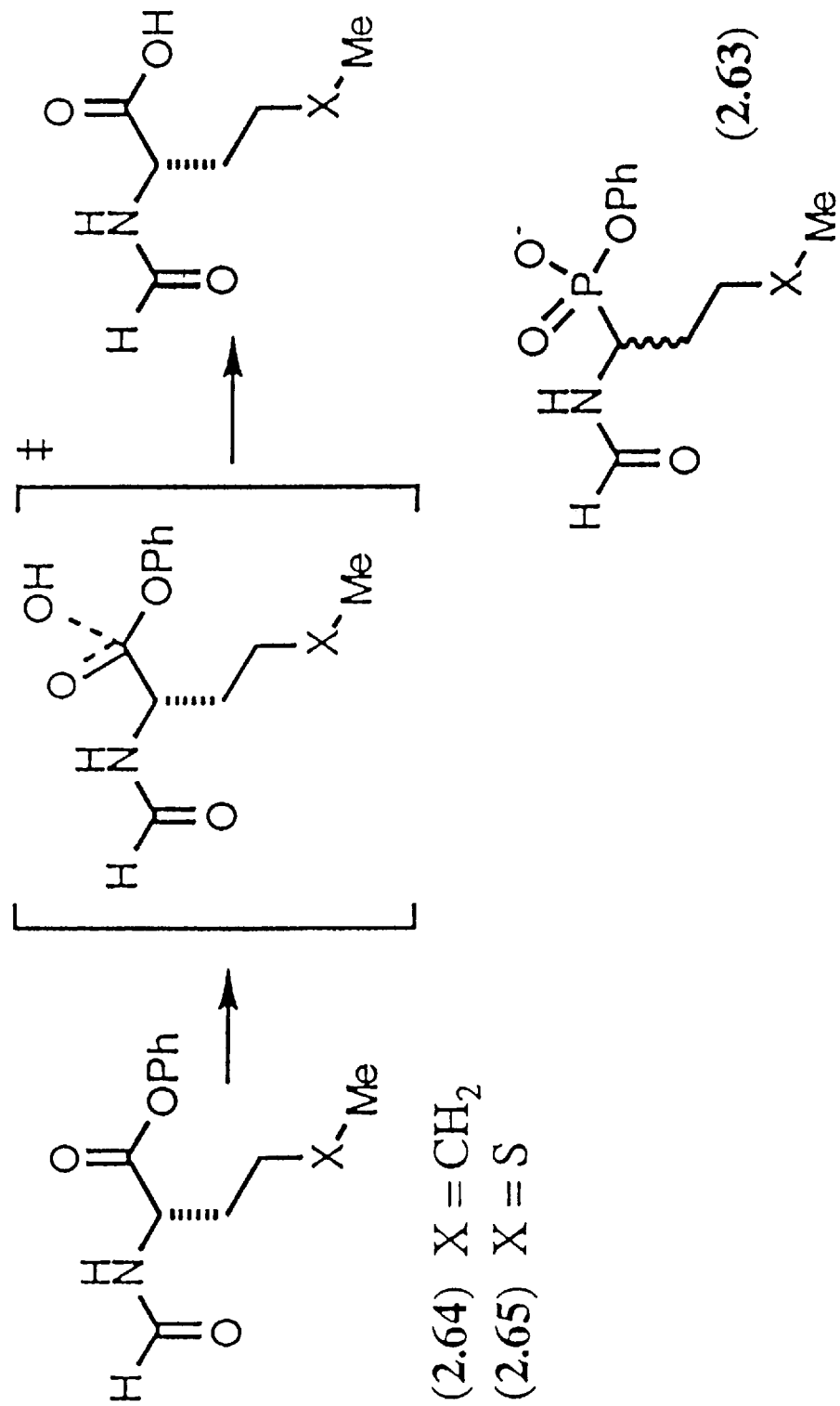
FIG. 2D2I

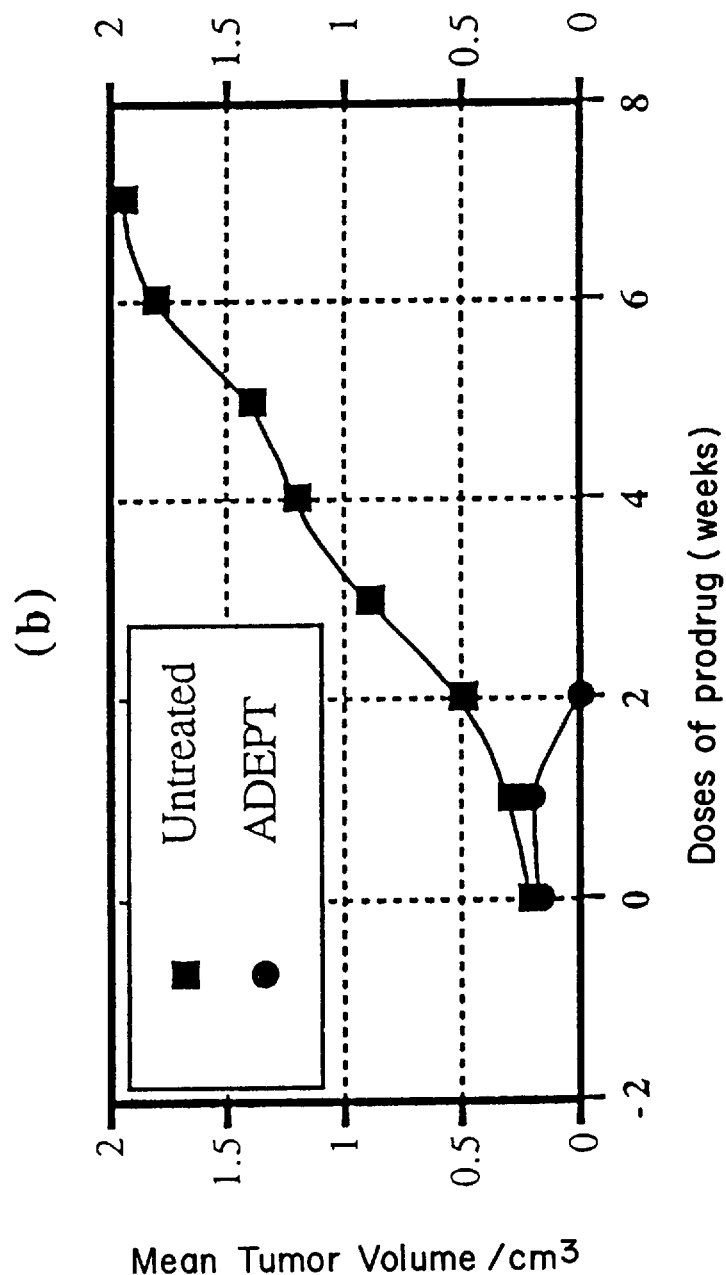
FIG. 3D2

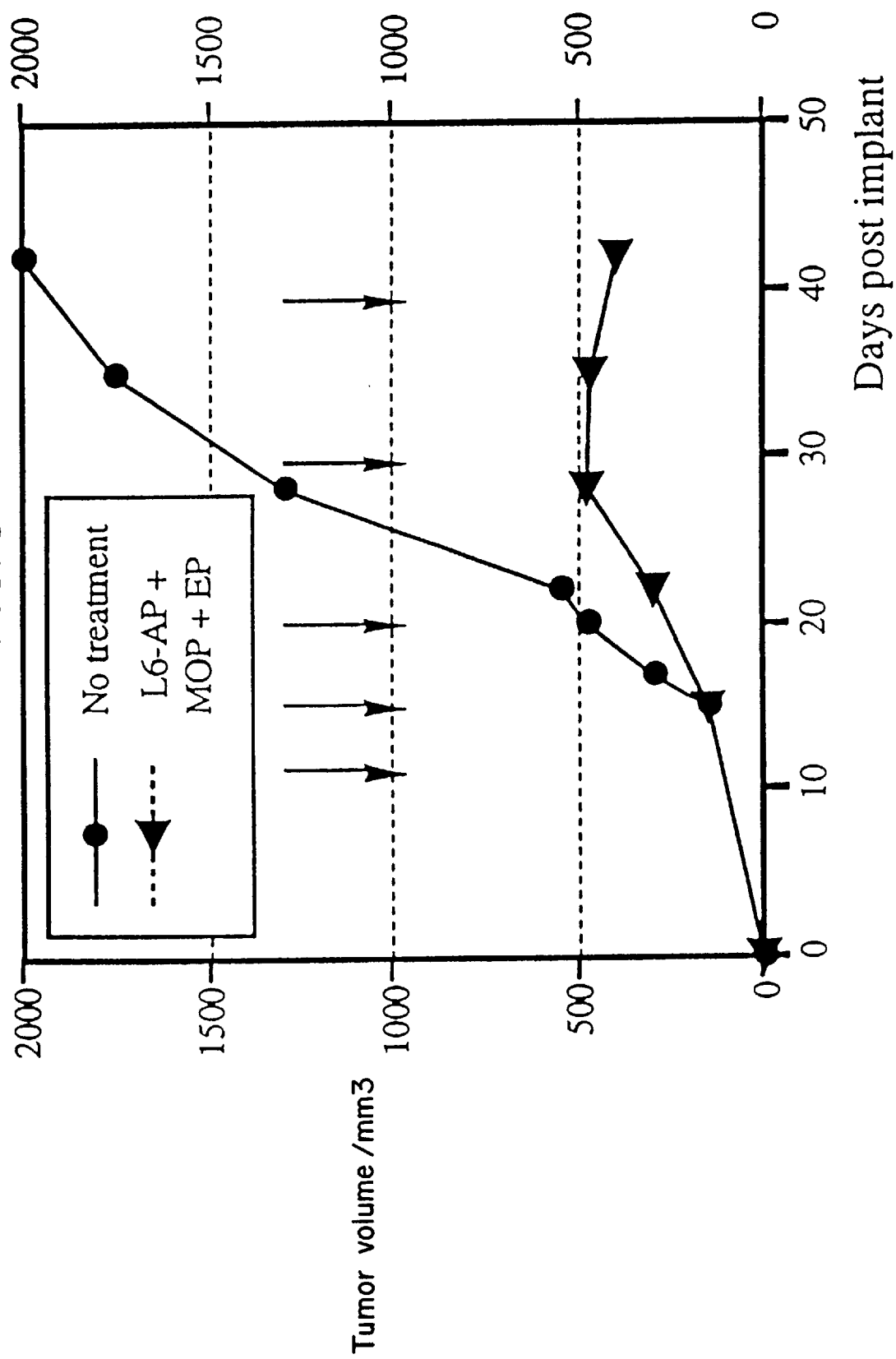

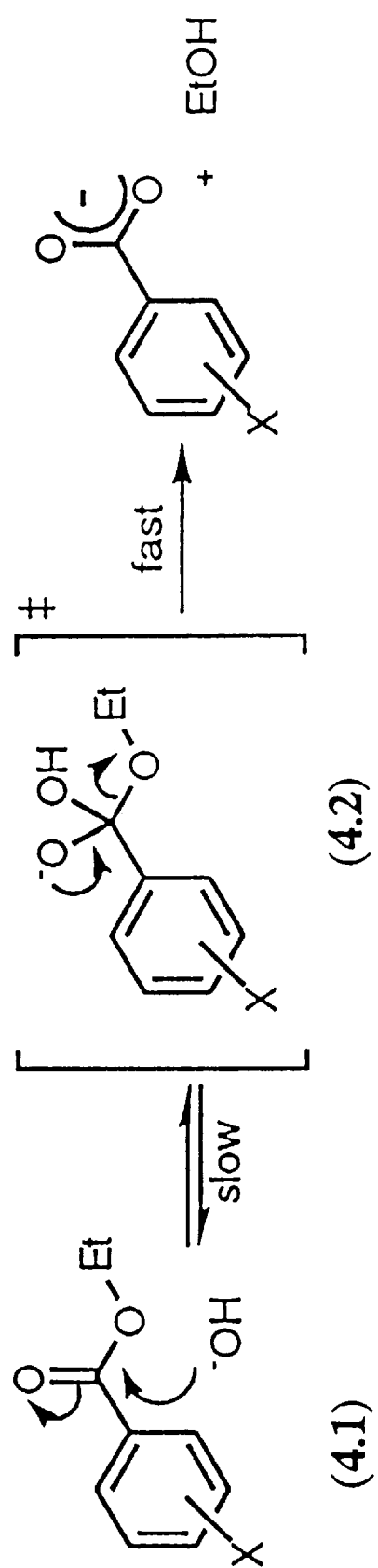
FIG. 4A1
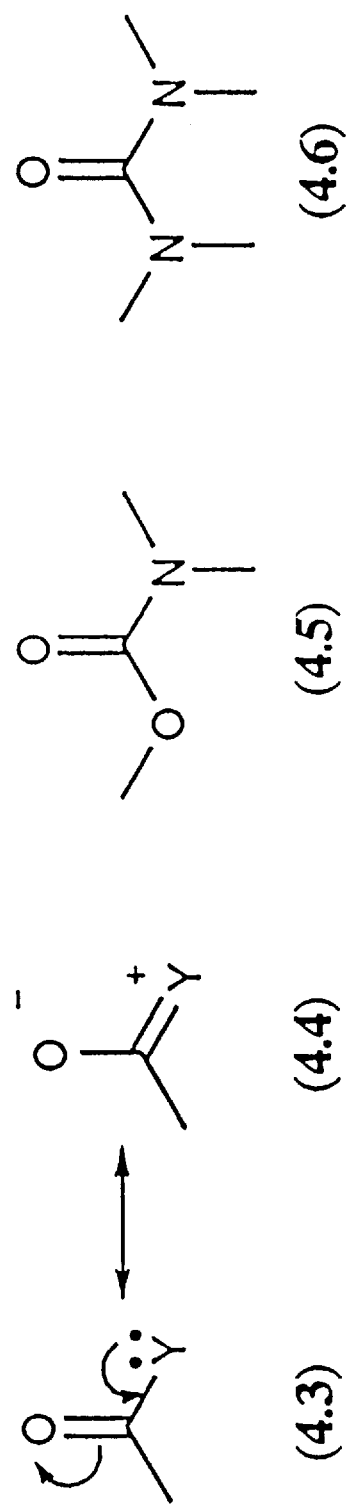
FIG. 4A2

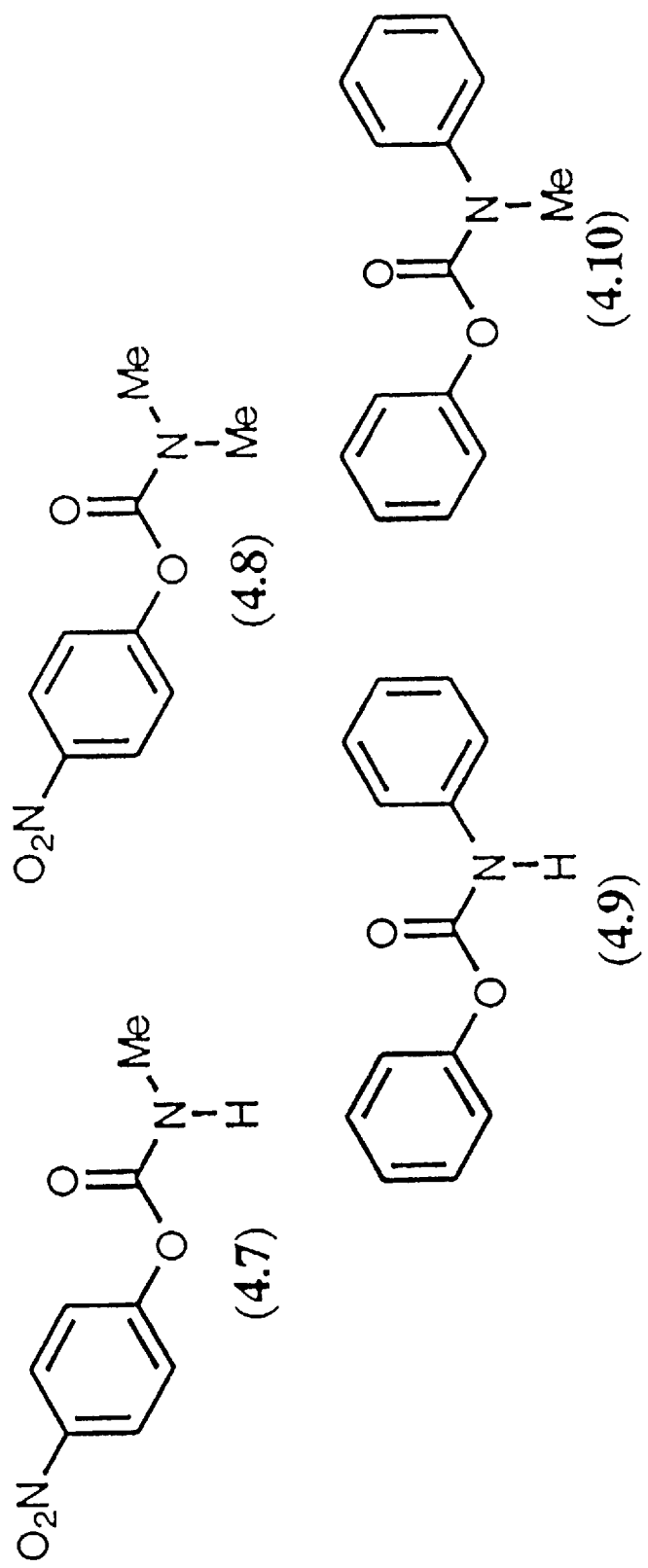
FIG. 4A3

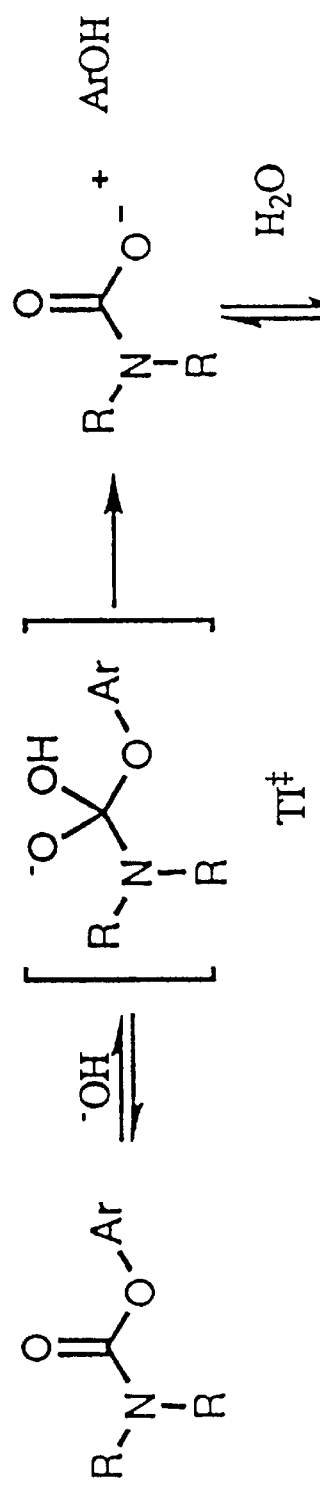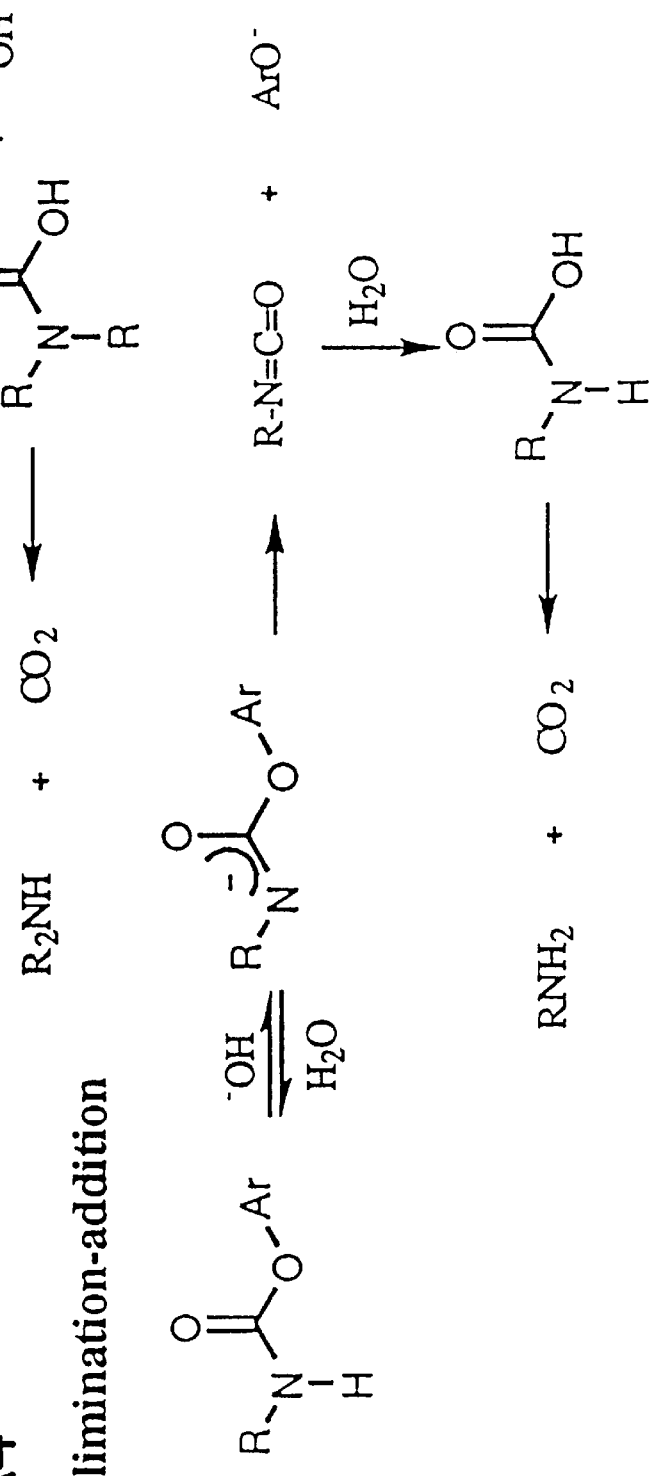
FIG. 4A4

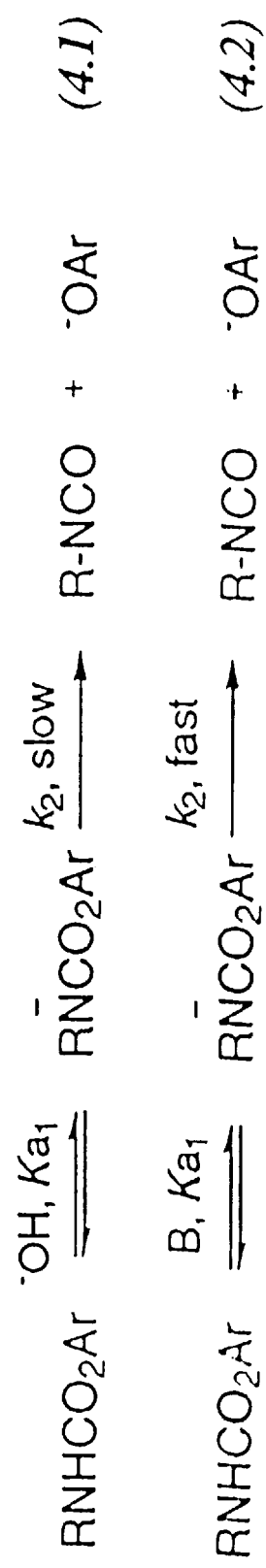
FIG. 4A5

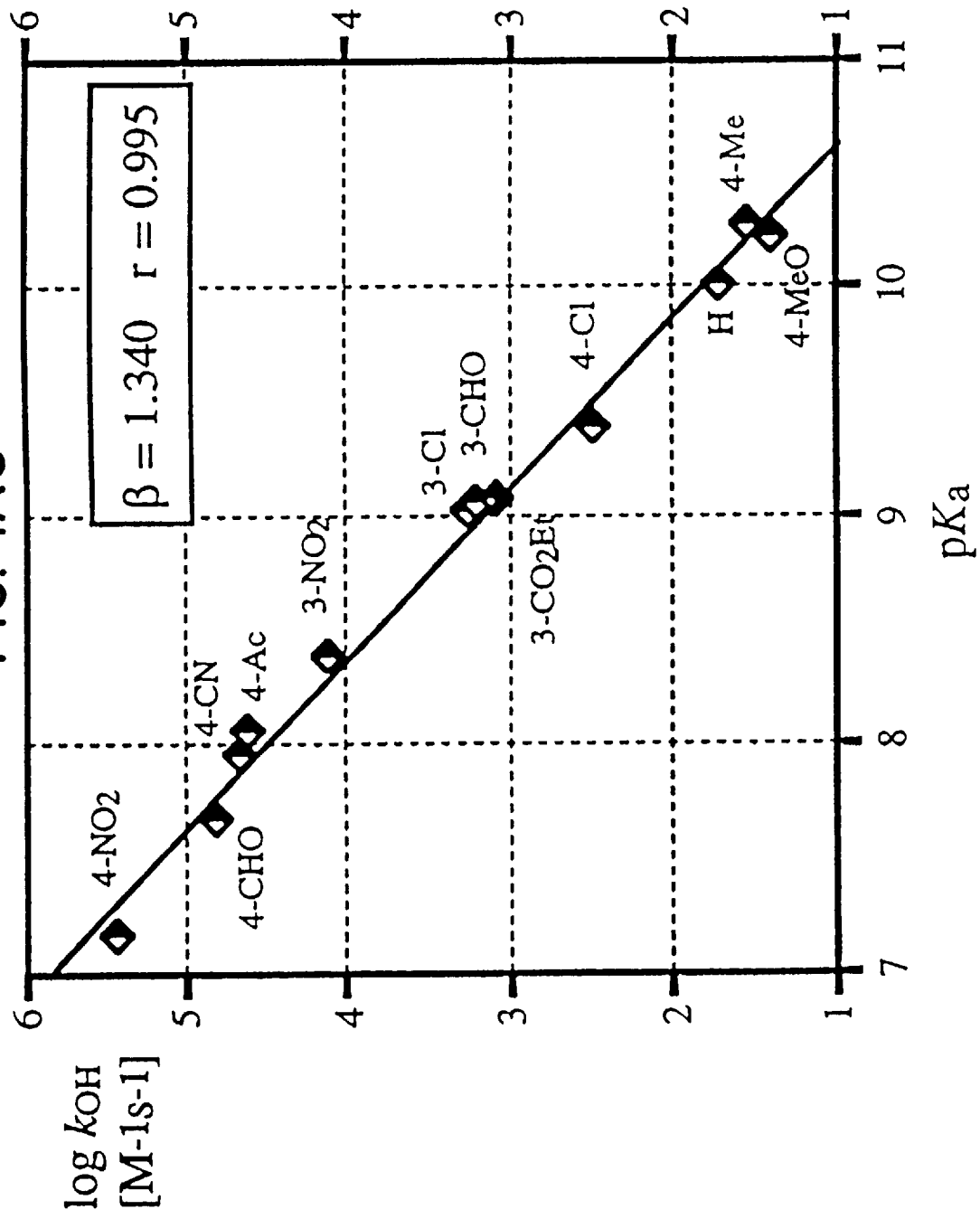

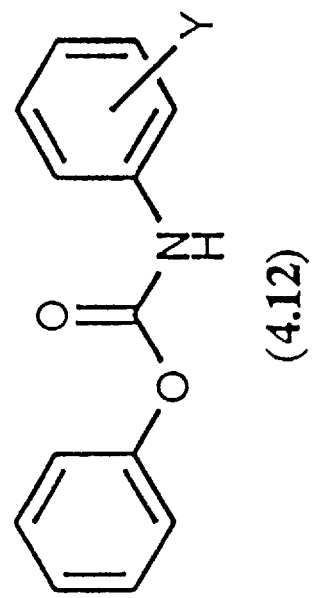
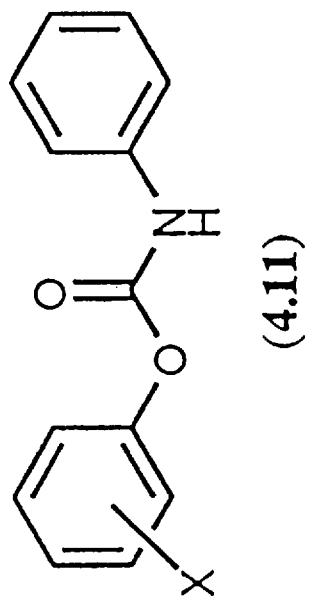
FIG. 4A7

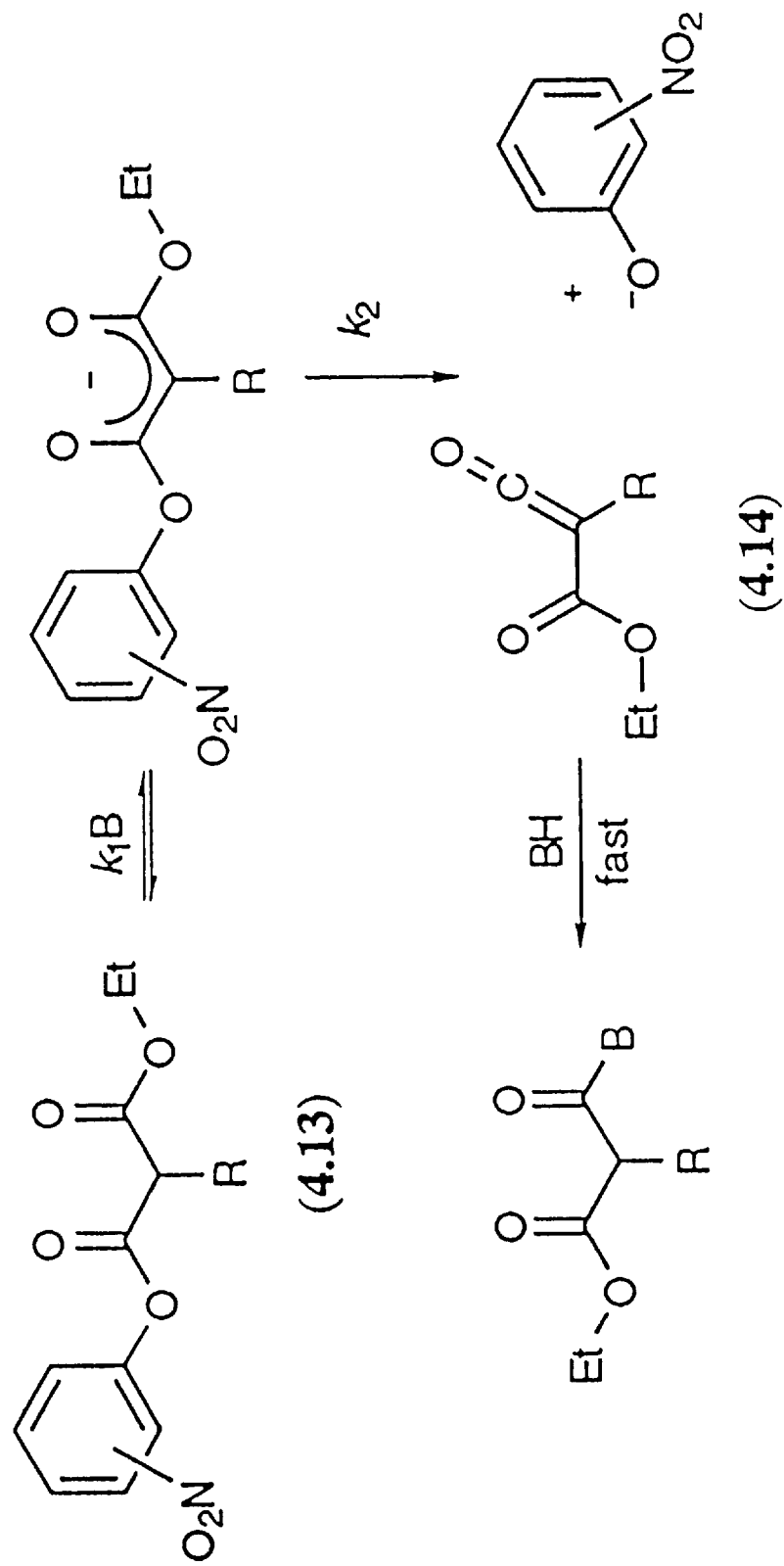
FIG. 4A8

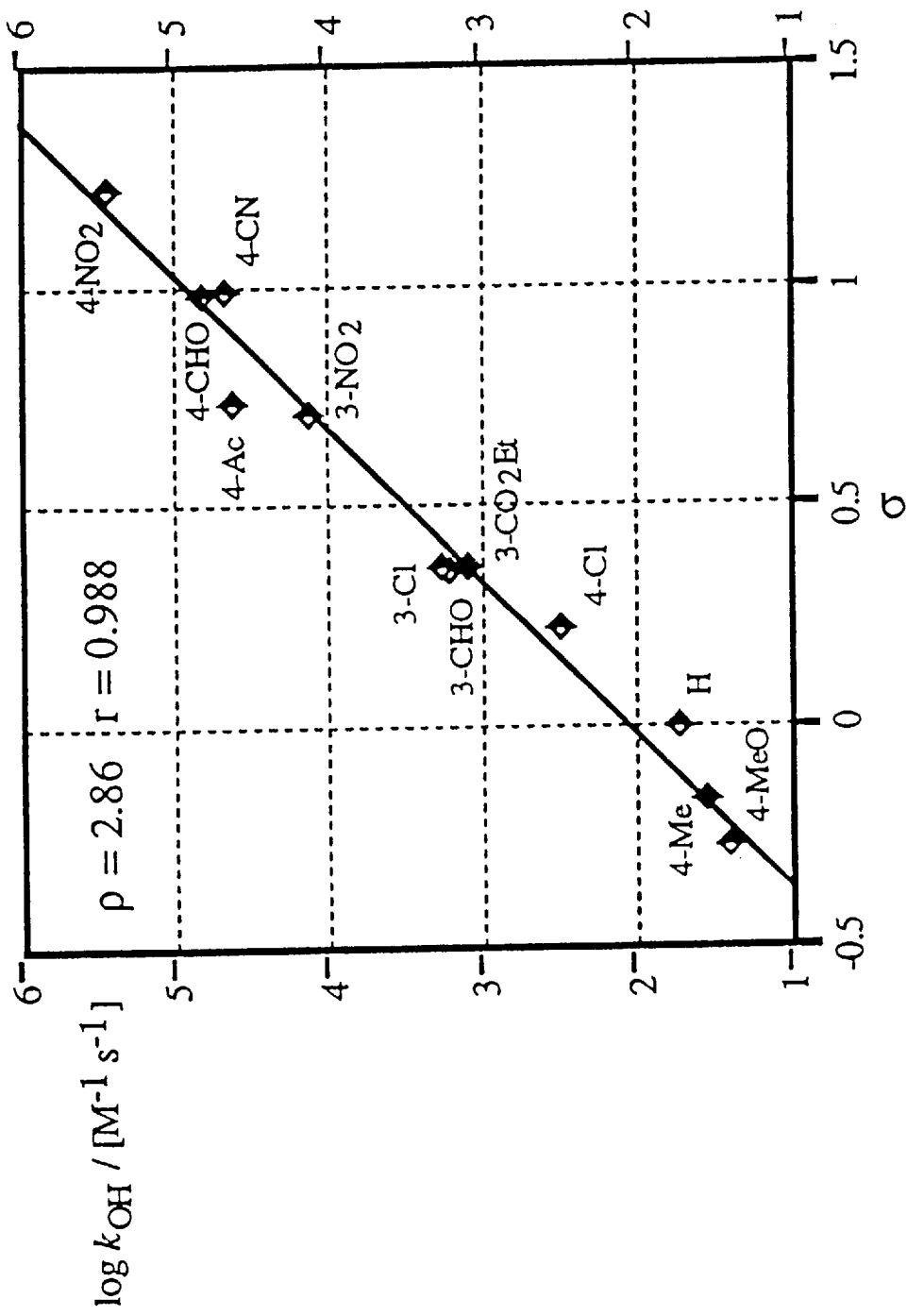
FIG. 4A9

FIG. 4A10
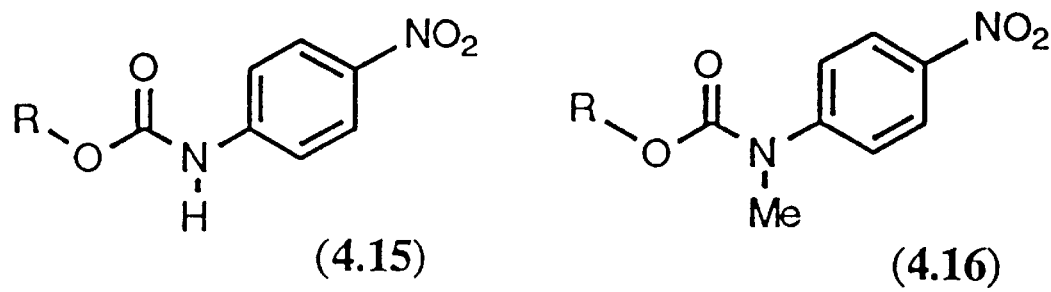
(4.15) (4.16)
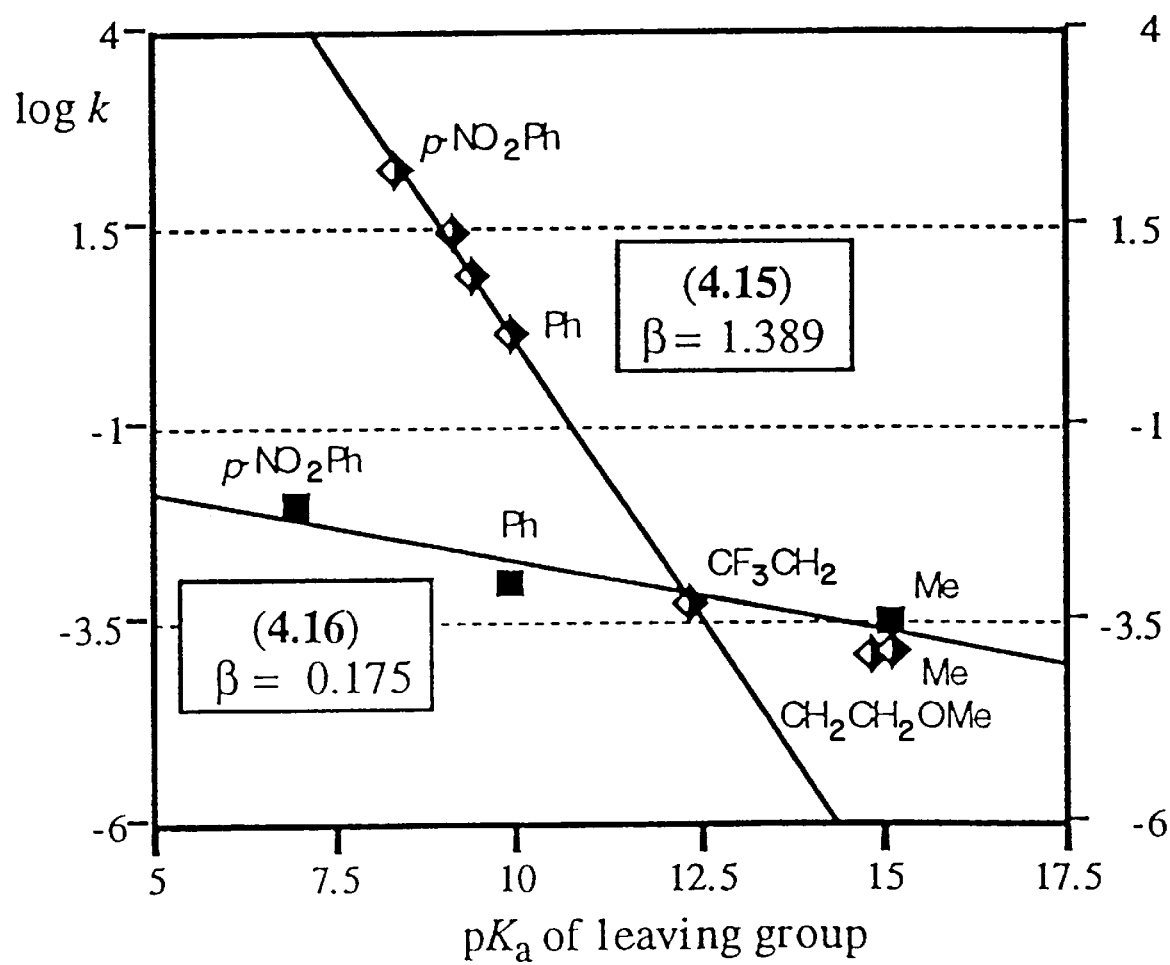

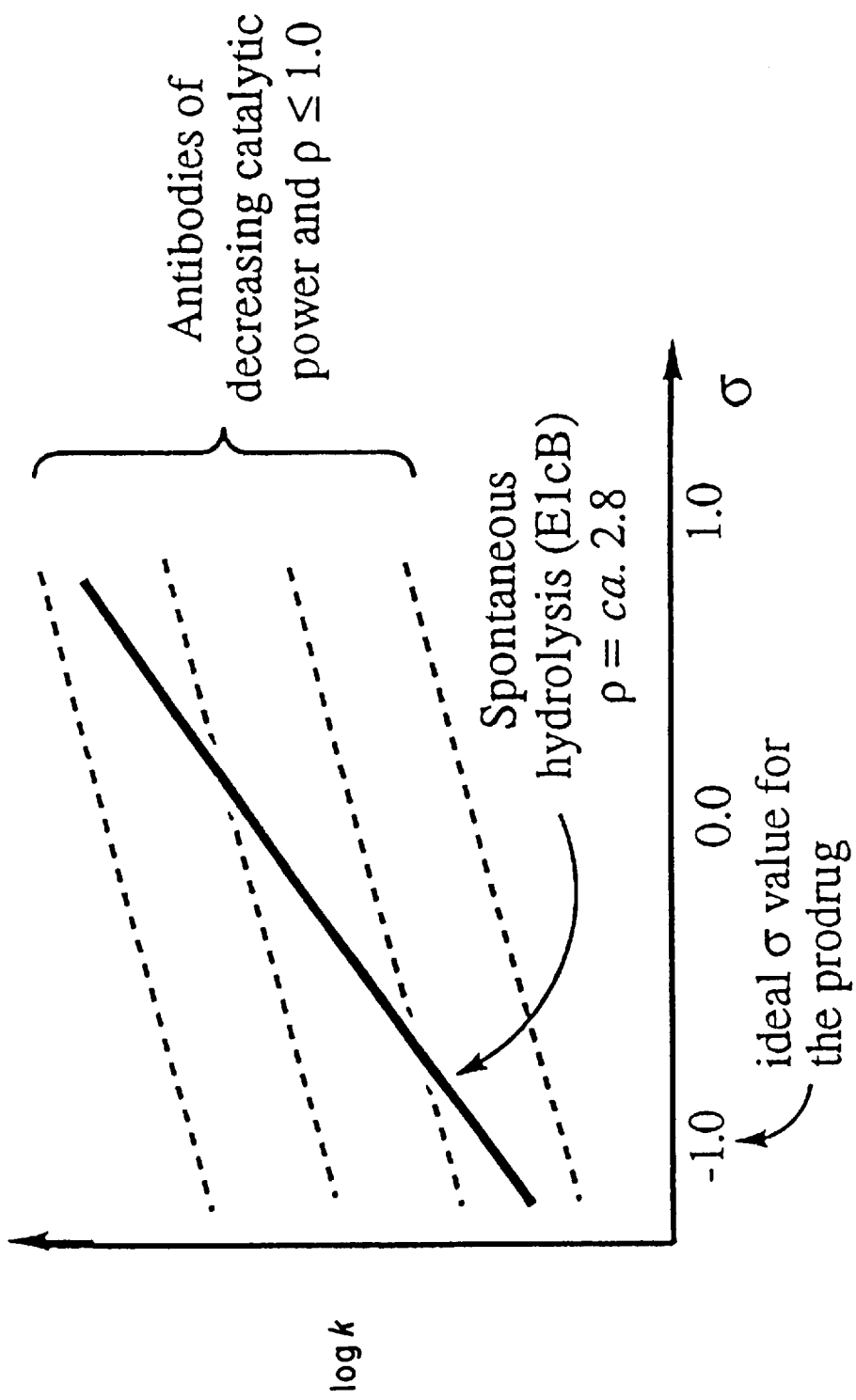
FIG. 4B2

FIG. 4B3
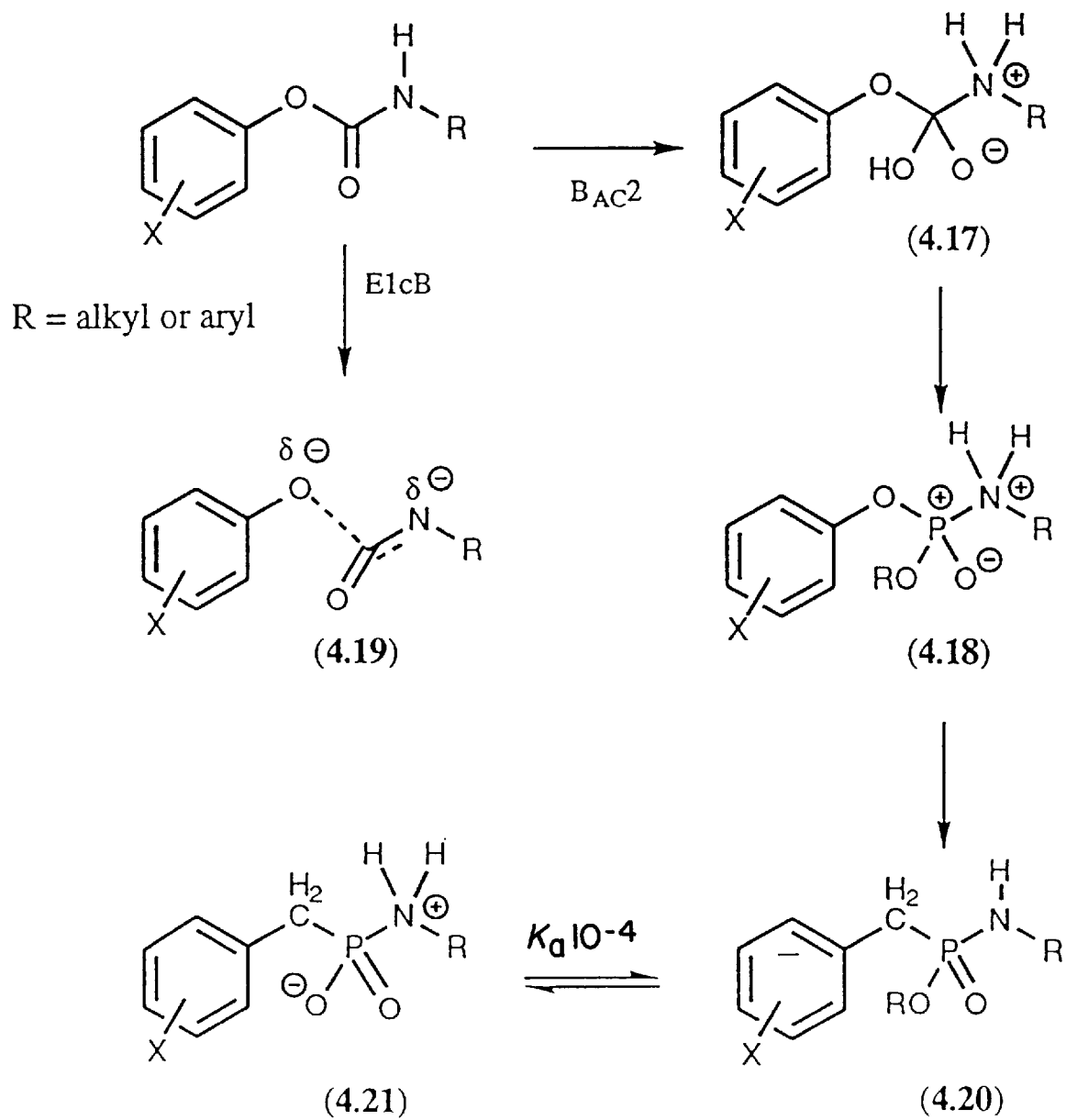

FIG. 4B4
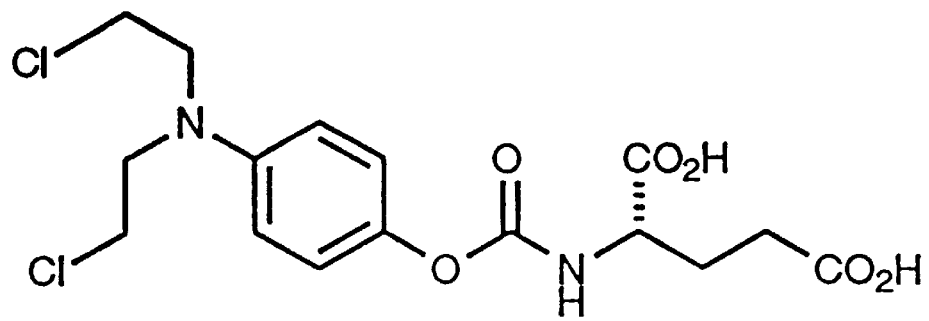
(4.22)
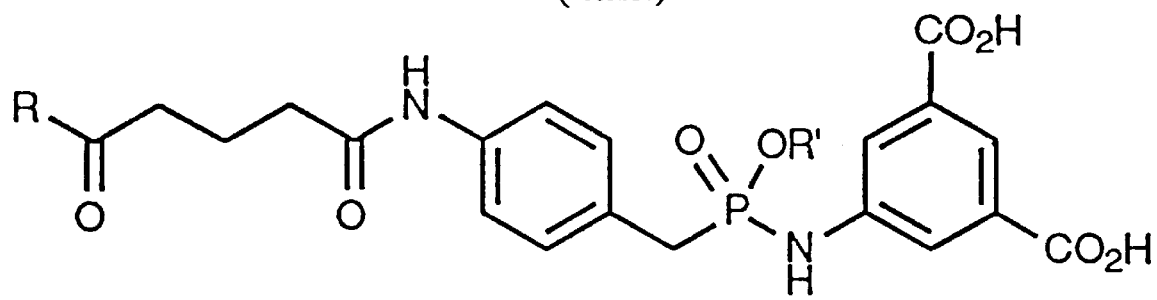
Hapten 1 (4.25) R = $N$-hydroxysuccinimide, R' = Et
Hapten 2 (4.26) R = $N$-hydroxysuccinimide, R' = H
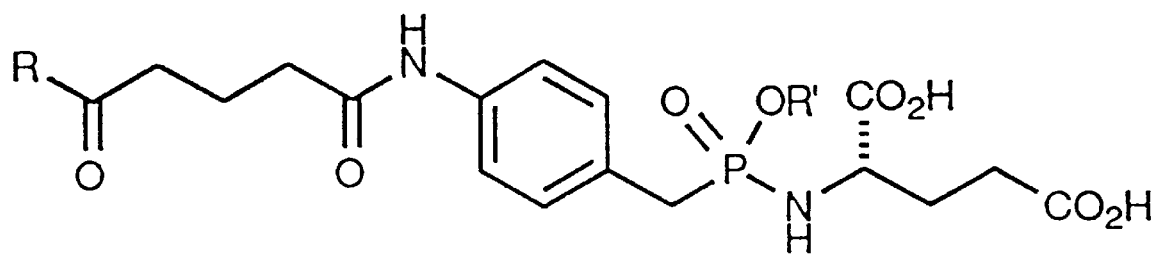
Hapten 3 (4.23) R = $N$-hydroxysuccinimide, R' = Et
Hapten 4 (4.24) R = $N$-hydroxysuccinimide, R' = H

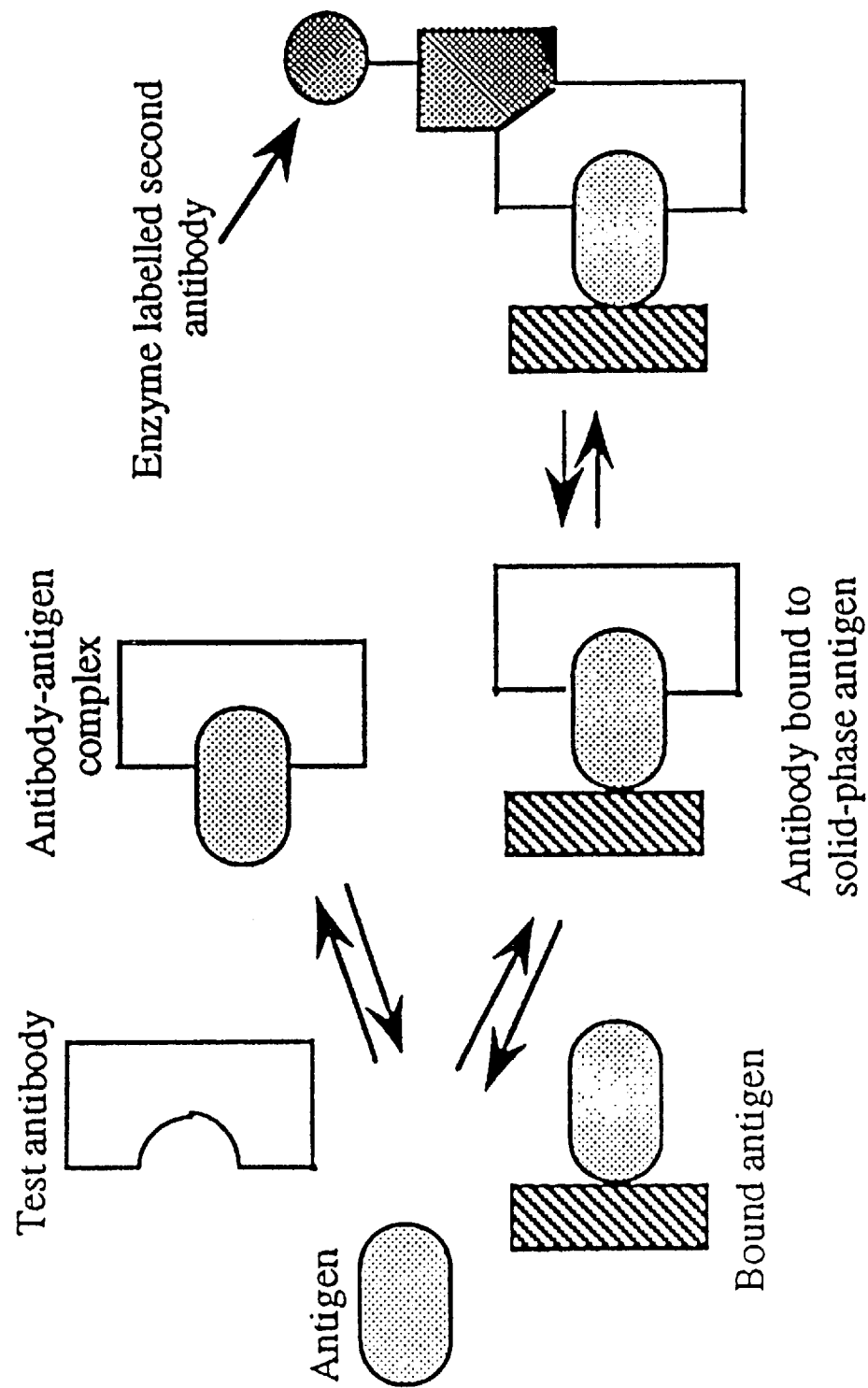

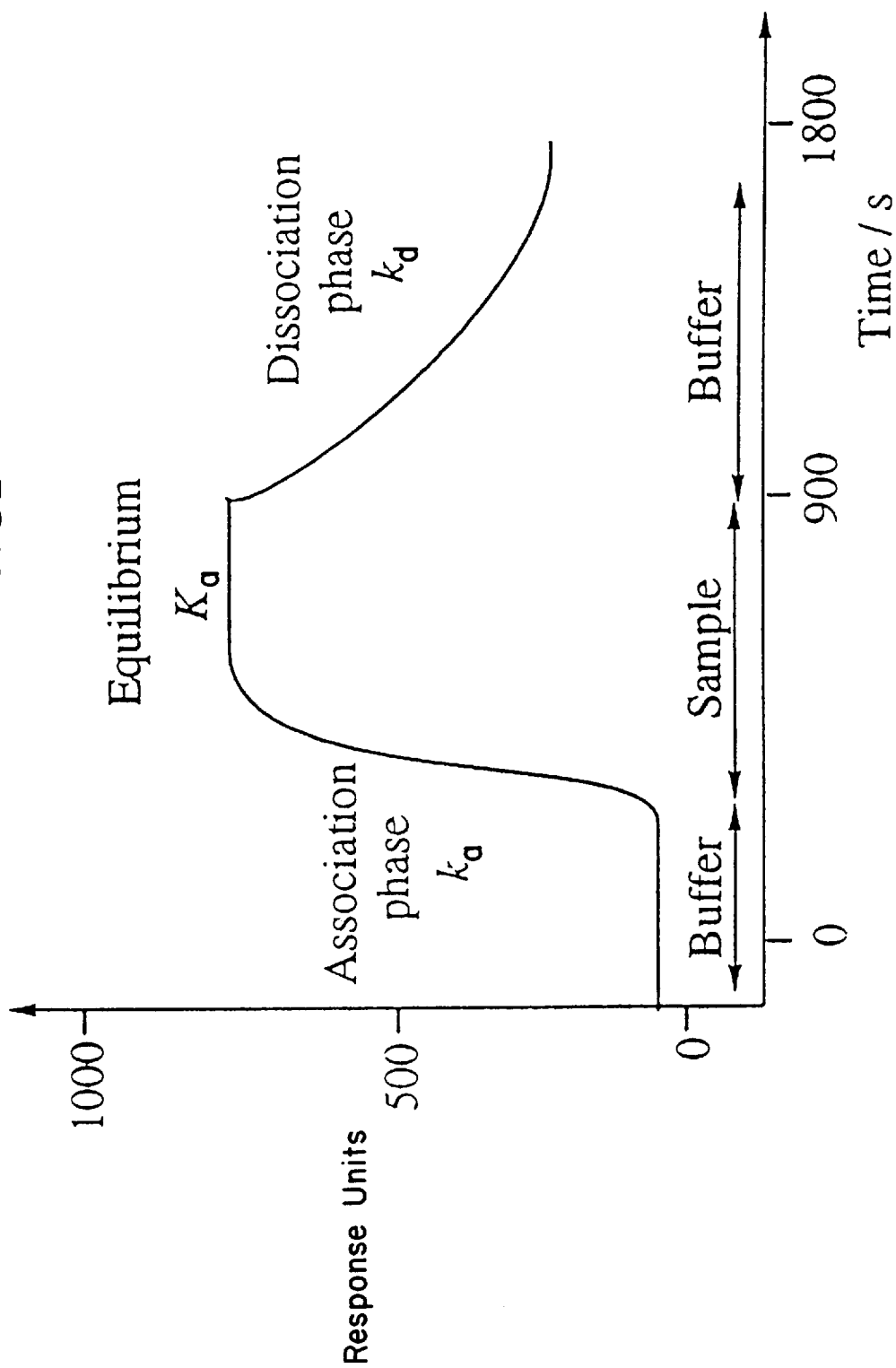

Hapten 1 (6.2)   R = N-hydroxysuccinimide   R' = Et
Hapten 2 (6.3)   R = N-hydroxysuccinimide   R' = H Hapten 3 (6.4)   R = N-hydroxysuccinimide   R' = Et
Hapten 4 (6.5)   R = N-hydroxysuccinimide   R' = H (6.6) X = N(CH$_2$)$_2$Cl$_2$
(6.12) X = NO$_2$ (6.13) Y = CH$_2$
(6.14) Y = NH$_2$ (6.7) X = NO$_2$
(6.8) X = Br
(6.9) X = F
(6.10) X = H
(6.11) X = MeO (7.1)

FIG. 7A2
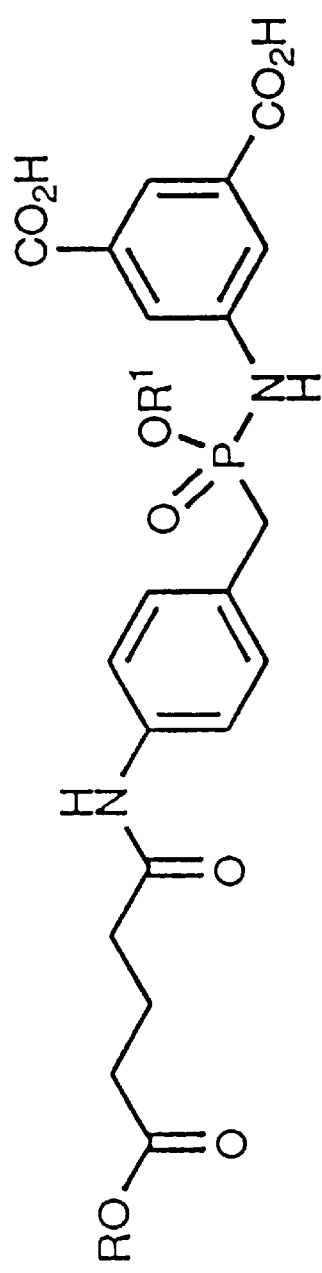
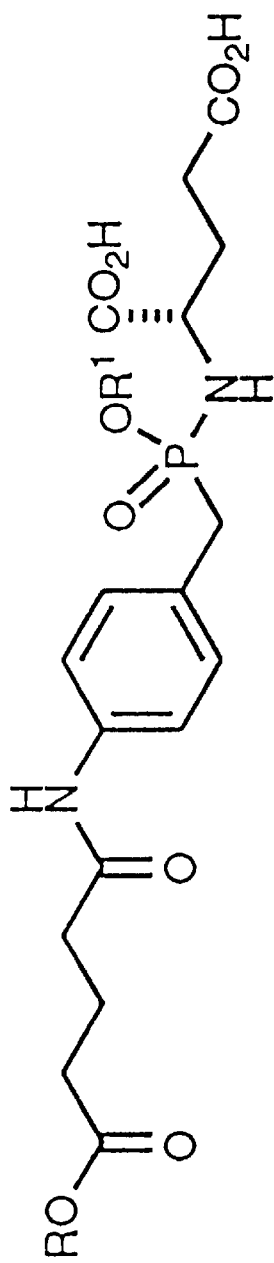
Hapten 1 (7.2)  R = N-hydroxysuccinimide  $R^1$ = Et
Hapten 2 (7.4)  R = N-hydroxysuccinimide  $R^1$ = H
(7.6)           R = H                     $R^1$ = Et
(7.7)           R = H                     $R^1$ = H
Hapten 3 (7.3)  R = N-hydroxysuccinimide  $R^1$ = Et
Hapten 4 (7.5)  R = N-hydroxysuccinimide  $R^1$ = H
(7.8)           R = H                     $R^1$ = Et
(7.9)           R = H                     $R^1$ = H

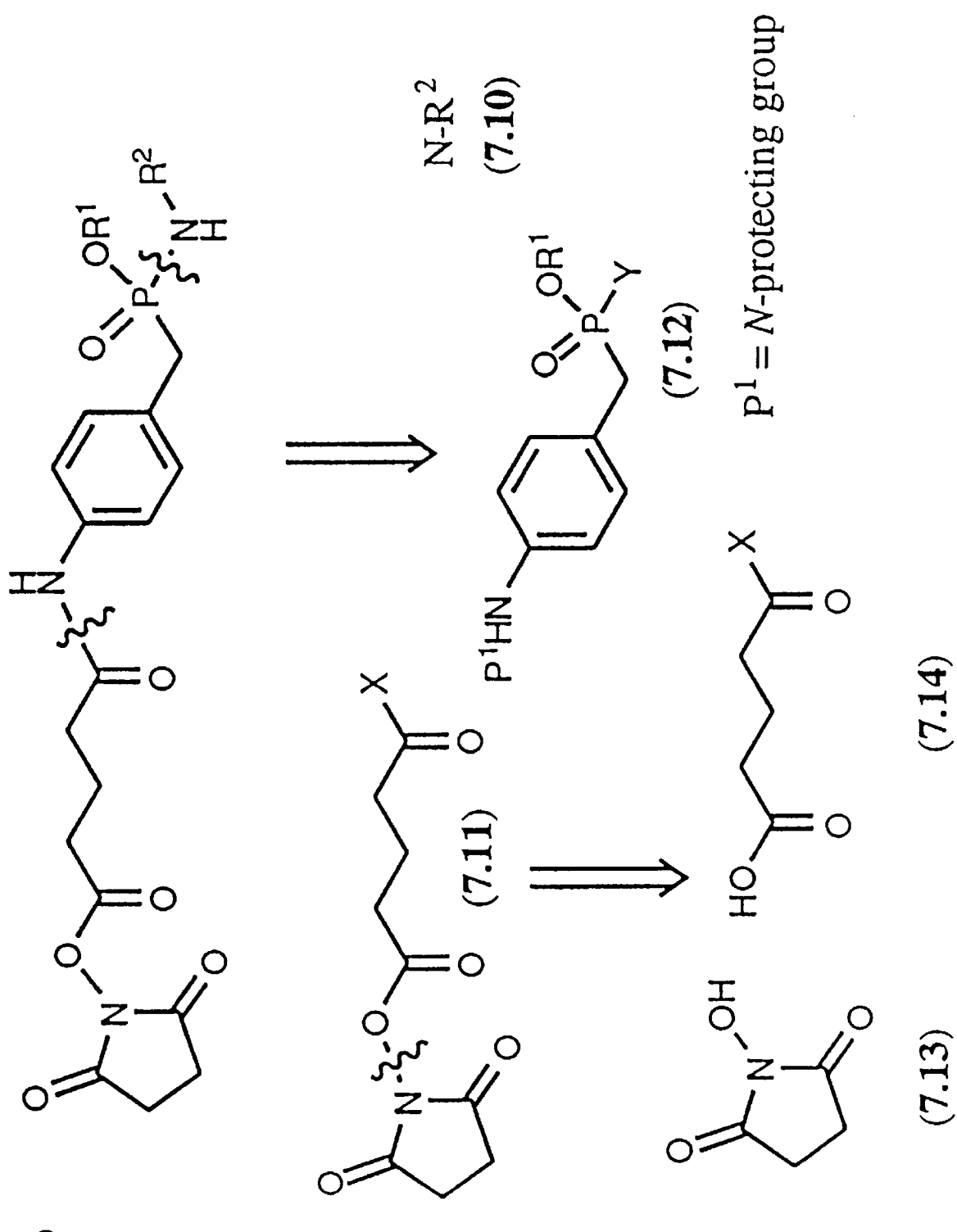
FIG. 7A3

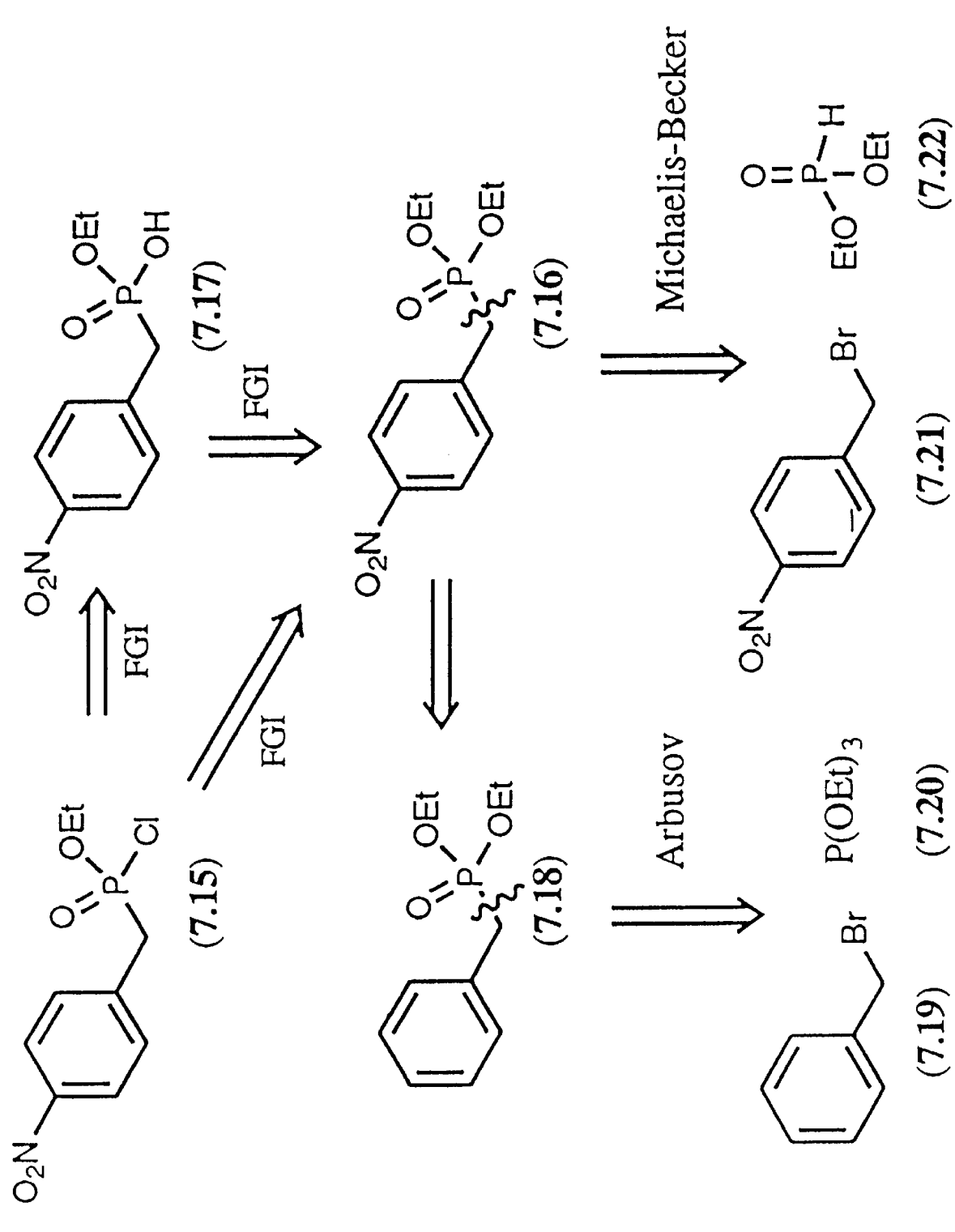
FIG. 7A4

FIG. 7A5
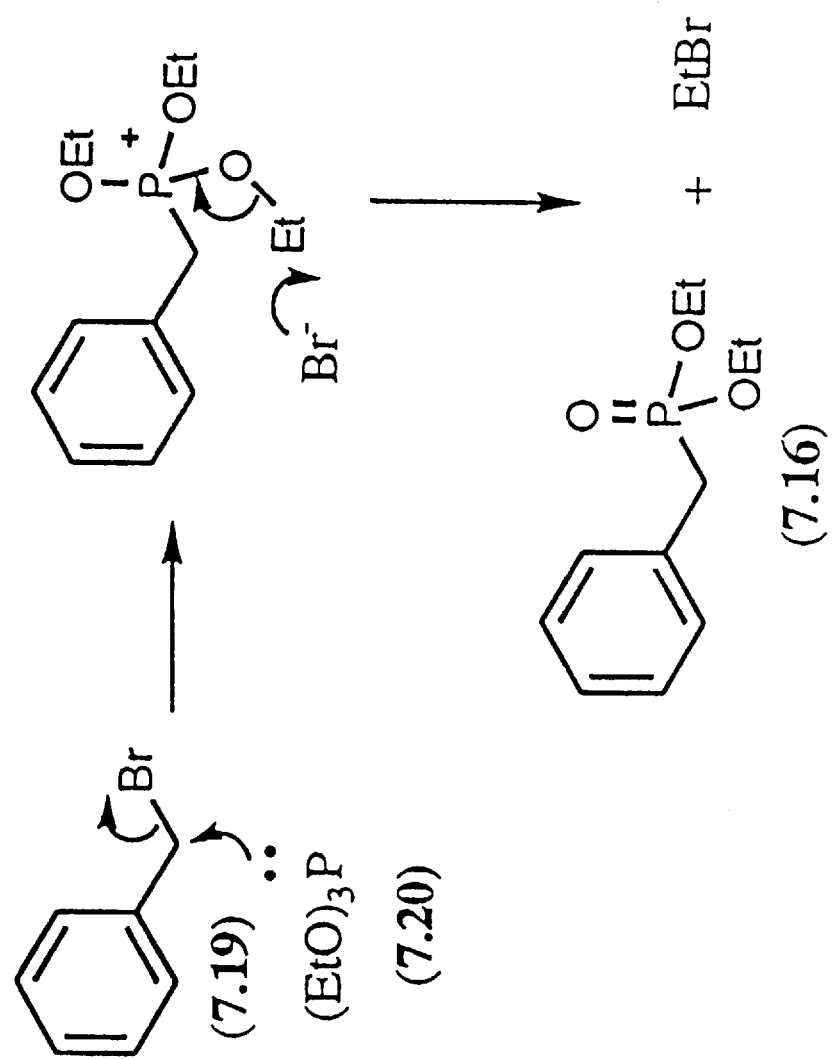

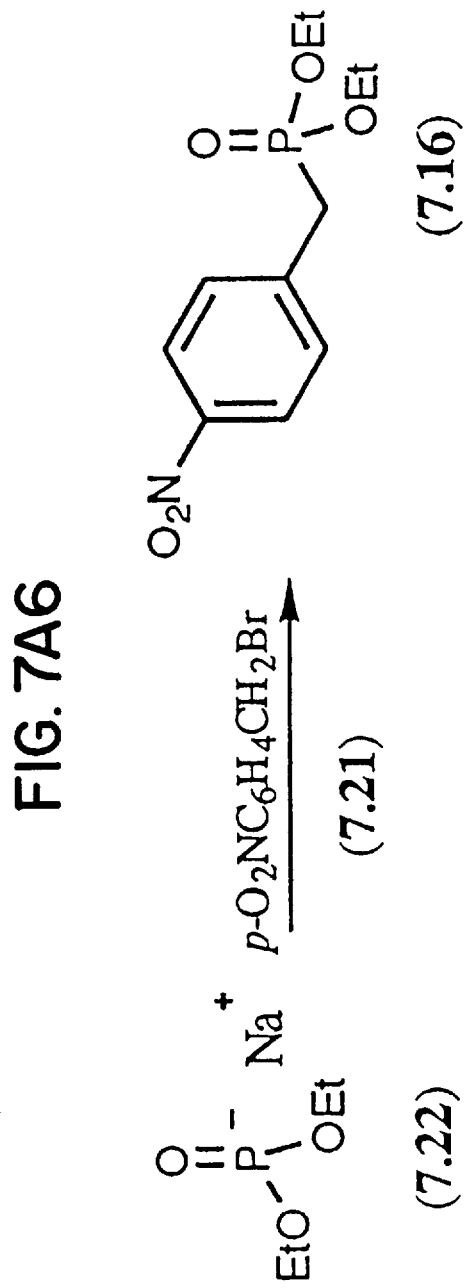
FIG. 7A6

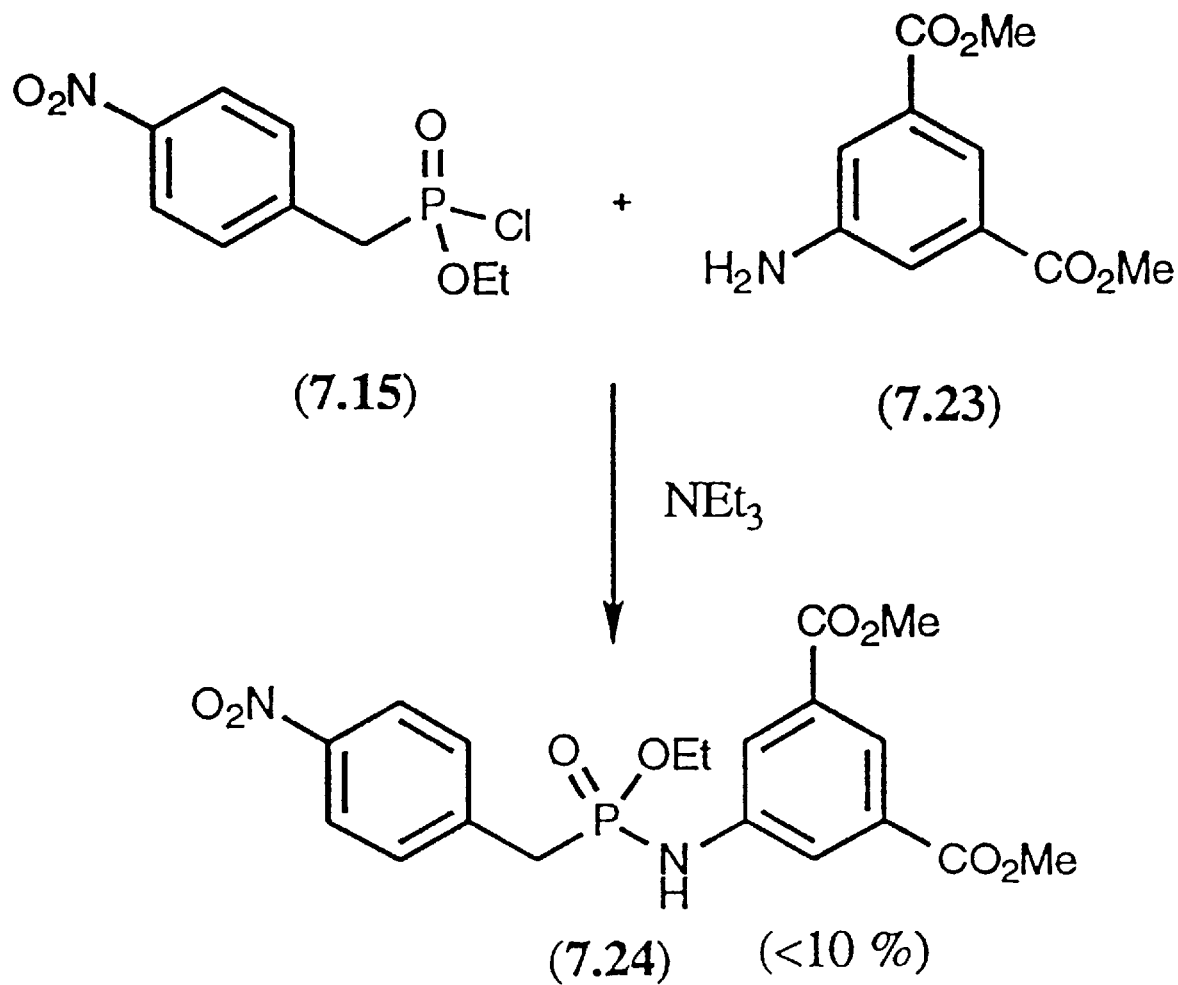
FIG. 7A7

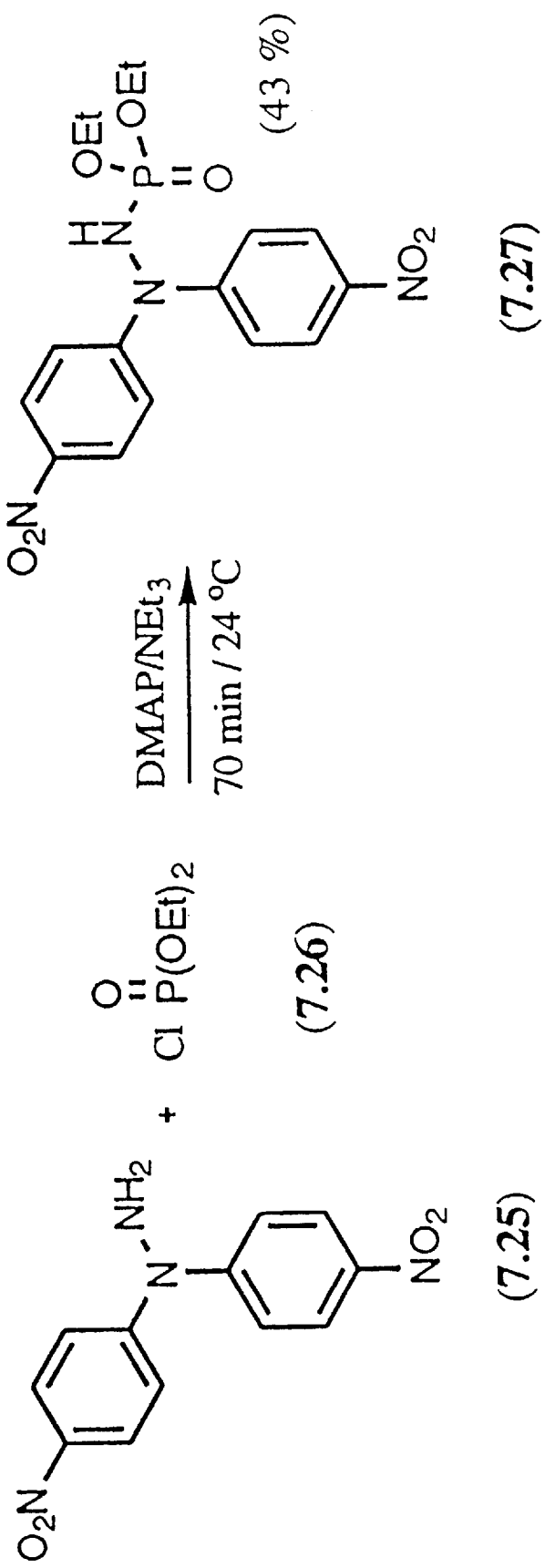
FIG. 7A8

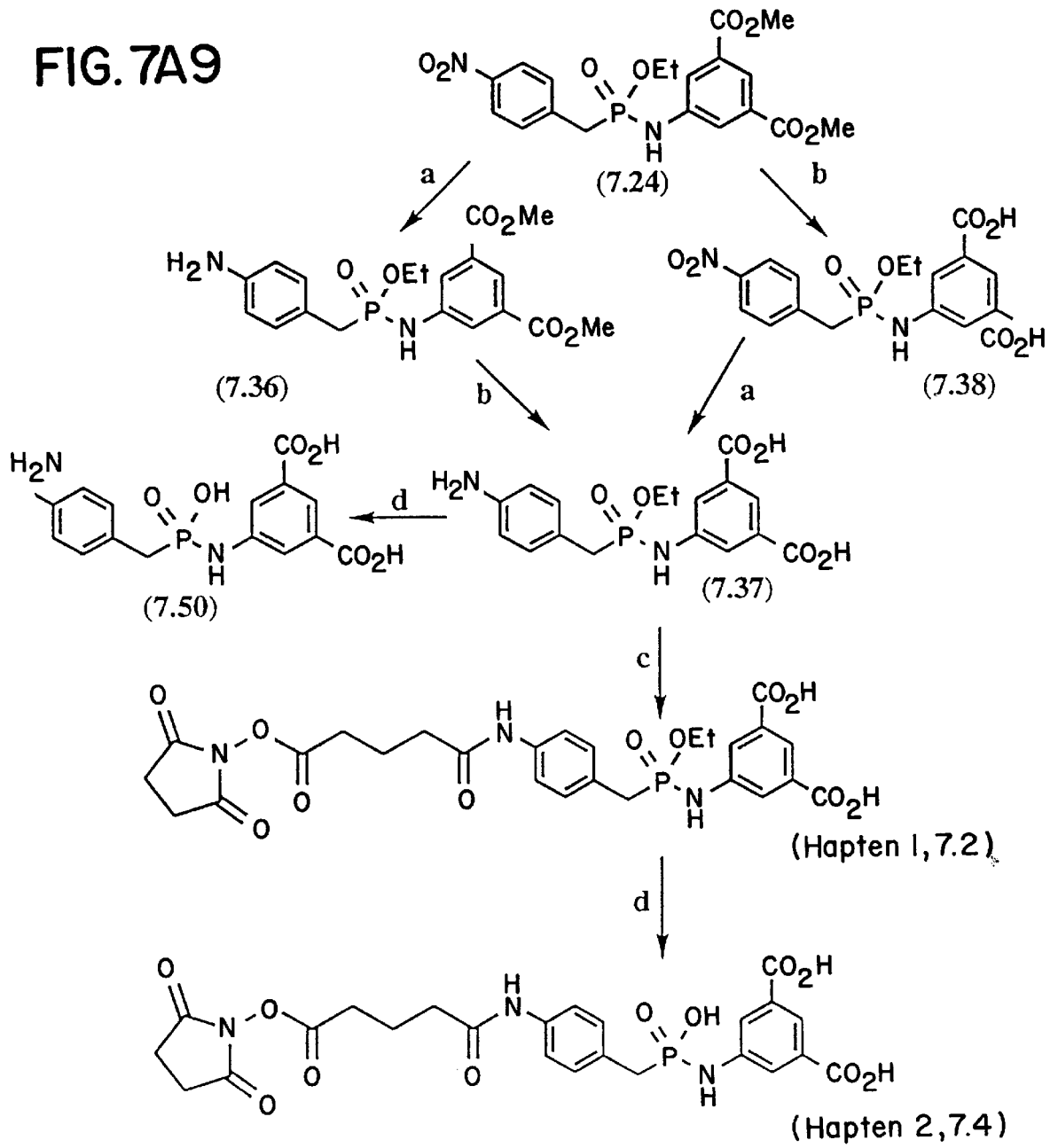
FIG. 7A9

FIG. 7A10
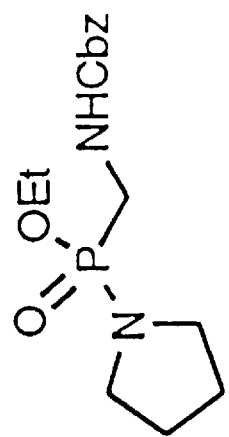
(7.41)
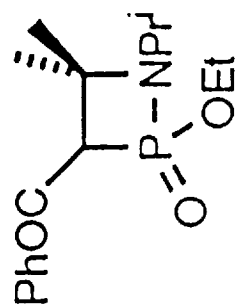
(7.40)

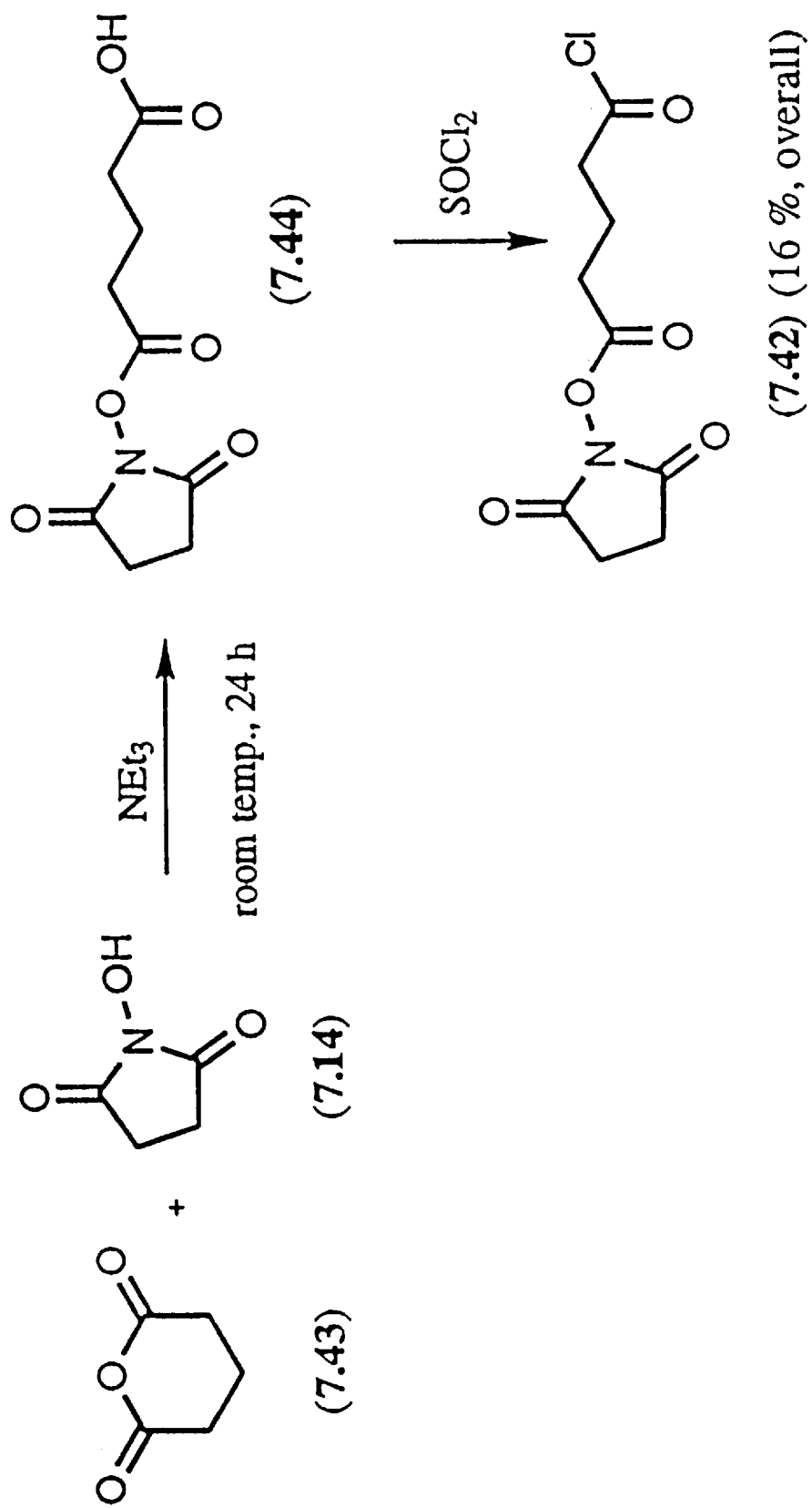
FIG. 7AII

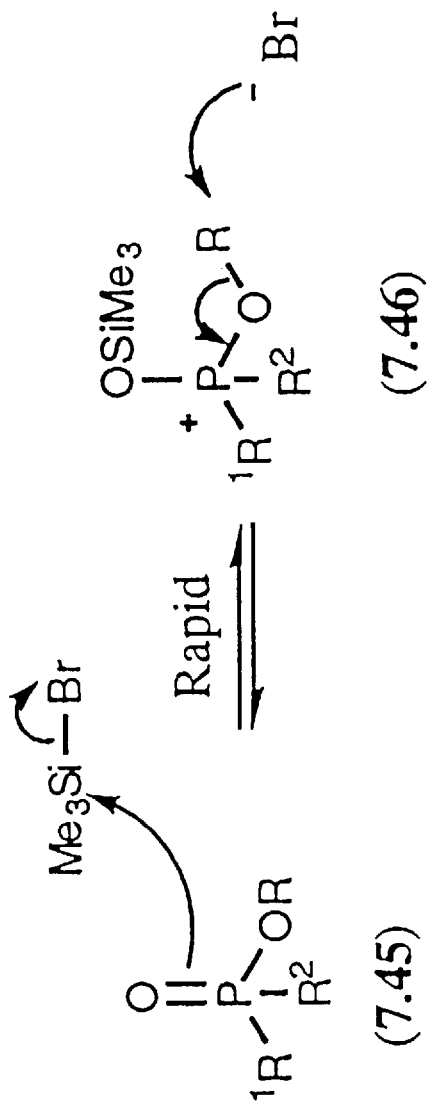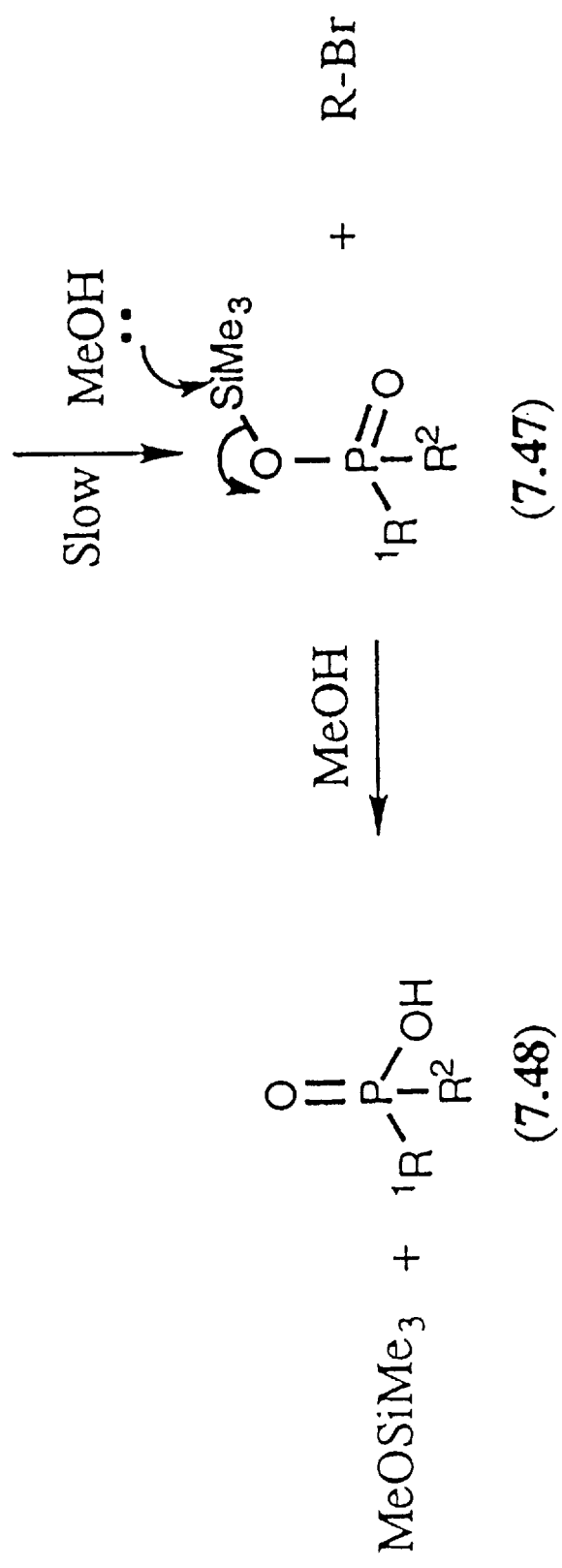
FIG. 7AI2

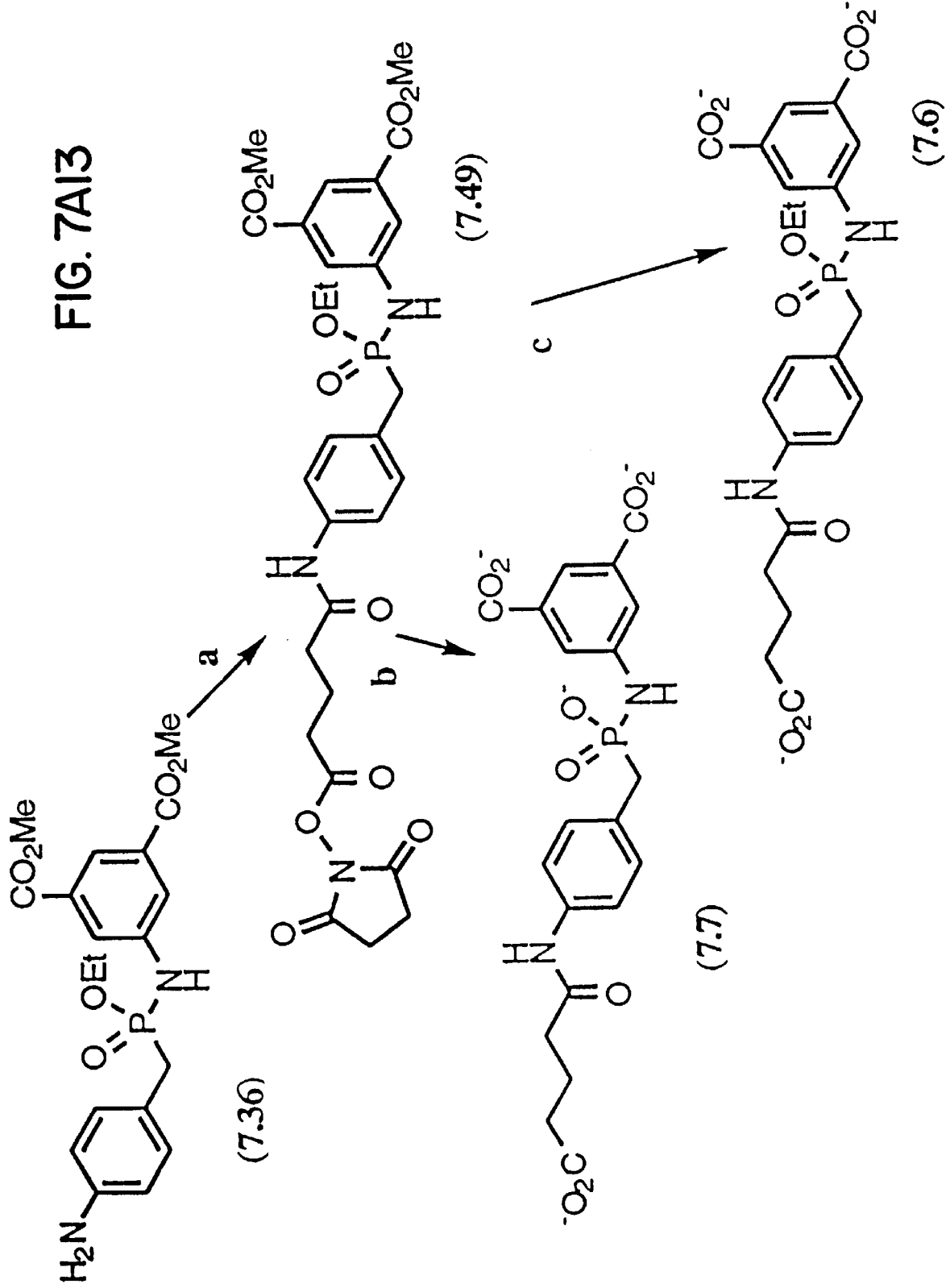
FIG. 7AI3

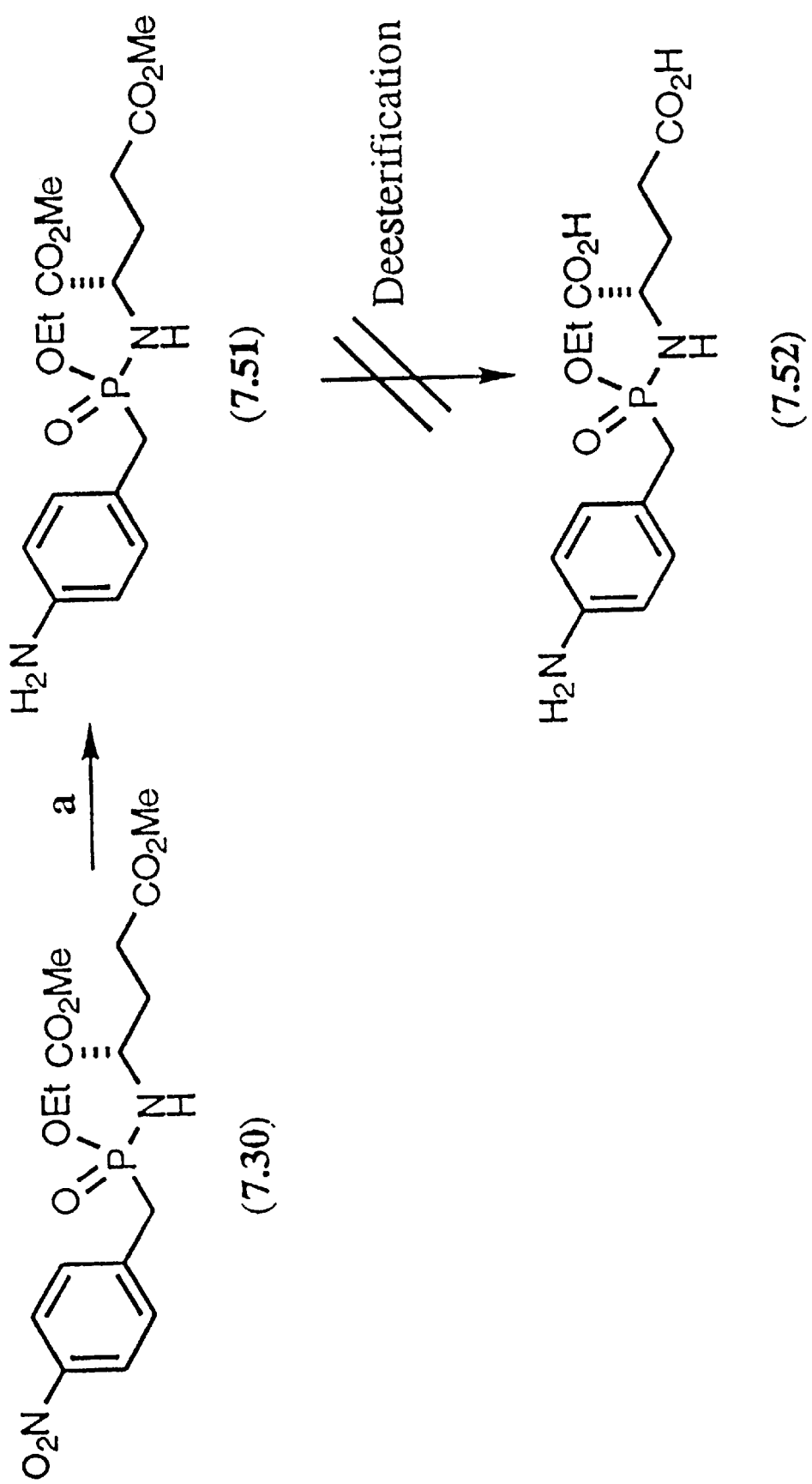
FIG. 7AI4

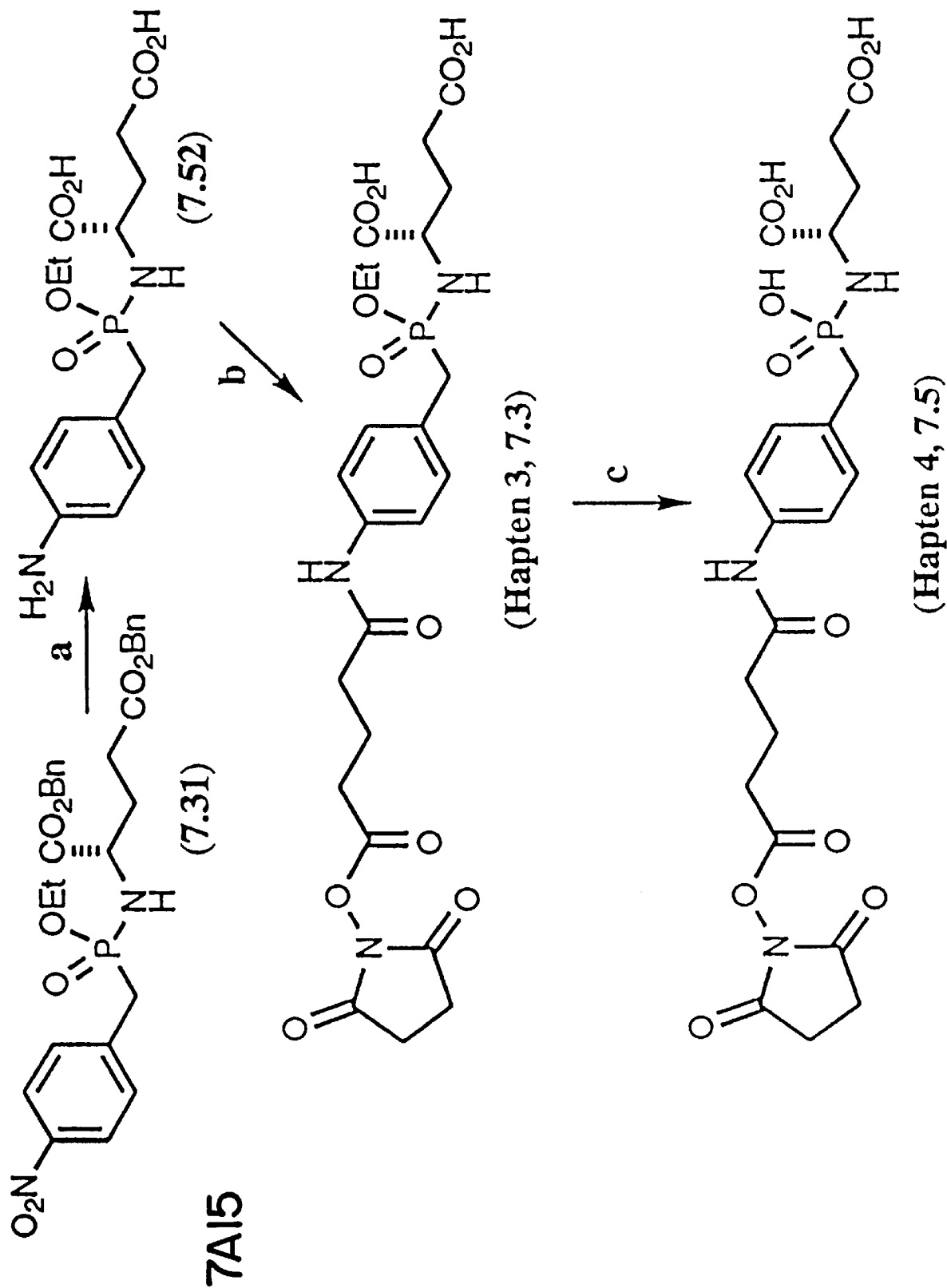
FIG. 7AI5

X = NO₂ (7.53)
X = Br (7.54)
X = F (7.55)
X = OMe (7.56)
X = H (7.57)

(7.39)

(7.58)

FIG. 7B2
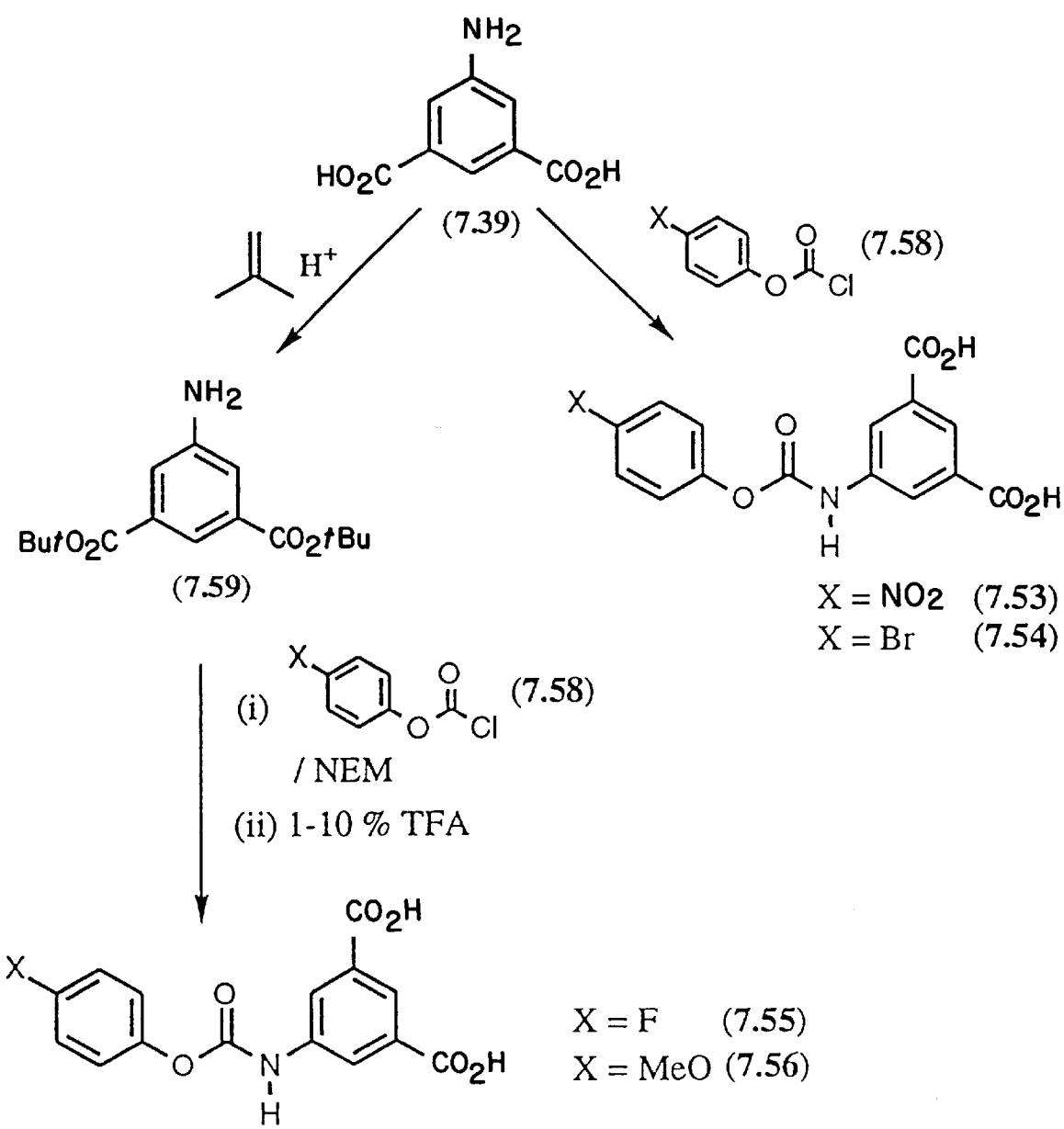

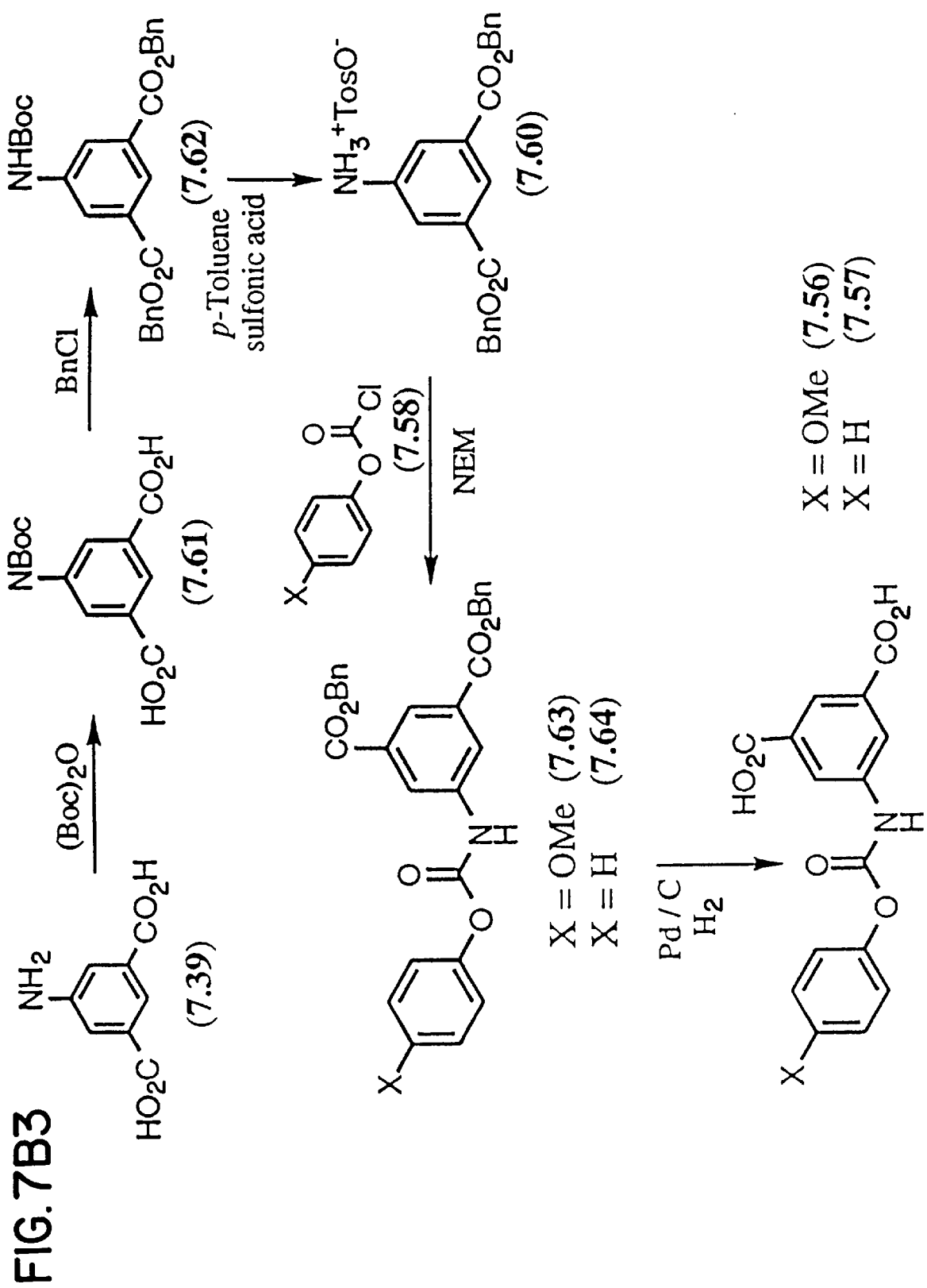
FIG. 7B3

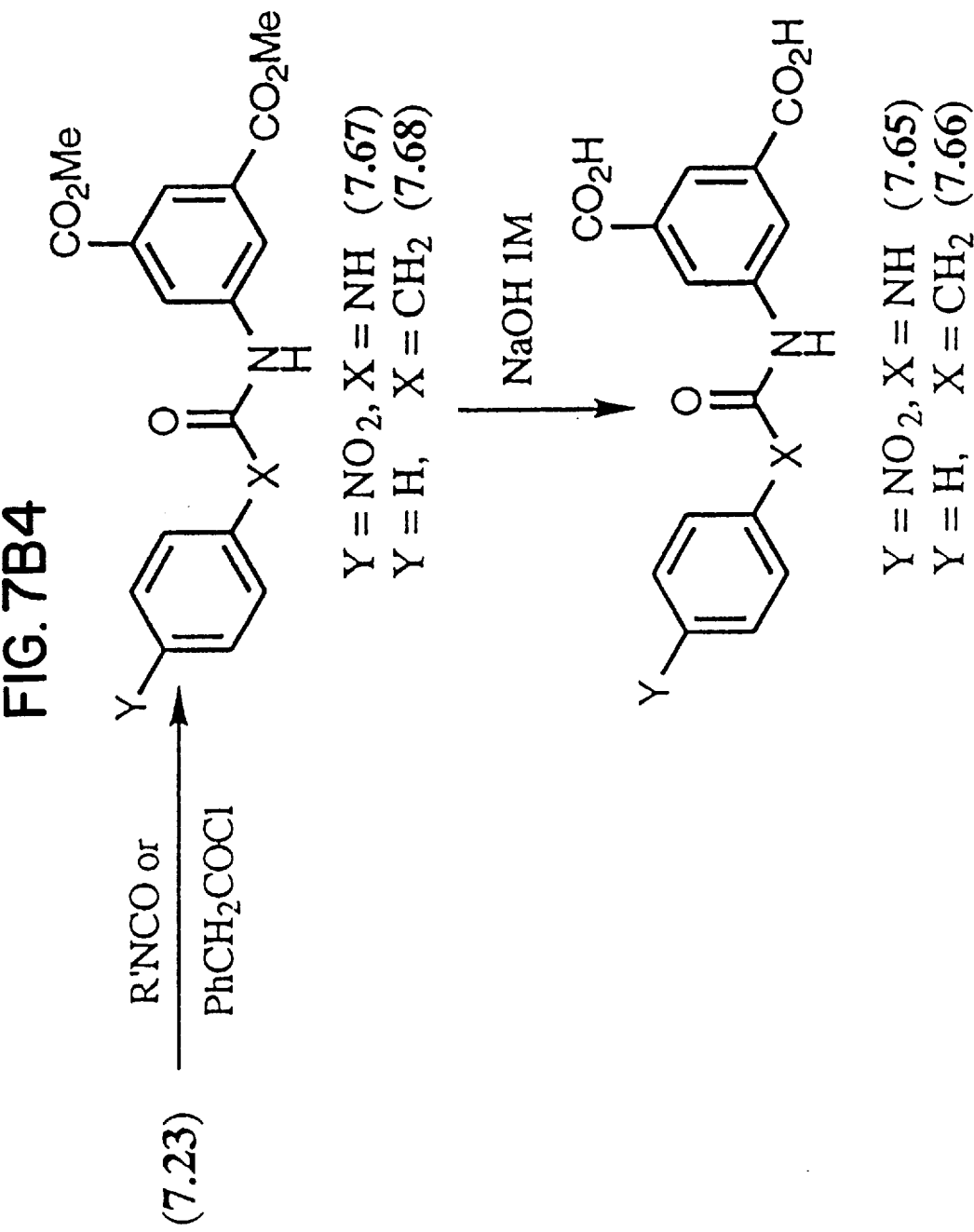
FIG. 7B4

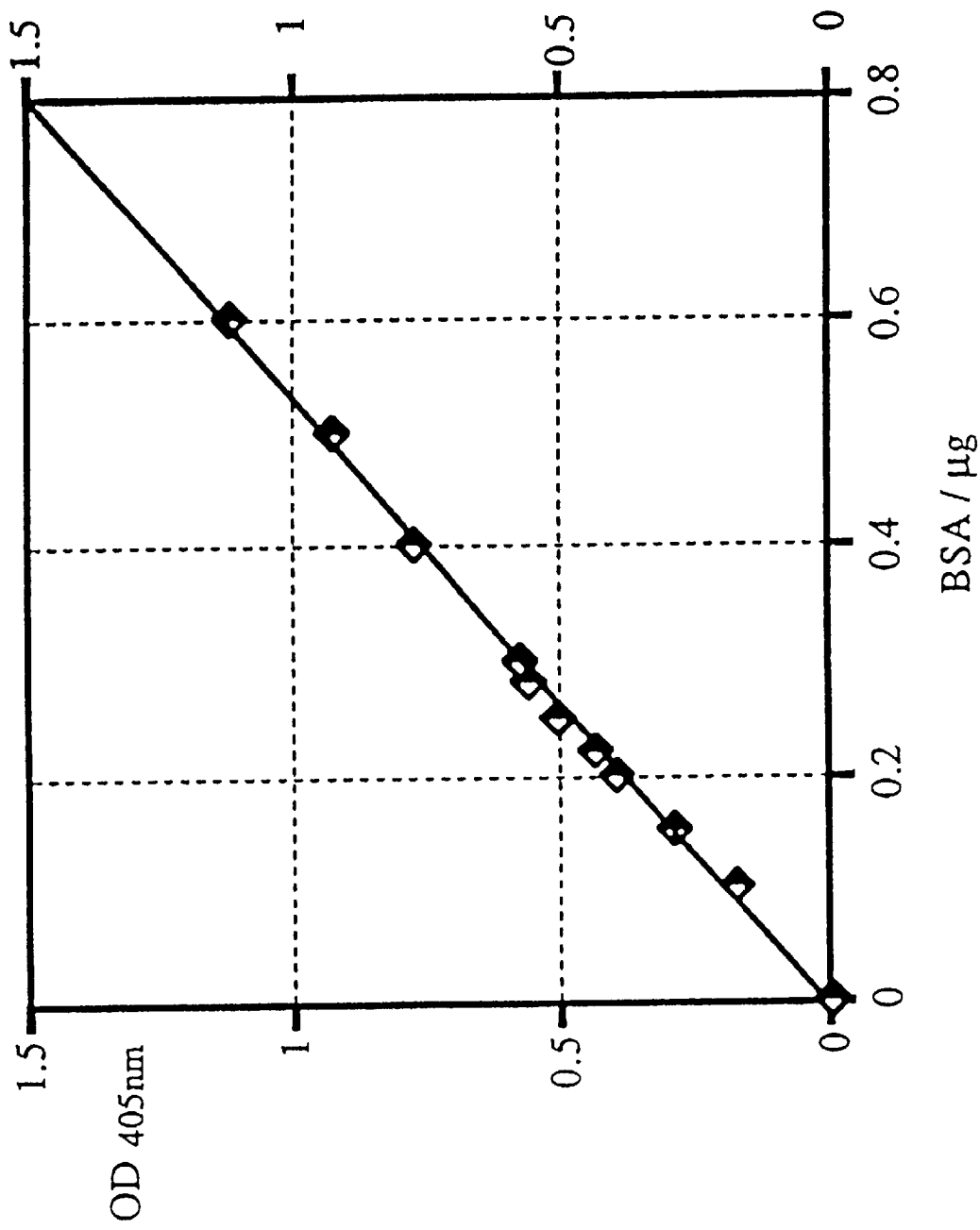
FIG. 8A2
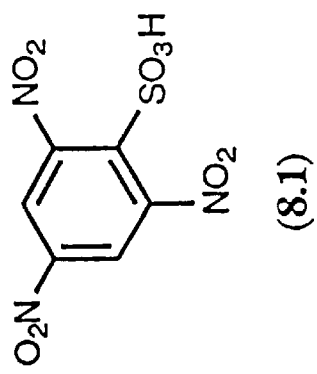
FIG. 8A1

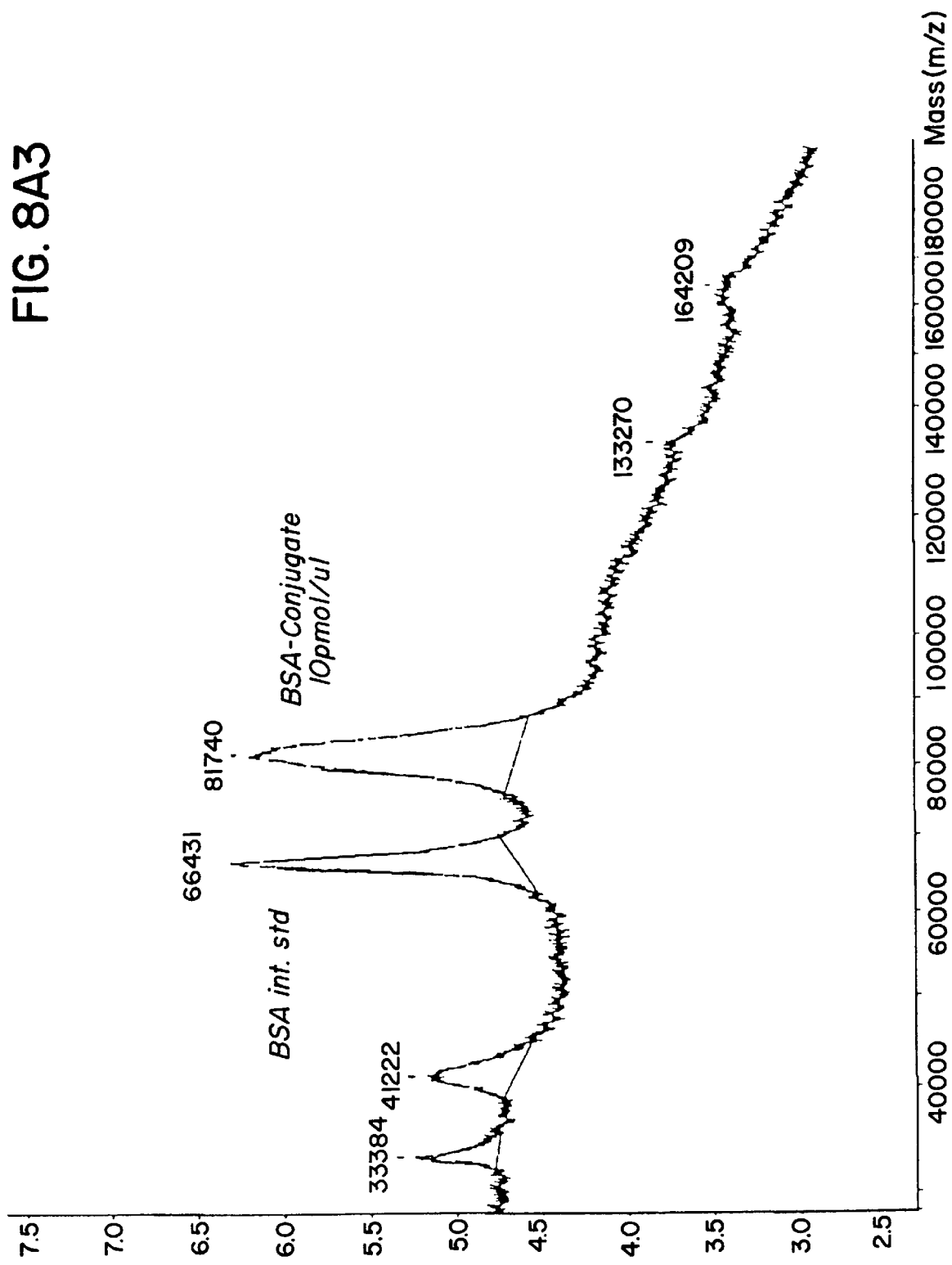
FIG. 8A3

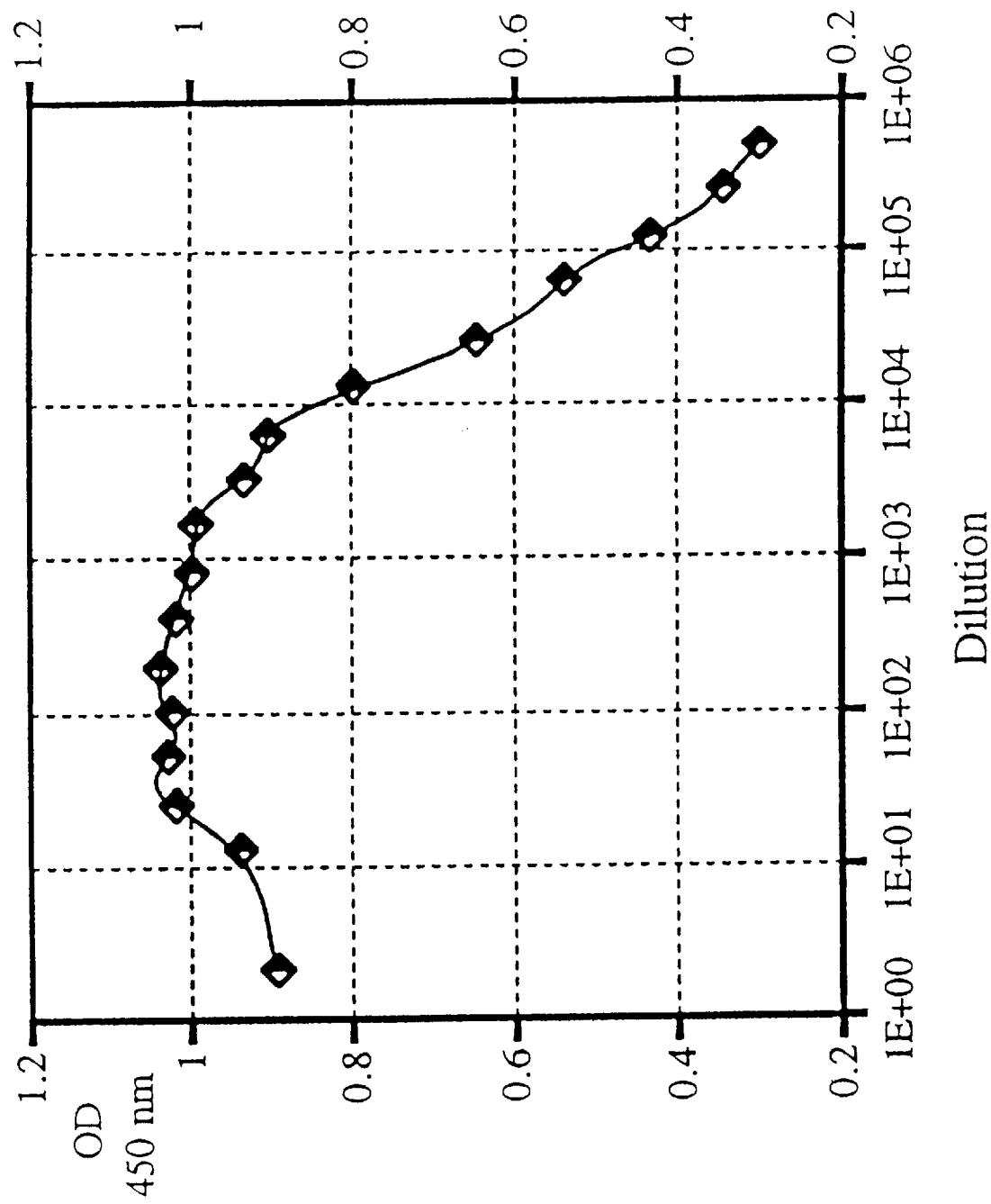

FIG. 8C2
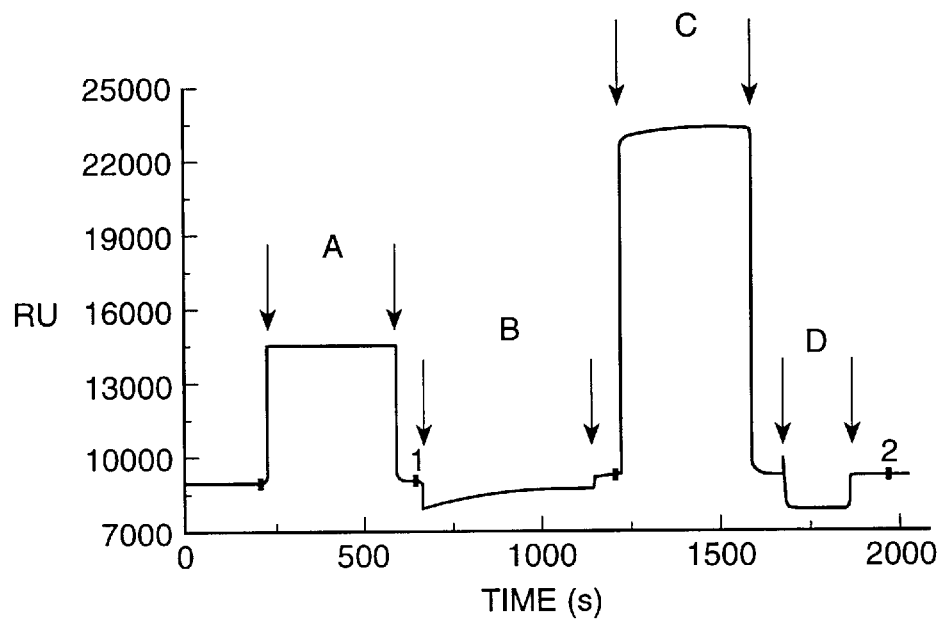
FIG. 8C3
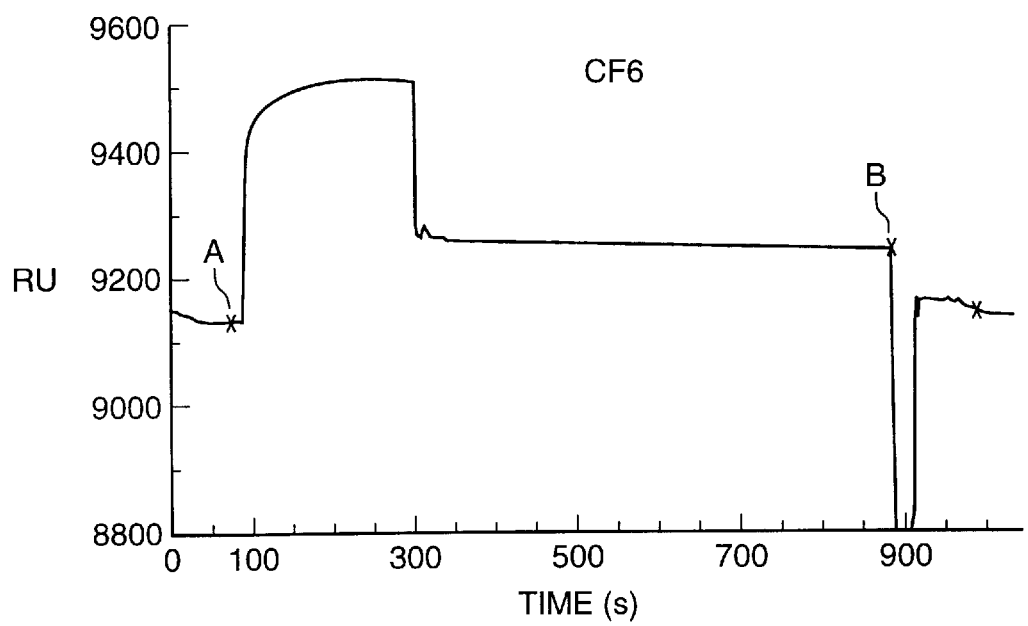

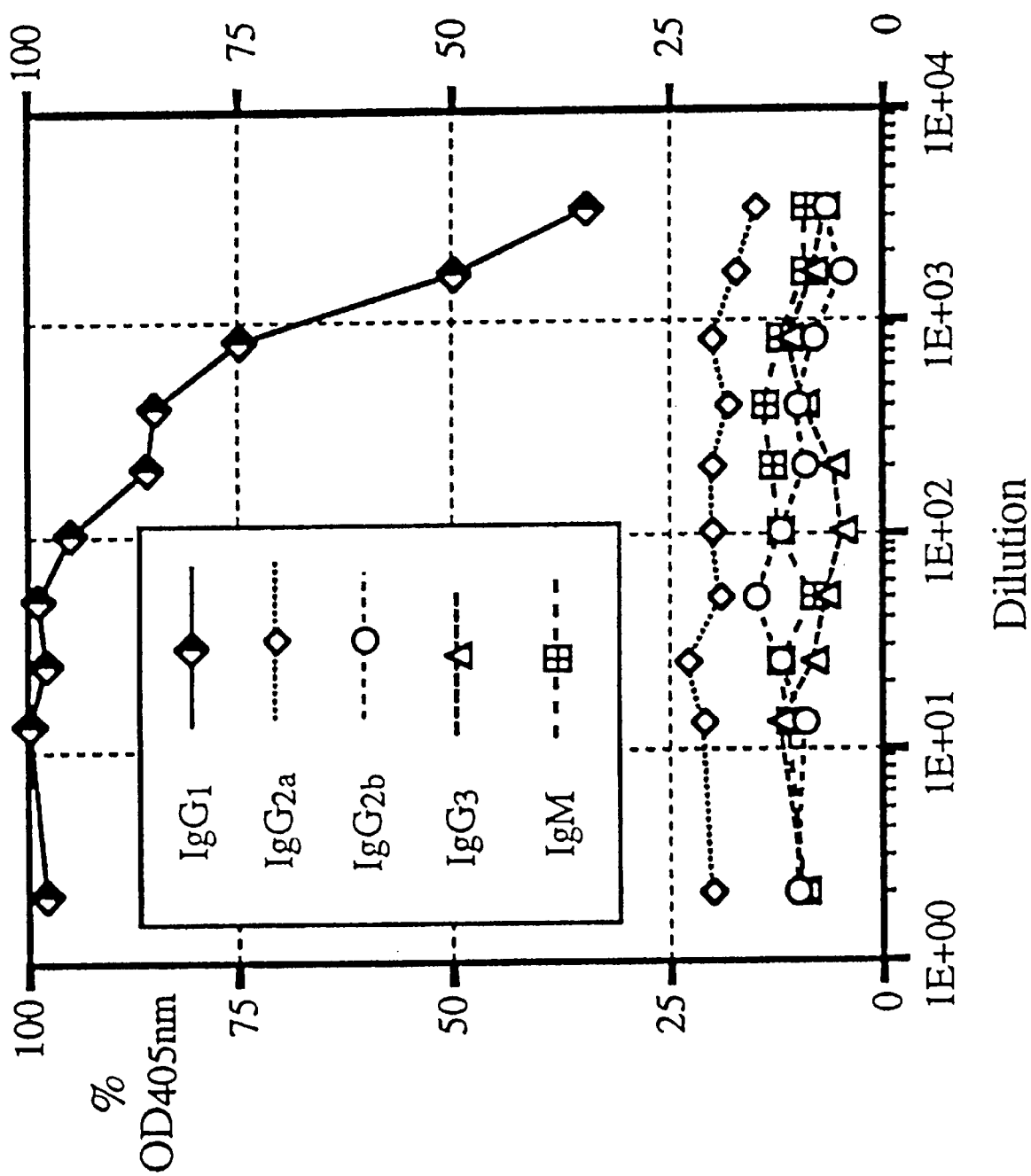
FIG. 8C4

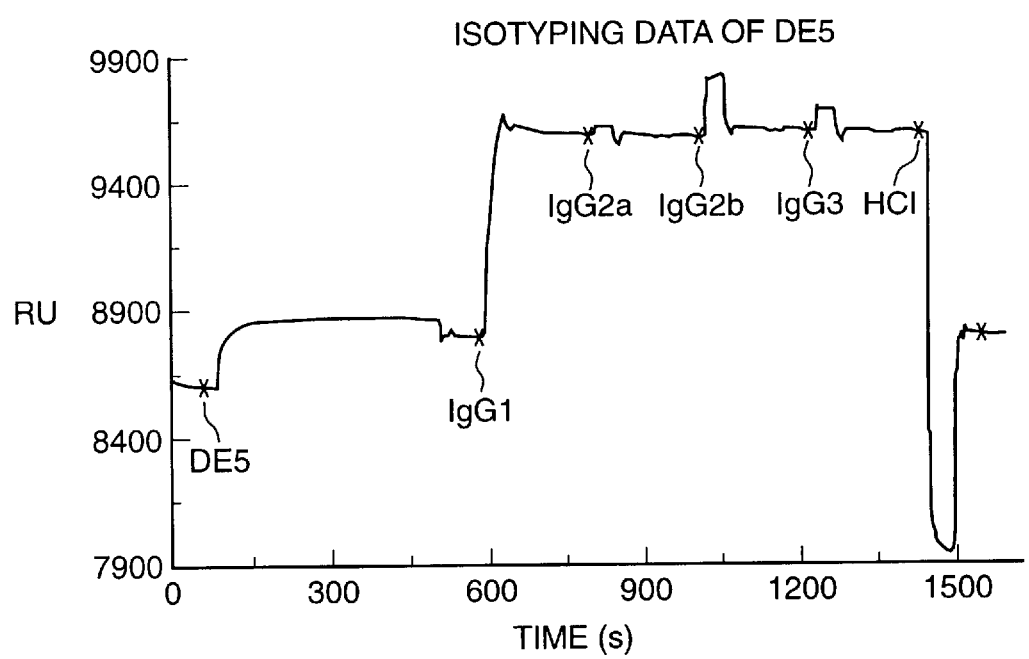
FIG. 8C5

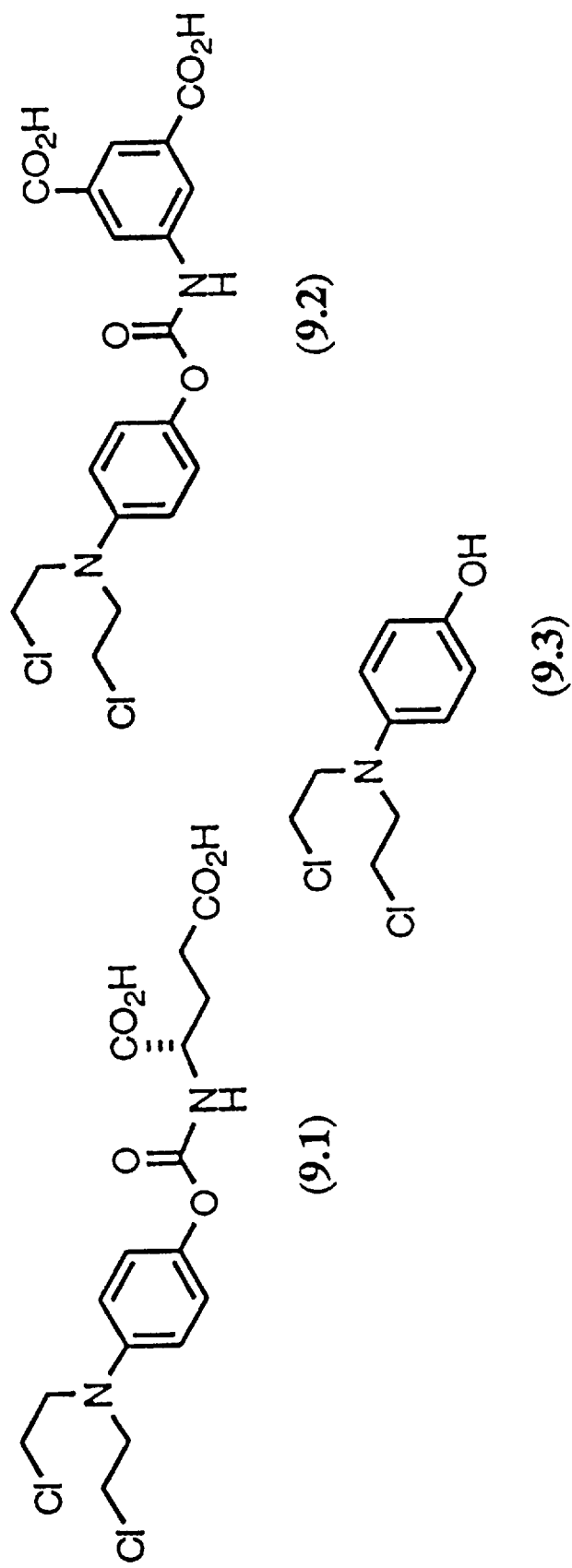
FIG. 9A2

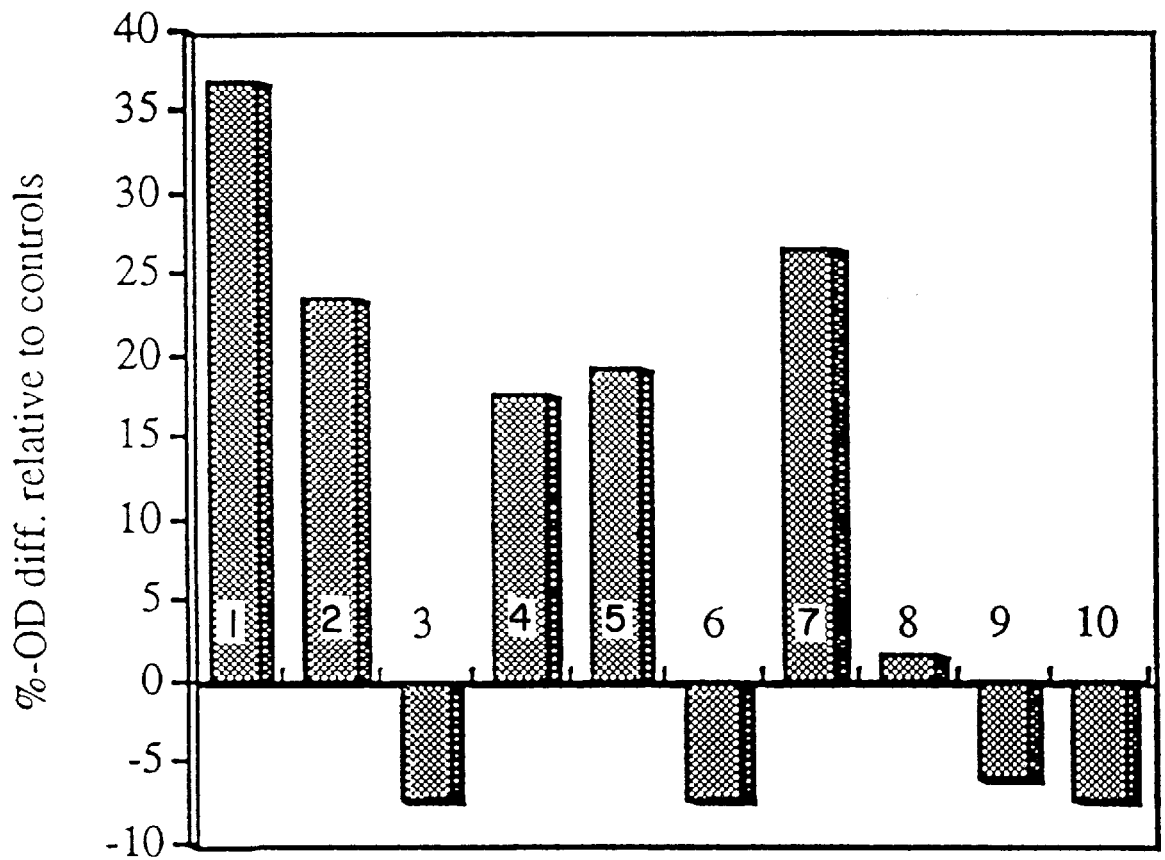
FIG. 9A3

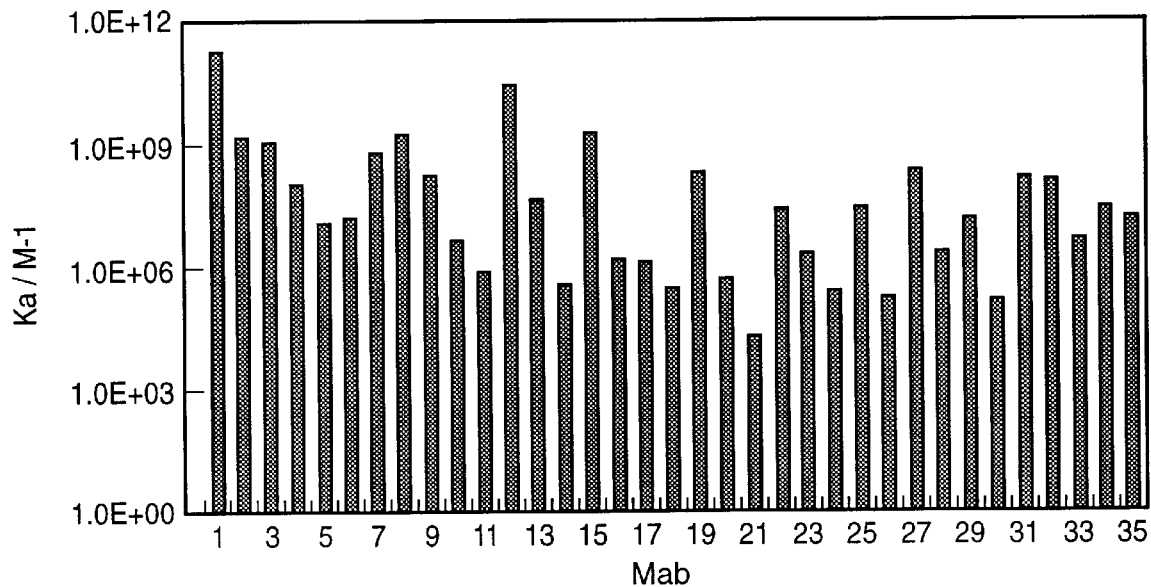
FIG. 9A4
AFFINITY FOR THE TSA (7.2)
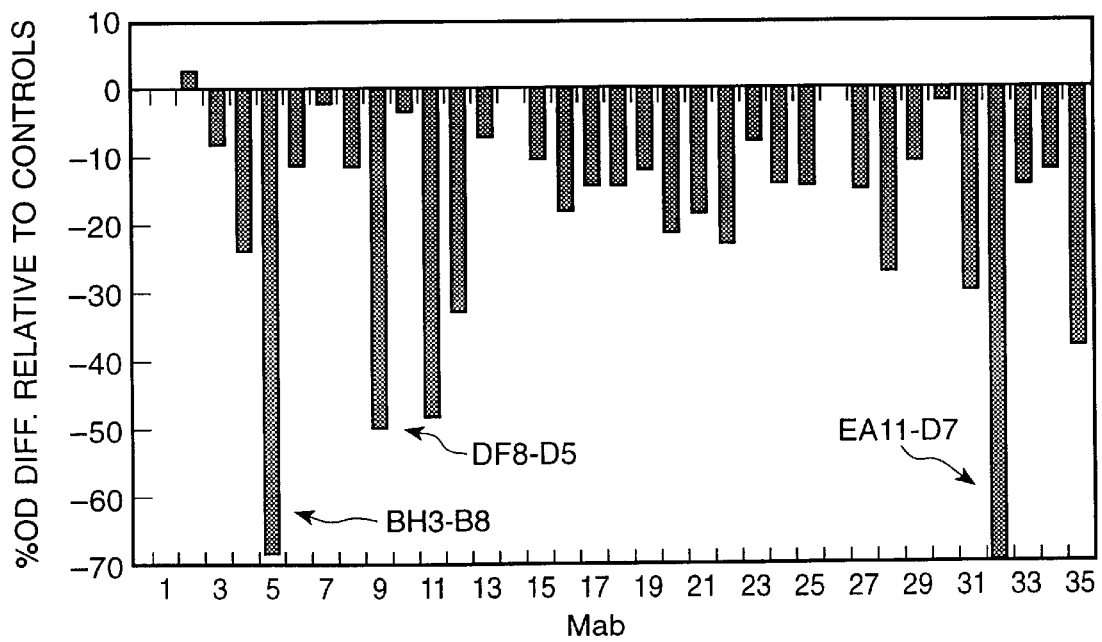
FIG. 9A5
CYTOTOXICITY

FIG. 9A6
AFFINITY FOR THE TSA (7.4)
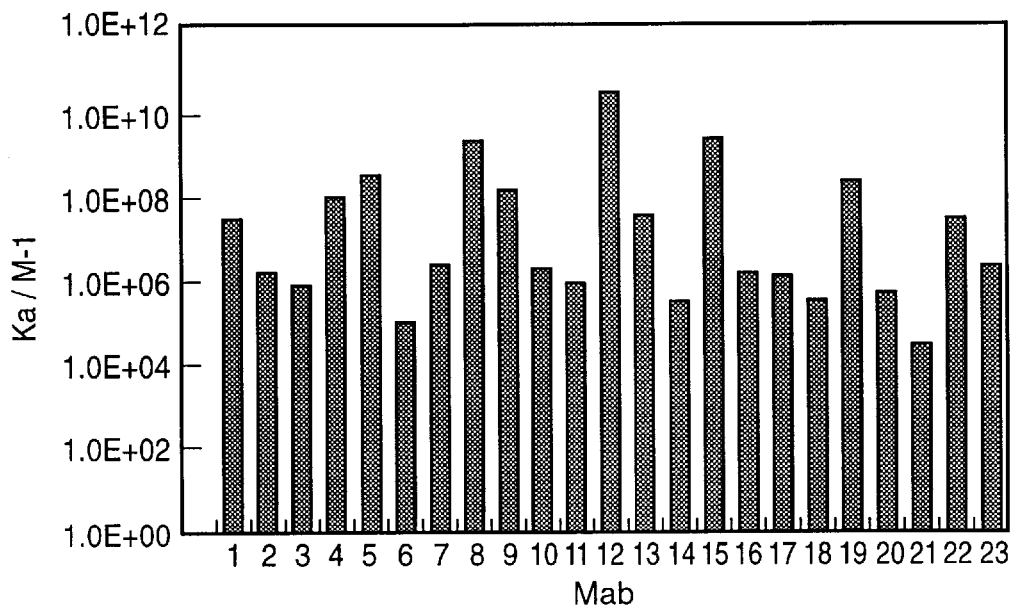
FIG. 9A7
CYTOTOXICITY
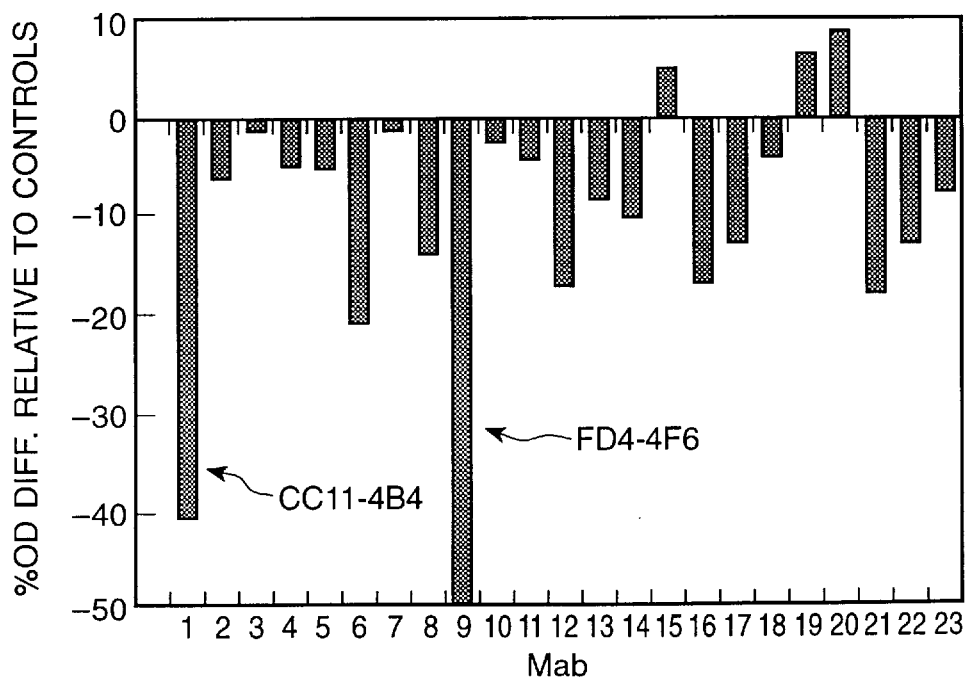

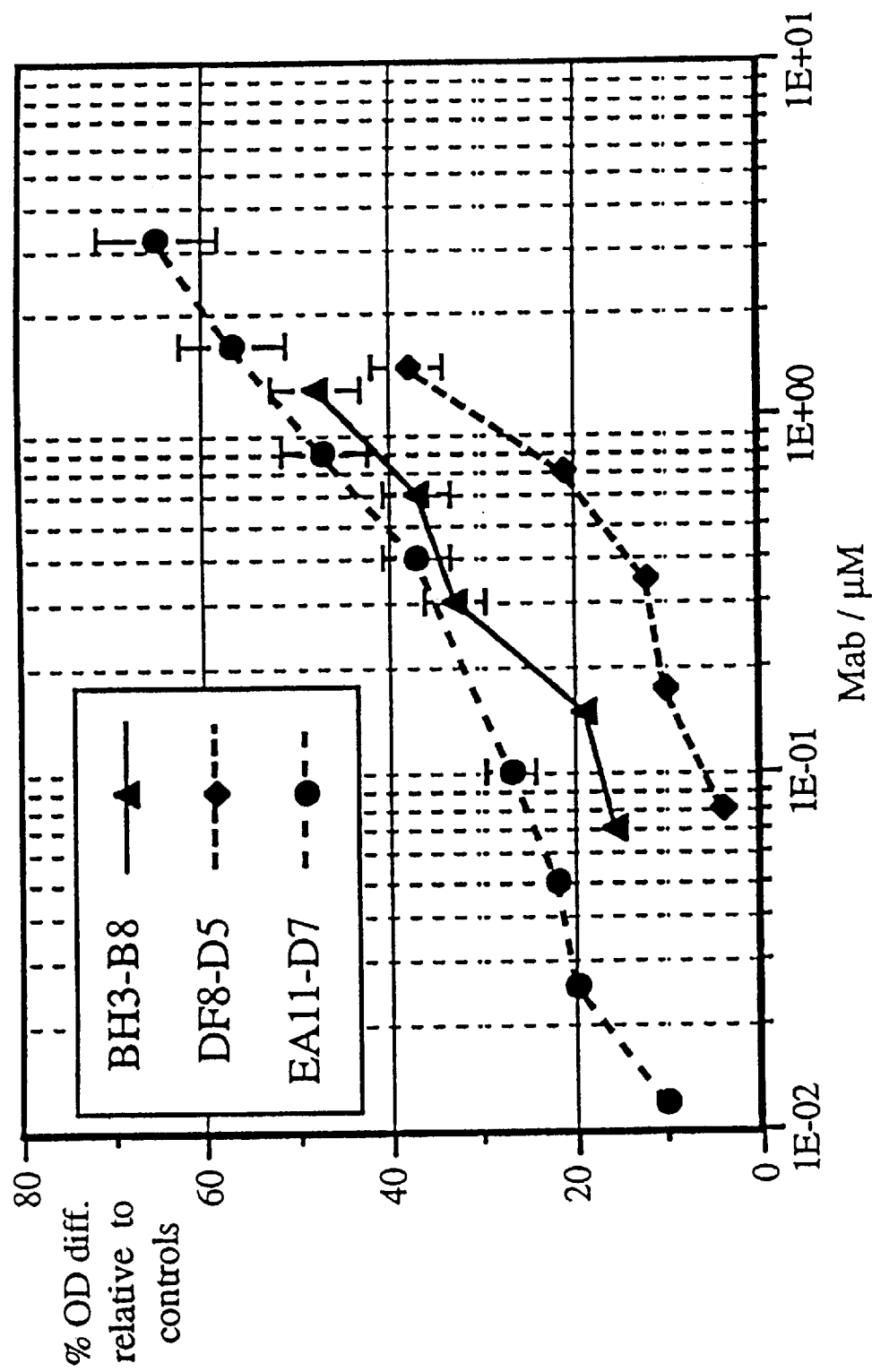

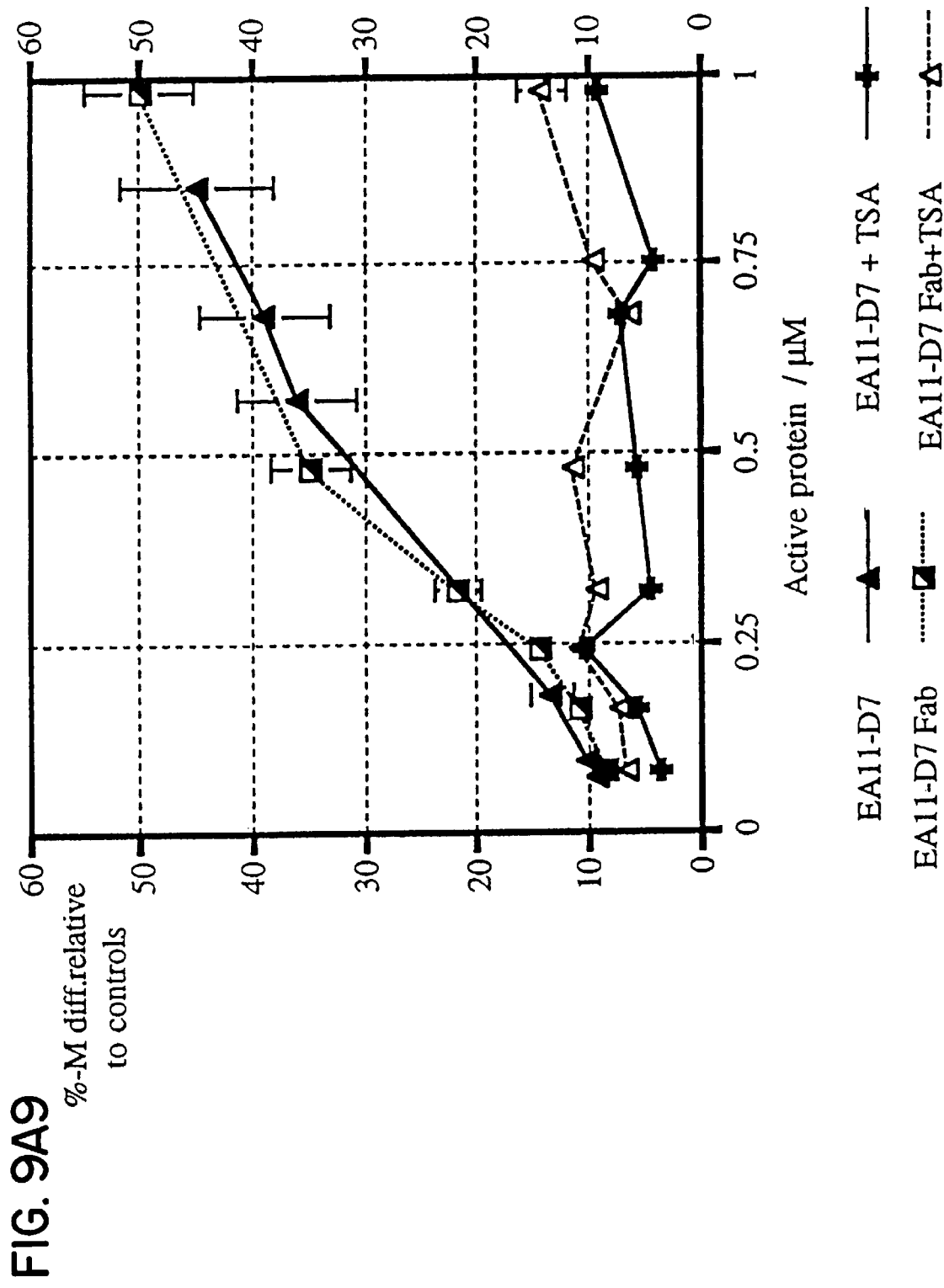
FIG. 9A9

FIG. 9B2
FIG. 9B3
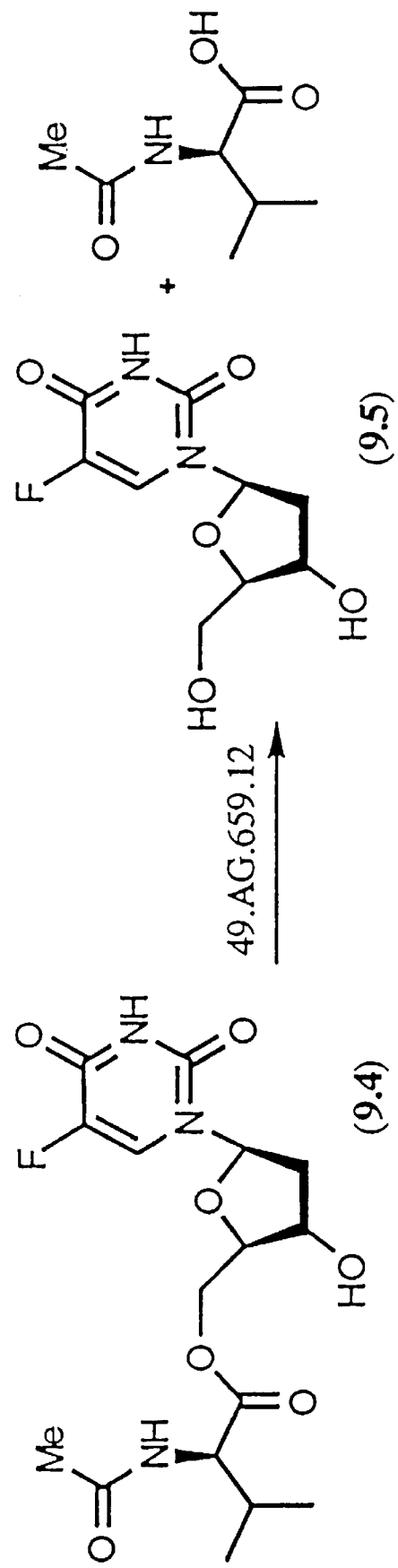

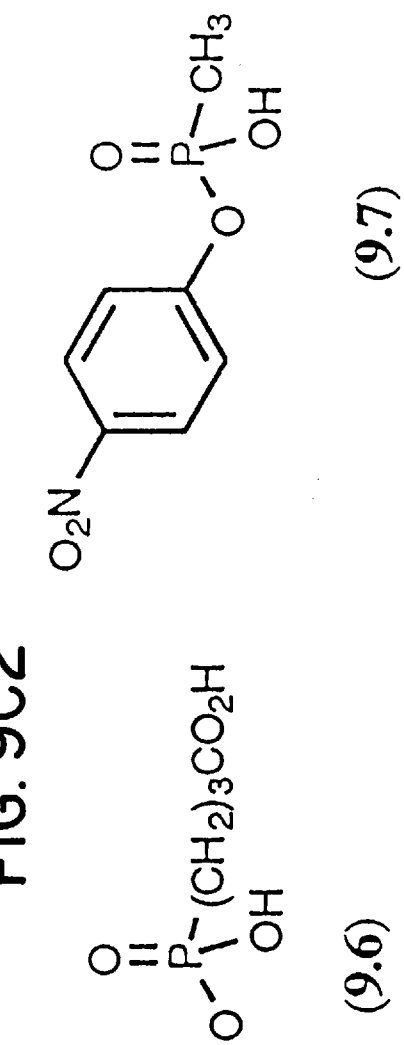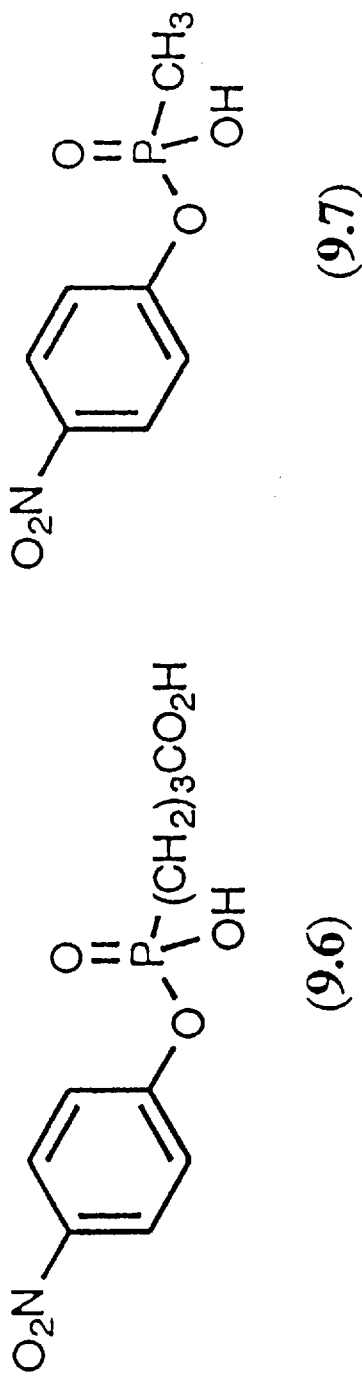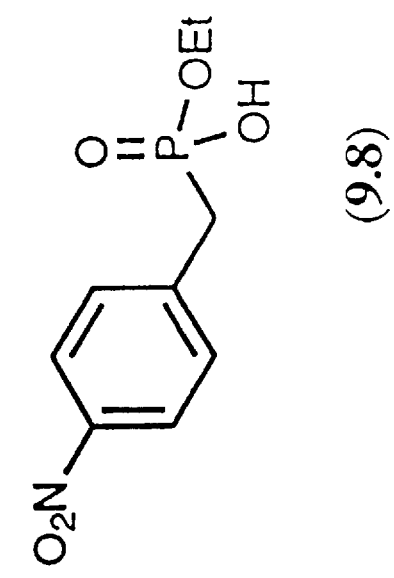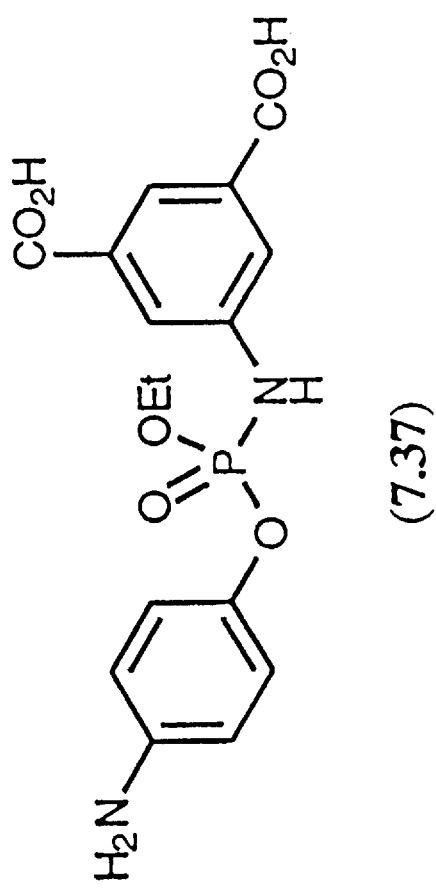
FIG. 9C2
FIG. 9C3

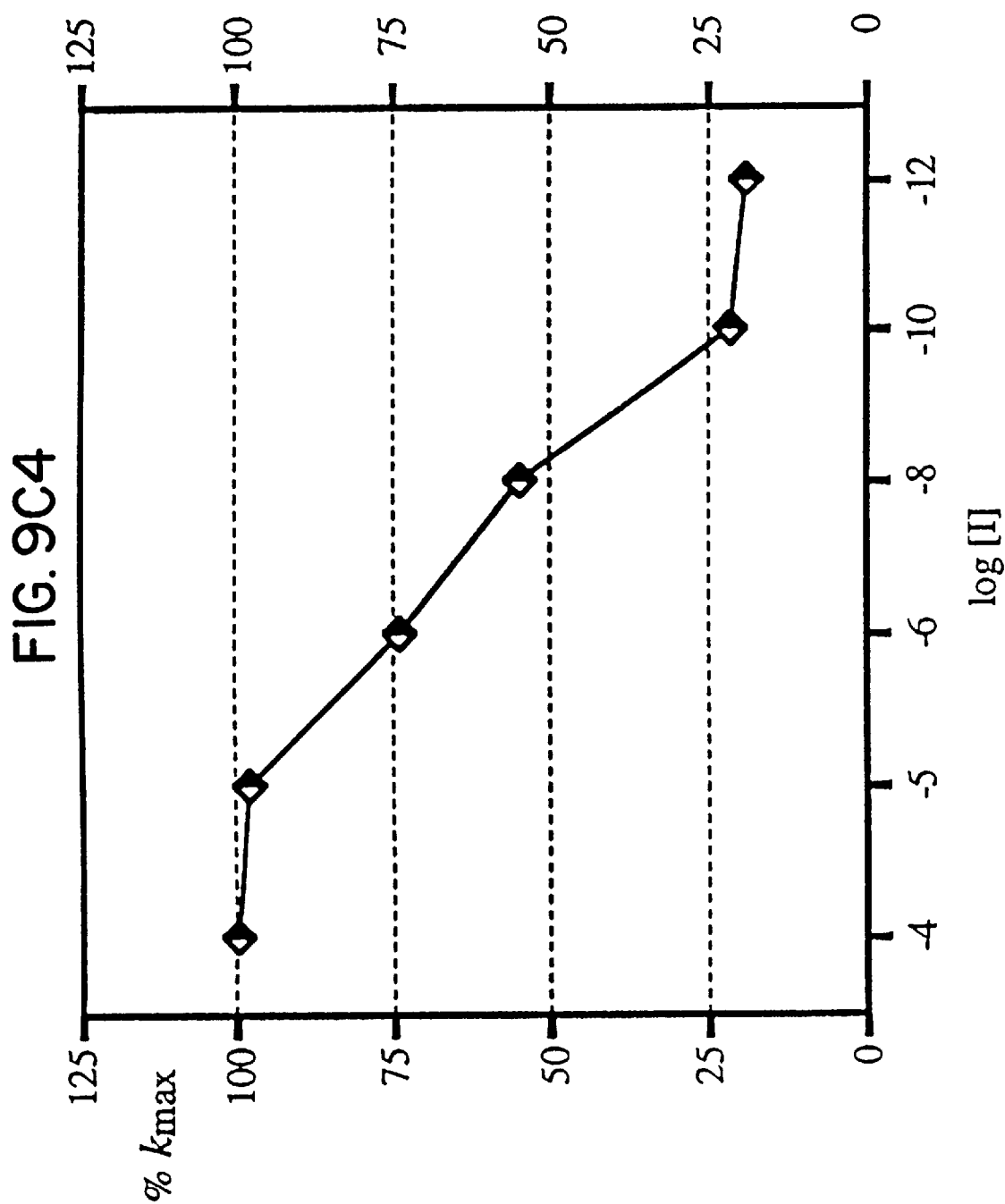

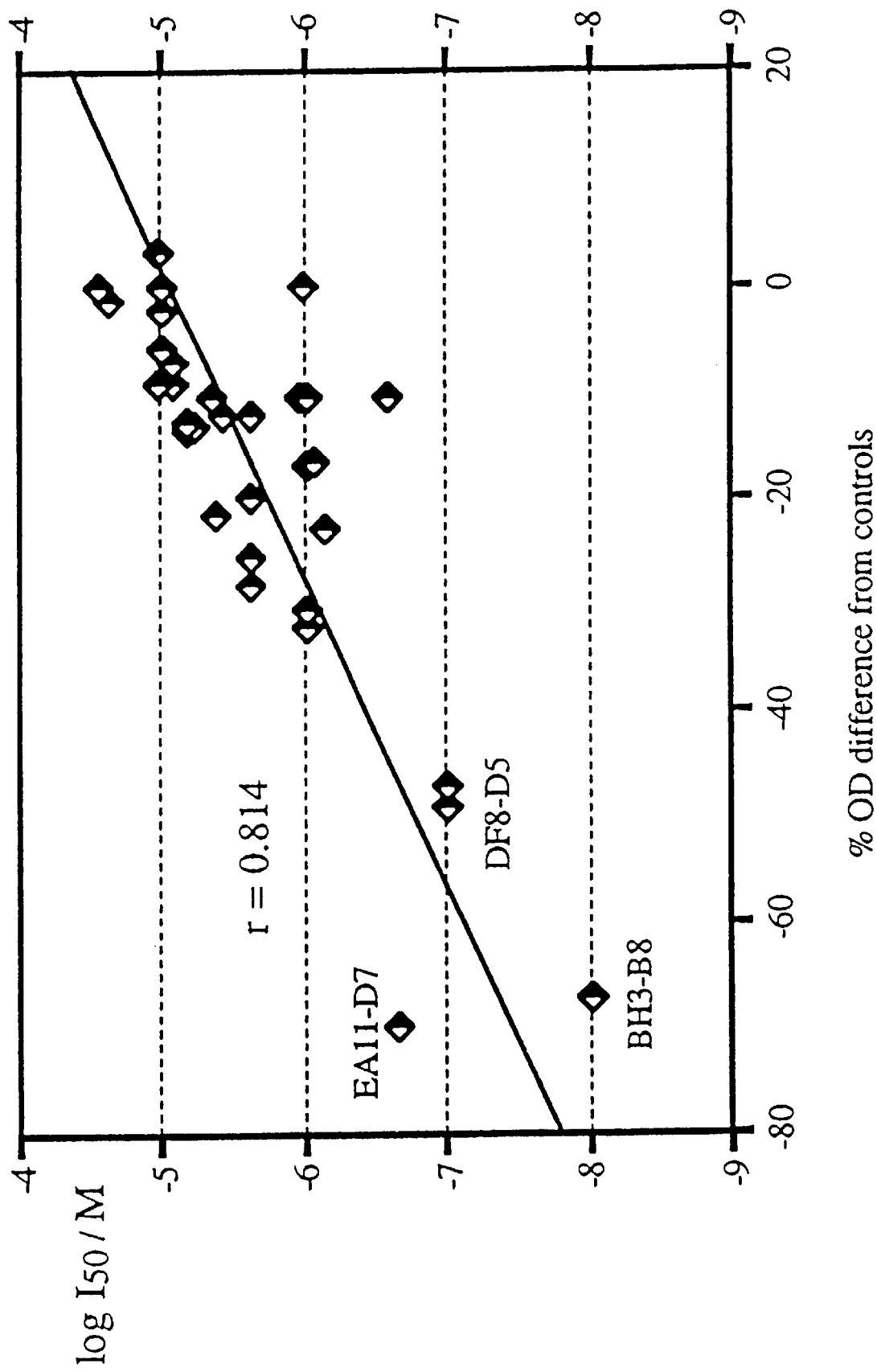

FIG. 9E2
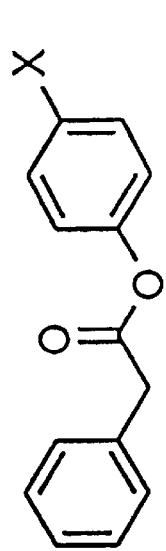
X = NO₂, MeCO, CHO, Cl, Me
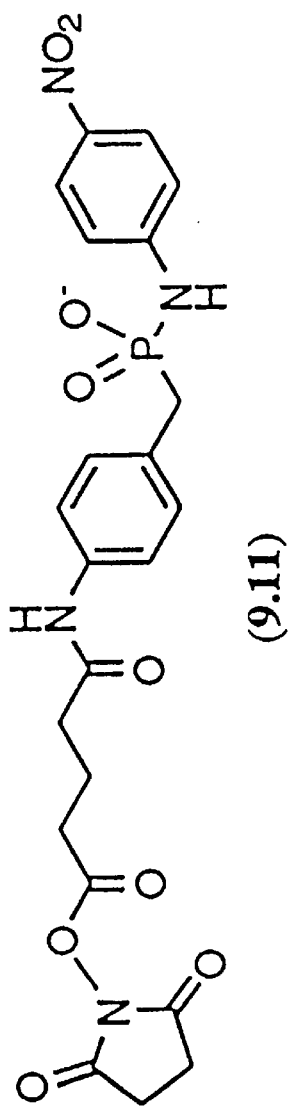
(9.11)
FIG. 9E3
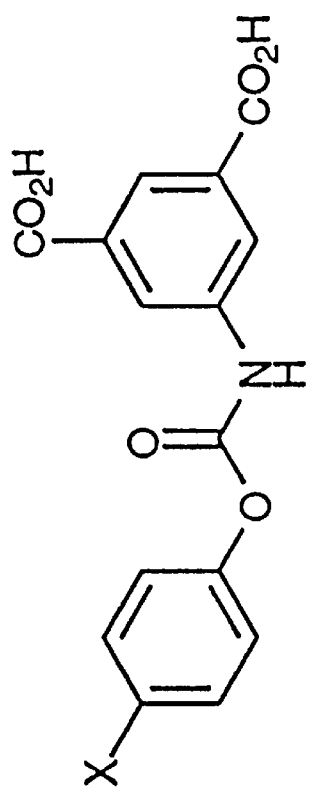
(9.9)  X = NO₂
(9.12) X = Br
(9.13) X = F
(9.14) X = MeO
(9.15) X = H
(9.16)

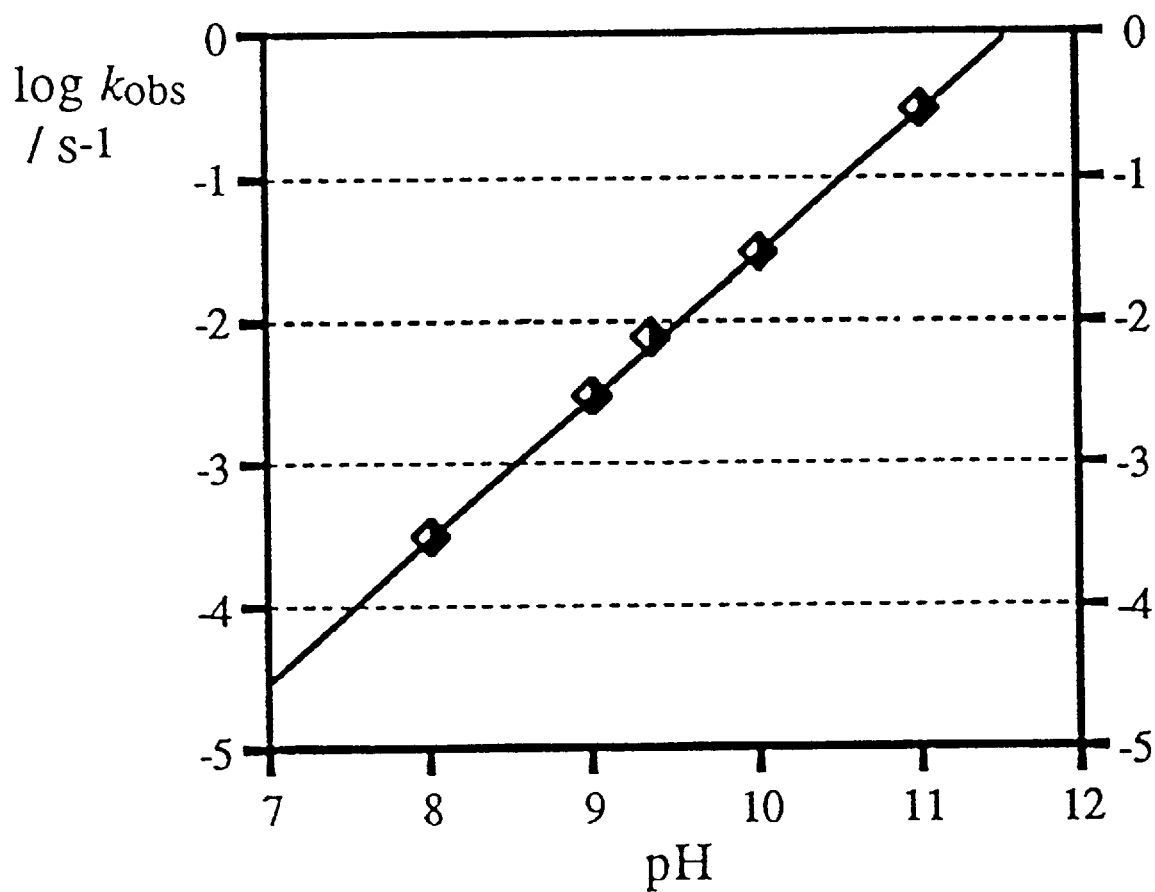
FIG. 9E4

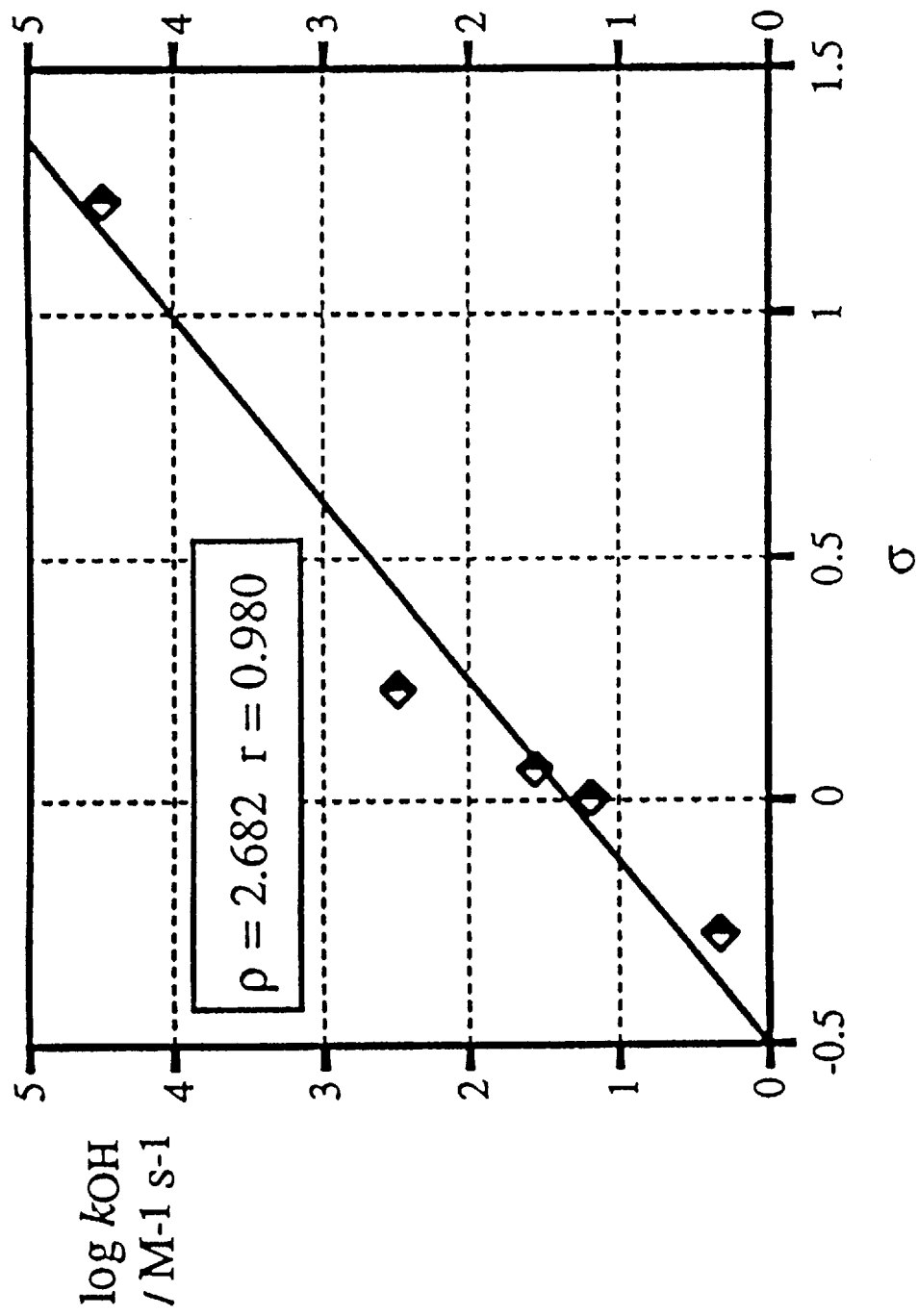
FIG. 9E5

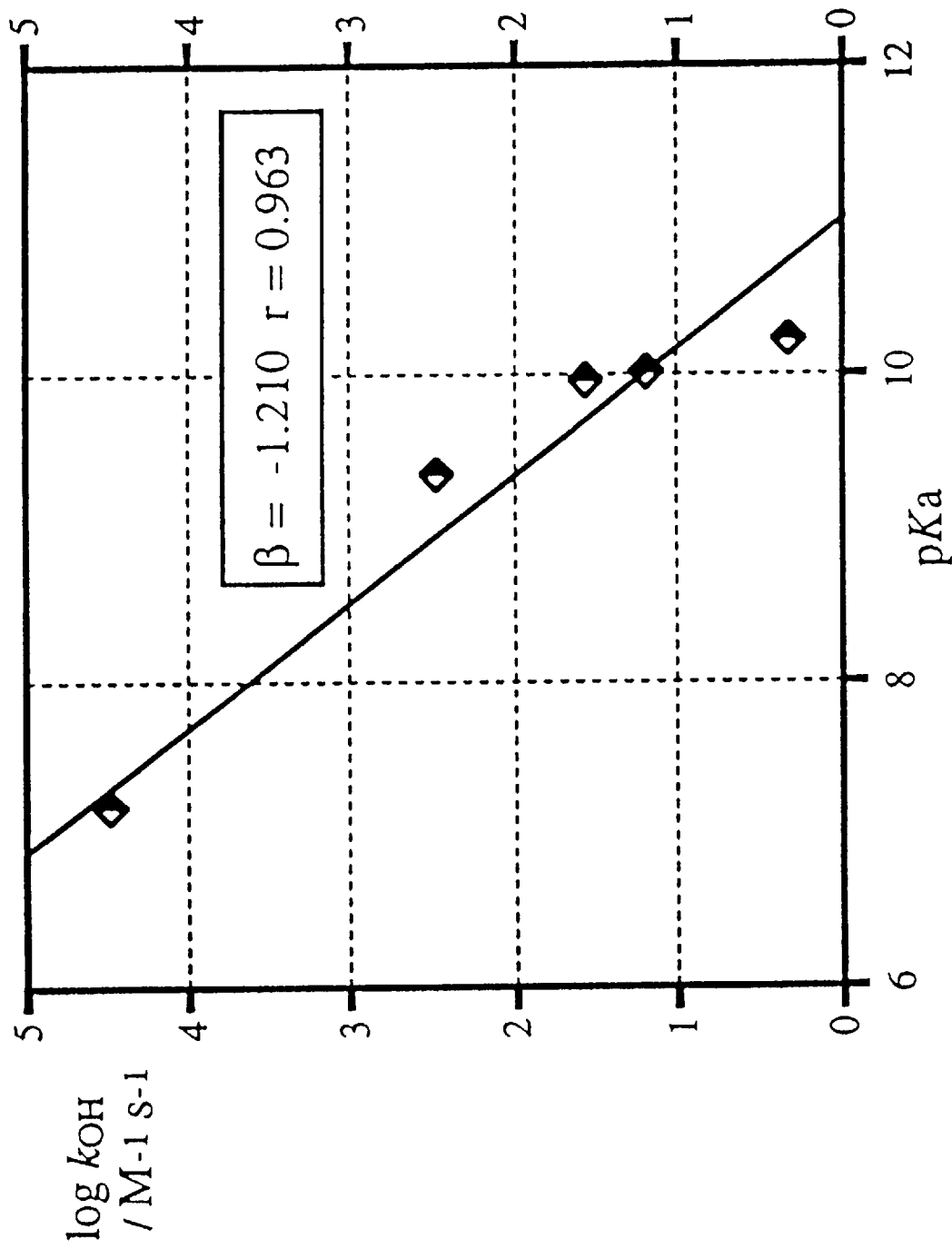
FIG. 9E6

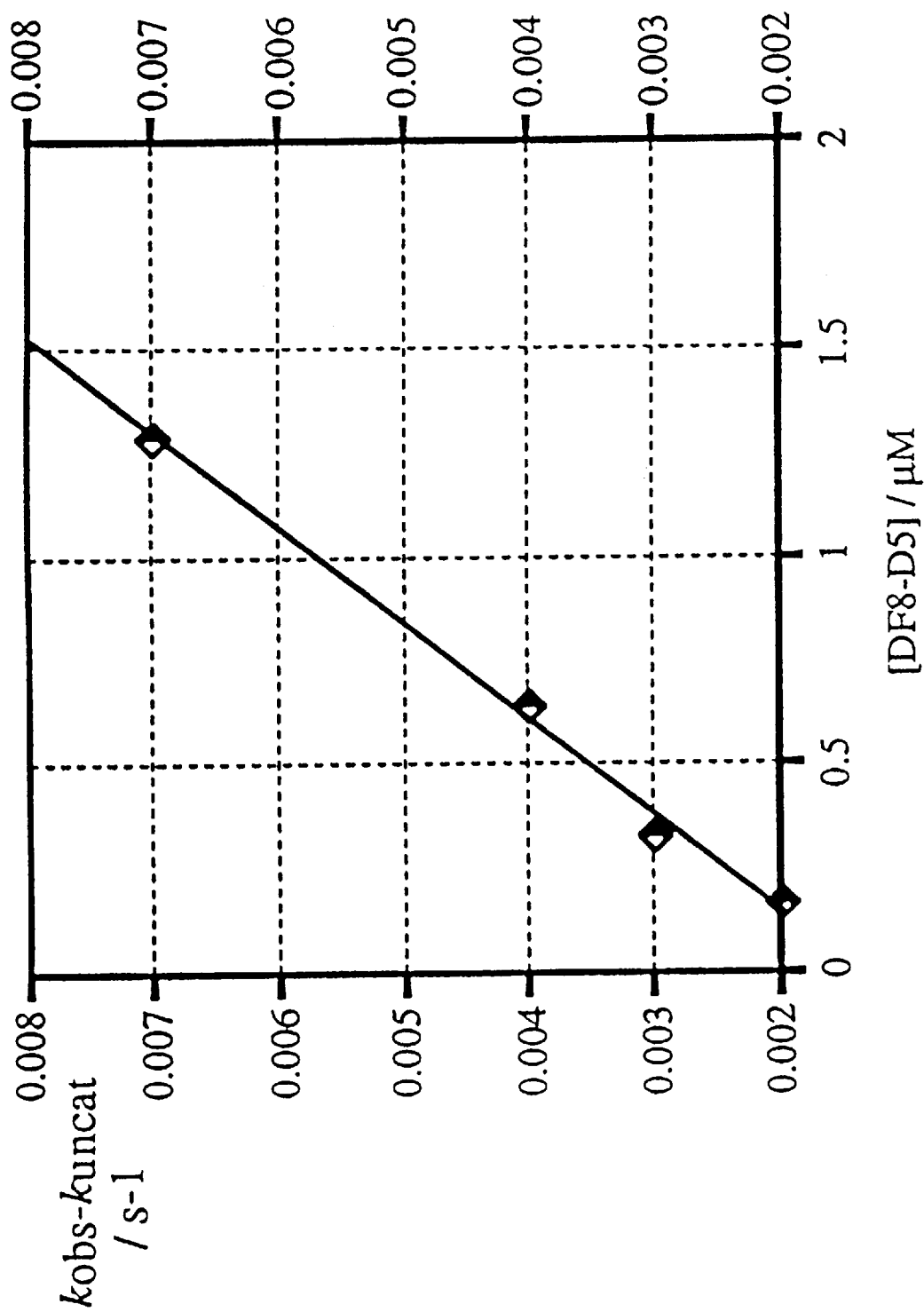
FIG. 9E7

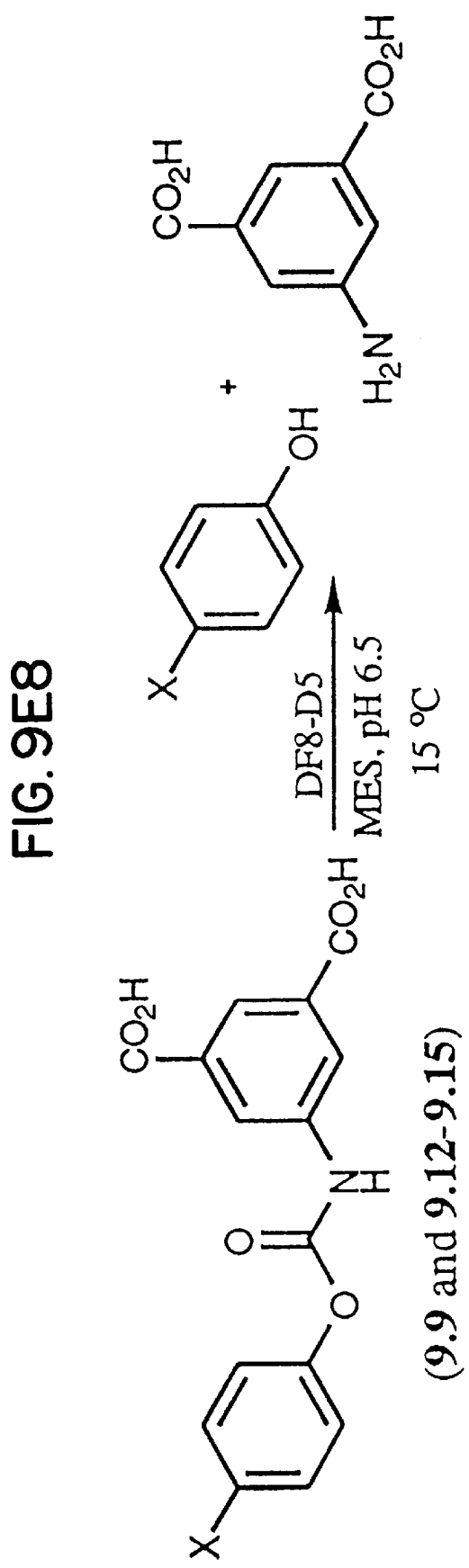
FIG. 9E8

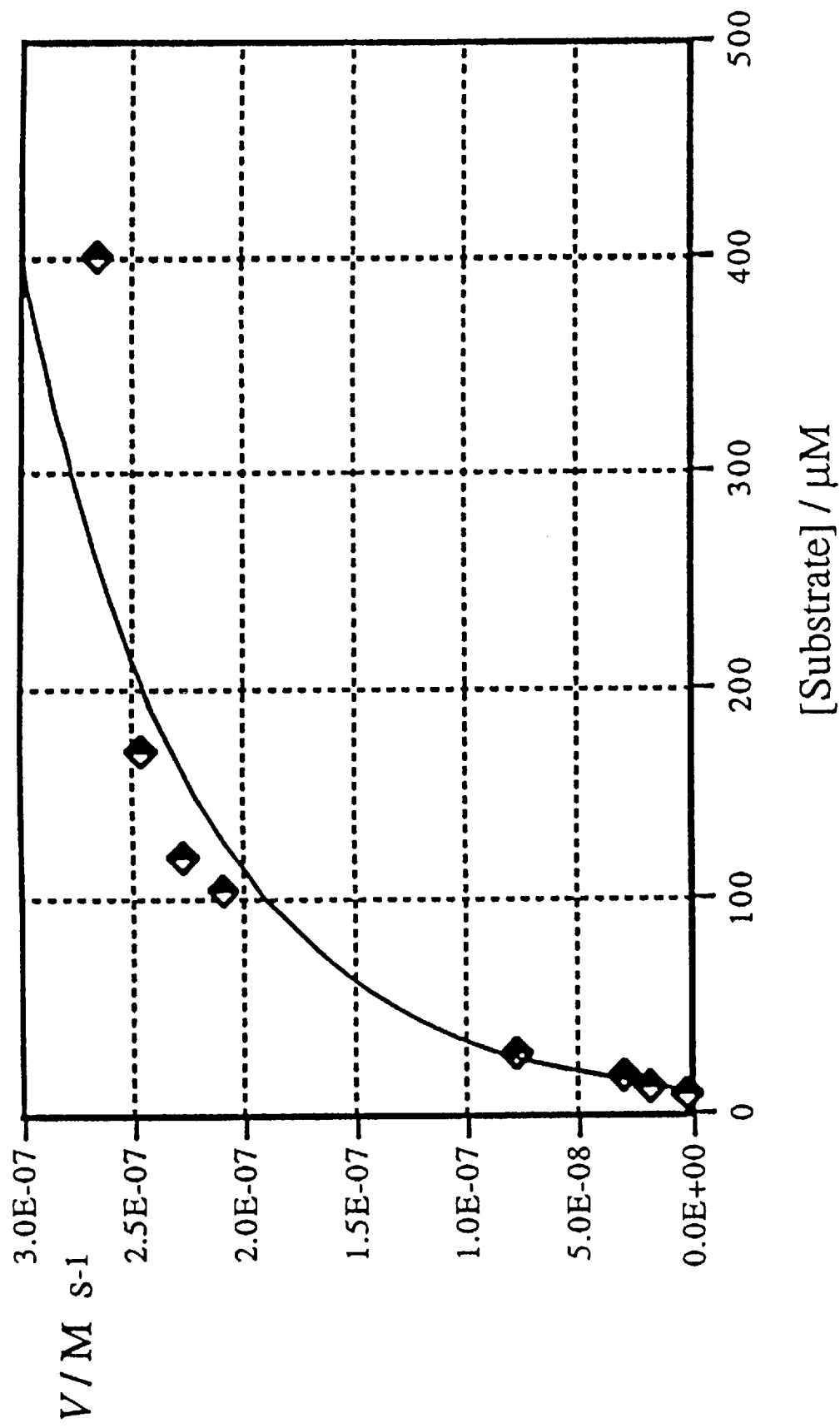
FIG. 9E9

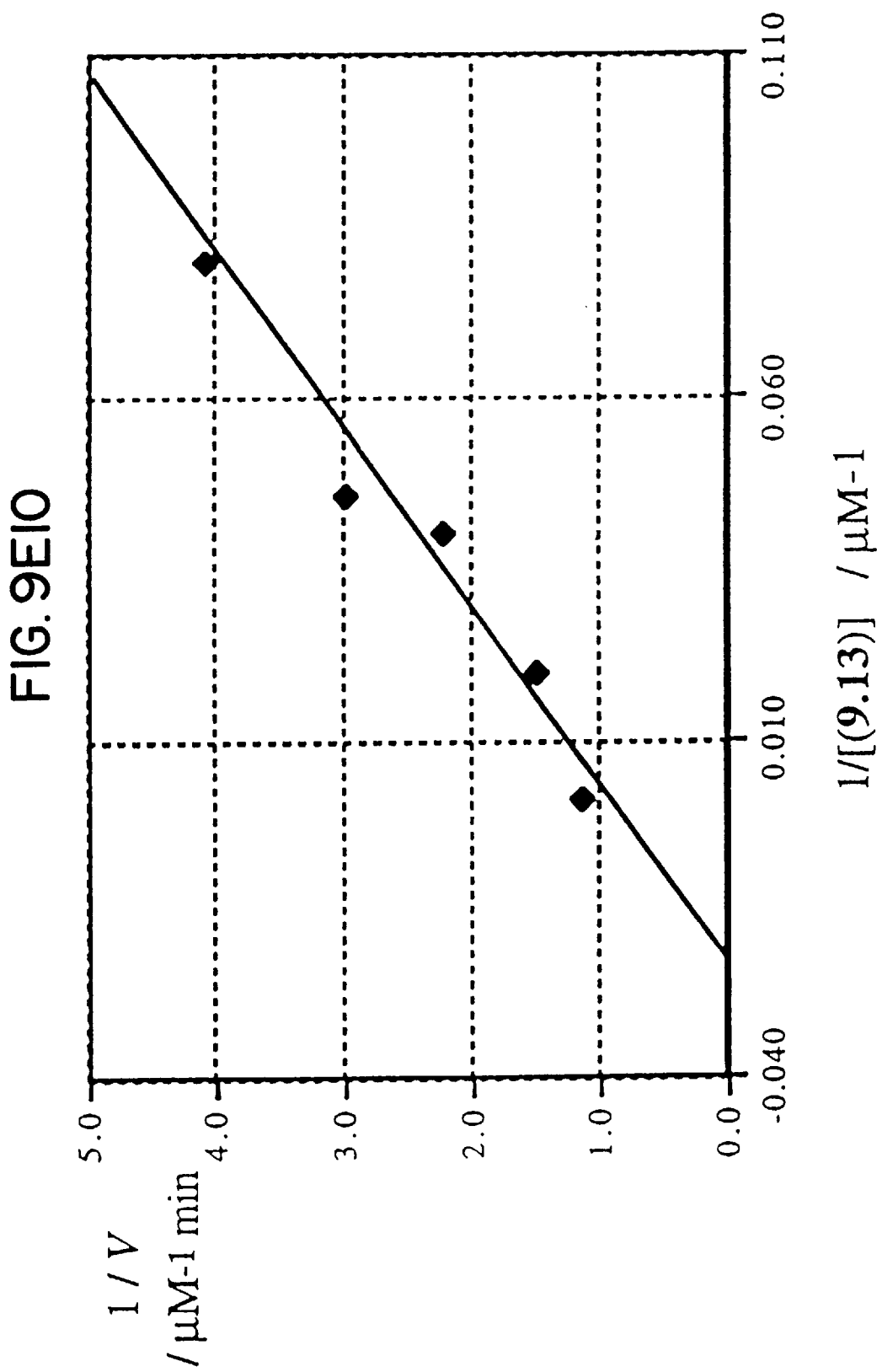
FIG. 9E10

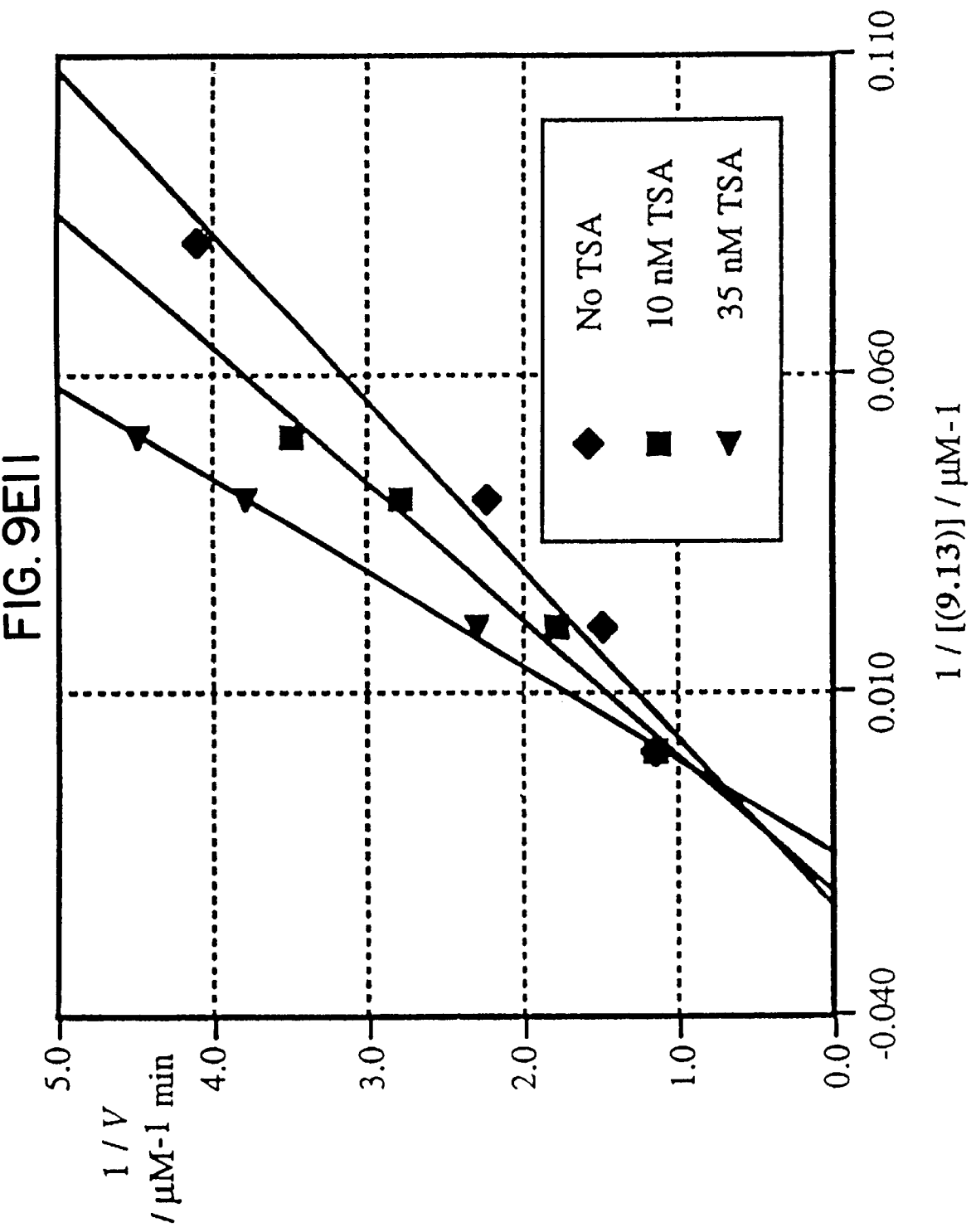

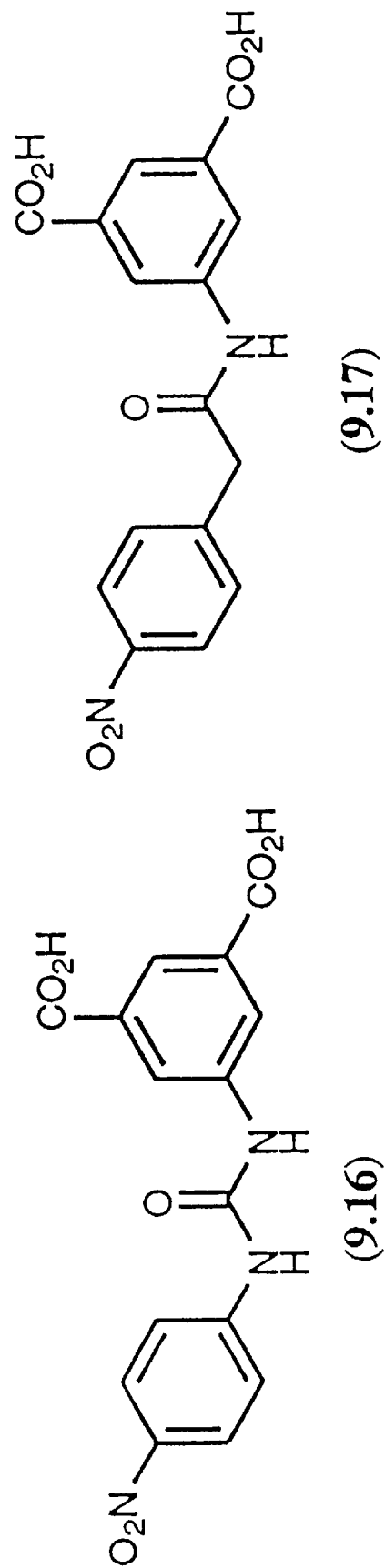
FIG. 9EI2

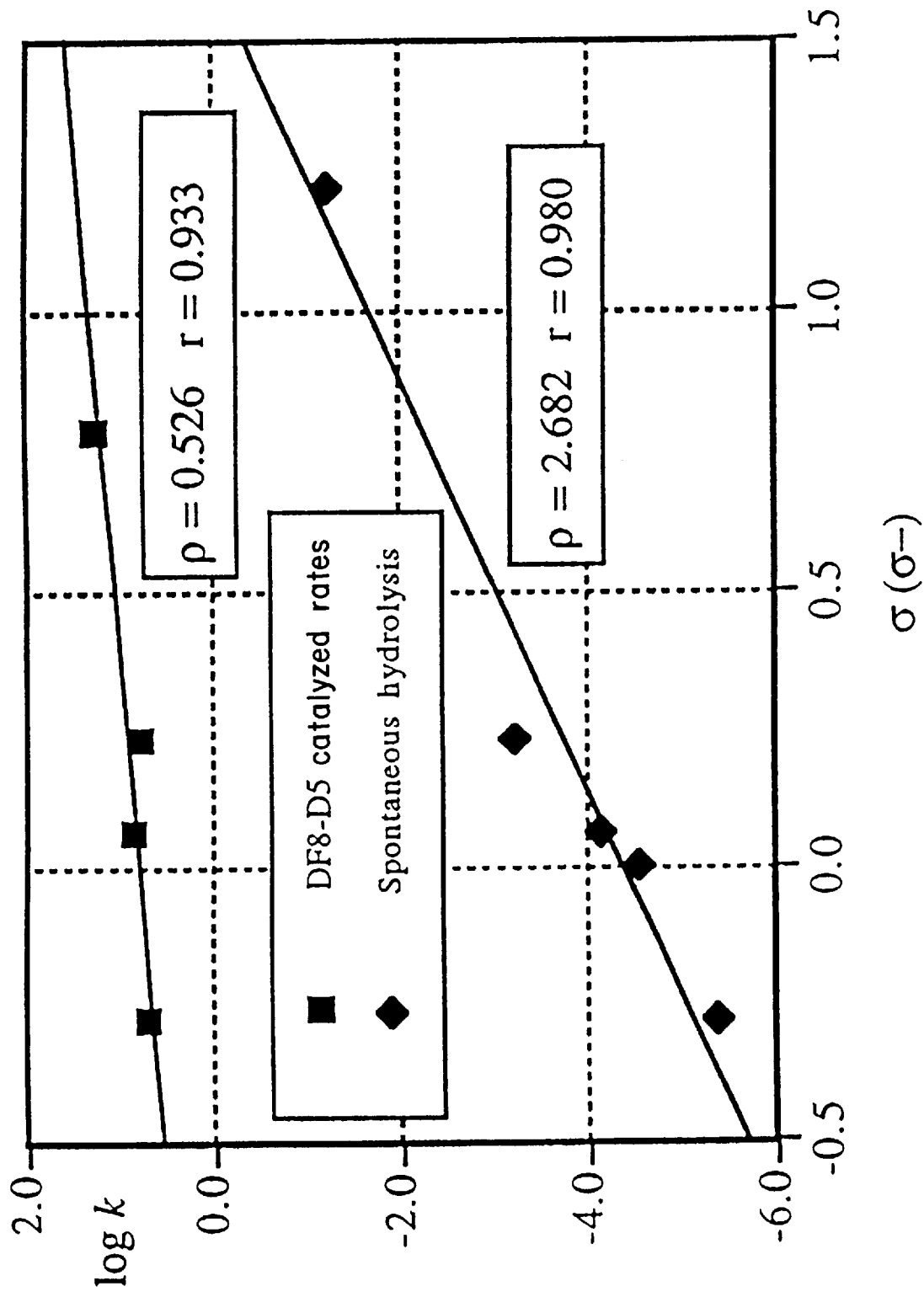
FIG. 9E13

FIG. 9F2
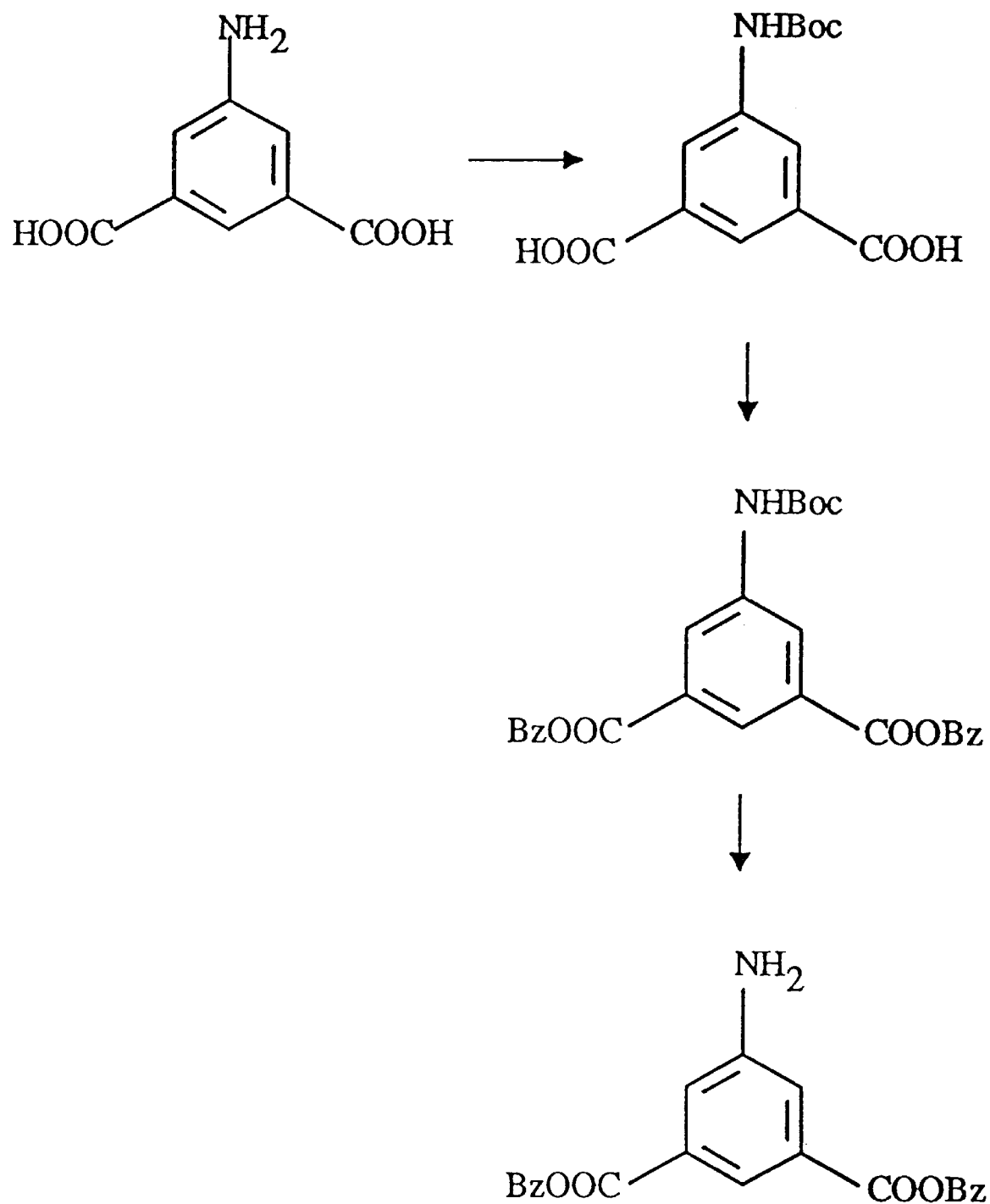

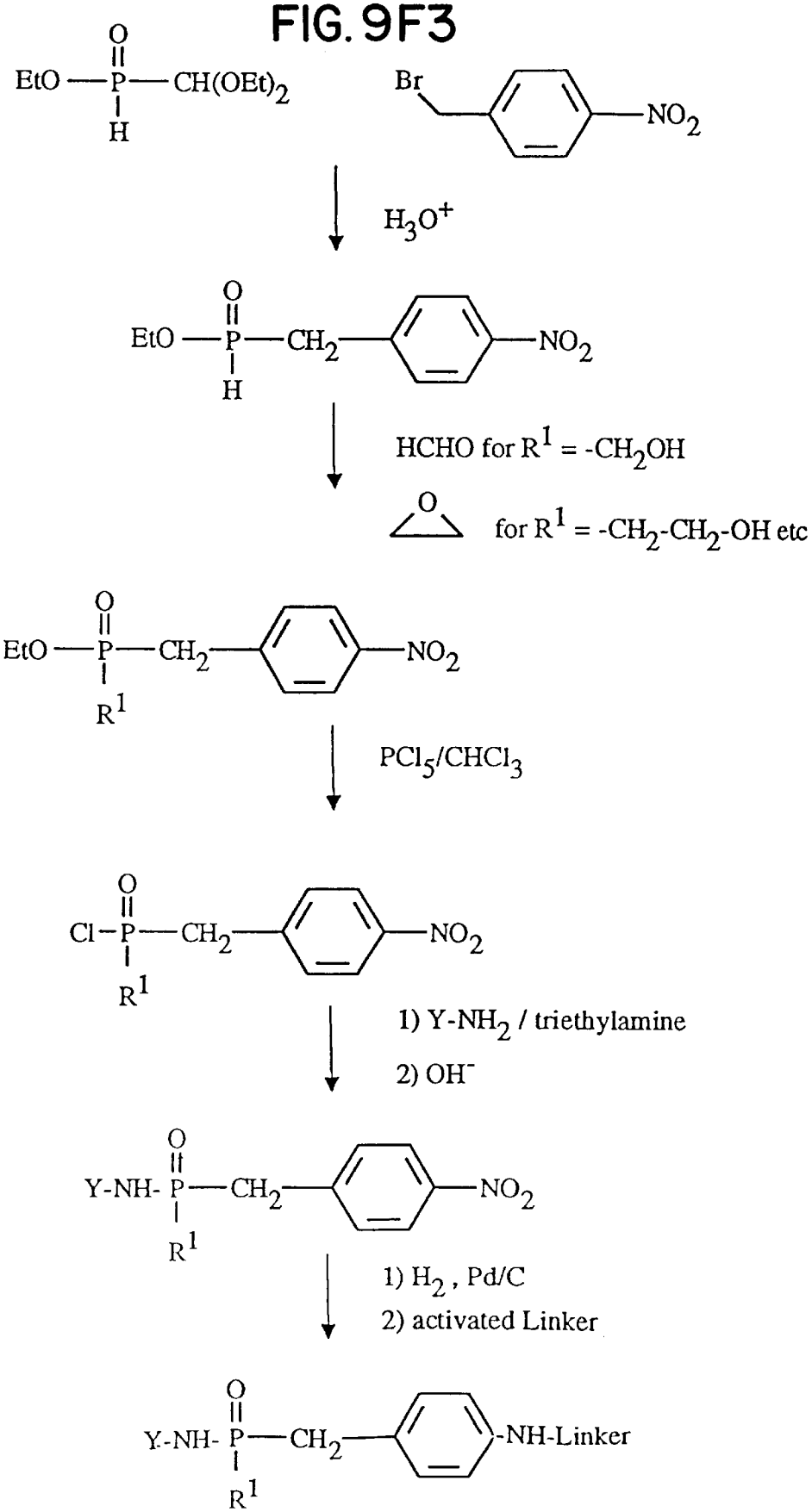
FIG. 9F3

CATALYTIC ANTIBODIES FOR CARBAMATE ACTIVATION BY A NON-SPONTANEOUS REACTION MECHANISM

CONTENTS

Introduction and Statement of Invention
1. Background to ADEPT
2. Background to Antibody Structure, Diversity and Catalysis
3. Cancer Treatment and ADEPT
4. Aryl Carbamate Ester Hydrolysis and Transition State Analogue Design
5. Monoclonal Antibody Production : Hybridoma Technology
6. Overview of Examples
7. Synthesis of Haptens and Substrates
   7.1 Synthesis of Transition State Analogues
   7.2 Synthesis of Substrates
   7.3 Materials and Methods
8. Example—Monoclonal Antibody Generation and Characterisation
9. Example—Catalytic Evaluation of TSA Specific Monoclonal Antibodies
10. References The invention principally relates to catalytic antibodies useful for activation of aryl carbamates, especially aryl carbamnate prodrugs for ADEPT.

Antibody directed enzyme prodrug therapy (ADEPT) has been developed to overcome the unwanted non-specific toxicity associated with anti-cancer agents and thus improve therapy. It is a 2 step targeting strategy. The first step involves administration of a tumour selective antibody linked to an enzyme. Following localisation of the conjugate at the tumour and clearance of the conjugate from blood and normal tissues the second step involves administration of a relatively non-cytotoxic prodrug which is cleaved by the enzyme at the tumour site to liberate a potent cytotoxic drug. In a recent clinical trial with an ADEPT system encouraging clinical results have been reported.

To diminish the extent of peripheral hydrolysis of the prodrug by non-specific enzymes in the plasma or normal tissues, the enzyme component selected for ADEPT has commonly been of bacterial origin. Bacterial enzymes are immunogenic in man and this immunogenicity reduces the clinical potential of ADEPT for repeated therapy. The alternative approach of using a mammalian enzyme, although circumventing the immunogenicity problem, reduces the specificity of the approach since endogenous enzyme will be present which can cleave the prodrug and enhance toxicity.

It is well established that antibodies against appropriate transition state analogues can catalyse a variety of chemical transformations. Furthermore, murine antibodies can be 'humanised' using existing technologies to reduce their immunogenicity in patients. Thus a humanised catalytic antibody (abzyme) could be prepared which replaces the bacterial enzyme and thus leads to an ADEPT system which combines both specificity and low immunogenicity. We have termed this approach antibody directed abzyme prodrug therapy (ADAPT).

The concept of using catalytic antibodies for ADEPT is known from WO 93/02703 but no disclosure of carbamate hydrolysis was made therein. Catalysis of carbamate hydrolysis by an antibody has been documented by Van Dranken et al in Tetrahedron Letters (1994) Vol 35: 3873–3876. However all catalytic antibodies to date have accelerated the reaction rate using the same mechanism as that identified for the spontaneous reaction.

The present invention is based on the discovery that carbamate prodrugs can be activated by catalysing a non-spontaneous reaction mechanism using a catalytic antibody.

According to one aspect of the present invention there is provided a catalytic antibody capable of catalysing activation of a carbamate (—O—CO—NH—) containing prodrug suitable for ADAPT by catalysing breakdown of the prodrug at the carbamate position by a non-spontaneous reaction mechanism. This has the advantage of obtaining maximum rate enhancement for catalytic antibody hydrolysis of carbamates that show minimal spontaneous hydrolysis.

Preferably the non-spontaneous reaction is a $B_{Ac}2$ mechanism. Preferably the spontaneous reaction proceeds by a E1cB mechanism. This approach has the advantage of overcoming the problem of stable intermediates by being a dissociative $B_{Ac}2$ process whilst the spontaneous E1cB mechanism is known to generate an electrophilic isocyanate intermediate, as shown in equation (4.1) (Ref 18). Preferably the prodrug is a nitrogen mustard aryl carbamate.

Preferably the antibody produces a reduced immune response in humans compared with mouse antibodies. Humanisation of non-human antibodies is contemplated to reduce the immunogenicity of such antibodies in humans such as for example described by Co and Queen in Nature (1991), 351:501–502 and in U.S. Pat. No. 5,225,539 (Medical Research Council). Catalytic antibodies may be whole or fragments (such as Fab or Fv) which have catalytic activity.

Preferably the catalytic antibody was raised to an immunogen of Formula I wherein Carrier represents any suitable carrier protein for immune system recognition (especially KLH); Linker represents any suitable linking moiety for linking the TSA to the Carrier (especially —CO—$(CH_2)_3$—CO—); Aryl represents a group selected from naphthyl and phenyl (preferably phenyl, especially para linked phenyl);

$R^1$ is selected from OH, $C_{1-4}$alkoxy, and —$C_{1-4}$alkylene-OH (especially $R^1$=—O-ethyl);

$R^2$ is selected from H and $C_{1-4}$alkyl (especially $R^2$=H);

Y represents a group of Formula II wherein:
   n is 0 to 4 (especially n=0),
   $R^3$ and $R^4$ are independently selected from —COOH, —$SO_3H$ and —$PO_3H_2$ (especially —COOH) and;
   X is selected from H, nitro, halogen, carboxy, —$SO_3H$, —$PO_3H_2$, —$SO_2NHCO$—$C_{1-4}$alkyl, tetrazol-5-yl (especially X=H); or, Y represents a group of Formula III wherein the asterisked chiral centre can be L or D configuration (preferably L).

In this specification the generic term "alkyl" includes both straight-chain and branched-chain alkyl groups. However references to individual alkyl groups such as "propyl" are specific for the straight-chain version only and references to individual branched-chain alkyl groups-such as "isopropyl" are specific for the branched-chain version only. An analogous convention applies to other generic terms.

It is to be understood that, insofar as certain of the compounds of the invention may exist in optically active or racemic forms by virtue of one or more asymmetric carbon atoms, the invention includes in its definition any such optically active or racemic form which possesses a desired property of the invention. The synthesis of optically active forms may be carried out by standard techniques of organic chemistry well known in the art, for example by synthesis from optically active starting materials or by resolution of a racemic form.

More preferred immunogens are shown in Formulae IV and V wherein $R^1$ represents —OH or —O-ethyl. An especially preferred immunogen has the structure of Formula IV wherein $R^1$ is —O-ethyl.

According to another aspect of the present invention there is provided catalytic antibody EA11-D7/B8 antibody obtainable from hybridoma no 94122025 as deposited under the Budapest Treaty at the European Collection of Animal Cell Cultures (ECACC), PHLS Centre for Applied Microbiology & Research, Porton Down, Salisbury, Wiltshire SP4 0JG, United Kingdom on 20th Dec. 1994.

According to another aspect of the present invention there is provided catalytic antibody BH3.B8.F9 antibody obtainable from hybridoma no 96042611 as deposited under the Budapest Treaty at the European Collection of Animal Cell Cultures (ECACC), PHLS Centre for Applied Microbiology & Research, Porton Down, Salisbury, Wiltshire SP4 0JG, United Kingdom on 26th Apr. 1996.

According to another aspect of the present invention there is provided catalytic antibody DF8.D5 antibody obtainable from hybridoma no 96042612 as deposited under the Budapest Treaty at the European Collection of Animal Cell Cultures (ECACC), PHLS Centre for Applied Microbiology & Research, Porton Down, Salisbury, Wiltshire SP4 0JG, United Kingdom on 26th Apr. 1996.

Optionally the catalytic antibody may be mutagenised to optimise catalytic activity. Preferably the catalytic antibody is monoclonal.

With respect to the deposit of antibody EA11-D7/B8 the reader should note the following. Testing of the antibody after deposit has revealed that although it still binds well to transition state analogue it no longer appears to exhibit catalytic properties.

Catalytic antibody generation techniques not involving immunisation are also contemplated such as for example using phage display technology to examine naive libraries (from non-immunised animals); see Barbas et al (1992), PNAS USA, 89: 4457–4461 and Waterhouse et al (1993), Nucleic Acids Research, 21:2265–2266.

Hybridomas no 96042611 and 96042612 represent another aspect of the present invention. Immunogens of Formula I represent another aspect of the present invention.

Hapten components of the immunogens described above represent another aspect of the present invention. The haptens are defined by Formula VI wherein the variable groups are as defined for Formula I above and optionally further containing an activating group (preferably N-hydroxysuccinimide) on the linker for linkage to carrier protein.

According to another aspect of the present invention there is provided the use of short transition state analogues of Formula VII wherein $R^1$ is as defined above, to screen for catalytic activity as described below, based on the immunogens described above. A preferred short transition state analogue has the structure of Formula VII wherein $R^1$ is —O-Ethyl. Preferably the short transition state analogue is attached to a solid phase through its —$NO_2$ group.

According to another aspect of the present invention there is provided the use of short transition state analogue immunogens of Formula VIII wherein $R^1$ is as defined above, to raise catalytic antibodies. A preferred short transition state analogue immunogen has the structure of Formula VIII wherein $R^1$ is —O-Ethyl.

To avoid alkylation of the abzyme by the mustard drug, haptens were linked to carrier proteins through a spacer linker introduced in place of the mustard function of the prodrug. This has the advantage of minimising the generation of strong contacts between the mustard portion of the prodrug and the combining site of the abzyme and thus optimises the opportunity for rapid diffusion of the drug out of the abzyme catalytic site. In addition this has the further advantage that a range of modifications of the drug moiety should be possible without impairing the enzyme activity of the abzyme.

According to another aspect of the present invention there is provided EA11D7/B8, BH3.B8.F9 and DF8.D5 antibodies in humanised form.

According to another aspect of the present invention there is provided a catalytic antibody containing the complementarity determining regions (CDRs) of EA11-D7/B8 antibody produced by hybridoma no 94122025 as deposited at the European Collection of Animal Cell Cultures (ECACC). The CDR sequences can be determined by standard techniques such as those described in "Generation of Antibodies by Cell and Gene Immortalisation" edited by C. Terhorst, F. Malavasi and A. Albertini. The Year in Immunology, Karger (Basel), 1993, volume 7, pp 56–62. The CDR sequences are defined from the alignment of antibody sequences according to "Sequences of Proteins of Immunological Interest" E. A. Kabat, T. T. Wu, M. Reid-Miller, H. M. Perry and K. S. Gottesman, U.S. Department of Health and Human Services, NIH (Bethesda) 1987." Humanised antibodies in the form of chimaeric antibodies are also contemplated.

According to another aspect of the present invention there is provided a method of making an immunogen of Formula I which comprises coupling an activated hapten to a carrier.

According to another aspect of the present invention there is provided a method of making a catalytic antibody which comprises immunising an animal with an immunogen of Formula I.

According to another aspect of the present invention there is provided an ADAPT system comprising a catalytic antibody as described above. Preferably the catalytic antibody is humanised. The catalytic antibody may be linked to a tumour selective antibody by chemical or recombinant fusion techniques. Bispecific antibodies are also contemplated wherein one binding site recognises the tumour and the other binding site possesses catalytic activity. Bispecific antibody technology is described in WO 91/09134 (Takeda) and WO 91/08770 (Immunomedics). These components may be used with prodrugs having carbamate linkages such as those described in WO 94/02450 (Cancer Research Campaign & Zeneca). The following abbreviations have been used in this text:

| MW | molecular weight |
|---|---|
| Da | Daltons |
| M | molar |
| KLH | keyhole limpet haemocyanin |
| BSA | bovine serum albumin |
| OVA | chick ovalbumin |
| d | days |
| Tyr | tyrosine |
| Arg | arginine |
| Glu | glutamic acid |
| His | histidine |
| Asn | asparagine |
| Lys | lysine |
| Asp | aspartic acid |
| Leu | leucine |
| Met | methionine |
| Phe | phenylalanine |
| Fab | antigen binding fragment Mab monoclonal antibody |
| TMED | N,N,N,N'-tetramethylenediamine |
| TNBS | trinitrobenzenesulphonic acid |
| PBS | phosphate buffered saline |
| HBS | hepes buffered saline |
| MES | 2-N-morpholino)ethanesulfonic acid |
| TRIS | tris(hydroxymethyl)aminomethane |
| HAT | hypoxanthine, aminopterin, thymidine |
| FCS | foetal calf serum |

| | |
|---|---|
| DMEM | Dulbecco's modified eagle media |
| PEG | polyethyleneglycol |
| TMB | 3,3',5,5'-tetramethylbenzidine |
| HRP | horse radish peroxidase |
| ALP/AP | alkaline phosphatase |
| SRB | sulforhodamine B |
| SPR | surface plasmon resonance |
| BIA | bi ospecific interactive analysis |
| RU | response units |
| NHS | N-hydroxysuccinimide |
| EDC | 1-(3-dimethylaminopropyl)-3-ethylcarbodiimide |
| NMR | nuclear magnetic resonance |
| LDMS | laser-desorption mass spectrometry |
| OD | optical density |
| Me | methyl |
| Et | ethyl |
| Ph | phenyl |
| Pri | iso-propyl |
| But | tert-butyl |
| Bn | benzyl |
| Boc | N-tert-butyloxycarbonyl |
| Z/Cbz | N-benzyloxycarbonyl |
| DMAP | 4-dimethylaminopyridine |
| TEAB | triethylammonium bicarbonate |
| r.t. | retention time |
| TLC | thin layer chromatography |
| h.p.l.c. | high performance liquid chromatography |
| m.p.l.c. | medium pressure liquid chromatography |
| TSA | transition state analogue |

The invention will now be illustrated by the following non-limiting Examples in which:

FIG. 1A shows prodrugs for ADEPT (1.1) and their activation (1.2);

FIG. 2A shows the Y-shaped antibody molecule. A schematic representation of an IgG molecule. Antigen binding occurs in the antibody binding site which is comprised of the VH (variable heavy) and $V_L$ (variable light) domains through non-covalent interactions of the antigen with CDRs (complementarity determining regions). $C_H1$, $C_H2$ and $C_H3$ represent the constant heavy chain domains 1, 2 and 3 respectively. CL is the constant light chain domain and H is the hinge region. Adapted from D. R. Burton[24]

Figure 1A:
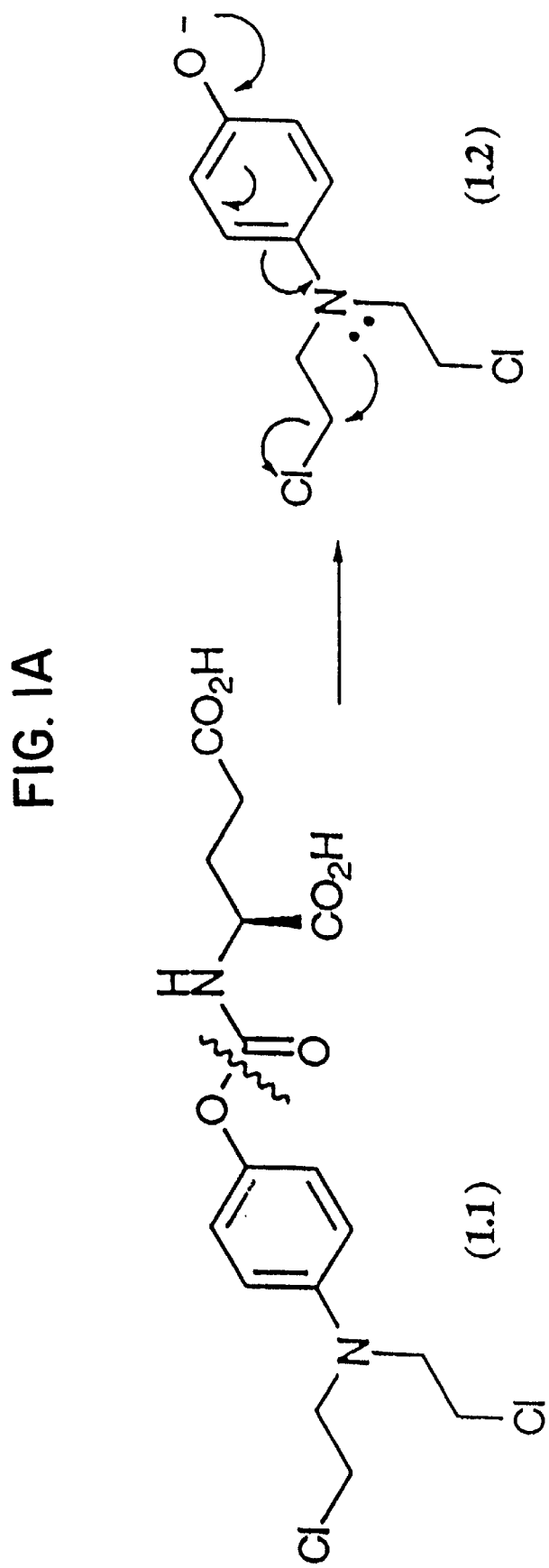

FIG. 2D2 shows a schematic representation of base catalysed ester hydrolysis showing progression through the tetrahedral intermediate, TI (2.5). The theorised transition structures both precede and follow formation of (2.5).

FIG. 2D3 shows geometry and charge distribution of the transition state for alkaline hydrolysis of methyl acetate and a phosphonate analogue.

FIG. 2D4 shows that Lerner (11) raised antibodies to the phosphonate TSA (2.9). One of the antibodies, 6D4, that bound the TSA hydrolysed the coumarin ester (2.8) but the acetanilide analogue (2.10) was not a substrate.

FIG. 2D5 shows the mechanism of catalysis of subtilisin. By going from the enzyme-substrate complex (E.S) to the transition state complex (E.S‡), the proton on Ser 221 (bold) is transferred to His 64, facilitating nucleophilic attack on the peptide bond. The proton is then transferred to the leaving amine and the acyl-enzyme intermediate is generated.

FIG. 2D6 shows the quaternary ammonium hapten (2.11) elicited an antibody, 43D4-3D12, by the 'bait and switch' principle which catalysed the beta-elimination of HF from (2.12)

FIG. 2D7 Three haptens (2.14–2.16) were designed to study the 'bait and switch' principle for abzyme generation. Both charged haptens produced antibodies that catalysed the hydrolysis of the benzoyl substrate (2.17), whereas the neutral hapten generated antibodies which only bound the substrate.

FIG. 2D8 shows (−)-Chorismic acid (2.18) isomerises to prephenic acid (2.19) via a [3,3]-sigmatropic rearrangement which proceeds through a highly-ordered transition state (2.20) having pseudo diaxial chair-like geometry. The endo oxabicyclic acid (2.21), was designed as a TSA for the reaction and inhibited the enzyme chorismate mutase with a $K_i$=0.15 $\mu$M.

FIG. 2D9 shows a schematic diagram showing the hydrogen bonding (dashed) and electrostatic interactions of the transition state analogue (2.21) with relevant side chain residues of the catalytic antibody 1 F7.

FIG. 2D10 shows the Diels-Alder condensation of TCTD (2.22) and (2.23) proceeds through an unstable transition state (2.26) which subsequently extrudes $SO_2$ to form the dihydro-phthalimide adduct (2.24). The hapten (2.25) was designed to be sufficiently different from the adduct to prevent product inhibition in antibody catalysis of this reaction.

FIG. 2D11 shows a scheme showing the binding site contacts, H-bonds (dashed) and electrostatic interactions of McPC603 and phosphorylcholine (2.27). This antibody catalyses the hydrolysis of p-nitrophenyl choline carbonates (2.28) because (2.27) is a TSA for this process.

FIG. 2D12 shows the production of thiolated Lys52H MOPC315 was achieved by treatment with (2.30) and subsequent reduction with $NaCNBH_3$ and DTT. The mutant abzyme catalysed the hydrolysis of (2.29).

FIG. 2D13 shows the monoclonal, 26D9, generated to the N-oxide hapten (2.33) regioselectively catalysed the disfavoured 6-endo-tet ring closure of the hydroepoxide (2.31). This is a formal violation of Baldwin's rules which predicts a 5-exo-tet process to generate the tetrahydrofuran derivative (2.32).

FIG. 2D14 shows the enantio- and diastereoselectivity of the Diels-Alder reaction for ortho approach.

FIG. 2D15 shows the Diels-Alder cycloaddition between the dienophile (2.36) and diene (2.35) yields two diastereoisomers (2.37) and (2.38).

FIG. 2D16 shows antibodies were raised to haptens (2.43) and (2.44) which are analogues of the favoured endo (2.41) or disfavoured exo (2.42) transition states respectively.

FIG. 2D17 shows that to effect the separation of four stereoisomers (2.49–2.52), BALB/c mice were immunised with one of four stereochemically related phosphonate haptens (2.45–2.48).

FIG. 2D18 shows the monoclonal, 6D9, raised to both (2.53) and (2.54) catalysed the hydrolysis of only one of the regioisomers (2.56) of the chloramphenicol prodrug.

FIG. 2D19 shows anticancer prodrug activation. The benzoic acid amide prodrug of doxorubicin (2.59) has lower toxicity than the parent drug, doxorubicin (2.58). By generating antibodies to the phosphonamidate hapten (2.60) IGEN hope to produce catalysts that will activate the prodrug in vivo thereby reducing the toxicity associated with doxorubicin treatment.

FIG. 2D20 shows unpredictability in abzyme generation. The hapten (2.61) elicited a powerful abzyme, 50D8, for the hydrolysis of the ester (2.62), but only after repeated immunisations.

FIG. 2D21 shows amino acid ester hydrolysis reaction catalysed by antibody 17E8 and the TSA used to elicit the antibody.

Figure 3A:
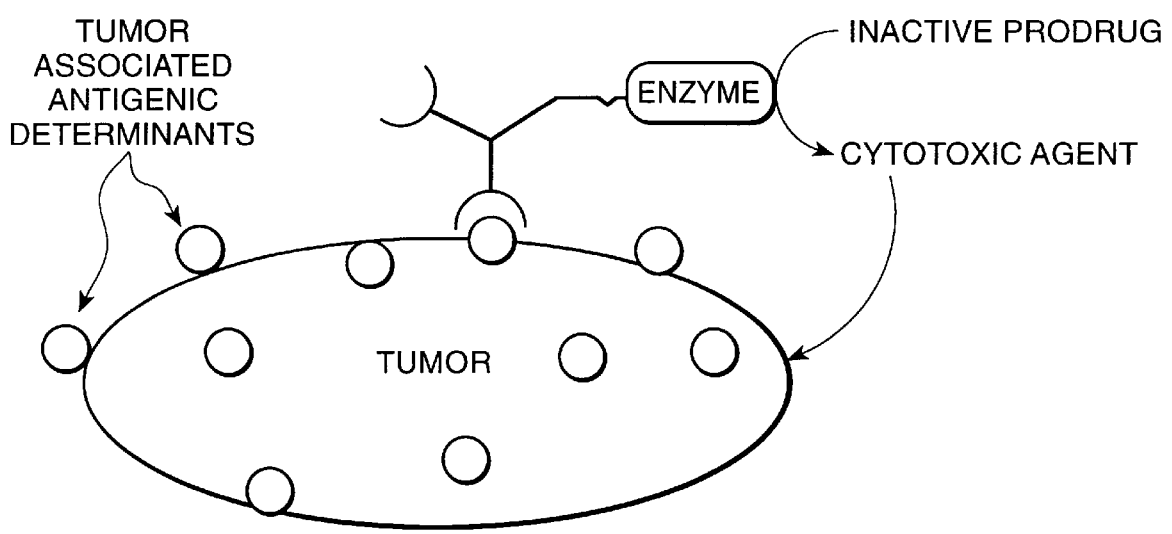

FIG. 3A shows ADEPT. Mab-enzyme conjugates targeted at tumour surfaces convert less toxic prodrugs into more active cytotoxic agents. The enzyme also acts as an amplification system, with each localised antibody-enzyme conjugate molecule catalysing the formation of many molecules of the active cytotoxic agent. Moreover, the cytotoxic drugs can be small molecules with the ability to diffuse through the tumour and destroy cells deep in the cancer.

Figure 3B:
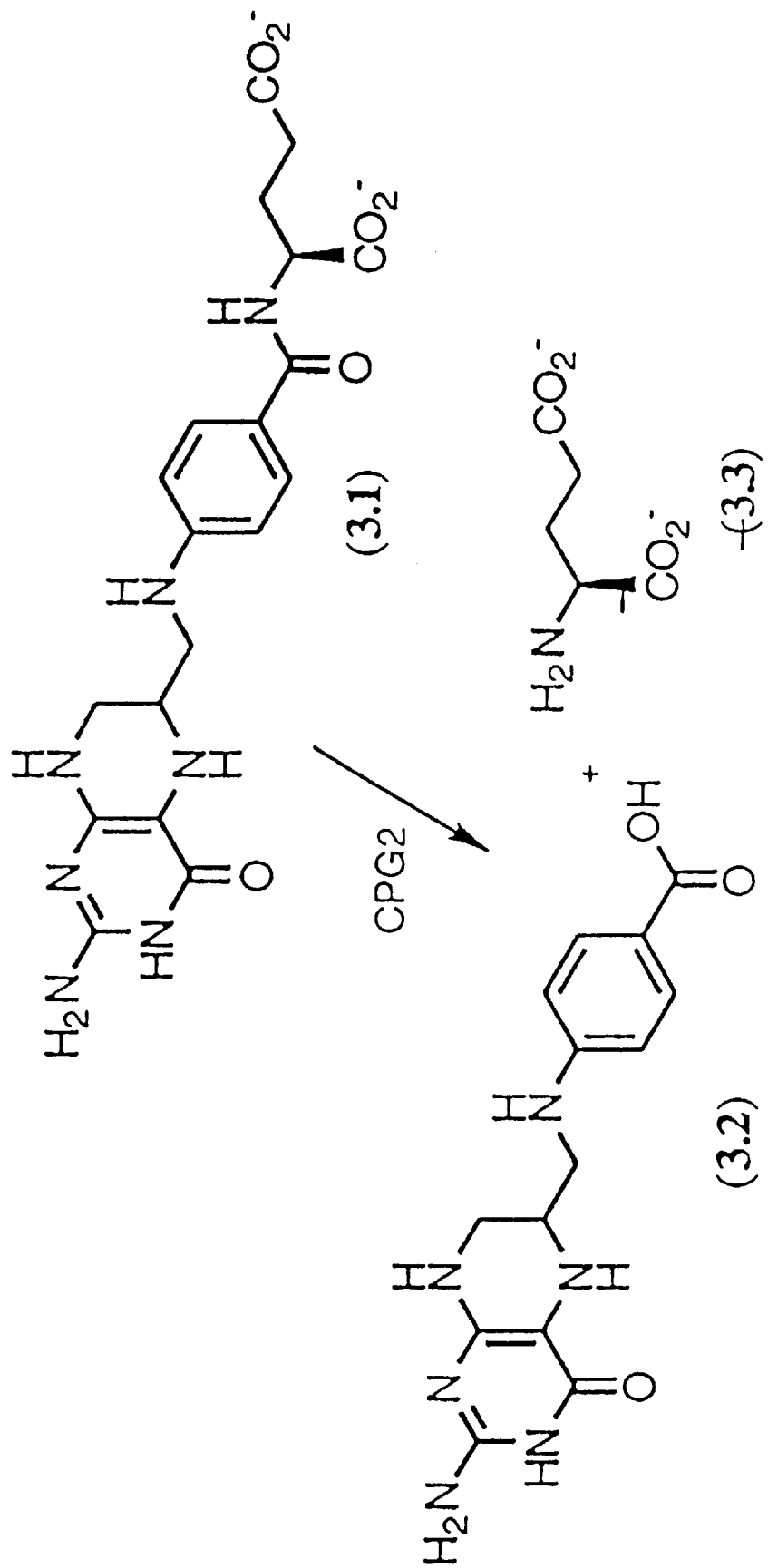

FIG. 3B shows hydrolysis of folates catalysed by CPG2.

Figure 3C:
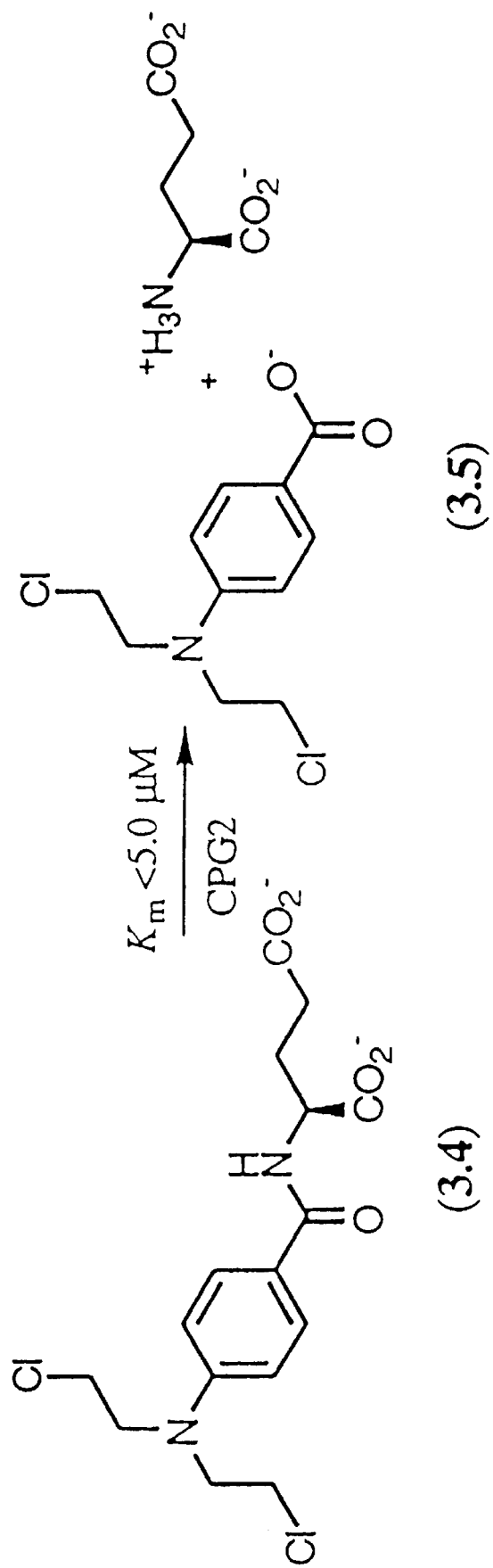

FIG. 3C shows the prodrug para-[bis(2-chloroethyl) amino]benzoyl-Lglutamic acid (3.4) is rapidly hydrolysed by CPG2 to para-[bis(2-chloroethyl)amino]benzoic acid (3.5) and glutamic acid.

Figure 2A:
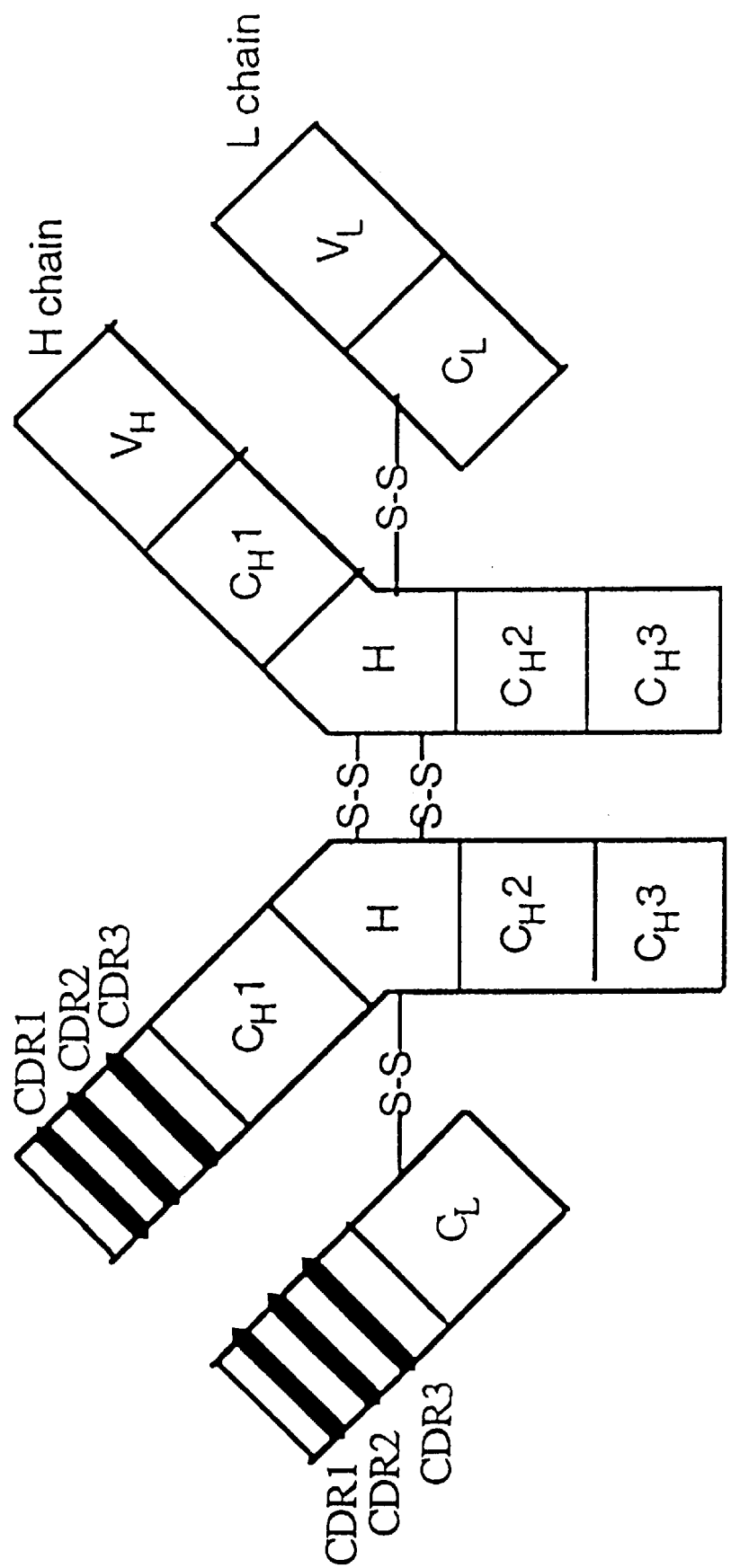
FIG. 2B shows selectivity of antibody recognition. Antibodies raised to (2.1) showed reduced affinity for both (2.2) and (2.3).
FIG. 2C shows engineered antibodies and fragments; adapted from reference 9.
FIG. 2D shows an energy potential diagram showing the importance of reducing the free energy of activation (the transition state energy) in order to achieve catalysis.
Figure 2C:
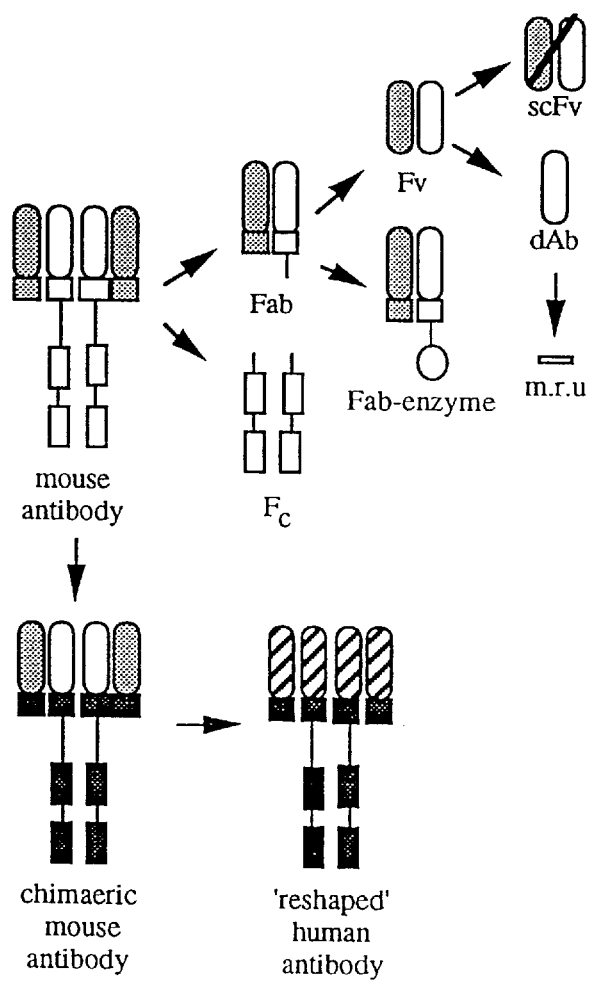
Figure 3D:
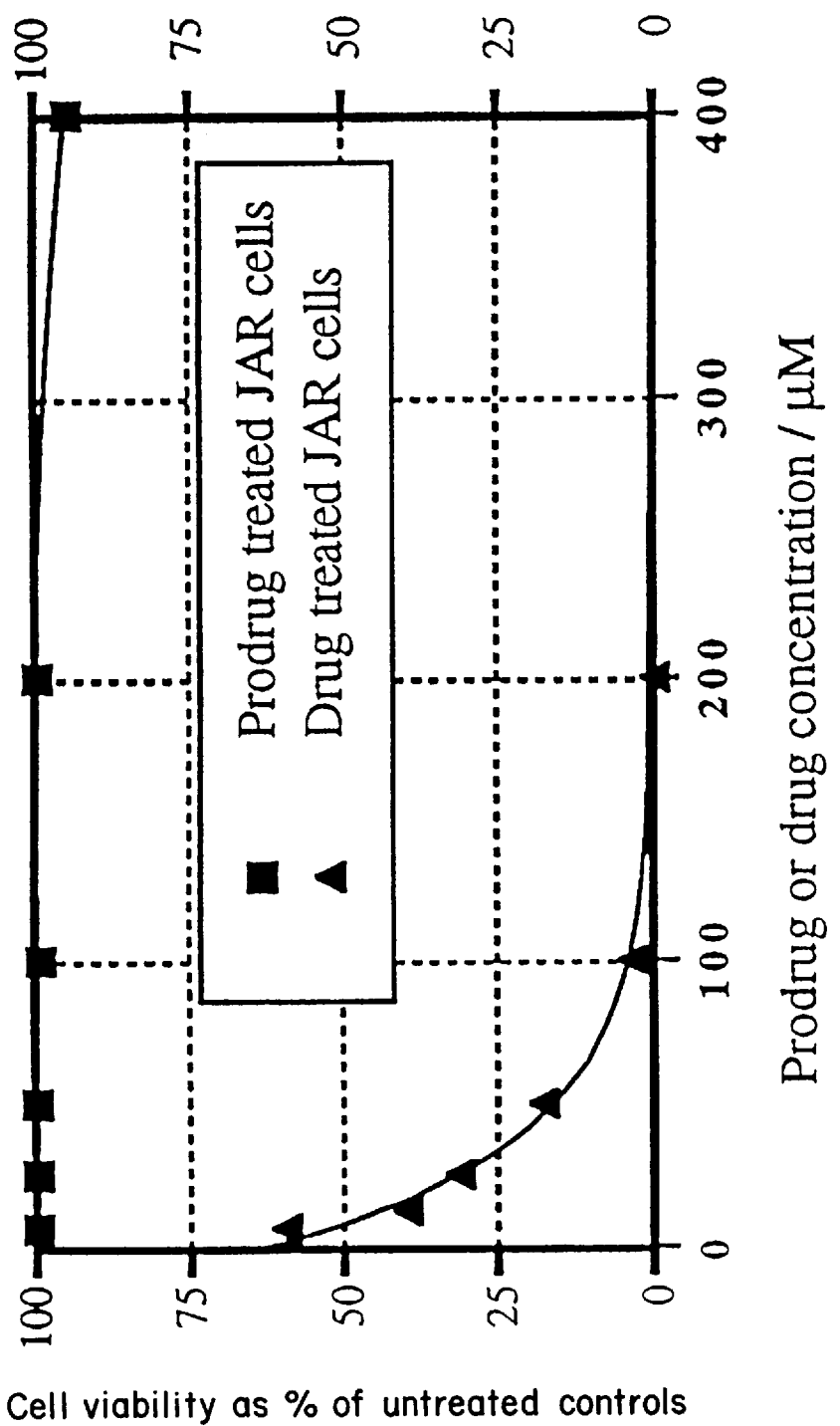

FIG. 3D1 shows Cytotoxicity of prodrug and drug against JAR human choriocarcinoma cell line. FIG. 3D2 shows the effect of ADEPT on CC3 xenograft bearing mice. The anti-hCG:CPG2 conjugate was followed by prodrug administration (after 52–76 h) and the tumour growth rates were compared with untreated controls.

Figure 3E:
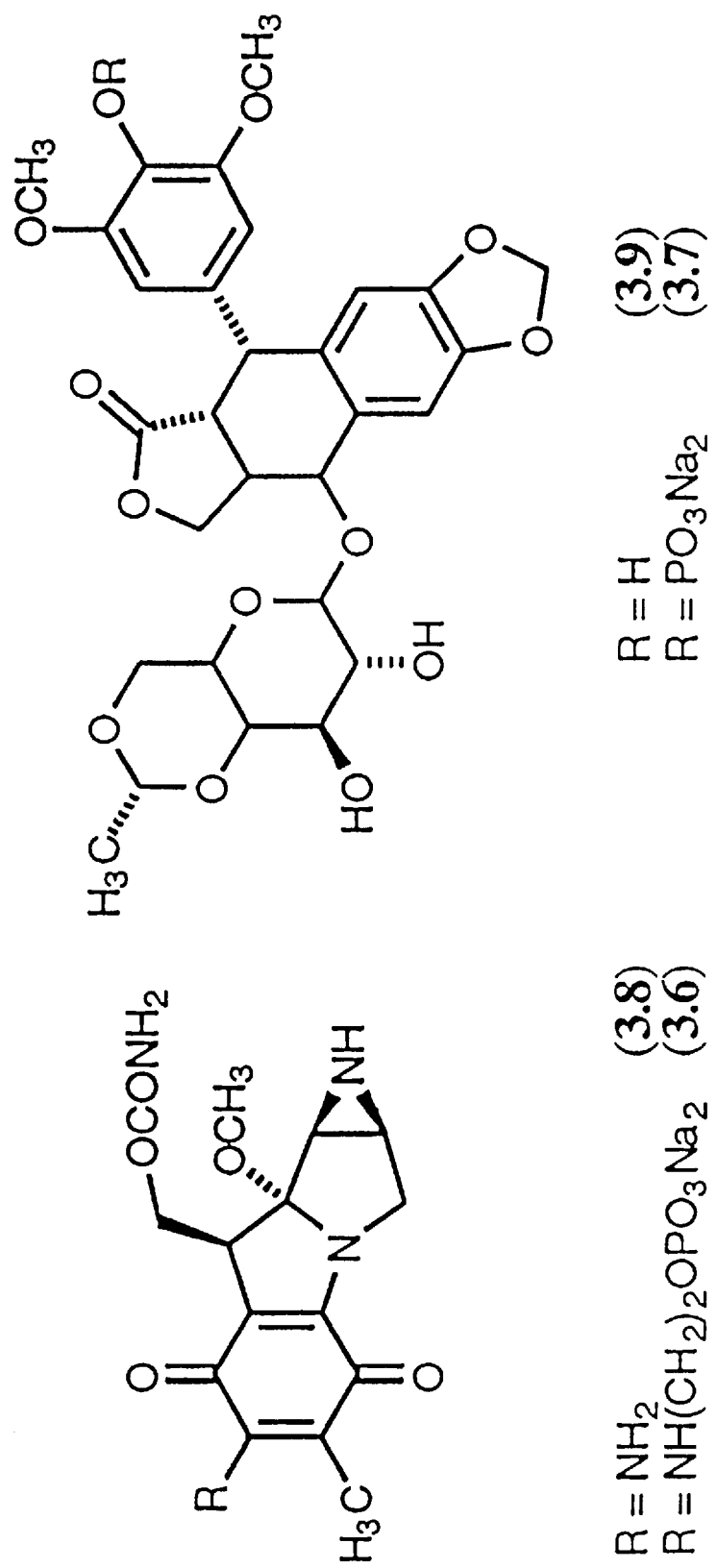

FIG. 3E shows Etoposide phosphate (EP) (3.7) and mitomycin phosphate (MOP) (3.6) prodrugs were hydrolysed to etoposide (3.9) and mitomycin C (MMC) (3.8) respectively by a Mab-AP conjugate for treatment of human adenocarcinoma xenografts in nude mice.

FIG. 3F shows the effect of MOP plus EP and conjugate (L6-AP) on H2981 tumours in nude mice. Arrows indicate the prodrug treatment schedule. Conjugates were administered 24 h before the first prodrug dose.

FIG. 36 shows DNA bases and their mechanism of alkylation by N-mustards. The most common alkylation of DNA occurs at $N^7$-guanine (3.12) and can lead to both inter- and intra-strand cross-linking. The other DNA bases (3.13–3.15) are alkylated by N-mustards to a lesser degree.

Figure 3G:
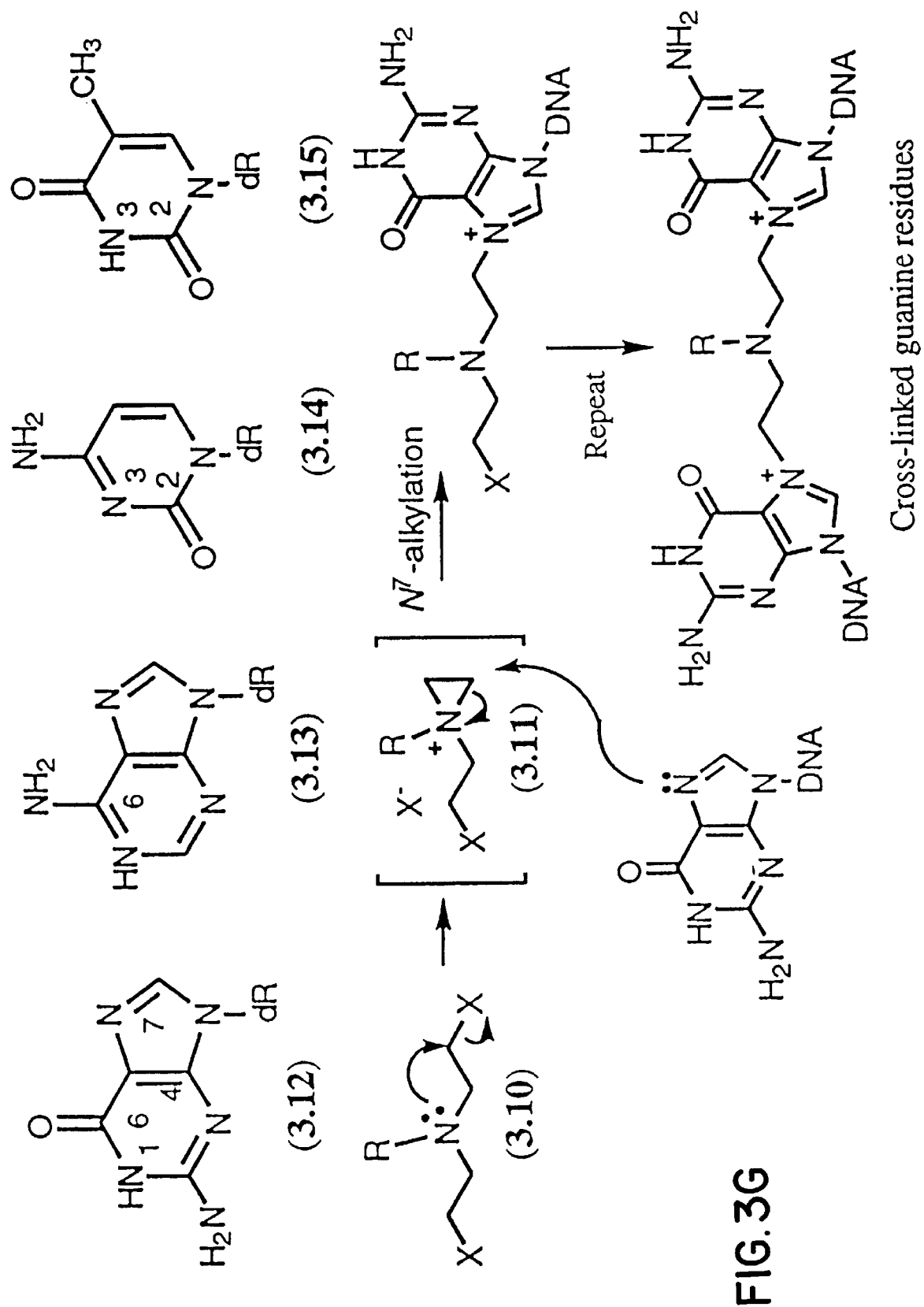
Figure 3H:
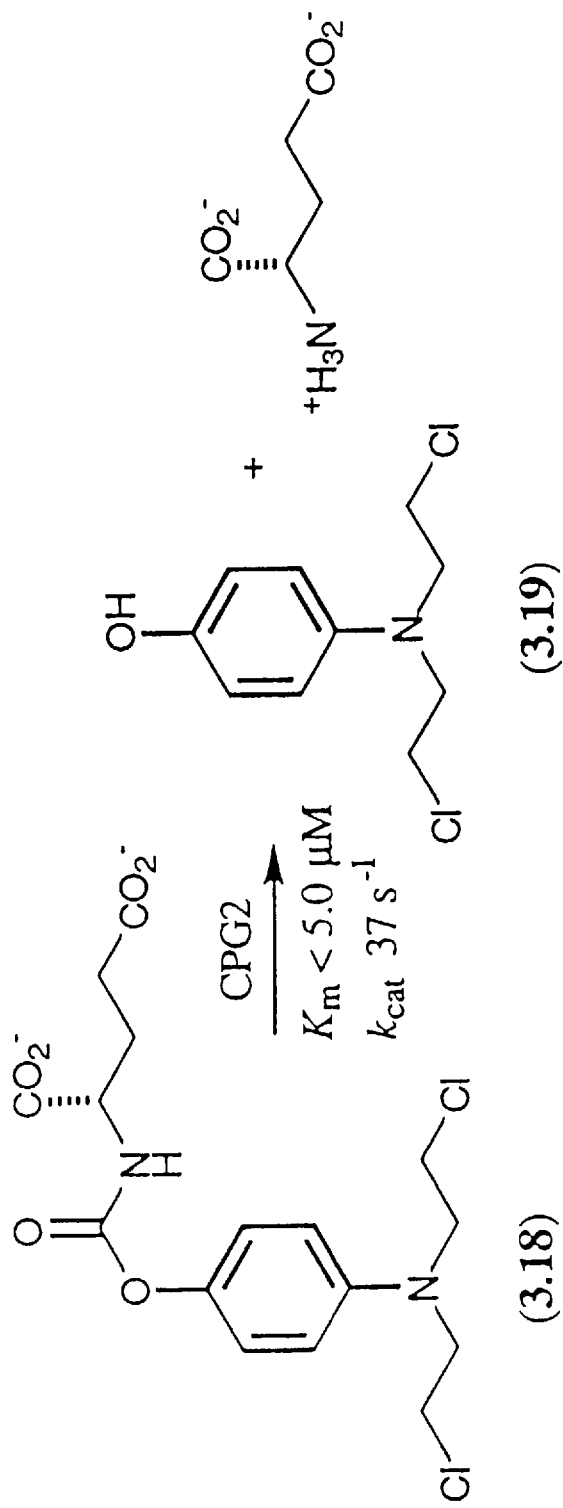

FIG. 3H shows the second generation N-mustard, 4-[N,N-bis-(2-chloroethyl)]aminophenol (3.19), possesses exceptional in vitro cytotoxicity to colorectal tumour cells (LoVo) ($IC_{50}$ 1 $\mu$M). Its prodrug, 4-[N',N'-bis-(2-chloroethyl)] aminophenyl N-[(1,3-dicarboxy)propyl]carbamate (3.18) is hydrolysed by CPG2 with $K_m$<5.0 $\mu$M and $k_{cat}$ 37 s$^{-1}$.

FIG. 4A1 shows the $B_{AC}2$ mechanism of ester hydrolysis.

FIG. 4A2 shows stability of carbamates (4.5) and ureas (4.6). Resonance structures such as (4.4) contribute to the lack of reactivity at the acyl centre of these compounds.

FIG. 4A3 shows the rate of hydrolysis of aryl carbamates shows tremendous variation. Where there is a proton on the nitrogen atom (4.7 and 4.9) alkaline hydrolysis is $10^6$ times faster than when the carbamate is N,N-disubstituted (4.8 and 4.10) (Refs. 145, 146).

FIG. 4A4 shows the duality of the mechanism for hydrolysis of carbamate esters. Depending on whether the nitrogen is mono- or di-substituted, alkaline hydrolysis of aryl carbamates can follow either an addition-elimination or an elimination-addition mechanism.

FIG. 4A5 shows two possible elimination-addition mechanisms. Alkaline hydrolysis can either be specific hydroxide catalysis eqn. (4.1) or general base catalysis eqn. (4.2).

FIG. 4A6 shows a Brønsted plot of rate constants for alkaline hydrolysis of substituted phenyl N-phenylcarbamate esters (4.11) versus pKa of the departing phenol.

FIG. 4A7 shows mechanistic studies were performed on substituted phenyl N-phenyl carbamates (4.11) and phenyl N-(substituted phenyl)carbamates (4.12) to elucidate their mechanism of alkaline hydrolysis.

FIG. 4A8 shows the carbanion mechanism (E1cB) of ester hydrolysis. Aryl acetoacetate ester (4.13) was shown to proceed via an E1cB mechanism with the formation of a ketene intermediate (4.14).

FIG. 4A9 shows a Plot of sigma ($\sigma^-$) vs. bimolecular rate constant ($k_{OH}$) for the alkaline hydrolysis of substituted phenyl N-phenylcarbamates (4.11).

FIG. 4A10 shows a Brønsted plot of log of the hydrolysis rates vs. pKa of a series of substituted N-(p-nitrophenyl) carbamates (4.15) and their N-methyl analogues (4.16).

Figure 4B:
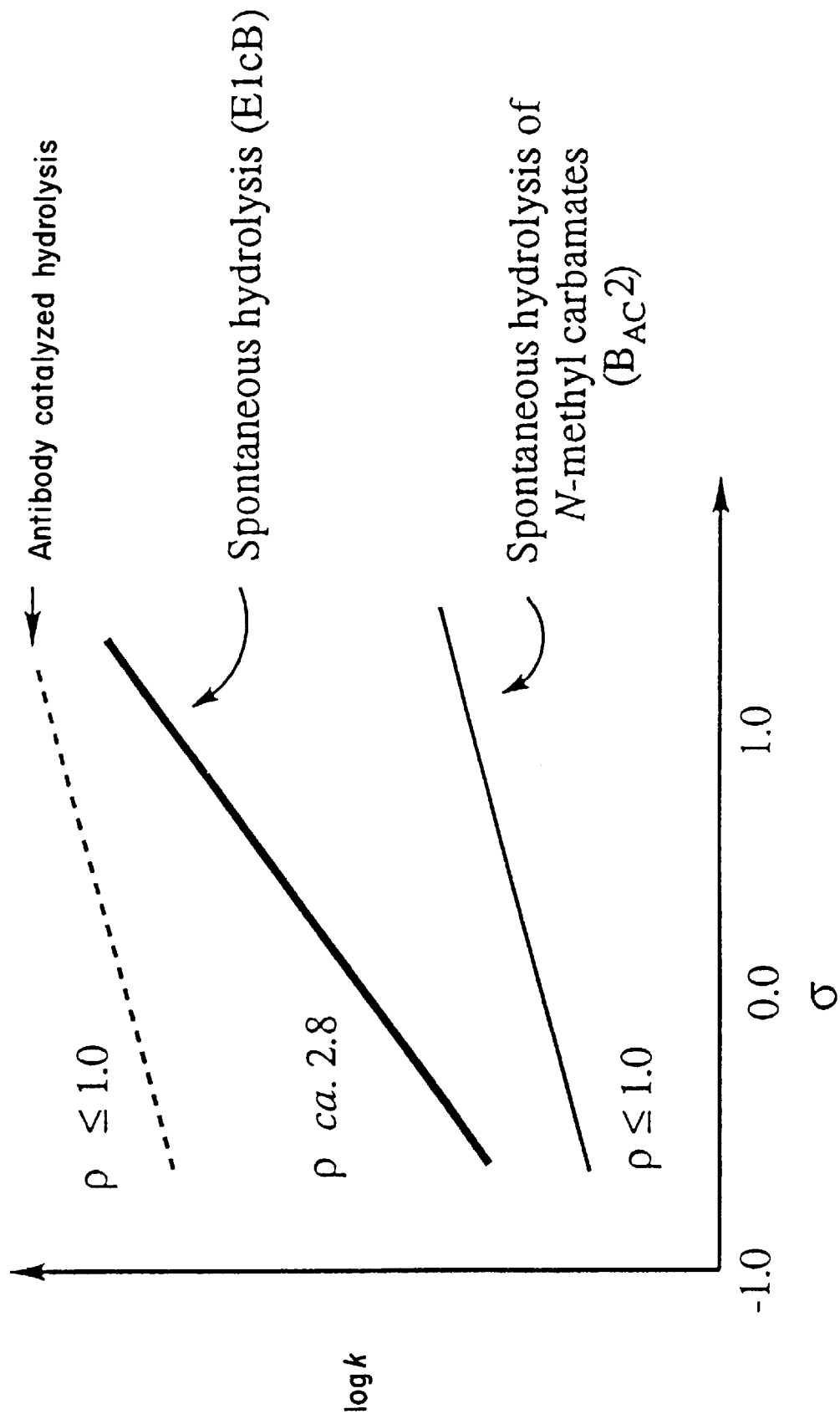

FIG. 4B1 shows a schematic representation of the effect of selectively catalysing the disfavoured $B_{AC}2$ mechanism of aryl carbamate ester hydrolysis.

FIG. 4B2 shows a schematic representation of the benefit of catalysing the $B_{AC}2$ process where the spontaneous rate is E1cB. If $\sigma$ for the cytotoxic substituent on the leaving phenolate is reduced sufficiently, $\sigma$ ca. $-1.0$, then antibodies of relatively poor catalytic power could well hydrolyse the compound with a detectable rate. However, the catalytic rate would be masked by the background decomposition where $\sigma>>-1.0$.

FIG. 4B3 shows the rational design of transition state analogues to elicit antibodies that would catalyse the disfavoured $B_{AC}2$ mechanism for hydrolysis of aryl carbamate esters.

FIG. 4B4 shows TSAs (4.23–4.26) are designed to elicit antibodies which would hydrolyse the aryl carbamate prodrug (4.22) via a $B_{AC}2$ process.

FIG. 5A shows the basis of the competitive inhibition ELISA

Figure 5B:
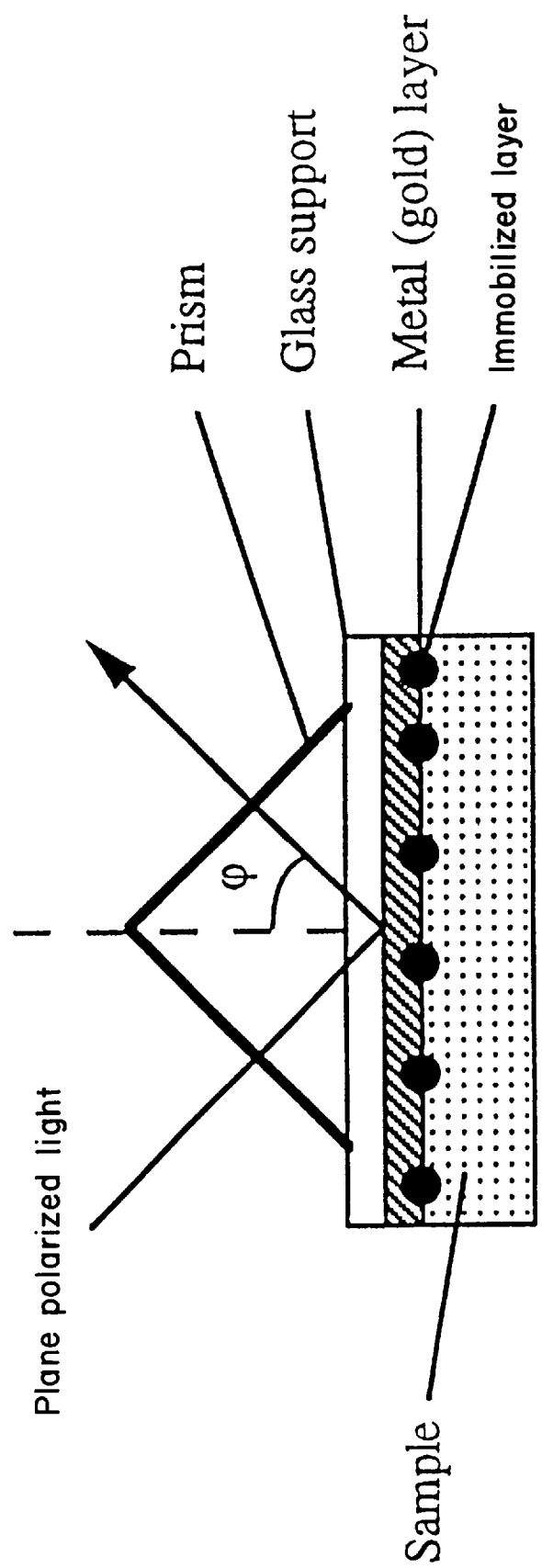

FIG. 5B shows a schematic representation of the experimental arrangement for surface plasmon resonance (SPR) detection of ligand binding. The angle of minimum reflection of the totally internally reflected laser light, $\phi$, changes with shifts in the refractive index of the sample medium adjacent to the gold layer allowing antibody-antigen interactions to be monitored.

Figure 5C:
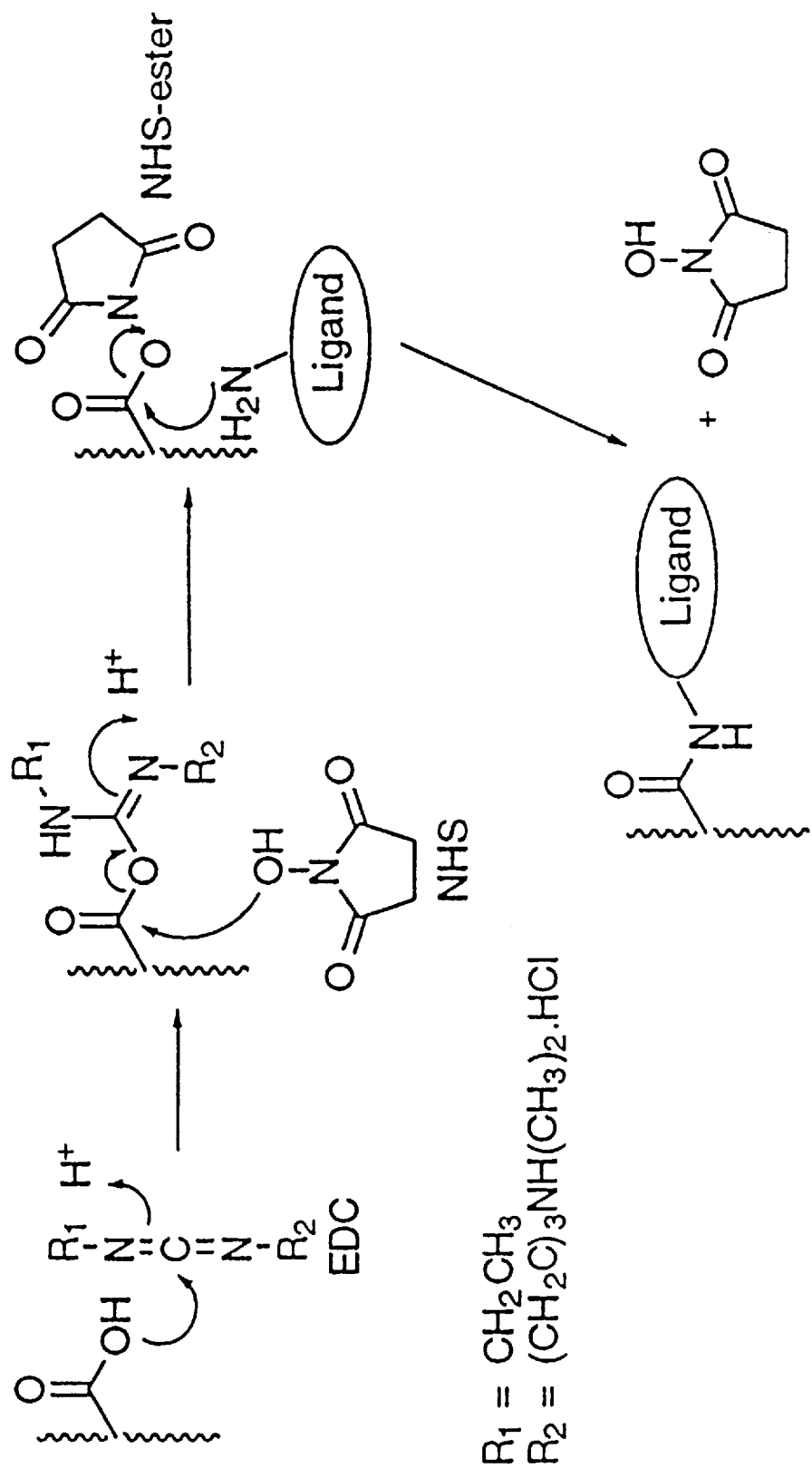

FIG. 5C shows the mechanism of activation of the carboxymethylated hydrogel with N-hydroxysuccinimide (NHS) and 1-(3-dimethylaminopropyl)-3-ethylcarbodiimide (EDC) and the coupling of antigens via their primary amine groups.

FIG. 5D shows a BIAcore sensorgram. As the sample is washed over the sensor chip, binding occurs to the immobilised antigen and the association phase is seen. At equilibrium ($K_a$), the antibody association rate is equal to the dissociation rate. As buffer replaces sample, the antibody dissociates and the response units (RU) fall.

Figure 6A:
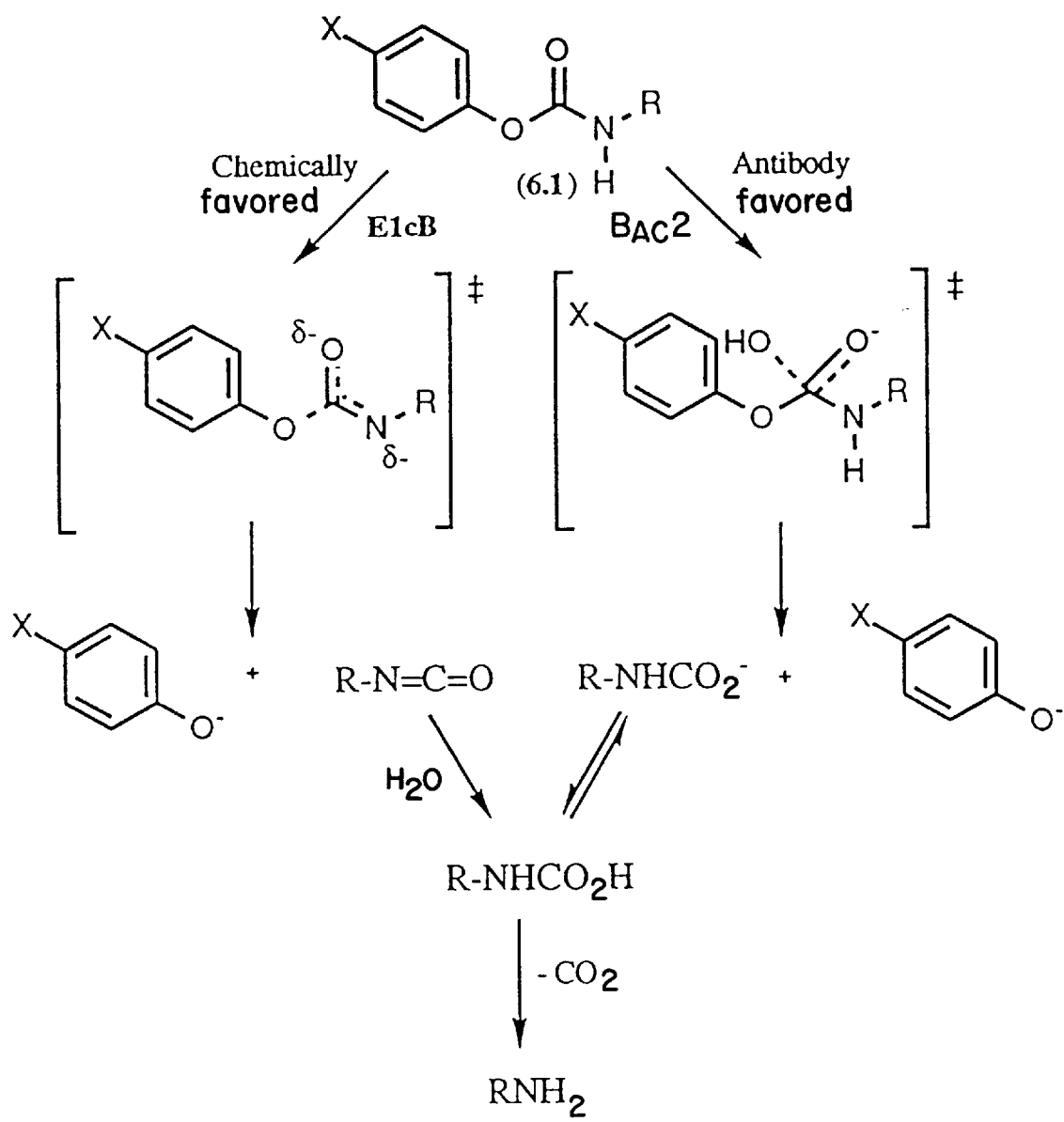

FIG. 6A shows the two mechanisms for carbamate hydrolysis. The chemically favoured mechanism is E1cB. By suitable hapten design, antibodies are generated that catalyse the disfavoured $B_{AC}2$ process.

Figure 6B:
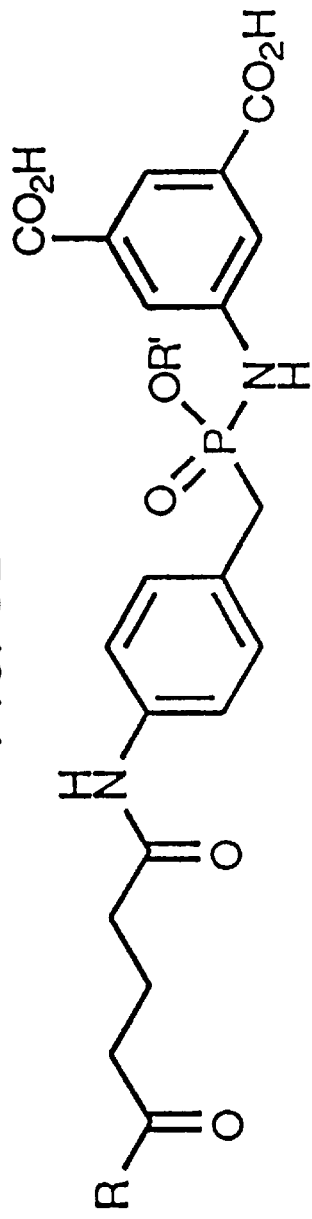
Figure 6B:
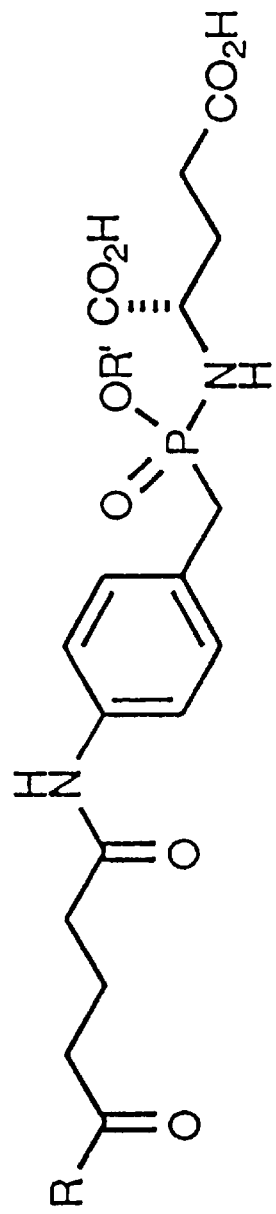

FIG. 6B shows haptens designed to elicit catalytic antibodies.

Figure 6C:
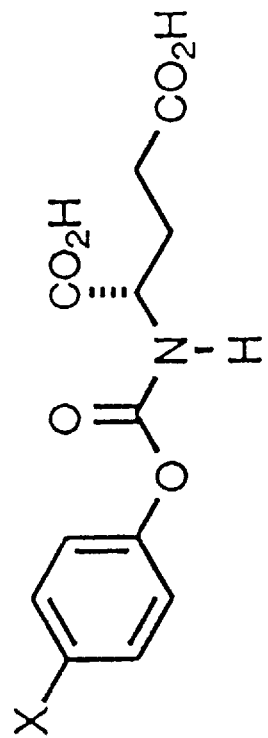
Figure 6C:
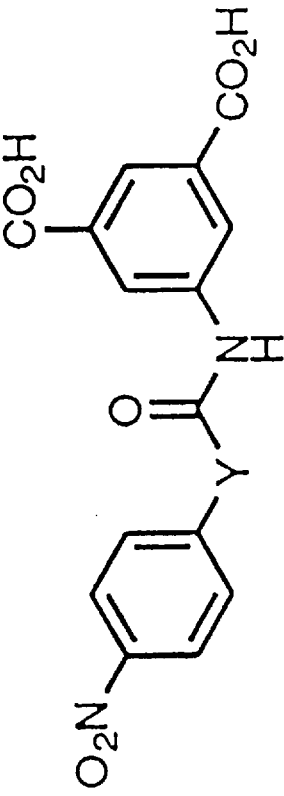
Figure 6C:
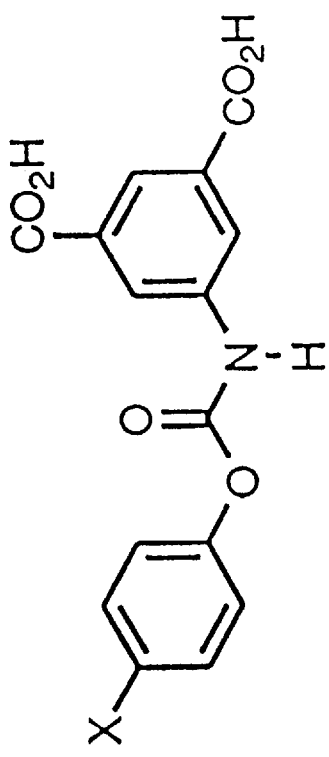

FIG. 6C shows substrates for the u.v. (6.7–6.14) and cytotoxicity (6.6) assays.

Figure 7A:
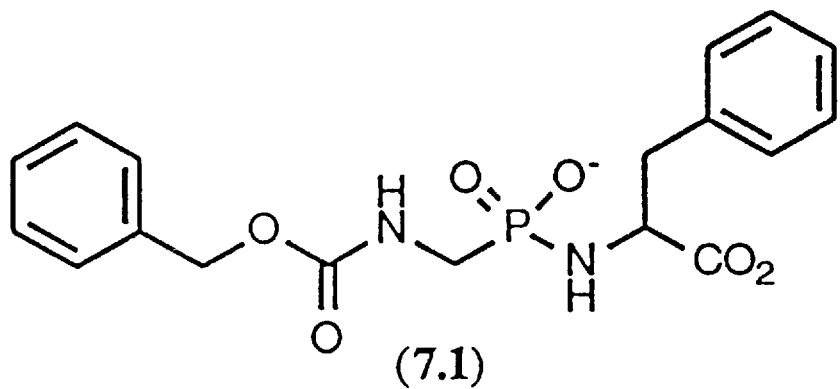

FIG. 7A1 shows the phosphonamidate (7.1) which is extremely acid sensitive, being hydrolysed with a $t_{1/2}$ of <2 min at pH 2.3.

FIG. 7A2 shows the target molecules required for antibody generation and characterisation.

FIG. 7A3 shows retrosynthetic analysis for synthesis of the haptens.

FIG. 7A4 shows retrosynthesis of the key phosphonochloridate intermediate in the hapten synthesis.

FIG. 7A5 shows the mechanism of the Michaelis-Arbusov reaction between benzyl bromide and triethyl phosphite.

FIG. 7A6 shows the Michaelis-Becker reaction between diethyl sodium-phosphite (7.22) and p-nitrobenzyl bromide (7.21).

FIG. 7A7 shows initially attempted phosphorylation of the amine (7.23) by phosphonochloridate (7.15) which was very poor yielding.

FIG. 7A8 shows catalysis by DMAP was observed for the phosphorylation of (7.25) by diethyl chlorophosphate (7.26).

FIG. 7A9 shows The synthetic scheme for Haptens 1 and 2 (7.2 and 7.4). (a) 10% w/w Adam's catalyst/$H_2$; (b) 1M NaOH; (c) 5-[(2',5'-dioxo-1'-pyrrolidinyl)oxy]-5-oxopentanoyl chloride (7.42)/$Et_3N$; (d) TMSBr/$NaHCO_3$, solvolysis.

FIG. 7A10 shows how Page (ref. 190) has studied the base hydrolysis of the acyclic (7.40) and cyclic (7.41) phosphonamidates.

FIG. 7A11 shows synthesis of the heterobifunctional spacer: 5-[(2',5'-dioxo-1'-pyrrolidinyl) oxy]-5-oxopentanoyl chloride (7.42).

FIG. 7A12 shows the mechanism of phosphonate deesterification using bromotrimethylsilane (TMSBr).

FIG. 7A13 shows a reaction scheme for the substrates (7.6 and 7.7) for ELISA studies: (a) 5-[(2',5'-dioxo-1'-pyrrolidinyl)oxy]-5oxopentanoyl chloride (7.42)/Et3N; (b) TMSBr (8 eq.), 35°–40° C.; (c) 1M LiOH.

FIG. 7A14 shows synthesis of the phosphonamidate (7.51): (a) 10% w/w Adam's catalyst/$H_2$.

FIG. 7A15 shows the synthetic scheme to haptens 3 and 4 (7.3 and 7.5): (a) Adam's catalyst 10% w/w/$NaHCO_3$ (2 eq.)/H2; (b) 5-[(2',5'-dioxo-1'-pyrrolidinyl)oxy]-5-oxopentanoyl chloride (7.42)/$Et_3N$; (c) TMSBr (2.2 eq.).

Figure 7B:
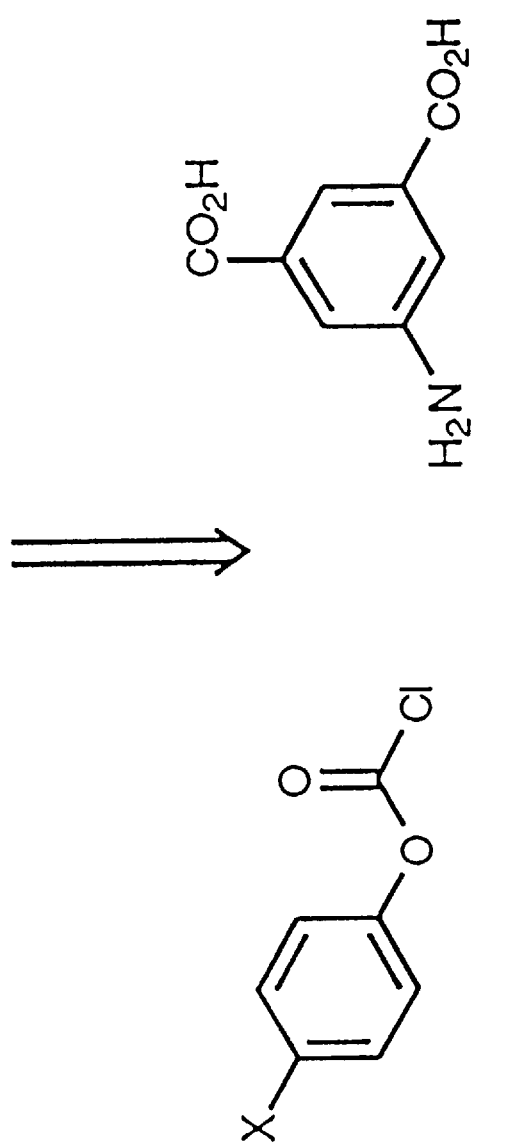

FIG. 7B1 shows retrosynthetic analysis of the target molecules (7.53–7.57) identifies the coupling of 5-aminoisophthalic acid (7.39) with a para-substituted-phenyl chloroformate (7.58).

FIG. 7B2 shows two of the primary routes to the aryl carbamates involving either direct reaction of 5-aminoisophthalic acid (7.39) with a chloroformate (7.58) or primary protection as a di-tert-butyl ester (7.59).

FIG. 7B3 shows carbamates from the benzyl protected route.

FIG. 7B4 shows routes to the urea (7.65) and the amide (7.66) substrate analogues.

FIG. 8A1 shows 2,4,6-Trinitrobenzenesulphonic acid (8.1) which is a reagent for the quantification of the free lysines on protein molecules.

FIG. 8A2 shows a calibration curve for TNBS coupled to BSA.

FIG. 8A3 shows an LDMS analysis of the BSA-hapten 1 conjugate. Key peaks to note are the m/z at 81 740 (conjugate) and 66 431 (BSA).

FIG. 8B shows a serum titration curve from a BALB/c mouse immunised with the KLH-hapten 3 (7.3) conjugate after 2 rounds of boosting. The serum titre (dilution giving half maximal OD405 nm) is ca. $8 \times 10^4$.

Figure 8C:
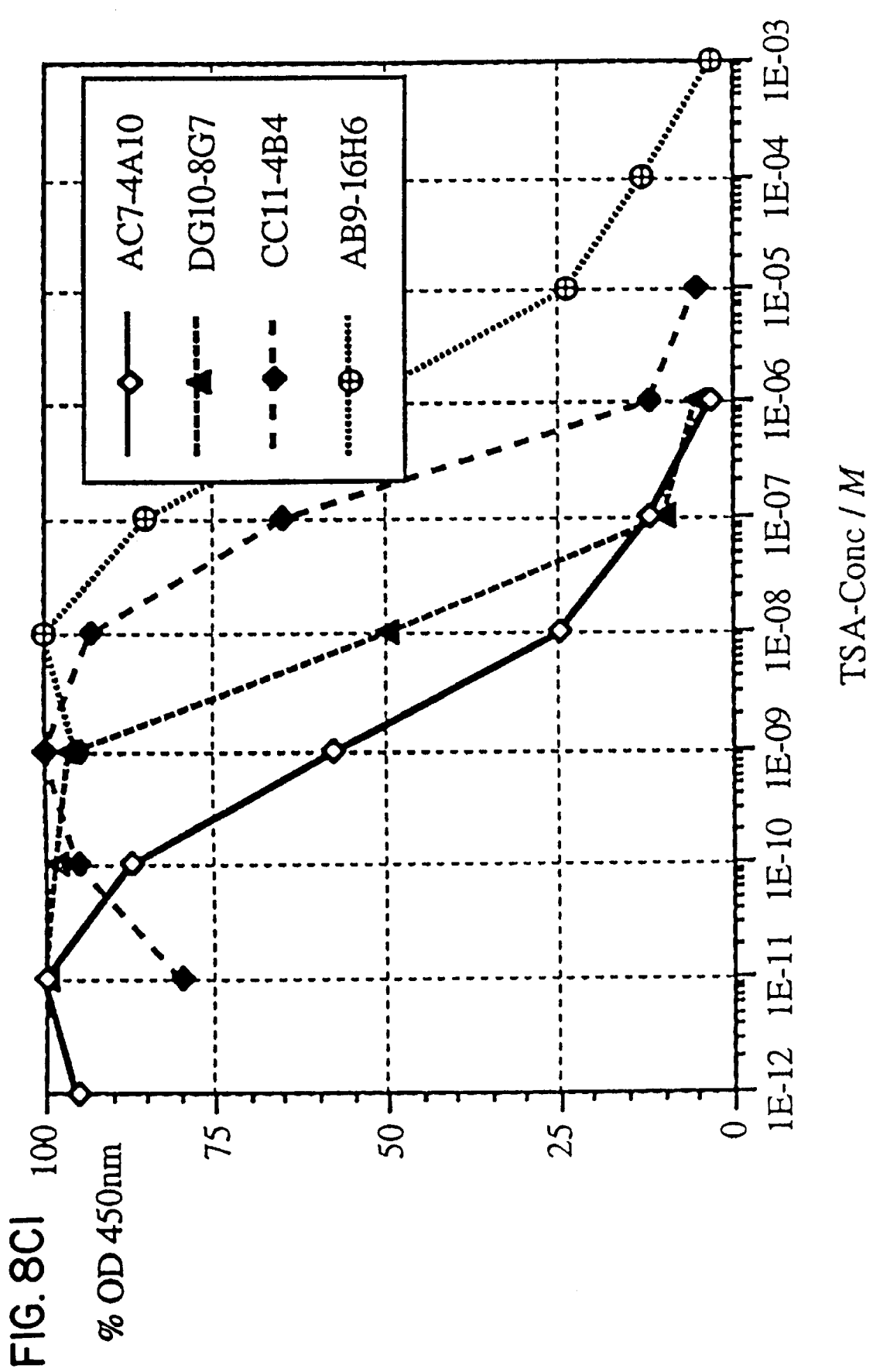

FIG. 8C1 shows the displacement ELISA traces for a panel of monoclonals elicited to the phosphonamidate ester hapten (7.4). The assay utilised the BSA conjugate of (7.4) bound to the solid phase and the displacing antigen (7.7) was added in increasing concentrations. The apparent affinity concentrations are determined as the concentration of free TSA (7.7) which causes 50% inhibition in the OD450 nm.

FIG. 8C2 is a sensorgram showing the immobilisation of TSA (7.37) on the CM5 sensor surface. The flow rate is 5 $\mu$l $min^{-1}$. (A) Activation of the carboxylated dextran matrix by the injection of 35 $\mu$l of an EDC/NHS mixture. The beginning and end of injection are indicated by arrows. The large variation in RU observed at the beginning and end of injection correspond to the difference in refractive index between the injected material and the buffer. (B) Injection of 40 $\mu$l of a 1 mg $ml^{-1}$ solution of the TSA in acetate buffer pH 4. (C) Inactivation of unreacted groups by 25 $\mu$l of ethanolamine. (D) Washing off noncovalently bound TSA with 35 $\mu$l of 50 mM HCl.

FIG. 8C3 shows an example of a typical kinetic run shown for the monoclonal antibody CF6. The run was performed with 50 $\mu$gml$^{-1}$ antibody in HBS pH 8.0. (A) 21 $\mu$l of antibody injected followed by (B) 6 $\mu$l of 50 mM HCl at 5 $\mu$l $min^{-1}$. Report points for dR/dt and RA values (Chapter 5, Section 5.4.1.2) were taken every 10 s between 60 s and 240 s after antibody injection. The data was analysed by BIAcore kinetic evaluation software to generate the kinetic parameters.

FIG. 8C4 shows isotyping ELISA of the supernatant from a monoclonal cell line, AC7-4A10, secreting hapten 1 (7.2) specific $IgG_1$ antibodies.

FIG. 8C5 shows a BIAcore sensorgram showing the isotyping experiment for the monoclonal antibody DE5. DE5 was injected at 50 $\mu$gml-1 and bound to the surface immobilised TSA (7.37). Isotype specific reagents were then injected and the highest RU change was seen on addition of the $IgG_1$ specific reagent. Therefore DE5 was determined to be an $IgG_1$ isotyped monoclonal.

Figure 9A:
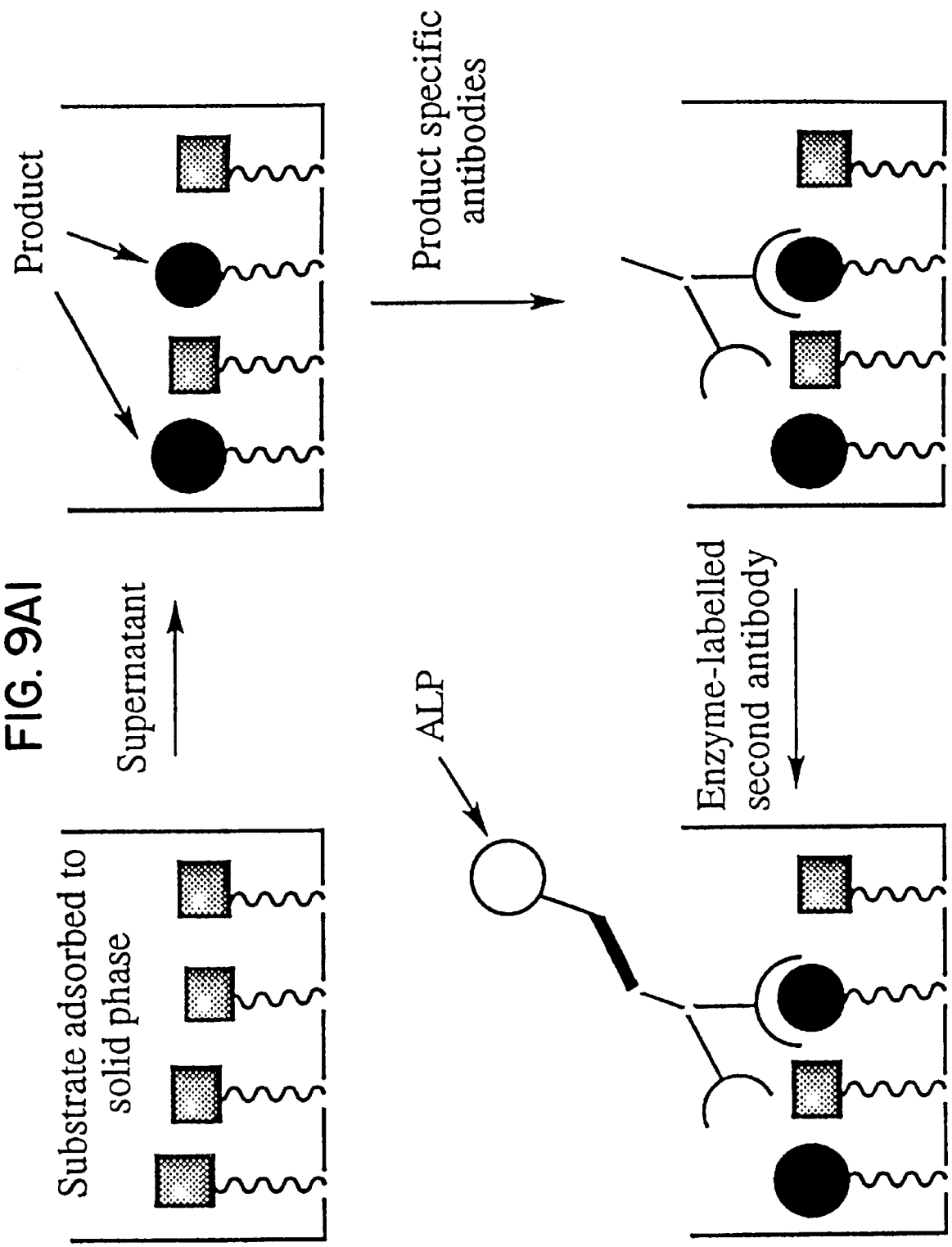

FIG. 9A1 shows a schematic presentation of catELISA.

FIG. 9A2 shows antibody catalysis was screened for conversion of the N-mustards (9.1 and 9.2) into product (9.3).

FIG. 9A3 shows cell viability in the presence of 10 $\mu$M prodrug (9.1) and hybridoma supernatants from 10 cell lines elicited to haptens (7.2–7.5).

FIG. 9A5 shows cell viability in the presence of: 20 $\mu$l of mAb (0.5 mgml-1): 10 $\mu$M prodrug (9.1) in DMEM. The Mabs were all elicited to the phosphonamidate ester (7.2).

FIG. 9A4 shows the affinity constants for the mAbs which are measured on a Pharmacia BIAcore. The three clones BH3-B8, DF8-D5 and EA11-D7 were expanded for further catalytic studies.

FIG. 9A7 shows LoVo cell viability in the presence of: 20 $\mu$l of mAb (0.5 mgml-1): 10 $\mu$M prodrug (9.1) in DMEM. The Mabs were all elicited to the phosphonamidic acid (7.4).

FIG. 9A6 shows the affinity constant for the mAbs which are measured on a Pharmacia BIAcore. The positive cell-lines CC11-4B4 and FD4-4F6 have been maintained in cryogenic store.

FIG. 9A8 shows the results of SRB studies to determine concentration effect of antibodies BH3-B8, EA11-D7 and DF8-D5. The assay conditions were: LoVo cells plated out at ca. $10^4$ cells per well in complete DMEM. The antibody (20 $\mu$l of a stock solution in PBS) was added to the wells and the assay initiated by addition of prodrug (9.1) in complete DMEM to a final volume of 200 $\mu$l. The cells were then incubated for 1 h at 37° C. and 5% $CO_2$ after which the medium was replaced with fresh DMEM and the cells allowed to grow for a further 3 d before being fixed with 50% TCA and stained with SRB. The assay was performed in quadruplicate on 4 separate plates, so n=16 and the mean values are reported ±S.E.M.

FIG. 9A9 shows a comparison between the activity of parent monoclonal EA11-D7 and its derived Fab in the SRB. In addition, the activity of both EA11-D7 and EA11-D7 Fab were studied in the presence of an equimolar concentration of TSA (7.6). The reaction conditions for the assay were identical to those outlined earlier. The concentration of Fab and parent Mab have been adjusted for 2 catalytic sites on the parent antibody.

Figure 9B:
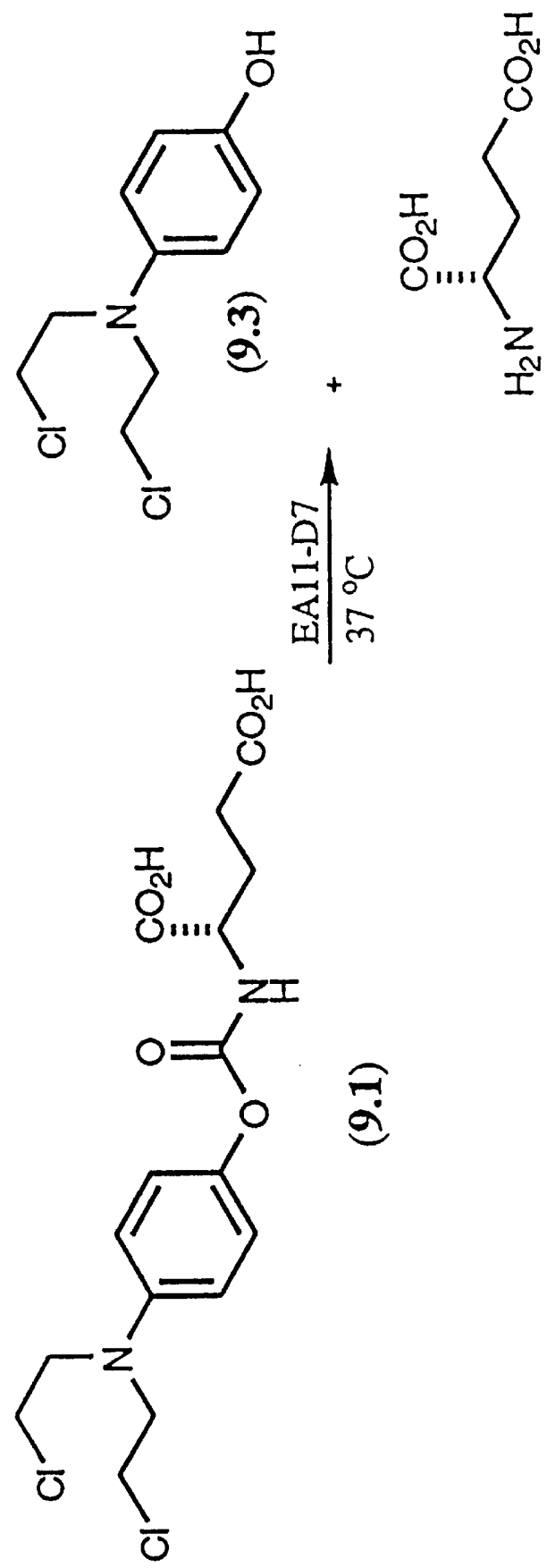

FIG. 9B1 shows the EA11-D7 catalysed hydrolysis of (9.1) was followed spectrophotomerically at 260 nm and 37° C.

FIG. 9B2 shows the Michaelis-Menten equation for EA11-D7 mediated catalysis.

FIG. 9B3 shows the monoclonal antibody, 49.AG.659.12, hydrolyses prodrug (9.4) to 5-fluorodeoxyuridine (9.5) with Km of 215 µM and kcat of 0.03 min$^{-1}$.

Figure 9C:
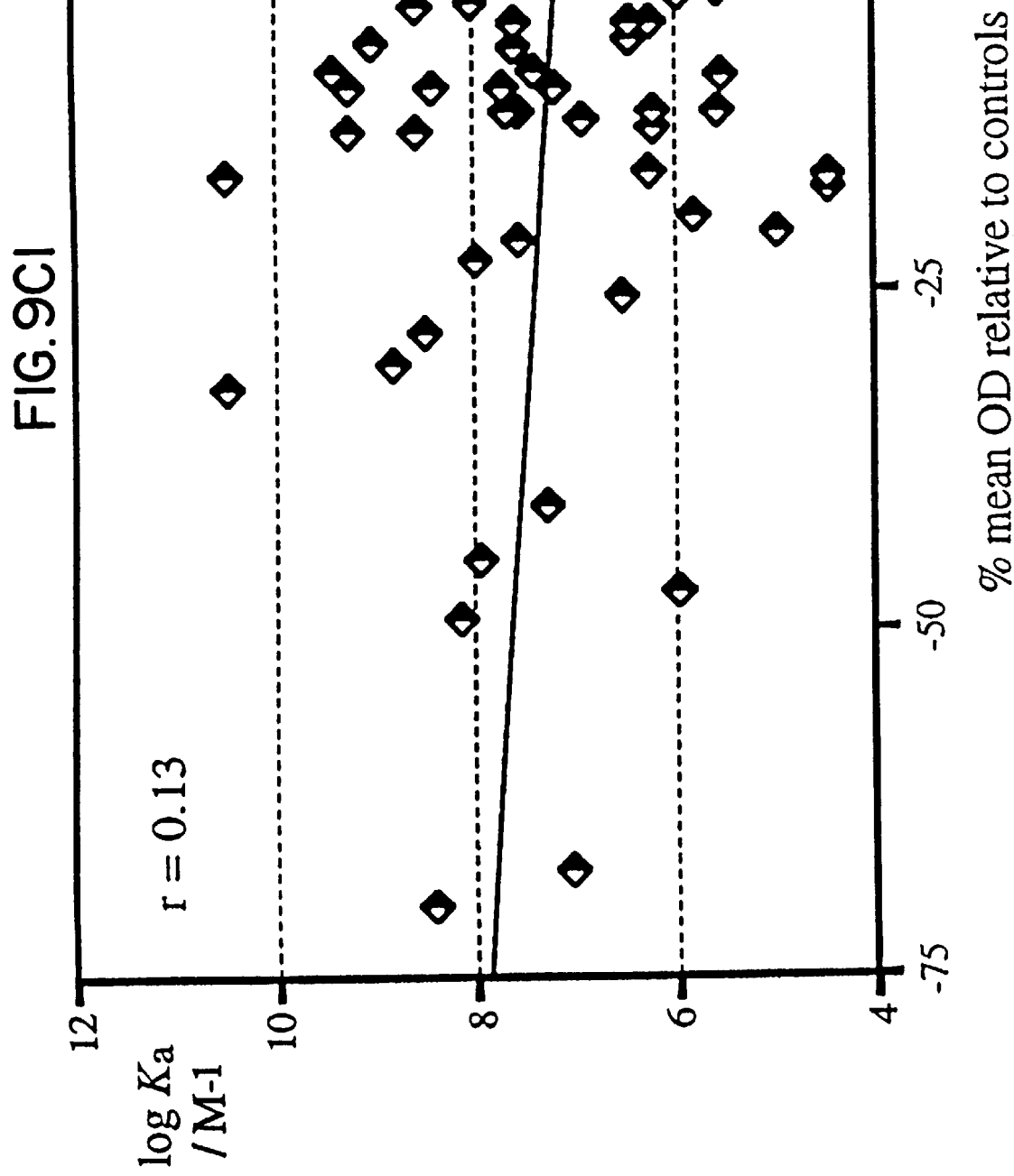

FIG. 9C1 shows a scatter plot between TSA affinity ($K_a$) and substrate activity measured as the fall in cell viability in the SRB assay (r=0.13).

FIG. 9C2 shows antibodies that bound both to the hapten (9.6) and the 'short' transition state analogue (9.7) were very often catalytic.

FIG. 9C3 shows the phosphonamidate (7.37) was bound to the hydrogel of the CM5 sensor chip and the relative binding affinities of a panel of 35 monoclonal antibodies was measured against the short transition state analogue (9.8).

FIG. 9C4 shows Determination of $I_{50}$. The graph shows the effect of concentration of inhibitor (9.8) on the dissociation constant for the antibody EA11-D7 as measured on a Pharmacia BIAcore machine. The antibody was injected onto the chip at a final concentration of 50 µgml$^{-1}$ in HBS (hepes buffered saline) buffer at a flow rate of 2 µl min$^{-1}$. The binding phase was followed for 120 s at which point inhibitor (9.7) was added and the kd measured. This gives $I_{50}$=3×10$^8$ M.

FIG. 9C5 shows a correlation of 'relative' affinities ($I_{50}$) of the antibodies elicited to the phosphonamidate (7.2) to the 'short transition state analogue' (9.8) vs. catalytic activity (% OD change in the SRB assay relative to controls).

Figure 9D:
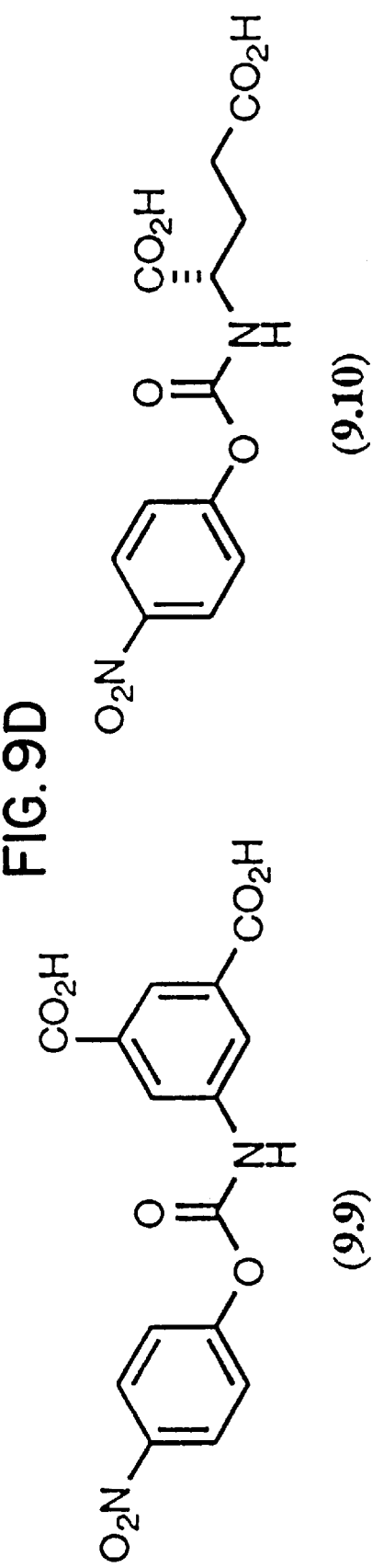

FIG. 9D shows the substrates used in a preliminary spectrophotometric screen designed to highlight purified catalytic clones.

Figure 9E:
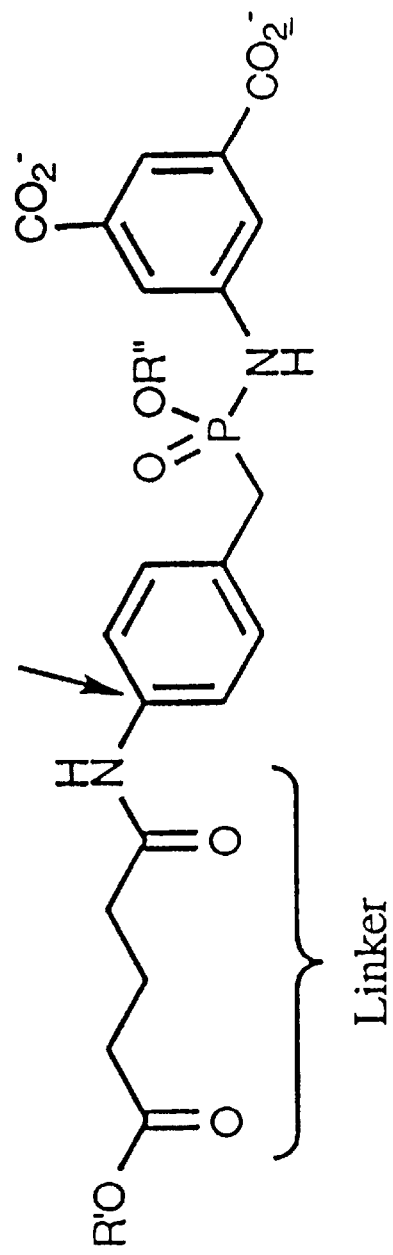

FIG. 9E1 shows hapten design has incorporated a feature which should allow structure-activity relationships to be examined for an antibody that hydrolyses carbamate esters.

Figure 9F:
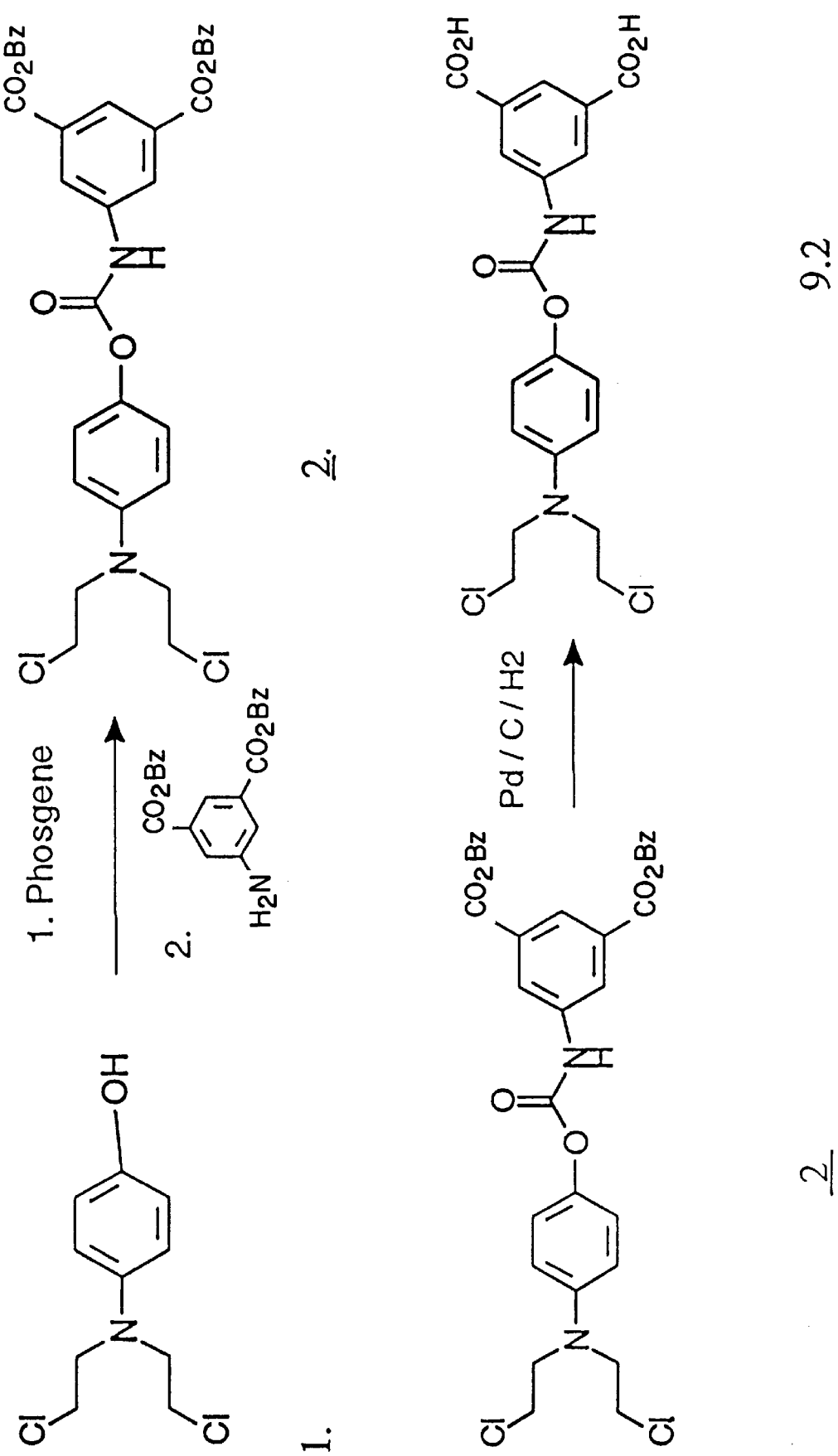

FIG. 9F2 shows that NPN43C9 an antibody elicited to the phosphonamidate hapten (9.11) hydrolysed a series of esters with high variability in the Km.

FIG. 9E3 shows that during the base catalysed hydrolysis of aryl carbamates (9.9 and 9.12–9.15), the reaction proceeds through a stable carbamate anion (9.16) which decomposes to aniline.

FIG. 9E4 shows variation of pseudo-first-order rate constant with pH for the hydrolyis of (9.12).

FIG. 9E5 shows the dependence on σ (σ$^-$) of the rate constant for the alkaline hydrolysis of substituted phenyl N-[(3,5-dicarboxy)phenyl]carbamates (9.9 and 9.12–9.15) (Table 9.3).

FIG. 9E6 shows the Brønsted plot of rate constant for alkaline hydrolysis of substituted N-[(3,5-dicarboxy)phenyl] carbamates (9.9 and 9.12–9.15) against pKa of departing phenol (Table 9.3). FIG. 9E7 shows the effect of increasing the concentration of DF8-D5 on the rate of hydrolysis (corrected for background) of the aryl carbamate (9.9).

FIG. 9E8 shows the reaction scheme catalysed by DF8-D5. The reaction was followed by monitoring either loss of carbamate (9.9 and 9.12–9.15) or formation of the phenol.

FIG. 9E9 shows a Michaelis-Menten plot for the hydrolysis of carbamate (9.14) by DF8-D5. The reaction condition were: 0.64 µM DF8-D5 at pH 6.5 in 50 mM MES and ionic strength 1.0 (KCl).

FIG. 9E10 shows a Lineweaver-Burke plot for the hydrolysis of carbamate (9.13) by DF8-D5 (0.15 mM). The parameters measured from this graph show a Km 42 µM and Vmax 1.1 µM min$^{-1}$.

FIG. 9E11 shows a Lineweaver-Burke analysis showing the inhibition by the TSA (7.6) on the rate of DF8-D5 catalysed hydrolysis of the carbamate (9.13).

FIG. 9E12 shows the urea (9.16) and amide (9.17) were tested as substrates for the abzyme DF8-D5. However, neither was hydrolysed.

FIG. 9E13 shows Hammett σ-ρ correlation for the hydroxide catalysed and DF8-D5 catalysed hydrolyses of carbamates (9.9 and 9.12–9.15). FIG. 9F1 shows synthesis of compound 9.2.

FIGS. 9F2 and 9F3 show synthetic reaction schemes.

Table 2.1 Combinational and somatic diversification of mouse V genes.

Table 2.2 shows kinetic and thermodynamic parameters for the spontaneous, enzyme-catalysed and antibody-catalysed conversion of chorismate into prephenate.

Table 2.3 shows Calculated activation energies of the transition structures relative to reactants for the reaction of acrylamide (2.39) with N-(1-butadienyl)-carbamic acid (2.40).

Table 2.4 shows stereoselectivity and kinetic parameters for the resolution of a diastereomeric mixture of fluorinated esters (2.49–2.52) by antibodies raised to one of four diastereomeric phosphonates (2.45–2.48).

Table 3.2 shows mean prodrug and drug concentrations (µgg$^{-1}$) in normal tissues and choriocarcinoma xenografts in nude mice. Intraperitoneal (i.p.) administration of prodrug occurred 48 h after intravenous (i.v.) injection of the W14-F(ab')$_2$-CPG2 conjugate.

Table 3.3 shows the effect of leaving group ability on N-mustard activity.

Table 4.1 shows catalytic coefficients of the hydrolysis of p-nitrophenyl N-methylcarbamate ester (4.7).

Table 4.2 shows $K_{al}$ values and observed plateau rates of decomposition of the anions ($k_2$) for hydrolysis of substituted carbamates (4.15).

Table 7.1 shows reaction yields for a series of [(N-acylamino)methyl]phosphonamides.

Table 7.2 shows the effect of DMAP catalysis on the synthesis of phosphonamidates (7.23), (7.29) and (7.30).

Table 8.1 shows the hapten densities for the BSA-conjugates of all 4 haptens (7.2–7.5).

Table 8.2 shows hapten density determined by LDMS

Table 8.3 shows the different myeloma cell lines utilised for fusions

Table 8.4 shows hybridoma production for the haptens (7.2–7.5)

Table 8.5 shows the aK values measured by displacement ELISA

Table 8.6 shows an Example of $k_a$, $k_d$ and $K_a$ values obtained in four independent experiments for the interaction between TSA (7.37) and monoclonal antibody EA11-D7.

Table 9.1 shows kinetic parameters for ester hydrolysis by NPN43C9.

Table 9.2 shows dependence of hydrolysis rate constant ($k_{obs}/S^{-1}$) on pH for (9.12).

Table 9.3 shows rate constants for alkaline hydrolysis of 4-substitutedphenyl-N-(3,5-dicarboxyphenyl)carbamates.

Table 9.4 shows epsilon values measured for the carbamates (9.9 and 9.12–9.15) and the phenol products.

Table 9.5 shows the kinetic parameters of DF8-D5 against the substituted aryl carbamates (9.9 and 9.12–9.15).

Appendix A shows characterisation of monoclonal antibodies elicited to transition state analogues 7.2 and 7.4.

1. BACKGROUND TO ADEPT

Next to heart disease, cancer is the major cause of death in the western world, accounting for 500,000 fatalities annually in the U.S. alone (Ref. 1). With present treatments, one third of patients can be cured with local measures (surgery or radiology) which are quite effective if the tumour has not metastasised by the time of treatment. However, micro metastases are a common feature of neoplasia and consequently, a systemic approach such as chemotherapy is often required. At present, about 50% of patients with cancer can be cured with chemotherapy contributing in about 17% of cases (Ref. 2). Bagshawe (Ref. 3) has described a means for achieving targeted delivery of cytotoxic agents in the form of a prodrug that is converted into the active agent by an enzyme which has been delivered selectively into the target tumour surface by means of a tumour specific antibody. This approach is known as ADEPT (Antibody Directed Enzyme Prodrug Therapy).

One ADEPT system involves an antibody-enzyme conjugate which binds to colorectal carcinoma cells and hydrolyses L-glutamic acid prodrugs of anticancer agents including phenolic N-mustards (1.1) (FIG. 1A ). (Ref. 4,5) This is because the reactivity of the mustard as a bifunctional alkylating agent calls for release of electrons from the phenolate oxygen through the benzene ring to nitrogen (1.2) which is impaired when the oxygen is a component of a carbamate ester. Carboxypeptidase G2 (CPG2), the enzyme component of the conjugate, is bacterial and thus is immunogenic in mammalian systems (Ref 6–8). Hence there is a need for an enzyme with low immunogenicity in humans, but whose substrate specificity is such that it will hydrolyse prodrugs with structures similar to (1.1).

An alternative strategy, mentioned in the original publications of Bagshawe (Ref. 6) is to use an antibody to catalyse the conversion of the prodrug into the cytotoxic agent. Since antibodies derived from rodents can be humanised, (Ref. 9) this idea provides a means of circumventing a major limitation of the ADEPT concept.

The first reports that some antibodies can manifest enzyme-like catalysis of the hydrolysis of esters appeared in 1986. (Ref. 11,12). One of the most common strategies employed to date for the identification of antibody catalysts has been mimicry of the transition state for the selected reaction. Through the design of a suitable transition state analogue, a catalyst can be generated for a given reaction. The target prodrug (1.1) is an aryl carbamate ester. The alkaline hydrolysis of such compounds has been investigated in considerable detail by Williams (Ref. 13–16) and by Hegarty (Ref. 17–19). In alkaline conditions they hydrolyse by an E1cB mechanism (Chapter 4), which is much faster than the alternative $B_{AC}2$ process found for the hydrolysis of N-methylcarbamate esters. (Ref. 18). By eliciting antibodies to haptens that mimic a $B_{AC}2$ transition state, catalysts would be generated that re-route carbamate hydrolysis through this 'disfavoured' process. This can then be used in design of prodrugs to increase their stability, in vivo, whilst optimising the substrate requirement [Michaelis-Menten constant ($K_m$) and catalytic rate constant ($k_{cat}$)] for the catalytic antibody (Chapter 4) to produce a catalytic antibody that can catalyse the hydrolysis of nitrogen mustard carbamate prodrugs (1.1). Following humanisation of such a catalytic antibody, the resulting protein catalyst should have the desired low immunogenicity required for use in ADEPT. To identify the significance of this change from an enzyme to an antibody catalyst, we have chosen the acronym ADAPT: Antibody Directed Abzyme Prodrug Therapy.

2. ANTIBODY STRUCTURE, DIVERSITY, AND CATALYSIS

Antibodies are mammalian host proteins that perform two distinct roles in immune defence. They recognise and bind to foreign material (the antigen) and secondly, by virtue of such complexation, they trigger its elimination (Ref. 20–22). They are synthesised by terminally differentiated B-lymphocytes (plasma cells) and circulate throughout the blood and lymph where they bind their antigens. The diversity of the immune response is vast: under appropriate conditions, any foreign macromolecule can elicit an immune response. In addition, the antibody response shows remarkable specificity such that any significant amount of cross reactivity between antigens is usually taken to indicate close similarity of their structure.

2.1 The Anatomy of the Antibody Molecule

In terms of structure, antibodies are probably the most studied of all protein classes. Amino acid and nucleotide sequence data are available for thousands of different chains (Ref. 23). Three-dimensional structures, obtained by X-ray crystallographic analysis, are available for both whole antibodies and a variety of their fragments and this has led to a more complete understanding of not just the structural features of antibodies but also how they interact with their antigens. Antibodies are a large family of glycoproteins that share a common functional structure comprised of two identical smaller or 'light' polypeptide chains (typically 110 amino acids in length, ca. MW 25 kDa) and two larger or 'heavy' chains (typically 220 amino acids in length, ca. MW 50 kDa). These chains are combined by both covalent bonds (via 4 disulphide linkages) and non-covalent interactions to form the characteristic four chain, Y-shaped structure (FIG. 2A). Closer examination of the protein sequences of the antibody chains reveals that the antibody molecules are arranged in globular domains which are critical to their functional characteristics. The light chain consists of two domains, the variable ($V_L$) and a constant region ($C_L$), both in the antigen binding fragment (Fab) of the antibody (FIG. 2A). The heavy chain shares a similar organisation and has 4 domains, a variable region, VH, and a constant region, $C_H1$, in the Fab and two constant domains, denoted $C_H2$ and $C_H3$ in the crystallisable fragment (Fc) of the molecule. The antigen binding site is formed in the Fab region of the molecule and is a result of the folding of the variable regions of the heavy and light chains, $V_H$ and $V_L$. Within these domains there are regions of high amino acid sequence variability and these so-called complementarity determining regions (CDRs) are involved directly in antigen recognition. Antibodies are divided into five classes, IgG, IgM, IgA, IgD and IgE, on the basis of the type of heavy chain they possess. The differences in the heavy chains allow the proteins to function in different types of immune response and at different stages in its maturation. The most abundant class, IgG, accounts for 70–75% of the immunoglobulin pool and, as such, has received the most intensive study in terms of its structure and function in the immune response (Ref. 25).

2.2 The Nature of Antibody-Antigen Interactions

The selectivity of antibody binding and recognition for its antigen was noted as early as 1936 when Landsteiner (Ref. 26) one of the dominant figures in early immunology, developed the concept of the antigenic determinant. He showed that antibodies could distinguish between the stereoisomers of tartaric acid and that anti-m-aminobenzene sulphonate (2.1) antibodies showed reduced affinity when exposed to the ortho- (2.2) and para- (2.3) isomers (FIG. 2B). (Ref. 26).

More recently, X-ray structures of antigen-antibody complexes have allowed an insight into the molecular construction of the antibody binding site. Antibodies utilise essentially non-covalent interactions in the recognition of their antigens: salt bridges, H-bonding and Van der Waals interactions all play a part in the binding energy associated with the antigen-antibody complex. Antibodies can bind to molecules of vastly differing sizes. McPC603, a mouse monoclonal antibody, binds to phosphorylcholine (MW 185) with an affinity constant of $2.0 \times 10^5$ $M^{-1}$. X-ray studies show that the antigen binds in a small pocket with the choline buried and the phosphate exposed to solvent (Ref. 27). By contrast, three different antibodies raised to the enzyme lysozyme (MW ca. 14.6 kDa) have large binding sites which are broad and flat (Ref. 28,29). The specificity of antibody-antigen interaction, regardless of size, is remarkable; depressions on one surface are filled by extensions from the other leaving no space for water molecules, which are rigorously excluded.

2.3 Antibody Diversity

Many theories of how the immune repertoire is constructed were developed in the first half of this century. How is it possible that a family of polypeptides can recognise and bind to any potential foreign invaders given the additional problem that some pathogens, e.g. HIV, can rapidly change their surface characteristics? In 1940, Linus Pauling proposed the variable folding theory of antibody formation. According to Pauling's theory, γ-globulin peptides (as they were then known) are folded in a complementary configuration in the presence of the antigen. This fitted the generally accepted 'unitarian' view of antibodies, which held that all antibodies were structurally identical but differed in their specificity. However Pauling's theory of antibody production and specificity was superseded by the cell or clonal selection theory of Sir Macfarlane Burnet, for which he received the Nobel Prize for Medicine in 1960. His theory predicts that virgin lymphocytes express antigen receptors before ever encountering antigen. Thus, the immune cell population is composed of a very large number of individual clones of lymphocytes, each with its own antigen receptor allowing it to respond to only a very small part of the total universe of antigenic epitopes. The antigen then serves as a selecting agent, only stimulating clones that recognise its epitopes. These clones are selectively expanded (clonal expansion) and their antibodies secreted without affecting the rest of the lymphoid population. It has been estimated that a human should make of the order of $10^7$–$10^9$ different antibody molecules before any contact with a foreign antigen occurs (Ref. 24,30). This naive repertoire is expected to generate enough diversity to cope with any invasive antigen. A naive repertoire of $10^7$ antibody molecules would appear to require $10^7$ genes, (Ref. 24) which is a considerable genetic demand. To avoid carrying this number of genes in every cell, the body carries a far smaller set of gene fragments which are recombined randomly in antibody-producing cells to generate the larger set. Each antibody molecule contains a heavy and light chain (FIG. 2A). The heavy chain gene is formed by recombination of a cluster of 3 genes: a $V_H$ gene, with a D gene, and with a JH gene. There are believed to be approximately 100 $V_H$ genes, 30 D genes, and 6 $J_H$ genes, giving potentially ca. 18 000 heavy-chain genes (Table 2.1). In fact, because of imprecise joining (variable boundary recombinations) which produce different junctional sequences, this number can be much higher. For the light chain, about 100 $V_L$ genes combine with 5 $J_L$ genes to give at least 500 combinations. Heavy-light chain combination (combinatorial association) then generates at least $18000 \times 500 = 9 \times 10^6$ antibody molecules.

2.4 Antibodies for Diagnostics and Therapy

Antibodies have many potential uses as diagnostic tools and in patient therapy. With the advent of hybridoma technology, monoclonal antibodies of almost any desired specificity can be produced (Chapter 5) (Ref. 32). However, these monoclonal antibodies are generally of rodent origin (mouse or rat) as human monoclonals are difficult to produce (Ref. 9) Murine monoclonals, when injected into human subjects for therapeutic purposes are very immunogenic and the human anti-mouse antibodies (HAMAs) produced either accelerate clearance of the monoclonals from the circulation or lead to hypersensitivity reactions (Ref. 33). In view of these problems, rodent antibodies have been 'humanised' by splicing the $V_H$ and $V_L$ mouse domains onto human $C_H$ and $C_L$ regions to yield chimaeric constructs of lowered immunogenicity (FIG. 2C) (Ref. 34). However, residual immunogenicity is retained by virtue of the alien variable framework (Ref. 35).

A more complete way of humanising rodent antibodies includes the replacement of the V region framework ('reshaped antibodies', FIG. 2C). The architecture of the V domains is a framework of β sheets topped with antigen-binding loops (Ref. 23). By grafting, the antigen-binding loops can be transferred from rodent to human antibodies (Ref. 36,37). Unfortunately, such reshaping may change the framework structure so that the packing of the $V_H$ and $V_L$ domains is affected which may well move key contacts in the binding site thus reducing antigen affinity. Although there are problems associated with the humanisation of rodent antibodies, it is by far the most practical approach to generating antibodies of low immunogenicity for therapy and allows access to a vast pool of rodent antibodies with good affinities and specificities for a range of human antigens.

2.5 Antibodies as Biocatalysts

The scientific world, in its quest to out-perform nature, has concentrated significant efforts in recent years in the field of biocatalysis. Jeremy Knowles (Ref. 40) has suggested that enzymes have evolved almost to the point of perfection and, therefore the discovery of novel biocatalysts from within a class of macromolecules composed of the same amino acid building blocks as enzymes, but possessing features with which enzymes could not compete, became an irresistible challenge. This was the nature of the search for catalytic antibodies.

2.5.1 Transition state theory and biocatalysis

The foundations of the search were laid long ago. Linus Pauling, (Ref. 41) in several sources published in the mid-1940s, clearly expressed the theory that an enzyme is able to accelerate a chemical reaction by having evolved an active site that is exquisitely complementary to the transition state (TS) for the reaction to be catalysed. That is, although an active site must bind substrate, it is the transition state (relative to all other species in the overall reaction) for which the binding interactions of the enzyme are maximised (FIG. 2D1). Simultaneously, transition state theory was being developed to account for chemical kinetics (Ref. 42,43). It assumes that the rate of any chemical reaction is proportional to the decomposition rate of the highest potential energy species along the reaction coordinate, namely the transition state. The rate constant for a reaction can be written as the product of the concentration of the TS‡ and the rate constant for its decomposition (v), (eqn. 2.1) (Ref. 44). Therefore, by lowering the energy of the TS under constant conditions, enzymes increase the number of molecules possessing sufficient energy to traverse the transition state and hence catalysis is observed.

$$k = v \cdot [TS‡]. \tag{2.1}$$

Knowles and Albery 45,46 have discussed the factors that increase the efficiency of an enzyme in detail and these are directly related to the way in which functional groups in the active site of the enzyme interact with the various chemical species along the reaction coordinate. Residues involved in 'uniform binding' interact equally strongly with all species (substrate, transition state, intermediates and products). There are functional groups involved in 'differential binding' which discriminate between binding of substrate and product. However, those residues that are essential to catalysis of an individual step preferentially bind one of the transition states in the reaction. Bill Jencks (Ref. 47) in his 1969 classic book on catalysis was the first to articulate the opportunity for the 'synthesis of an enzyme' by means of antibodies: "One way to do this is to prepare an antibody to a haptenic group which resembles the transition state of a given reaction." Whilst Jencks's notion was theoretically elegant, numerous practicalities prevented its realisation for many years: accurate transition state elucidation, suitable analogue design, poor immunogenicity of small organic molecules and identification of putative catalysts from within a polyclonal antibody mixture all served to confound would-be entrepreneurs in this field until the mid-1980s. The breakthrough was achieved simultaneously in 1986 by Richard Lerner at the Scripps Research Institute (Ref. 1) and Peter Schultz (Ref. 12) in Berkeley who both reported the production of antibodies that catalysed chemical transformations.

2.5.2 Catalytic antibodies and transition state stabilisation

Acyl transfer reactions were early targets for antibody catalysis. Lerner et al (Ref. 11) at La Jolla focused on attempts to generate monoclonal antibodies that would be potential aryl carboxylic esterases. Representation of the transition state for this reaction was straightforward, as it was well known that the course of hydrolysis of such esters (2.4) proceeds through a high energy tetrahedral intermediate (TI) (2.5) (FIG. 2D2) (Ref. 47). These intermediates have significant changes in geometry and charge relative to both reactants and products.

Design of stable mimics of this transient tetrahedral intermediate was vital to Lerner's success because antibodies cannot be generated in vivo to short lived species. Phosphonamidate and phosphonate esters, by nature of their geometry and charge, were known to be stable TS‡ mimics of esterases and amidases (Ref. 48). These molecules are tetrahedral and the free phosphonic acid, are negatively charged. In addition the interatomic distances of groups bound to phosphorus are elongated with respect to their carbon counterparts. This is thought to accurately represent the lengths of bonds forming and breaking in the TS‡ (Ref. 49). The stereoelectronic features of the TS‡ (2.6) and the corresponding phosphonate hapten transition state analogue (TSA) (2.7) for the hydrolysis of methyl acetate have been determined by ab initio calculations (FIG. 2D3) (Ref. 50). The data confirms that the phosphonate TSA (2.7) has similar bond lengths and angles compared to the TS‡ (2.6), but the charge distribution is more polarised, suggesting a close but imperfect representation of the transition state.

However, the similarity of phosphonates to anionic tetrahedral intermediates persuaded Lerner to use these molecules, with added structural complementarity to the coumarin substrate (2.8), as his hapten (2.9) for catalytic antibody generation (FIG. 2D4). From an immunological perspective, these molecules were too small to stimulate antibody production. Landsteiner's (Ref. 51) prerequisite for immunogenicity was met by tethering the TSA (2.9) via a five carbon chain to an immunogenic carrier protein, typically keyhole limpet haemocyanin (KLH) or bovine serum albumin (BSA). These conjugates were then able to stimulate an immune response.

The next phase of the work involved producing and identifying catalytic antibodies from the vast murine repertoire. In the mid-seventies several attempts had been made to produce catalytic antibodies in polyclonal sera, all had proved unsuccessful (Ref. 52,53). From the outset, Lerner concentrated on producing monoclonal antibodies by the new 'hybridoma technology' developed by Köhler and Milstein (Chapter 5) (Ref. 32). One of the monoclonal antibodies generated, 6D4, bound the phosphonate TSA (2.9) and catalysed the hydrolysis of the coumarin ester (2.8) with a Km=1.25 mM, a Vmax=0.78 nM s$^{-1}$, and a rate enhancement, kcat/kuncat, of $10^3$. One of the features of enzymes is their substrate specificity and this was exhibited by 6D4 which turned over the trifluoroacetanilide containing molecule (2.8), whereas the acetanilide containing analogue (2.10) was not a substrate. A high percentage of early catalytic antibody generation was achieved by utilisation of the dogma of Pauling and Jencks concerning transition state stabilisation (Ref. 54). These antibodies follow classic Michaelis-Menten kinetics, display substrate specificity, and bind the transition state analogue with higher affinity than the substrate, consistent with this notion.

As more catalytic antibodies were produced, it became clear that they were at first not on a par with enzymes as catalysts. Rate enhancements of $10^6$ to $10^9$ and turnover numbers of $10^3$ to $10^5$ s$^{-1}$ achieved in enzyme-catalysed reactions were not accomplished by antibodies. Elaborating hapten design, mutagenesis, and expansion of the immune repertoire are all strategies that were subsequently employed to increase the catalytic efficiency of abzymes. In addition, antibody catalysis has been directed at reactions for which either no natural enzyme exists (so no direct comparison of catalytic rates is available) or which are difficult to achieve by synthetic methodology so their rate enhancement is of secondary importance to the isolation of specific products.

2.5.3 Elaborating Hapten Design

General acid or base catalysis, entropy reduction, strain, proximity effects, and nucleophilic interactions all serve to assist transition state stabilisation in enzymatic catalysis. For example, subtilisin, one of the serine proteases, has evolved a so-called 'catalytic' triad (characterised by the residues Ser, His, and Asp) and other features which stabilise the transition state in its active site (FIG. 2D5). (Ref. 55,56). For Bacillus amyloliguefaciens subtilisin, these functional elements impart a total rate enhancement of at least $10^9$ to $10^{10}$ times the non-enzymatic hydrolysis of amide bonds (Ref. 57). Mechanistically, the proton on Ser-221 is transferred to His-64, thus facilitating nucleophilic attack on the peptide bond. The proton is then transferred to the amine leaving group resulting in an acyl-enzyme intermediate (E-Ac), which is hydrolysed by attack of water to regenerate active enzyme. Hapten design began to reflect this more complex view of biocatalysis as attempts were made to incorporate features other than transition state complementarity into antibody catalysis.

2.5.3.1 Bait and switch catalysis

From binding studies (Ref. 58) and crystallographic data (Ref. 59) of antibody-antigen interactions, it was clear that structural features of the hapten induce complementary structural features in the combining site. Charged groups are stabilised by oppositely charged entities and hydrophobic groups are surrounded by an apolar environment. Antibodies elicited to negatively charged haptens were shown to contain specific Arg and Lys residues in the binding sites.

Conversely, positively charged ammonium-containing haptens elicited antibodies with Asp and Glu residues in their combining sites (Ref. 58,60) Shokat and Schultz (Ref. 61) showed that electrostatic complementarity could be used to generate catalytic antibodies with a precisely positioned negatively charged residue in the combining site. They raised an immunoglobulin, 43D4-3D3, to the charged hapten (2.11) (FIG. 2D6). The monoclonal catalysed a β-elimination reaction on the β-fluoroketone (2.12) to give the trans enone (2.13) product.

The hapten (2.11) bore significant structural complementarity to the substrate, but with the key additional functionality of a quaternary ammonium species to induce a general base. Kinetic studies of the active clone showed a significant pH dependence for the catalytic rate due to a single group titrating with a $pK_a$ of 6.2. The kcat/kuncat of $10^5$ was attributed to a glutamic acid residue with depressed acidity due to its hydrophobic environment.

This principle for hapten design was expanded further by Janda and Lerner, (Ref. 62,63) who saw its applicability to acyl transfer reactions, previously the domain of tetrahedral phosphonate and phosphonamidate TSAs (Ref. 64,65). They generated antibodies to a methylpyridinium containing hapten (2.14), a benzoate containing hapten (2.15) and a neutral pyridine containing hapten (2.16), and assessed the monoclonal IgGs produced for their ability to catalyse the hydrolysis of a benzoyl ester (2.17) (FIG. 2D7). To mimic the tetrahedral centre in the transition state, a secondary alcohol was placed adjacent to the 2-position of the aromatic ring in all the antigens but. notably, no anionic charge was present at the tetrahedral centre as this may have interfered with the charge characteristics in the antibody active site. The results confirmed the necessity of point charges in the hapten for induction of catalysis. No abzymes were obtained after immunisation with the neutral hapten (2.16), only antibodies with high affinity recognition for the substrate. Catalysts were generated with both the carboxylate (2.15) and the N-methylpyridinium species (2.14). In fact, a very high proportion of the antibodies that bound the N-methylpyridinium hapten were catalysts. Confirmation that a complementary base had been induced was determined for one of these abzymes, which utilised the basic form of an ionisable group ($pK_a$ 6.26) in the catalytic process (Ref. 62,66). 'Bait and switch' hapten design has proved a successful technique for catalytic antibody production and it offers, in conjunction with transition state stabilisation, the potential to yield catalysts of heightened activity.

2.5.3.2 Catalysis by control of entropy (entropic trap)

Until 1971, the view generally held among biochemists was that the maximum rate acceleration in an enzyme catalysed process that resulted from the contiguity of two reactants in the enzyme site was of the order of 55, that being the effective concentration of small molecules such as water. Jencks and Page (Ref. 67) changed that view through the application of the thermodynamic principles of bimolecular processes and argued that the loss of translational and rotational freedom for two molecules brought into proximity in an enzyme binding site could result in effective molarities (EM) of $10^8$M. Therefore, by preorganising reactants through favourable binding interactions, an antibody should be able to minimise the entropy of activation and hence effect catalysis (Ref. 68,69).

Antibody catalysis of a Claisen rearrangement.

The enzyme chorismate mutase (EC 5.4.99.5), accelerates the conversion of chorismicacid (2.18) into prephenic acid (2.19) by $3\times10^6$ and appears to work exclusivelyby restriction of the free rotation of bonds in the substrate, thereby achieving intramolecular juxtaposition of the reacting carbons (FIG. 2D8) (Ref. 70). This Claisen rearrangement has a spontaneous, unimolecular counterpart that proceeds at a measurable rate at room temperature. Several years ago, Knowles (Ref. 71) established the transition state (2.20) for the enzymecatalysed process as having a pseudo diaxial chair-like conformation. Using that information, Bartlett (Ref. 72) produced a transition state analogue (2.21) which proved to be a powerful inhibitor of the enzyme, Ki of $1.5\times10^{-7}$M, binding much more strongly than chorismate (Km $1.5\times10^{-5}$M for the *E.coli* enzyme).

Since the inhibitory activity of this bicyclic species is independent of the substituent on the pendant hydroxyl group, Schultz (Ref. 73) and Hilvert (Ref. 74) used this locus to join the inhibitor to a carrier protein. This hapten was used to raise antibodies that catalysed the conversion of chorismate into prephenate. Their results provide an instructive contrast (Table 2.2). The best of the antibodies elicited by Schultz, 11F1-2E11, achieves a $10^4$ acceleration of the reaction, primarily by reducing the entropic barrier of the process almost as effectively as does the enzyme from *E. coli*. However, the enthalpy of activation is significantly higher than that for the enzymatic reaction. Thus, this antibody has been described as working as an Entropic Trap.[75] By contrast, Hilvert's antibody, 1F7, which is a rather poorer catalyst, has a lower enthalpy of activation than that for the enzymatic process while the entropic barrier is much higher! The conjunction of these results offers the tantalising prospect that a Fab engineered to combine the best features of 1F7 and 11F1-2E11 might outperform the natural enzyme by two to three fold. The genes encoding abzyme 1F7 have been sequenced and expressed in a yeast strain which lacks wild-type chorismate mutase activity (Ref. 76). The Fab produced in this system possesses sufficient activity to maintain the strain on unsupplemented media (Ref. 77). A 1F7 Fab'-hapten complex has been crystallised (Ref. 78) and its three dimensional structure determined to 3.0 Å resolution (Ref. 79). The structural data suggests that the antibody does indeed stabilise the same conformationally restricted pericyclic transition state as occurs in the uncatalysed reaction (FIG. 2D9). An important feature in the antibody recognition is that the region around the pendant hydroxyl at the opening of the binding site is highly solvent accessible. This area, where the spacer was attached, therefore offers the potential for further substitution which will not affect the overall rate of the Claisen reaction.

Antibodies and the Diels-Alder cycloaddition.

Another reaction which proceeds through an entropically disfavoured, highly ordered transition state is the Diels-Alder cycloaddition. This bimolecular process has large activation entropies in the range of $-30$ to $-40$ cal mol$^{-1}$ K$^{-1}$ (Ref. 80). The Diels-Alder reaction is one of the most important and versatile transformations available to organic chemists and involves the concerted addition of a conjugated diene to an olefin to give a cyclohexene derivative. This reaction is essentially non-biological as only one naturally occurring enzyme has been isolated which performs this transformation (intramolecularly). Therefore, attempts to generate antibodies which could catalyse this reaction were seen as an important landmark in the abzyme field. The major problem in generating a 'Diels-Alderase' antibody lies in the choice of a suitable haptenic structure because the transition state for the reaction resembles the product more closely than the starting material (FIG. 2D10). However, the reaction product would not be an appropriate hapten since severe product inhibition, preventing efficient turnover of the catalyst, would result. Tetrachlorothiophene dioxide (TCTD) (2.22) reacts with N-ethylmaleimide (2.23) to give an unstable, bicyclic intermediate that spontaneously extrudes $SO_2$ to give a dihydrophthalimide (2.24) as the bicyclic adduct (Ref. 81). This allowed haptenic design to comprise of a bridged dichloro tricycloazadecene derivative (2.25) which closely mimics the transition state (2.26) whilst being sufficiently different from the product (2.24) to avoid the possibility of end-product inhibition (Ref. 82).

Several antibodies raised to the hapten (2.25) accelerated the Diels-Alder cycloaddition between (2.22) and (2.23). The most efficient antibody, 1E9, performs multiple turn-overs suggesting that product inhibition has been avoided. Comparison of kcat with the second order rate constant for the uncatalysed reaction (kuncat=0.04M−1min-1) gives an EM of 110M. The EM is equivalent to the concentration of substrate that would be needed in the uncatalysed reaction to achieve the same rate as achieved by the antibody ternary complex. The observed value is several orders of magnitude larger than the physically accessible concentration of substrate in aqueous solution, therefore the antibody binding site confers a significant kinetic advantage over the bimolecular Diels-Alder reaction.

2.5.4 Modification of the abzyme combining site

In addition to hapten elaboration, direct modification of abzymes has been performed in the hope of either increasing the catalytic efficiency of these proteins or gaining information about the specific residues involved in the catalytic process (Ref. 64,83). Following antibody production two main strategies have been employed to modify the combining site residues: mutagenesis (Ref 84) or chemical modification (Refo 85–87).

2.5.4.1 Mutagenesis

There is a series of phosphoryicholine (PCho) (2.27) binding antibodies, produced by mouse myelomas, (Ref. 88,89) that were subsequently found to hydrolyse p-nitrophenyl cholyl carbonates (2.28) (FIG. 2D11) (Ref. 84). The structure of one of this class of proteins, McPC603, has been elucidated by X-ray crystallography and the residues important in the catalytic process have been determined (Ref. 90). Two conserved heavy chain residues, Arg52H and Tyr33s, were thought to be critical in the catalytic process. Jackson et al. (Ref. 84) performed mutagenesis at these loci on a related PCho binding antibody, S107. Tyr33H mutants had little effect on catalysis whereas the Arg52H mutants showed a significant reduction in catalytic power, thus highlighting the importance of electrostatic stabilisation of the TS‡ on catalytic rate. This technique is of limited use at present because X-ray structures are required to highlight potential residues important in binding and catalysis. As more catalytic antibody crystal structures become available, this method of enhancing catalysis will become increasingly powerful.

2.5.4.2 Chemical Modification

It has been shown that enzymes can be selectively altered by cofactors to give enzymes of modified activity (Ref. 91). The major problem when derivatising a protein is to develop mild procedures for the selective introduction of groups onto the residue of interest without destroying the integrity of the whole protein. These groups are subsequently modified to incorporate a chemical functionality (e.g. cofactor, fluorophore).

The Fab of another PCho binding antibody, MOPC315, was labelled with a nucleophilic thiol to enhance the hydrolysis of a coumarin ester (2.29) (Ref. 85,86). Affinity labelling reagents were produced which contained the dinitrophenyl (DNP) group linked to an electrophilic aldehyde through a cleavable disulphide (2.30) (FIG. 2D12). The lysine52H residue in the active site reacted with (2.30) to generate an imine which was reduced with $NaCNBH_3$. The thiol was then generated by cleavage of the cross link with dithiothreitol (DTT). The resulting semisynthetic antibody exhibited saturation kinetics and showed a rate acceleration relative to dithiothreitol of $6\times10^4$ for hydrolysis of the coumarin ester (2.29).

2.5.5 Antibody catalysis of difficult chemical processes

In the earliest examples of antibody-mediated catalysis, simple transformations with well studied mechanisms were chosen (Ref. 54,64,65,83). More recently, the field has begun to focus on selective chemical transformations that are difficult to achieve via existing chemical methods. For these types of process the catalysis achieved by the antibody is secondary to the isolation of a specific product. These include 'disfavoured' chemical reactions (Ref. 92) reactions along one of many nearly equivalent reaction coordinates, (Ref. 93) and reactions where the inherent reactivity of the components is reversed (Ref. 94).

2.5.5.1 Reversal of kinetic control in a ring closure reaction

For reactions under kinetic control in which a number of reaction products are possible, the product distribution reflects the relative free energies of each transition state (Ref. 92). Janda et al. (Ref. 95) showed that an antibody can selectively stabilise one transition state in a reaction where multiple, alternative transition states exist.Baldwin's rules (Ref. 96) predict that for acid-catalysed ring closure of the hydroepoxide (2.31), the product arising from the preferred 180° transition state geometry is a result of 5-exo-tet attack leading to the tetrahydrofuran product (2.32) (FIG. 2D13). By raising antibodies to the charged hapten (2.33), Janda (Ref. 95,97) produced a catalyst which accelerated 6-endo attack, a formal violation of Baldwvin's rules, to yield the tetrahydropyran adduct (2.34) exclusively. The N-oxide antigen (2.33) was designed to mimic both the electrostatic requirements of oxirane (2.31) opening under acidic conditions and the six membered ring geometry required to overcome the necessary steric constraints for the 6-endo-tet process. The most efficient abzyme generated, 26D9, was a completely regioselective catalyst and followed Michaelis-Menten kinetics.

2.5.5.2 Control of the exo- and endo-pathways of the Diels-Alder reaction

As discussed earlier, the Diels-Alder pericyclic reaction is one of the most useful carbon-carbon bond forming reactions available to the organic chemist. However, in the reaction between an unsymmetrical diene and dienophile up to eight stereoisomers can be formed (Ref 98). By increasing the electron-withdrawing ability of the substituent on the dienophile, the regioselectivity can be enhanced so that only the four ortho adducts are seen (FIG. 2D14) (Ref. 99). However, control of the stereochemical outcome of the Diels-Alder reaction, to yield disfavoured exo products in enantiomerically pure form, has proved to be very difficult. Gouverneur et al. (Ref. 100) at the Scripps Institute, were interested in controlling the outcome of the reaction between the diene (2.35) and N,N-dimethylacrylamide (2.36) (FIG. 2D15). From experimental work, they had shown that regioselectivity dictated that only two stereoisomers were obtained, the ortho endo (cis) (2.37) and the ortho exo (trans) (2.38) adducts in an 85:15 mixture respectively. This was supported by ab initio transition state modelling for the reaction of acrylamide (2.39) with N-vinylcarbamic acid (2.40), which showed that the relative activation energies of the ortho endo and ortho exo transition states were of considerably lower energy than the meta endo and meta exo transition structures (Table 2.3).

In order to generate abzymes that would be completely regio and diastereo-selective, hapten design was crucial. To develop catalysts with regioselectivity, the TSAs had to incorporate features which were compatible with either the disfavoured endo (2.41) or favoured exo (2.42) transition states (FIG. 2D16). Furthermore, because the transit in state for Diels-Alder processes are very close to products, the haptens (2.43) and (2.44) were developed to represent a high energy boat conformation of each product, a rationale developed by Hilvert (Ref. 82) to reduce product inhibition.

Two of the monoclonal antibodies produced, 7D4 and 22C8, are completely stereoselective, performing either the endo or exo Diels-Alder reaction, with a kcat of $3.44 \times 10^{-3}$ and $3.17 \times 10^{-3}$ min$^{-1}$ respectively. The poor turnover number was attributed in part to inaccuracies in transition state representation. Modelling studies had shown that the transition states for both the exo and endo processes were asynchronous whereas both TSAs mimicked synchronous transition states (Ref. 100).

2.5.5.3 Controlling the stereoselectivity of reactions

Several catalytic methods have been developed in recent years for the regio- and stereo-selective synthesis of enantiomerically pure compounds (Ref. 101). These include chiral epoxidations, (Ref. 102) asymmetric dihydroxylations, (Ref. 103,104) and chiral reductions (Ref. 105,106). However, the design of such catalysts is still in its infancy and high stereoselection is usually dependent on neighbouring ligands or is limited to specific substituents (Ref. 101). Given the specificity of the immune system, it was thought that antibodies would make excellent stereoselective catalysts. Antibodies can be generated that recognise enantiomeric transition states regardless of their chemical environment or complexity. A number of such reactions have been reported including enantioselective ester hydrolysis, (Ref. 83,107,108) transesterification reactions (Ref. 109, 110) and Claisen rearrange-ments (Ref. 73,74). A recent report has shown that antibodies can stabilise selectively one of a number of transition states in a diastereoselective esterolytic reaction (Ref. 93). Antibodies were raised to each of four diastereoisomeric phosphonate analogues (2.45–2.48) of the transition states for the hydrolysis of the corresponding 1-(benzyloxy)-2-fluoro-2-methyl-3-hydroxybutane esters (2.49–2.53) (FIG. 2D17). Each of the four esters was hydrolysed by the corresponding antibody in >97% ee, with greater than 23% overall conversion from an equal mixture of all four diastereoisomers (Table 2.4).

Throughout this section, the potential of antibodies for the synthetic organic chemist has been emphasised. Their use as regioselective and stereoselective catalysts has been outlined and additional work has shown that they can catalyse reactions for which enzymes have not yet been found (Ref. 82,111). Recently, it has been shown that antibodies can perform large scale (multigram) organic transformations either by conjugation to a solid phase, (Ref. 112) or in a biphasic system (Ref. 113). It may be only one step to put these abzymes to work in a bioreactor to move into the kilogram scale of production (Ref. 114). Moreover, by virtue of their programmability, abzymes may well replace enzymes as the biocatalysts of choice in synthetic chemistry.

2.5.6 Therapeutic applications

The major imminent thrust of industrial development of catalytic antibodies is to be found in the medical field. Antibodies that have the ability to recognise foreign antigens in vivo and destroy them could revolutionise the field of immunology (Ref. 115). Antibodies that can perform the function of the complement system and phagocytes could have exciting possibilities in effector disease states, for example in autoimmune disorders or after organ transplant, where the immune system of the body is destructive. Abzymes could be targeted to the body's own immune system components and destroy them, thus causing an amelioration of the disorder. Conversely, where high levels of effector functions are necessary, as in HIV or septicaemia, abzymes could be used to destroy the invasive organisms. Furthermore, in direct analogy with vaccination, a patient could be immunised with the requisite TSA for a reaction which would destroy a specific structural motif of a known pathogen. For example, *Clostridium tetani*, the cause of tetanus, secretes a potent neurotoxin called tetanospasm. This blocks normal postsynaptic inhibition of spinal reflexes, leading to a generalised muscular spasm or 'tetany'. The exotoxin responsible is a protein. Therefore, if a patient were to be immunised with the TSA for amide hydrolysis of this specific protein, at initial exposure to the toxin the patient would already possess immunity which would directly destroy the protein.

2.5.6.1 Prodrug activation by antibodies

Many therapeutic agents are administered as prodrugs. The prodrug is a chemically modified form of the therapeutic agent designed to improve either its pharmacokinetic, pharmacological, or toxicological profiles. Antibody mediated prodrug activation was first exemplified by Fujii's group in Osaka (FIG. 2D18) (Ref. 116). By raising antibodies to both phosphonate haptens (2.53) and (2.54), he generated abzymes that hydrolysed a single regioisomer of the ester prodrug (2.55) or (2.56) of chloramphenicol (2.57) (FIG. 2D18). One of the active clones, 6D9, hydrolysed the prodrug (2.56) with Michaelis-Menten kinetics and a rate enhancement, kcat/kuncat, of $1.8 \times 10^3$. It was inhibited selectively by hapten (2.54), with a Ki of 0.06 mM. Furthermore, Fujii (Ref. 116) showed unequivocally that the principle was viable by effecting growth inhibition of *Bacillus subtilis* on a confluence plate by means of the ester (2.56) only in the presence of 6D9. Biotechnology companies in the U.S., including IGEN (FIG. 2D19)(Ref. 117) and Affymax (Ref. 118) have been seeking to develop the use of abzymes for activation of prodrugs for cancer therapy. It is well known that anticancer agents suffer from severe side effects. Therefore, administration of a prodrug of reduced toxicity which can be activated in vivo would be of invaluable use in cancer treatment (Chapter 3, Section 3.1.2).

2.5.7 Conclusion

The increasing subtleties associated with the generation of catalytic antibodies have been reflected by increasingly complex hapten design. Transition state stabilisation, charged active site residues, distortion, desolvation, proximity effects, and enantioselectivity are all features of antibody catalysis that can be induced by ingenious hapten design. However, hyper-rational hapten design or mimicry of the nth component of a reaction mechanism may well be unnecessary and lead to surprising results in terms of the antibodies isolated.

For example, the hapten (2.61) was designed to elicit antibodies to catalyse the hydrolysis of an ester (2.62) (FIG. 2D20). No catalysts were isolated in initial experiments (Ref. 121). However, after repeated immunisations with the same hapten, antibody 50D8 was isolated which is one of the most efficient antibody catalysts known for ester hydrolysis (Ref. 122).

Scanlan (Ref. 123) was eliciting antibodies that would catalyse the hydrolysis of esters of L-amino acids. The hapten (2.63) was designed as a simple transition state analogue for the reaction (FIG. 2D21). One of the isolated antibodies, 17E8, accelerates the hydrolysis of norleucine (2.64) and methionine (2.65) phenyl esters and is selective for amino acid esters that have the natural α-arbon L configuration. The antibody-catalysed hydrolysis reaction gave a bell-shaped pH rate profile suggesting that two ionisable residues with $pK_a$s of 9.1 and 10.0 were mediating catalysis. Maximum activity for 17E8, $k_{cat}$ of 223 min$^{-1}$ and a rate enhancement of $2.2 \times 10^4$, is achieved at pH 9.5 where the residue with $pK_a$ 9.1 is deprotonated and the residue with $pK_a$ 10.0 is protonated. An acyl-antibody intermediate was detected in mechanistic experiments and the rate-limiting step in catalysis was defined as formation of this intermediate. The Fab of 17E8 was crystallised in the presence of the hapten (2.63) and the structure was determined by X-ray crystallography. The antibody active site contains a Ser-His dyad structure proximal to the phosphorus atom of the bound hapten. This resembles two of the three components of the Ser-His-Asp catalytic triad of serine proteases (Chapter 2, Section 2.5.3). The remarkable feature of this antibody is that the HisH35 SerH99 dyad was completely unanticipated from the hapten design. Furthermore, none of the three residues that participate in the hydrolytic mechanism (TyrH101, SerH99, and HisH35) appear to have significant interactions with the bound hapten (2.63). Therefore, the key catalytic component of the antibody is achieved by pure chance. While this is an excellent discovery for the Scanlan group, it rather confirms the desirability for a simple pragmatic philosophy regarding hapten design.

3. CANCER TREATMENT AND ANTIBODY DIRECTED ENZYME PRODRUG THERAPY (ADEPT)

3.1 Drug Targeting
3.1.1 Antibody-drug conjugates

A major boost to the use of antibodies in cancer treatment came with the hybridoma technology developed by Kohler and Milstein (Ref. 32) which enabled monoclonal antibodies of unique specificity to be produced (Chapter 5).

3.1.2 Antibody directed enzyme prodrug therapy (ADEPT)

It was recognised by Bagshawe (Ref. 3) at the CRC and Senter (Ref. 132) at Oncogen that a targeted pharmaceutical agent requires two distinct features, a delivery and effector function. The delivery function (an antibody fragment) should carry an activating principle (an enzyme), which can either deplete an essential substrate or, as is fundamental to this project, convert a subsequently administered prodrug into an active form. This latter option offered remarkable advantages over any other previous forms of targeted therapies because the prodrug administration can be delayed until the enzyme has localised in the tumour tissue and has cleared from the general circulation so that the catalytic action occurs predominantly at tumour sites (FIG. 3A).

3.1.2.1 ADEPT and carboxypeptidase G2 (CPG2)

Bagshawe focused on the bacterial enzyme CPG2 as the active component for ADEPT. Its natural function is the hydrolysis of tetrahydrofolate (3.1) to tetrahydropteroate (3.2) and L-glutamic acid (3.3) and it has no known equivalent activity in a tumour bearing host (FIG. 3B) (Ref. 133).

CPG2 was conjugated to a F(ab')$_2$ fragment of a monoclonal antibody, W14, specific for the tumour associated antigen human chorionic gonadotrophin (hCG). The prodrug (3.4) was a bifunctional alkylating agent (Chapter 3, Section 3.1.2.4) in which the activating effect of the carboxylate anion was masked by linking the benzoic acid moiety through an amide bond to L-glutamic acid (FIG. 3C).

Kinetic studies showed that this prodrug is an excellent substrate for CPG2, with a $K_m$ of 4.9 μM. The W14-CPG2 conjugate localised in a human choriocarcinoma xenograft in nude mice and considerable turnover of prodrug to drug was observed. Half an hour after administration, the prodrug was detected in all sites except the tumour, a finding consistent with a more complete conversion of prodrug to drug at that site than in other tissues (Table 3.2).

3.1.2.2 ADEPT and alkaline phosphatase (AP)

Senter (Ref. 134) utilised a mammalian enzyme in the development of a monoclonal antibody (L6)-alkaline phosphatase (AP) conjugate for hydrolysis of phosphorylated mitomycin C (3.6) and etoposide (3.7) (FIG. 3E). The in vitro cytotoxicity studies of the prodrugs (3.8 and 3.9) and drugs (3.6 and 3.7) against a lung adenocarcinoma cell line (H2981) showed that the phosphorylated derivatives were more than 100 times less toxic than the active agents. Comparative in vivo studies showed that growth of H2981 xenografts in nude mice were delayed by treatment with the conjugate followed by the prodrug (FIG. 3F).

3.1.2.3 Optimising the prodrug and drug features for ADEPT

Selection of the prodrug for ADEPT is the most modifiable part of the treatment. It should ideally be 10–100 times less cytotoxic than the active drug and be a good substrate for the enzyme, i.e., it should have a low $K_m$ and a high $k_{cat}$, so it can be administered in as low concentrations as possible to minimise toxicity. Preferably the active drug has high lipophilicity to promote diffusion across tumour cell membranes, high efficacy and a low plasma half life to reduce the potential of peripheral toxicity.

3.1.2.4 Nitrogen mustards

Nitrogen mustards (3.10) belong to a class of anticancer agents that are not cell-cycle specific (FIG. 3G). They diffuse well through tissues, are equally toxic to oxygenated and hypoxic cells, and so should be lethal to all cells in high enough concentration (Ref. 135). Mechanistically, they act by alkylating various cellular constituents (Ref. 136). While alkylations of DNA represent the major interactions that lead to lethality, these drugs can also react with thiol, amino. hydroxyl, and phosphate groups throughout the cell further potentiating their cytotoxicity. Their mechanism of action involves an intramolecular cyclisation to form the aziridinium intermediate (3.11) which can then react either directly, or after subsequent rearrangement, as an electrophile with cellular nucleophiles. The major site of alkylation in DNA is N7 of guanine (3.12). However, other bases are alkylated to lesser degrees including N1 and N3 of adenine (3.13), N3 of cytosine (3.14) and O6 of guanine (3.12) as well as phosphate groups in the nucleic acid backbone (FIG. 3G) (Ref. 1). Alkylation of guanine results in miscoding through abnormal base pairing with thymine or in depurination by excision of guanine residues. The latter effect leads to DNA breakage through scission of the sugar-phosphate backbone. To increase the alkylating power of a N-mustard (3.10), R must be electron donating (alkyl or aryl) to activate the tertiary amine and X must be a good leaving group. Springer et al. (Ref. 4,5,137,138) at the CRC have modified these functions in a series of studies to increase the cytotoxicity of aryl N-mustards for use in ADEPT. The starting point for comparison was the para-[bis(2-chloroethyl)amino]benzoic acid mustard (3.5) (Table 3.3). By replacing either or both chlorines with mesyloxy groups (3.16 or 3.17 respectively) the N-mustards became increasingly active. This was reflected both in the half-lives of these compounds and in their $IC_{50}$s against a JAR cell line (FIGS. 3D1 and 3D2)(Ref. 5). Trials have commenced on a series of phenolic N-mustards and their L-glutamic acid prodrugs for use in ADEPT (Ref. 139). The phenolic N-mustards are more potent alkylating agents than the benzoic acid mustards because phenol is more activating than the carboxylate of benzoic acid. The prodrug (3.18) has an $IC_{50}$>100 times that of the drug (3.19) and it is an excellent substrate for the enzyme CPG2, with a $K_m$ of <5.0 µM and a kcat of 37 $s^{-1}$ (FIG. 3H).

3.1.2.5 The ADEPT system in cancer patients

It is desirable to reduce the immunogenicity of the conjugate. The human anti-mouse antibody (HAMA) response may well be minimised by humanisation techniques (Chapter 2) (Ref. 9). Unfortunately the enzyme component of the conjugate be cannot so easily modified. The accepted necessity for the use of non-mammalian enzymes such as CPG2 is that they have the specificity of activation which is required to reduce peripheral toxicity. (Ref. 8). Human enzymes such as AP will induce less hypersensitivity but also will be less specific (Ref. 132,134). Therefore, there exists a real need to be able to produce a protein catalyst with non-mammalian selectivity but with a human structural motif, so that its immunogenicity does not preclude therapeutic use.

3.1.3 Antibody directed 'abzyme' prodrug therapy (ADAPT)

With the advent of antibody-enzymes (Ref. 12,121) (Chapter 2, Section 2.5) the 'synthesis' of protein catalysts of exquisite specificity is possible. Because they are immunoglobulins, they can be humanised by techniques already described (Chapter 2, Section 2.4).

4. ARYL CARBAMATE ESTER HYDROLYSIS AND TRANSITION STATE ANALOGUE DESIGN

4.1 Aryl Carbamate Ester Hydrolysis

Alkaline hydrolysis of aryl carboxylic acid esters (4.1) involves acyl-oxygen fission ($B_{AC}2$) in a two step process involving the addition of hydroxide ion to the carbonyl centre to form a tetrahedral intermediate (4.2) followed by the decomposition of this intermediate to give products (FIG. 4A1). This mechanism has been distinguished from a direct displacement reaction ($S_N2$) at the carbonyl carbon atom by means of isotopic exchange (Ref. 141) and kinetic arguments (Ref. 142). By direct analogy, it was suggested that alkaline hydrolysis of carbamic acid esters may proceed via a $B_{AC}2$ mechanism (Ref. 142). However, several observations made when studying the hydrolysis of these compounds were inconsistent with this idea.

4.1.1 Duality of mechanism for carbamate hydrolysis (FIG. 4A4)

The reactivity of the acyl function (4.3) (FIG. 4A2) is enhanced when the group Y is electron withdrawing and is markedly reduced when Y is capable of donating electrons by resonance (4.4). When two electron donating groups are present, as with carbamate esters (Ref. 143) (4.5) or ureas (Ref. 144) (4.6), nucleophilic attack on these acyl centres is very slow. Several workers noted that N-monoalkylcarbamate esters hydrolyse more rapidly than do N,N-dialkylcarbamate esters. Dittert (Ref. 145) and Christenson (Ref. 146) who reviewed early work in this area, found that p-nitrophenyl N-methylcarbamate (4.7) is hydrolysed about $10^6$ times faster than p-nitrophenyl N,N-dimethylcarbamate (4.8) and phenyl N-phenylcarbamate (4.9) is hydrolysed $10^6$ times faster than phenyl N-phenyl-N-methylcarbamate (4.10) (FIG. 4A3). The novelty of the elimination-addition process inspired a number of kinetic studies designed to clarify differences between this mechanism and the more classical addition-elimination route. In particular, experiments were performed to assess which step in this elimination-addition mechanism was rate determining (FIG. 4A5). The process can involve either a rapid proton abstraction followed by a slow decomposition (4.1) or, slow proton transfer followed by a fast decomposition of the anion (4.2). These two mechanisms can be distinguished from each other because (4.2) leads to general base catalysis whereas (4.1) leads to a specific hydroxide ion catalysis. With this in mind, Bender (Ref. 147) studied the effect of various buffers on the rate of hydrolysis of (4.7) (FIG. 4A3). The catalytic rate coefficients (kb) of substances other than hydroxide ion were exceedingly small (Table 4.1). A plot of pH vs. log kobs (not corrected for buffer catalysis) showed a slope of exactly 1 from pH 5.5 to 9 consistent with a first order process (with respect to hydroxide ion concentration) indicating that buffer catalysis makes a very small contribution to the overall rate.

There was rapid isotopic exchange of the carbamate proton of (4.7) with solvent deuterons at neutral pD. This exchange rate was >200 times the rate of the hydrolytic reaction. All these data: first order dependence of hydrolysis on hydroxide concentration, low buffer catalysis and rapid deuterium exchange supported a specific base catalysed, E1cB, mechanism for carbamate hydrolysis, as shown in eqn. (4.1) (FIG. 4A5).

4.1.2 E1cB and the Brønsted catalysis law

The relationship between the thermodynamic acid-base property of a compound and its ability to act as a catalyst is expressed as the following linear relationship (4.3) (Ref. 148).

$$\log k_B = -\beta \cdot \log K_{BH} + \text{constant} \quad (4.3)$$

or, since $PK_{BH} = -\log K_{BH}$ $$\log k_B = \beta \cdot PK_{BH} + \text{constant} \quad (4.4)$$

where $k_B$=the second-order catalytic constant for the reaction catalysed by a general base B, β=the Brønsted parameter for the particular reaction being catalysed, and $K_{BH}$=the acidity constant of the conjugate acid of the catalytic base B. As the β value increases (usually from 0 to 1) then the sensitivity of the reaction to basic catalysis increases. A β value of ca. 0 indicates a reaction for which bases of widely different strengths are broadly comparable in their catalytic effect. Consequently, the major part of the reaction in aqueous solution will be catalysed by water. By comparison, a β of ca. 1 is very sensitive to base strength of the catalyst. If different bases are present at comparable concentrations, the strongest will be most effective and provide the major reaction route. In alkaline solution this would indicate specific base catalysis, i.e. catalysis by hydroxide ion. Typical general base catalysis is associated with a Brønsted coefficient in the range 0.2<β<0.8. Bender and Homer (Ref. 147) had established that the alkaline hydrolysis of aryl carbamates follows specific base catalysis (4.1) with little or no buffer catalysis, predicting a Brønsted β value of ca. 1. However, a Brønsted $β_{lg}$ value of 1.34 was measured for a series of substituted phenyl N-phenylcarbamates (4.1 1) (FIG. 4A7). The $pK_a$ of the leaving group phenol was plotted vs. the log of the rate (FIG. 4A6) and Williams (Ref. 13) suggested that this high β was a result of a combination of ionisation ($K_a$), bond formation (—N═C—) and bond fission (—C—OAr) in the E1cB transition state.

4.1.3 Hammett reaction parameters for $B_{AC}2$ and E1cB

Since a polar reaction consists of the interaction between a nucleophile and an electrophile, the electronic demands of the reactions, i.e., the factors that facilitate this process, are either a supply of electrons to the nucleophilic centre or withdrawal of electrons from the electrophilic centre. The degree to which a given reaction responds to electronic perturbation by a substituent depends upon the reaction type and its electronic demand.

Hammett drew attention to the fact that a plot of log $K_a$ for benzoic acid ionisation against log k for ester hydrolysis is linear over many substituents. The proviso was that the substituents had to be located at meta or para positions in the benzene ring. Rates and equilibrium constants for ortho compounds do not fall on the line. The reason for this is that changes in k or $K_a$ (i.e. $\Delta G\ddagger$, $\Delta G$) brought about by m- or p- substituents are virtually all due to changes in whereas o-substitution alters both $\Delta H\ddagger$ and $\Delta S\ddagger$. Quantitatively, the effect of each substituent, relative to that of hydrogen, is obtained by a comparison of $\Delta G_o$ for dissociation constants of substituted benzoic acids ($K_X$) with that of benzoic acid ($K_H$) (4.5). Thus:

$$\text{Substituent effect} = \Delta G_X - \Delta G_H = \log (K_X/K_H) = \sigma_X \quad (4.5)$$

in which sigma$_X$ is known as the substituent parameter. Electronwithdrawing substituents are characterised by positive values of sigma and electron donating groups give negative sigma values, with the magnitude being a measure of their effect. It follows that:

$$\log k_X/k_H \alpha \log K_X/K_H \quad (4.6)$$

If $k_X/k_H = k_{rel}$ and introducing a constant of proportionality $\rho$, known as the reaction constant, and substituting in eqn. (4.5)

$$\log k_{rel} = \rho\sigma \quad (4.7)$$

This is the Hammett (Ref. 149) expression (4.7) and is followed with varying precision by very many reactions. The reaction parameter, $\rho$, is a measure of the sensitivity of a reaction to the introduction of substituents into the aromatic ring relative to the effect of the same substituent on the acidity of benzoic acid, since from eqn. (4.5) $\rho=1.00$ for the dissociation of benzoic acid.

The rate determining step in the bimolecular attack of hydroxide ion ($B_{AC}2$) on phenyl esters, for example phenyl acetates, is the initial formation of the tetrahedral intermediate (FIG. 4A1). There is little acyl-oxy bond cleavage which minimises phenolate character in the transition state. This results in low reaction sensitivity ($\rho \leq +1.0$) for hydroxide ion attack on related aryl acetates. (Ref. 150,151). Furthermore, for the $B_{AC}2$ process, Hammett relationships are observed where sigma (as opposed to $\sigma^-$) is employed. (A modified substituent parameter $\sigma^-$ was defined to account for deviations in a plot $pK_a$ of substituted phenols and $\sigma$. Substituents which could conjugatively delocalise the negative charge, e.g. $\rho$-$NO_2$, $\rho$-CHO and $\rho$-CN all increased the acidity of phenol to a greater degree than was expected for simple inductive delocalisation. Wherever conjugative delocalisation can occur, the $\sigma$ parameter value is used). This suggests that conjugative delocalisation does not accelerate hydrolysis relative to simple inductive delocalisation, consistent with there being little phenolate character in the transition state.

The E1cB pathway for the hydrolysis of aryl acetoacetate ester (4.13) was known to be very sensitive to the nature of the leaving group, since the transition state is reached with almost complete acyl-oxy bond cleavage (FIG. 4A8) (Ref. 152). Williams (Ref. 13) in Canterbury and Hegarty (Ref. 17,18) in Cork independently measured the effect of changing the substituent on the departing phenol on hydrolysis rates for a series of phenyl N-phenylcarbamates (4.11) (FIG. 4A9) (Ref. 13). They found that there was indeed a high sensitivity to leaving group ability, with reaction parameters being measured as $\rho=+2.86$ and $+3.17$ respectively.

Having shown that electron withdrawing groups on the phenol ring activate the carbamate to hydrolysis (both inductively and mesomerically), substitutions in the aniline ring for a series of phenyl N-(substituted phenyl)carbamates (4.12) were undertaken to study their effect on both the hydrolysis rate and the $pK_a$ of the carbamate proton (Ref. 18). The results showed a much lower substituent effect ($\rho=+0.64$) than modifications in the phenol ring. This is because the effect of modifying $\sigma$ or ($\sigma^-$) in the N-aryl ring has two opposite effects. The $pK_a$ of the carbamate is reduced by electron withdrawing groups (a result of a more stabilised anion) but the rate of decomposition of the anion decreases. Therefore, direct correlation of the reaction sensitivity parameter to carbamate hydrolysis is more difficult for substitutions in the aniline ring than in the phenol ring.

Hegarty (Ref. 18) noted that by increasing the electron withdrawing ability in the aniline ring the $K_a1$ of the carbamate proton for a series of aryl N-(p-nitrophenyl) carbamates (4.15) could be measured (Table 4.2). Furthermore, a plateau rate ($k_2$) was observed at pHs above the $pK_a$, supporting the theory that hydrolysis proceeds with rate determining decomposition of the carbamate anion.

If the observed hydrolysis rates of the anions ($k_2$) are plotted against the $pK_a$ of the leaving phenol (Brønsted plot), as the leaving group ability decreases there is suddenly a marked positive deviation away from the expected E1cB relationship (FIG. 4A10). Hegarty compared these results with the hydrolysis rates of a series of N-methyl substituted analogues (4.16) of the carbamates (4.15) which are known to hydrolyse by the $B_{AC}2$ mechanism (Section 4.1.1). The points which deviated from the E1cB correlation fitted well onto the $B_{AC}2$ line, suggesting that the $pK_a$ of the leaving group reaches a critical point ($pK_a$ 12.5 for carbamates) above which the hydrolysis mechanism switches from E1cB to $B_{AC}2$. A similar changeover in mechanism has been noted for the acetoacetate esters (4.13), the slope of the log $k_2$ vs. $pK_a$ (of ROH) being close to zero when the $pK_a$ of ROH<ca. 11 (Ref. 152).

4.2 Example—Hapten Design and Carbamate Hydrolysis

Antibodies which have the capability to perform a reaction by a disfavoured mechanism are believed to be novel. From kinetic studies it was known that there is a much lower dependence on leaving group ability in a $B_{AC}2$ process compared with an E1cB route, $\rho=-$ca. 1.0 and 2.8 respectively (Chapter 4, Section 4.1.3). It is possible that if a catalyst could selectively accelerate the disfavoured $B_{AC}2$ process for carbamate hydrolysis, by means of suitable substrate design the background hydrolysis might become negligible under conditions where the enhancement is optimal (FIG. 4B1). Such a catalyst would meet the criterion for ADEPT, where the prodrug substrate for the catalyst should have low peripheral toxicity, i.e. a low decomposition rate, but should be an excellent substrate for the enzyme (Chapter 3, Section 3.1.2.3).

A number of features in FIG. 4B1 are noteworthy. Firstly, as $\sigma(\sigma^-)$ decreases, because of the difference in sensitivity of the mechanisms to leaving group ability, the theoretical distance between the catalysed and uncatalysed hydrolysis rates increases. Therefore the apparent enhancement ratio, $k_{cat}/k_{uncat}$, becomes quite large. This ratio is not, however, the true rate acceleration because the two mechanisms are different. The actual rate of spontaneous hydrolysis via the $B_{AC}2$ process is immeasurably small. Hegarty (Ref. 17,18) has shown that N-methyl-N-(p-nitrophenyl) substituted carbamates (4.16) in which there is no carbamate proton (N—H group), hydrolyse via a $B_{AC}2$ mechanism. Therefore, a more direct enhancement ratio can be estimated by comparing the relative rates of hydrolysis of the N-methyl analogues (4.16) and the antibody catalysed rate. Secondly, because of the high spontaneous hydrolysis rates of carbamates with leaving group $\sigma(\sigma^-)>1.0$, coupled with the poor catalytic rates of antibodies, it would be conceivable that the antibody catalysed line would lie much lower than shown in FIG. 4B1. Thus, the lower the $\sigma(\sigma^-)$ value of the phenolate in the substrate (prodrug), the greater the chance of identifying an antibody that will catalyse its hydrolysis by a detectable amount (FIG. 4B2). Two further issues for catalytic antibodies are product inhibition and the formation of stable intermediates. The former should be negligible for the dissociative $B_{AC}2$ process. However, the latter might be a drawback for antibodies that catalyse an E1cB reaction, which is known to generate an electrophilic isocyanate intermediate, as shown in equation (4.1) (Ref. 18).

All of the above considerations suggested that eliciting antibodies for the hydrolysis of carbamates via the disfavoured $B_{AC}2$ process would be advantageous.

Clearly, hapten design has to reflect the features of the $B_{AC}2$ mechanism whilst minimising features of the E1cB transition state (FIG. 4B3). The two processes have quite different stereoelectronic features. The $B_{AC}2$ high energy intermediate (4.17) has been well characterised (Chapter 2, Section 2.5.2) as an anionic tetrahedral structure which should be similar to the true transition state of the reaction (Ref. 154). Consequently, the incorporation of a tetrahedral phosphorus to replace the carbonyl carbon was seen as a primary requirement (4.18). The E1cB transition state (4.19) is less well known but kinetic studies have shown it to involve a significant degree of acyl-oxygen bond cleavage (Ref. 13,17). Furthermore, the transition state is planar with the carbonyl carbon being essentially trigonal allowing resonance stabilisation of the carbamate anion. The phenolic oxygen was replaced with a methylene group to minimise any phenolate anionic character being recognised by the antibody (4.20). A nitrogen atom was placed adjacent to phosphorus to generate a hydrogen bond (H-bond) donor-acceptor system in the antibody active site. It was felt that the problems of instability of such phosphonamidates would be outweighed by the benefits to substrate and transition state binding of utilising H-bonding as a component of antibody recognition. In addition, they are rather easier to prepare than the corresponding dibenzylphosphinic acids.

Evidence from enzyme inhibition studies (Ref. 155,156) and catalytic antibody generation (Ref. 110,157) suggests that the negative charge in the TSA is non-essential. Antibodies which catalyse acyl cleavage reactions have been generated to neutral phosphonate esters (Ref. 110) and secondary alcohols (Ref. 157) with the inherent polarity of these bonds sufficient to mimic the negative charge in the transition state. To further clarify the electronic requirements of acyl transfer transition state analogues, both the neutral phosphonamidate ester (4.20) and the anionic phosphonamidic acid (4.21) were proposed for synthesis.

The issue of product recognition marl also be diminished at this stage of hapten design. The intended substrate, prodrug (4.22), contains a nitrogen mustard which could potentially alkylate the antibody binding site (FIG. 4B4). Therefore, to reduce any binding recognition in this region of the hapten, a heterobifunctional linker was introduced at the para position of the benzyl ring which also produces a handle for attachment of the carrier protein. To study the effects of substrate and product recognition on antibody catalysis, the L-glutamic acid moiety in the substrate (4.22) was either retained [Hapten 3 (4.23) and Hapten 4 (4.24)] or replaced by a planar 5-aminoisophthalic acid group [Hapten 1 (4.25) and Hapten 2 (4.26)].

Several advantages appeared to attach to the use of the isophthalate group in place of the glutamate residue. The phosphonamidates were thought to be more stable and therefore easier to synthesise. The reduced population of rotamers potentially offered the opportunity of a lower $K_m$ of the substrate to the antibody and may allow the switch to the glutamate prodrug (4.22) in due course.

5. MONOCLONAL ANTIBODY PRODUCTION : HYBRIDOMA TECHNOLOGY

The majority of research groups generating abzymes have used monoclonal antibodies as their active protein. However there are exceptions. In particular, the work of Gerry Gallacher at Queen Mary College, London, has shown that catalytic activity can be detected in a polyclonal mixture (Ref. 158–162).

During the production of catalytic antibodies, it is important to accurately measure the binding and kinetic profiles of any antibodies produced and to be sure that any catalysis observed is derived from the immunoglobulin and not from a contaminating enzyme. Whilst polyclonal antibody preparations are cheaper and can be produced much faster than monoclonals, assumptions have to be made to assess even the most routine parameters. Binding affinities for the antigen and enzyme kinetics are all directly related to the fraction of anti-haptenic IgG in the polyclonal mixture and this is largely unmeasurable (Ref. 159,163).

5.1 Example—Hydridoma Technology
5.1.1 Cell fusion

The traditional technique, pioneered by Köhler and Milstein (Ref. 32,164) involves the fusion of two cell types: splenocytes from a mouse hyperimmunised with an antigen and cells from a myeloma cell line.

5.1.2 Screening for antigen (TSA) binding by ELISA

Once a successful fusion has been effected and hybridomas isolated by HAT selection, a rapid and efficient screening technique is vital to highlight antibodies which bind the antigen, in this case the TSA.

In recent years, labelled reagent assays, especially enzyme linked immunosorbent assays (ELISA), have played an increasing role in the qualitative and quantitative analyses of antibody-antigen interactions. ELISA is an ideal screen for antibodies in cell fusion supernatants.

Hapten-protein conjugate is adsorbed onto the polyvinyl surface of a 96-well microtitre plate. The hapten is then exposed to the test solution (cell supernatants) and any monoclonal antibody with an affinity for the solid phase bound hapten will bind and resist subsequent washing. This antibody-hapten complex is highlighted when the plate is further incubated with a secondary anti-murine IgG specific antibody which has been prelabelled with an enzyme. The two most commonly used enzymes are alkaline phosphatase (ALP) and horse radish peroxidase (HRP), the latter being favoured in the present work because of its relative cheapness and ease of conjugation. After incubation and washing steps, the plate is exposed to a solution containing a specific chromogenic substrate for the enzyme and hydrogen peroxide which invokes a clearly visible colour change if enzyme is present. For this study, the substrate 3,3'5,5'- tetramethylbenzidine (TMB) has been used for HRP, which yields a primary blue colour which turns yellow on acidification. TMB is the most sensitive reagent available and as such is ideal for the early screening of hybridoma supernatants (Ref. 166).

In the search for catalytic antibodies it would save time if selection for catalysis were available at this early stage of hybridoma development. However, because of the low antibody concentrations (0.1–10 µg/ml) and potential enzyme contamination in hybridoma supernatants, very little success has been achieved to date. Whilst initial screening of supernatants has been based on recognition of the TSA, attempts have been made to measure turnover of the carbamate prodrug (4.22) by cell supernatants in a cytotoxicity assay (Chapter 9, Section 9.1.1).

5.1.3 Cloning by limiting dilution

Once the hybridomas that are secreting antibody specific for the required antigen have been highlighted, the hybrid cell lines must be cloned.

5.1.4 Determination of affinity constants

The importance of being able to measure the affinity of monoclonal antibodies for the hapten with a high degree of certainty cannot be underestimated. In situations where the antibodies are being developed as tools for immunoassay, their affinity for a specific antigen is important for assessing how well they recognise their antigen. The affinity of the antibodies for the TSA may well give a fundamental insight into potential catalysts. If substrate and product binding effects are disregarded, it is inherent from transition state theory (Chapter 2, Section 2.5.1) that the higher the affinity of the antibody for the transition state, the greater the catalysis that should be observed. Theoretically the higher the affinity of the Mabs for the hapten (TSA) the greater chance that those monoclonals should be catalytic. Care has been taken to generate panels of monoclonals to all the haptens and to assess, using two orthogonal techniques, their affinity for the transition state analogues. Furthermore, antibodies can recognise any part of the haptens. Therefore studies have been undertaken to clarify which region (if any) of the hapten is important for the generation of catalysts.

5.1.4.1 Apparent affinity (aK) determination using ELISA

The first techniques used to determine the affinity constants ($K_a$) of antibodies were equilibrium dialysis (Ref. 169) and fluorescence quenching (Ref. 170) both of which were either difficult to perform or gave inaccurate data because the antibody was binding to a modified antigen. More recently Nieto (Ref. 171) has developed a rapid and simple technique for affinity determination based on a competition ELISA. These assays depend on the competition between a fixed amount of immobilised antigen and a variable concentration of hapten in solution for a limiting amount of antibody (FIG. 5A). The amount of enzyme-labelled antibody subsequently bound to the solid phase decreases with increasing free antigen in solution.

$$aK = 1/[H]_{50} \quad (5.2)$$

Nieto defined an apparent affinity constant (aK) as the reciprocal of that concentration of free hapten (H) required to give 50% inhibition of antibody binding to immobilised antigen (5.2). This is determined as 50% of the maximum OD, where 100% is the OD containing no free hapten. Nieto showed both by derivation and by experimental comparison with equilibrium dialysis techniques that the apparent affinity constants (aK) measured by ELISA were comparable to actual affinity constant ($K_a$) values measured by classical methods. As with all techniques used to determine antibody affinities, competition ELISA is limited both in its degree of accuracy and in practical terms, but nevertheless it is a rapid and useful index for scaling antibody affinities.

5.1.4.2 Affinity determination using BIAcore

Most available methods for determining affinities of antigen-antibody interactions, including ELISA, are based on equilibration of the reactants followed by the free and bound reactants being separated and at least one of these components then being quantified. Biospecific interaction analysis (BIA) is a new technique developed for measuring the binding of macromolecules to surface immobilised interactants. It offers a unique insight into both equilibrium constants and kinetic rate constants for biomolecular interactions (Ref. 172). The net association rate for antibody-antigen interaction enables a panel of monoclonal antibodies to be graded on the rate at which they bind their antigen. This is proving of use in developing more rapid immunoassay techniques, where the prime requisite of high affinity is being superseded by a need for a more rapid rate of detection. For this work the BIAcore method offered an opportunity not only to measure the binding affinities of the antibodies but also to assess the kinetic events arising from the binding of monoclonal antibodies to their TSAs.

The central feature of the BIA process is the biosensor. Biosensors are instruments that combine biological recognition with a sensing device or transducer. The biosensor for BIA utilises an optical phenomenon called surface plasmon resonance (SPR) (FIG. 5B). At an interface between two transparent media of different refractive index (e.g. glass and water), light coming from the side of higher refractive index is partly reflected and partly refracted. Above a certain critical angle of incidence, determined by the ratio of the refractive indices, no light is refracted across the interface and total internal reflection is observed. Although the incident light is reflected, an electromagnetic field component of the light called the evanescent wave penetrates a short distance (approximately one wavelength) into the medium of lower refractive index. If the interface between the media is coated with a thin layer of metal and the light is monochromatic, a sharp 'shadow' or intensity dip appears in the reflected light at a specific incident angle. This phenomena is called SPR and the incident angle is called the SPR angle.

The biosensor is housed in a sensor chip and is comprised of a gold film embedded in a glass support. For SPR a number of metals can be used, but gold gives an SPR signal at a convenient combination of reflectance angle and light wavelength. In addition, it is chemically inert to solvents and solutes used in a biochemical context. The gold film on the sensor chip is coated with a carboxymethylated dextran hydrogel. Biomolecules can be immobilised on the hydrogel using standard NHS/EDC chemistry (FIG. 5C).

When one of the reactants is immobilised, the other is introduced in solution flowing over the sensor surface. The flow system is miniaturised to provide efficient mass transport. The reaction is monitored by changes in the refractive index at the gold surface over time and is presented in a sensorgram (FIG. 5D). The y axis of the sensorgram is the resonance signal and is expressed in response units (RU). The running buffer defines the baseline and all responses are expressed relative to this level. At a given time the relative response, R, can be expressed as:

$$R = R_R + R_L + R_A \quad (5.3)$$

where $R_R$ is the refractive index component for the sample buffer, $R_L$ is the component for immobilised ligand and $R_A$ is the component for analyte bound to immobilised ligand. The change in signal level with respect to time is:

$$dR/dt = dR_R/dt + dR_L/dt + dR_A/dt \quad (5.4)$$

Except for the 10–20 seconds at the beginning and at the end of an injection $dR_R/dt=0$, and hence $R_R$ is constant. Furthermore, because the ligand is immobilised, $dR_L/dt=0$. Therefore, the change D in response level reflects binding of the analyte and:

$$dR/dt = dR_A/dt \quad (5.5)$$

Theoretical Background.

When analyte A reacts with ligand B to form the complex AB, the net rate of complex formation (at equilibrium) depends on the free concentration of the A and B components and on the stability of the complex formed. This can be expressed in eqn. (5.6):

$$d[AB]/dt = k_a[A][B] - k_d[AB] \quad (5.6)$$

The association rate constant is $k_a$ ($M^{-1}s^{-1}$) and kd is the dissociation rate constant ($s^{-1}$). In the biosensor, the ligand B is immobilised on the sensor surface. Therefore, the concentration of the complex [AB] is identical to the concentration of the bound analyte. From eqn. (5.4) the concentration of bound analyte is proportional to the response $R_A$. Free ligand concentration [B] is the difference between total and bound ligand concentration. The total concentration of active immobilised ligand is obtained indirectly as it is saturated with analyte. The maximum response due to analyte binding, $R_{max}$, will therefore be proportional to total ligand concentration and ($R_{max}-R_A$) will be proportional to free ligand concentration. When the analyte is injected in a stream over the sensor surface the analyte solution is constantly replenished and hence the free concentration of the analyte is constant and identical to total analyte concentration. The reaction between immobilised ligand and analyte in solution can therefore be assumed to follow pseudo-first-order kinetics and the concentration of complex [AB] and free ligand can now be expressed in terms of analyte response. Given that C is the concentration of injected analyte, equation (5.6) can be rewritten:

$$dR_A/dt = k_aC(R_{max}-RA) - k_dRA \quad (5.7)$$

Rate and Equilibrium Constant Determination.

A rearrangement of eqn. (5.7) gives $$dR_A/dt = k_aC\,R_{max} - (k_aC+k_d)R_A \quad (5.8)$$

Rate constants can now be evaluated by a plot of $dR_A/dt$ vs. $R_A$ provided that $R_{max}$ and C are known and therefore:

$$dR/dt = \text{constant} - (k_aC+kd)R \quad (5.9)$$

Using this equation, the detector response, R, can be used directly and no correction for responses due to differences in refractive index from the buffer components are necessary.

To determine the association constant, $k_a$, several concentrations of analyte are injected and the slope value ks, obtained from each dR/dt vs. R plot, are introduced into a new plot vs. analyte concentration such that:

$$k_s = k_aC + k_d \quad (5.10)$$

From relationship (5.10) the association rate constant is readily obtained as the slope of the plot. Theoretically, the dissociation rate is obtained from the intercept on the y axis. However, this intercept cannot be determined accurately when kd is low. A more useful experiment is measuring dissociation of the analyte in pure buffer flow (FIG. 5D). No analyte is present in the buffer, therefore $dR_A/dt = -kdR_A$. The dissociation follows a simple exponential decay such that:

$$ln(R_A1/R_n) = k_d(t_n-t_l) \quad (5.11)$$

where $R_A1$ is the response level at t=1, the start time for the assay. $R_n$ and $t_n$ are points along the dissociation curve. Therefore, because at equilibrium the rates of association and dissociation of the analyte (A) with the bound ligand (B) are equal:

$$k_a[A][B] = k_d[AB] \quad (5.12)$$

$$K_a = [A][B]/[AB] = k_a/k_d \quad (5.13)$$

Therefore, as a result of being able to monitor the antibody binding over time, it is possible to determine both the association and dissociation constants very rapidly and hence the equilibrium affinity constant ($K_a$).

6. OVERVIEW OF EXAMPLES

The aim is to produce monoclonal antibodies that can hydrolyse aryl carbamate esters (6.1) via the disfavoured $B_{AC}2$ mechanism (FIG. 6A). In Chapter 4, the alternative mechanisms for carbamate hydrolysis were discussed. The two transition states have sufficiently different steric and electronic features such that design of transition state analogues for the $B_{AC}2$ process should elicit antibodies which selectively stabilise this transition state in preference to accelerating the E1cB mechanism.

Section 4.2 outlined the design of the haptens (6.2–6.5) which include a number of important components (FIG. 6B). The central feature is a tetrahedral phosphorus atom to mimic the geometry of the $B_{AC}2$ transition state. A nitrogen atom is α to phosphorus to elicit a hydrogen bond donor-acceptor system in the antibody active site for increased substrate binding. A benzylic methylene group is designed to reduce any recognition of the phenolic oxygen by the antibody thus preventing stabilisation of the E1cB transition state. The phosphonamidate group is either esterified (6.2 and 6.4) or as a free phosphonic acid (6.3 and 6.5). to study the effects of anionic charge on abzyme production. The N-substitution of the phosphonamidate is either isophthalic or L-glutamic acid to study the effects of substrate recognition and product inhibition on antibody catalysis.

The activated haptens are linked via their N-hydroxysuccinimide esters to a carrier protein (KLH, BSA, or OVA) for immunisation. After successful conjugation, determined by methods outlined in Chapter 8, antibodies are generated by hybridoma technology (Chapter 5). Monoclonal antibodies that bind the transition state are fully characterised by ELISA and BIAcore (Chapter 8) and screened for catalysis (Chapter 9).

Catalysis is assessed by both a u.v. and a cytotoxicity assay. In the cytotoxicity screen, N-mustard prodrug (6.6) is the substrate and catalytic efficiency is related to cell kill of a colorectal tumour cell line (FIG. 6C). While previous work has shown that antibody catalysis of prodrug activation can cause inhibition of bacterial growth (Ref. 116) despite the keen industrial interest in anticancer prodrug activation by antibodies (Chapter 2, Section 2.5.6.1), there is no literature precedence for assessing the effect of catalytic antibody mediated hydrolysis of an anticancer prodrug on a tumour cell line.

A number of substrates (6.7–6.12) and substrate analogues (6.13 and 6.14) have been generated to either highlight the presence of active clones or to generate Hammett σ-ρ correlation data (FIG. 6C). By measuring the rates of antibody catalysed hydrolysis of these substrates, it is hoped to elucidate the mechanism by which any catalytic clones are working.

The linker was attached at the para position of the phenyl ring, in a position corresponding to where substrate modification occurs in the substrates (FIG. 6B). From results highlighted by Hilvert et al. (Ref. 79) there should be little antibody recognition of this part of the substrate, thus allowing the Hammett analysis to reflect the direct relationship between structure and kinetics, rather than being complicated by additional changes in substrate affinities arising from large changes in $K_m$. The stability of ureas (Section 4.1.1) has meant that there has been no report of their hydrolysis by catalytic antibodies. Because of the generality of phosphonates as TSAs for acyl transfer processes the amide (6.13) and urea (6.14), are screened to see if their hydrolysis can be catalysed by any antibodies generated to the haptens (6.2–6.5).

7. EXAMPLES—SYNTHESIS OF HAPTENS AND SUBSTRATES

7.1. Example—Synthesis of Transition State Analogues

Phosphonamidates have been employed as strong inhibitors for a number of enzymes (Ref. 48). By correlation of $K_i$ values of a series of such inhibitors with $K_m/k_{cat}$ for the corresponding substrates, it has been shown that they do indeed work as transition state analogues. Unfortunately, they suffer from marked instability under acidic conditions and consequently their use has been restricted to enzymes that do not employ acidic residues in their active site, for example carboxypeptidase A (Ref 174–176). To assess the potential of phosphonamidates as inhibitors of enzymes with acidic groups, for example the aspartyl proteases, phosphonamidate esters have been employed. The results have shown considerable variation (Ref. 155,156). Phosphonamidate methyl esters retain a potency comparable to that of their phosphinic acid counterparts for the HIV-1 protease (Ref. 156). By contrast, in the inhibition of the metalloprotease, angiotensin converting enzyme (ACE), an enzyme which works by proximity effects, ethyl phosphonamidate esters show a 700–4000 fold increase in $K_i$ values when compared to their de-esterifed analogues (Ref. 177). Paul Bartlett (Ref. 175) has studied the pH dependence of the hydrolysis of the phosphonamidate (7.1) (FIG. 7A1). At pH 2.3 the half life was a few minutes, whereas at pH 6.5 this increased to 4 h and at pH 7.5 it was more than 8 days.

The haptens for this work were either phosphonamidate esters (7.2 and 7.3) or phosphonamidic acids (7.4 and 7.5) (FIG. 7A2) (see also Chapter 4, Section 4.2). The incorporation of an ethyl ester at phosphorus which ostensibly increases the stability of the phosphonamidates was seen as a rational component of hapten design, in no way contradictory to transition state analogue theory. The acid sensitivity of the phosphonamidate linkage results from the poor delocalisation of the nitrogen lone pair into the vacant phosphorus d-orbitals, making it much more basic than in a carboxylic amide (Ref. 177).

It was envisaged that the haptens containing the isophthalic acid group (7.2 and 7.4) would have a greater stability than the haptens derived from L-glutamic acid (7.3 and 7.5) by direct analogy with the relative basicities of an aniline and an amino acid ($pK_a$ ca. 5 and 9.5 respectively).

Therefore, the first stage of synthesis focused on production of the more robust isophthalic acid haptens, with the L-glutamate series being deferred until after the immunisation protocols for haptens 1 (7.2) and 2 (7.4) were under way (Chapter 8, Section 8.1).

It is standard practice to use a molecule of structural similarity to the hapten for ELISA studies (Ref. 11,121). We have followed the example of Tramontano(Ref. 11) and synthesised analogues (7.6–7.9) of the four haptens that do not contain the activated N-hydroxysuccinimide ester. These molecules are designed for incorporation into displacement ELISA protocols for determination of affinity constants of any antibodies which bind to their parent hapten.

The target molecules can be subject to disconnection analysis at two points to give three fragments: an amine (7.10), a heterobifunctional spacer (7.11) and a benzylphosphonic acid derivative (7.12) (FIG. 7A3). The spacer can be further disconnected to N-hydroxysuccinimide (7.13) and a glutaric acid derivative (7.14).

7.1.1 Routes to the activated benzylphosphonic acid intermediate (7.15)

To prevent cross reactions during activation of the benzylphosphonic acid intermediate (7.12), the p-amino function was masked as a nitro group. Therefore the first step in the hapten synthesis involved the production of ethyl (4-nitrophenyl)methyl-phosphonochloridate (7.15). It was anticipated that following mono de-esterification of the phosphonate diester (7.16), the resulting phosphonic acid (7.17) could be chlorinated by standard procedures (FIG. 7A4) (Ref. 178).

Diethyl (4-nitrophenyl)methylphosphonate (7.16) (Ref. 179) was first synthesised by Kosolapoff (Ref. 180) by nitration of diethyl phenylmethylphosphonate (7.18), which, in turn, he prepared by a standard Michaelis-Arbusov (Ref. 181) reaction between benzyl bromide (7.19) and triethyl phosphite (7.20) (FIG. 7A5). A more direct route is through the Arbusov reaction between p-nitrobenzyl bromide (7.21) and triethyl phosphite (7.20), but both Kosolapoff (Ref. 180) and others (Ref. 182) have reported very low yields from this particular reaction.

By following the two-step procedure, the phosphonate (7.16) was synthesised in good yields (71% over two steps). Unfortunately, the nitration produced both the para and ortho isomers in a ratio of 85:15 respectively (determined by $^{31}P$ NMR). They could not be separated by either silica gel chromatography or distillation and repeated attempts to increase the para selectivity by temperature control also proved fruitless. An alternative route to the phosphonate (7.16) employed a Michaelis-Becker (Ref. 183) reaction between p-nitrobenzyl bromide (7.21) and diethyl phosphite (7.22) (FIG. 7A6). This afforded the diethyl phosphonate species (7.16), after distillation, as a single isomer in moderate yields (65%).

The next stage was selective removal of one ethyl group from the phosphonate diester (7.16) prior to activation to the phosphonochloridate (7.15). The standard procedure involves stirring the diester (7.16) in an excess of aqueous NaOH. Only one ester is hydrolysed because the electron density on phosphorus after monodeesterification prevents further nucleophilic attack (Ref. 184). On addition of NaOH to a methanolic solution of (7.16), a vivid red colour was seen. This was ascribed to resonance stabilisation of the carbanion formed by abstraction of one of the benzylic protons. Unfortunately all attempts to de-esterify the phosphonate by this method proved unsuccessful, perhaps due to partial stabilisation of the carbanion onto phosphorus which reduces the potential for nucleophilic attack by hydroxide.

This problem was overcome by following a one-step activation procedure, as described by Yamauchi (Ref. 185). The phosphonate (7.16) was smoothly chlorinated by phosphorus pentachloride by stirring in chloroform or carbon tetrachloride at 30° C. The reaction was monitored by $^{31}$P NMR [δP (7.16) 24.59 (s) and (7.15) 35.94 (s)] which showed the reaction was complete after 24 h. Because of the moisture sensitivity of these compounds, instability on silica gel, and reported decomposition to metaphosphates during distillation,[186] the phosphonochloridate (7.15) was not further purified following removal of the phosphorus oxychloride by-product in vacuo. The yields for this reaction were consistently over 80%, contributing to an overall yield of ca. 64% for the production of this key intermediate (7.15) via the Michaelis-Arbusov route.

7.1.2 Synthesis of the phosphonamides

Initial attempts to condense dimethyl 5-aminoisophthalate (7.23) with the phosphonochloridate (7.15) in the presence of triethylamine using the method of Doak (Ref. 178) resulted in very poor yields of the phosphonamidate (7.24) (ca.<10% ) (FIG. 7A7). Following addition of the phosphonochloridate (7.15) to a stirred suspension of the amine (7.23) and triethylamine in DCM, the reaction mixture rapidly turned a deep brown colour. $^{31}$P NMR showed that within 6 h of the addition, the chloridate had completely disappeared although only a low conversion into product (7.24) [$δ_p$ 23.23 (s)] was obtained after work up. This same brown colour (with fuming) was observed when triethylamine was added to the chloridate in isolation, suggesting that the tertiary amine was effecting a side reaction with the chloridate which was far faster than nucleophilic attack by the amine (7.23). The problems were compounded by poor solubility of (7.23) in most organic solvents making the reaction inherently slow. Initial modifications, using a less nucleophilic base (diisopropylamine) to replace triethylamine, improved the yield of the phosphonamidate (7.24) to ca. 20%.

7.1.2.1 4-Dimethylaminopyridine (DMAP) as an acylation catalyst

There are many reports of DMAP catalysing the acylation of alcohols, phenols, enolates, and isocyanates, but few examples exist for the acylation of amines (Ref. 187,188). Litvinenko and Kirichenko (Ref. 189) have shown that enormous increases in the observed rate of amine acylations occur when DMAP is used as a catalyst in aprotic solvents. These authors have determined the relative rate constants (in parentheses) for the amine-catalysed acylation of m-chloroaniline with benzoyl chloride in benzene to be N,N,-dimethylaniline (0.1); triethylamine (0.072); 2,6-dimethylpyridine (0.03); pyridine (1.80); 4-methylpyridine (10.0); and DMAP (10 600).

Höfle et al. (Ref. 188) have reported unpublished results on the catalytic effect of DMAP on the phosphorylation of 1,1-bis(p-nitrophenyl)hydrazine (7.25) with diethyl chlorophosphate (7.26) (FIG. 7A8). The desired hydrazine derivative (7.27) was not formed in repeated attempts with pyridine or triethylamine alone. Therefore, the reaction between the phosphonochloridate (7.15) and dimethyl 5-aminoisophthalic acid (7.23) was attempted with triethylamine as base and DMAP (10% mol equivalent) as a catalyst. Almost complete acylation of the amine (7.23) occurred with the yields of the phosphonamidate (7.25) being increased to 60% in a reduced reaction time.

When the reactions between the phosphonochloridate (7.15) and either dimethyl or dibenzyl L-glutamate (7.28 and 7.29 respectively) were carried out in the presence of triethylamine alone, the yields of the phosphonamidates (7.30 and 7.31) were ca. 60 to 75% respectively and the reactions were complete within 4 to 6 h. The relative success of these phosphorylations comparative to that achieved with the aniline (7.23), was attributed to the increased solubility and nucleophilicity of the alkylamines (7.28 and 7.29). The results for the condensation of the L-glutamic derivatives are in accord with the observations of Elliot et al. (Ref. 177) who have synthesised a series of peptide ACE inhibitors (7.32–7.34). They reacted the phosphonochloridate (7.35) and a protected amino acid in the presence of triethylamine and found that the yields varied from 47–75%, with reaction times varying from 5 to 72 h (Table 7.1).

The reactions of L-glutamic esters (7.28 and 7.29) with the phosphonochloridate (7.15) were repeated with DMAP to see if the catalysis observed for the formation of (7.24) would be repeated. In both cases, the yields were improved and the reaction times were reduced (Table 7.2).

The synthetic routes from the phosphonamidates, (7.23), (7.28) and (7.29), to the target compounds (7.2–7.9) presented distinct aspects and therefore, from this point onward, the discussion treats the isophthalic acid and the L-glutamic acid series separately.

7.1.3 Routes to the isophthalic acid series

The synthesis of the isophthalate series of haptens was to follow the scheme outlined in FIG. 7A9.

The phosphonamidate (7.24) was smoothly reduced with hydrogen and Adam's catalyst to the aniline (7.36) in near quantitative yield after similar attempts with a palladium on carbon (Pd/C) catalyst had proved unsuccessful (FIG. 7A9). Reduction prior to deesterification gave (7.37) in higher overall yield (83%) than that (28%) for the alternate route involving deesterification to (7.38) as the first step.

The purification of the deprotected product (7.38) by h.p.l.c. was very low yielding. There are many literature reports highlighting the instability of phosphonamidates after deesterification. As free phosphonamidic acids, they suffer from considerable decomposition during reversed-phase, ion-exchange, or silica gel chromatography (Ref. 155,156,175,177,185). However, we found that the free dicarboxylic acid (7.38) also suffered from decomposition on the h.p.l.c. column. It was felt that this could have been caused by the use of 0.1% TFA in the eluant but subsequent runs without TFA showed similar decomposition. Three major fractions were isolated and characterised. Fraction one (r.t. 2.14 min): ethyl (4-nitrophenylmethyl)-phosphonic acid (7.17). Fraction 2 (r.t. 4.31 min): the required deesterified phosphonamidate ester (7.38), Fraction 3 (r.t. 5.59 min): the 5-aminoisophthalic acid (7.39).

The isolation of these products confirmed that the P-N linkage had been hydrolysed. Professor Mike Page (Ref. 190) has studied the effect of hydroxide ion on the hydrolysis of acyclic and cyclic phosphonamidates. He has shown that the acyclic phosphonamidate (7.40) hydrolyses exclusively by P-O fission and with a second-order rate constant, consistent with hydroxide attack at phosphorus and loss of alkoxide (FIG. 7A10). By contrast, the strained cyclic phosphonamidate (7.41) hydrolyses exclusively with P—N bond fission. These data suggest that the hydrolysis of the phosphonamidate (7.38) is occurring on the h.p.l.c. column, not during the NaOH mediated deesterification reaction.

After reduction and deprotection of (7.24), the resultant phosphonamidate (7.37) was purified by m.p.l.c. on a DEAE-Sephadex column. This yielded the stable bis-triethylammonium salt of the phosphonamidate which was identified by $^{31}$P and $^{1}$H NMR. A sample of this compound was then converted into the di-sodium salt by the technique of Langston (Ref. 191) for characterisation. No attempt was made to generate the free carboxyl groups for risk of the acid hydrolysis, as described previously.

The triethylammonium salt of the phosphonamidate (7.37), which was soluble in DMF, was then reacted with triethylamine and 5-[(2',5'-dioxo-1'-pyrrolidinyl)oxy]-5-oxopentanoyl chloride (7.42) which had been synthesised in two steps from glutaric anhydride (7.43) and N-hydroxysuccinimide (7.14) in an overall yield of 16% (FIG. 7A11).

This yielded a crude residue which showed significant decomposition during purification attempts on silica gel, DEAE Sephadex, and ODS spherisorb reversed-phase h.p.l.c. columns. Fortunately, because the earlier parts of the synthesis had been relatively high yielding, a significant amount of the reduced phosphonamidate could be sacrificed in an attempt to generate enough of pure hapten 1 (7.2) for immunisations and for subsequent phosphonamidate deprotection to yield hapten 2 (7.4), purified by semi-preparative h.p.l.c. The phosphorus ester deesterification of (7.2) was problematic. The standard methods employed for removal of phosphonate and phosphinate esters such as refluxing in concentrated HCl (Ref. 192) or stirring in 2M NaOH (Ref. 184) were completely inappropriate for this molecule due the P-N bond and the N-hydroxysuccinimide linkage respectively. There are only a few neutral methods (Ref. 193) available for deesterification of phosphonates, of which the classical approach involves the use of trimethylsilyl halides (Ref. 194–196).

The deprotection is carried out routinely for phosphonates using romotrimethylsilane (TMSBr) in either $CCl_4$ or DCM. Although only one equivalent of TMSBr is required per alkyl ester function (FIG. 7A12), the literature shows examples of where up to 20 equivalents have been used which indicates the sluggishness of the reaction (Ref. 197, 198). The mechanism by which TMSBr (and indeed chloro- and iodo-trimethylsilane) deesterifies phosphorus esters such as (7.45) involves nucleophilic displacement of bromide from silicon by the phosphoryl oxygen (Ref. 199,200). The phosphonium bromide intermediate (7.46) generated undergoes a second bimolecular nucleophilic displacement reaction to yield the trimethylsilyl ester (7.47) which is readily solvolysed with methanol or water to afford the free phosphinic acid (7.48) (FIG. 7A12). This is purified by the addition of a base such as cyclohexylamine and subsequent recrystallisation (Ref. 201). These pure cyclohexylammonium salts can be converted smoothly into their sodium salts in aqueous sodium hydroxide solution, with removal of cyclohexylamine by organic solvent extraction. After neutralisation of the strongly basic aqueous solution with a cation exchange resin (H+ form), the required phosphonic acid (7.48) is obtained as its sodium salt.

Hapten 1 (7.2) contains both a phosphorus and a carboxylate ester and it has been reported that selectivity in removal of these functions is limited when using TMSBr (Ref. 196). Furthermore, Olah (Ref. 202) and Jung (Ref. 203) have reported that carboxylic acid esters can be hydrolysed by TMSI under mild conditions (25°–50° C.). This suggested that TMSCl would offer the best selectivity but, perhaps, with the slowest reaction time. Therefore initial attempts to selectively deesterify (7.2) involved stirring at room temperature with one equivalent of TMSCl in DCM. However, no dealkylation of the trimethylsilyloxyphosphonium chloride intermediate was detected by $^{31}P$ NMR. (Ref. 204). LiI was added in an attempt to generate TMSI in situ (Ref. 205) to accelerate the reaction but no further dealkylation was seen. Therefore, following the example of Janda (Ref. 206) for the deesterification of phosphonamidates in the presence of activated esters, the reaction was performed with 1.2 eq. of TMSBr at room temperature. After 3 days ca. 70% of the phosphonamidate had been dealkylated. A further equivalent of TMSBr was added and this was sufficient to complete the conversion. Repeated evaporation of the volatiles and solvolysis with $NaHCO_3$ to create a basic solution yielded the crude residue as a salt which was purified by h.p.l.c. to give the phosphonamidate [hapten 2, (7.4)] as the free acid. This was converted into the trisodium salt to prevent decomposition and to enhance water solubility for conjugation to the carrier protein.

The synthesis of the hapten derivatives required for ELISA (7.6 and 7.7) and BIAcore (7.50) was relatively straightforward. The phosphonamidate (7.37) was smoothly deesterified with TMSBr as described above to give (7.50) in acceptable yields (44%). The phosphonamidate intermediate (7.49) was synthesised in good yield (58%) by acylation of the aniline derivative (7.36) with 5-[(2',5'-dioxo-1'-pyrrolidinyl)oxy]-5-oxopentanoyl chloride (7.42) in the presence of triethylamine (FIG. 7A13) and was sufficiently stable to allow purification of the crude residue by silica gel chromatography. By utilising the method of Jacobsen and Marlowe, (Ref. 175) who reported the selective deesterification of carboxylic acid esters in phosphonopeptides, the methyl esters of the phosphonamide (7.49) were smoothly dealkylated with LiOH in excellent yields (77%) whilst leaving the phosphorus ester untouched. The crude residue was purified by m.p.l.c. and a solution of the resulting triethylammonium salt of (7.6) was converted into the trilithium salt by addition of ca. 1 equivalent of 1M LiOH per acid function, followed by lyophilisation. Initial attempts to produce (7.7) by the same procedure were ineffective. Jacobsen and Marlowe (Ref. 175) had reported successful hydrolysis of a phosphonamidate ethyl ester by increasing the concentration of LiOH used to deesterify the carboxylic acid esters. However repeated attempts with increasing base strength resulted only in the isolation of (7.6).

Ultimately, the synthesis of (7.7) was achieved by using an excess of TMSBr (8 eq.) and stirring the reaction mixture at 35° C. for 6 days. The phosphonamidate was sufficiently stable to allow purification on m.p.l.c. and was converted into the tetra-sodium salt for stability and to increase the water solubility of the compound.

7.1.4 Routes to the L-glutamic acid series

The starting point in the route to the glutamate series was the phosphonamidate (7.30), the synthesis of which was described earlier (Section 7.1.2). It was hoped that by reduction to the aniline derivative (7.51) and selective deesterification by methods already described, the phosphonamidate (7.52) would be produced very readily (FIG. 7A14). The reduction to the aniline derivative (7.51) was high yielding (84%), with the phosphonamidate being sufficiently stable to allow purification by silica gel chromatography. However, repeated attempts to deesterify with LiOH (Ref. 175) or with NaOH proved fruitless. Other methods including refluxing with LiCl and lutidine in toluene (Ref. 207) and refluxing with NaCl in pyridine were also unsuccessful. Therefore this intermediate (7.30) was replaced with the dibenzyl analogue (7.31), synthesised as described previously (Section 7.1.2).

The new path to the haptens envisaged reduction as both deprotecting the carboxylates and generating the amine in one step, to be followed by condensation with the linker (7.42) to give hapten 3 (7.3) and deprotection to give hapten 4 (7.5) (FIG. 7A15). Initial attempts to reduce both the aromatic nitro group and debenzylate the carboxylic acid esters of (7.31) by hydrogenation in MeOH with $PtO_2$ were successful. Unfortunately, the product was unstable and, following evaporation to dryness, a preliminary $^{31}P$ NMR seemed to show the presence of two components. Analysis by h.p.l.c. confirmed the presence of both the target phosphonamidate (7.52) (r.t. 2.97 min) and ethyl (4-aminophenylmethyl)phosphinic acid (r.t. 3.87 min). This result was confirmed by mass spectroscopic analysis which showed a molecular ion (m/z) of 216. To avoid this hydrolysis, the method of Elliot (Ref. 177) was adopted where the reduction is performed in aqueous ethanol with the addition of $NaHCO_3$ (2 eq.). This gave the disodium salt of the phosphonamidate (7.52) in good yields (58%) with minimal hydrolysis.

This phosphonamidate salt was then reacted with the acyl chloride (7.42) in DMF by the same procedure mentioned above (Section 7.1.3), to give hapten 3 (7.3) in good yield (62%) after purification by semi-preparative h.p.l.c. Surprisingly, little decomposition of the phosphonamidate was seen on the reverse-phase column. Therefore attempts have been made to recrystallise the hapten as the free acid from isopropanol/ether for the purpose of X-ray analysis.

The synthesis of hapten 4 (7.5) was achieved by TMSBr deprotection of hapten 3 (7.3) in acceptable yield (58%) by the method described earlier for the synthesis of hapten 2 (7.4) (Section 7.1.3). The compound (7.5) was purified by h.p.l.c. and converted into the trisodium salt to increase its stability and water solubility for conjugation to carrier proteins. Having generated the L-glutamate haptens, the corresponding compounds (7.8 and 7.9) for ELISA were produced by deesterification of the N-hydroxysuccinimide ester of the corresponding hapten in 1M NaOH with good yields (ca. 68%).

7.2 Synthesis of Substrates
7.2.1 Routes to the substituted aryl carbamates

The synthesis of the target aryl carbamate esters (7.53–7.57) involved N-substitution of 5-aminoisophthalic acid (7.39) with a para-substituted phenoxycarbonyl group (FIG. 7B1). Carbamate esters are widely used, especially in peptide synthesis, as nitrogen protecting groups. Common examples include the benzyloxycarbonyl, or 'Z' group, and the tert-butyloxycarbonyl or 'Boc' group. In amino acid chemistry, the more active nitrogen function is usually protected before the carboxylic acid which would allow the synthesis of compounds (7.53–7.57) to be a one step process. However, such urethane forming reactions between a chloroformate or dicarbonate and an amino acid take place under Schotten-Baumann conditions where the aqueous layer is ca. pH 9. Aryl carbamates, unlike their benzyl and t-butyl counterparts are very base sensitive by virtue of their E1cB mechanism of breakdown; therefore their synthesis via this route results in very low yields (Ref. 208).

Hansen (Ref. 209) and Kruse (Ref. 210) have developed a direct method of combination, using one equivalent of a phenyl chloroformate and two equivalents of amine in anhydrous ethyl acetate for the synthesis of a series of phenyl carbamates of amino acids. They found that they could improve the yields of compounds previously synthesised by the Schotten-Baumann procedure from 5–25% to 31–67%.

Initial attempts to make the carbamates (7.53) and (7.54) adopted this direct route (FIG. 7B2). The virtual insolubility of 5-aminoisophthalic acid in ethyl acetate and in most other organic solvents resulted in incomplete reactions and tremendous difficulty in isolating the carbamate products, which showed the same solubility problems as the starting material. Very low yields were isolated by purification using reverse phase h.p.l.c.

It was inevitable that the solubility of the starting material had to be improved and this necessitated esterification of the carboxylate groups. Initially, this was attempted by the use of the readily available dimethyl 5-aminoisophthalate (7.23). Unfortunately, the solubility characteristics of this ester were not too different from that of the parent acid which meant that low yields and difficulties in isolating the carbamates were still a problem. In addition, the methyl esters were stable to neutral hydrolysis conditions such as NaI or LiCl in pyridine, hydrazine, etc. Because alkaline hydrolysis was not an option, other protecting groups were sought. The tert-butyl ester (7.59) is very lipophilic and is acid labile, being rapidly hydrolysed in TFA (Ref. 211).

The di-tert-butyl ester of 5-aminoisophthalate was successfully synthesised by reaction of (7.39) with isobutylene in chloroform in the presence of an acid catalyst (Ref. 212,213). The reaction was low yielding because of the low solubility of the amine in the reaction solvent. The di-tert-butyl ester (7.59) was then coupled with the chloroformates of 4-fluoro- and 4-methoxyphenol to yield the respective carbamates after deprotection with 1–10% TFA in good yields (FIG. 7B2). The complete solubilisation of the amine starting material markedly enhanced the rate of reaction.

The dibenzyl ester derivative (7.60) was sought as another easily modifiable starting material. However, its preparation required three steps which gave an overall yield of only ca. 20% (FIG. 7B3). Reaction with a substituted chloroformate and subsequent reduction led to the isolation of (7.56) and (7.57) in good yields (ca. 91%).

7.2.1.1 Physical properties of the carbamates.

The isophthalic acid derived carbamates are high melting (>300° C.) solids, yet their FAB mass spectra always show a high degree of decomposition to starting material (7.39) and the corresponding phenol. Consequently, high resolution mass spectra was not obtained to confirm the identity of these substrates. Analyses on most of these compounds is provided in the form of LRMS and analytical h.p.l.c. analysis coupled with $^1H$ NMR.

7.2.2 Preparation of the urea (7.65) and the amide (7.66) substrate analogues

The syntheses of this pair of more-stable compounds were less problematic and allowed the employment of the dimethyl ester of 5-aminoisophthalic acid (7.23), which is readily obtained in 85% yield. Coupling of the amine (7.23) with 4-nitrophenylisocyanate alone or phenylacetyl chloride with N-ethylmorpholine yielded the urea (7.65) and the amide (7.66) respectively after alkaline deprotection (FIG. 7B4).

7.3 Materials and Methods
7.3.1 Materials

All solvents required in the following reactions were dried and distilled before use as described in either Vogel's Textbook of Practical Chemistry (Ref. 214) or Casey's Advanced Practical Organic Chemistry (Ref. 215). Solvents used for chromatography were distilled before use.

Melting points were measured on a Koffler hot stage micro-melting point apparatus and are uncorrected.

Infra-red spectra were recorded on a Perkin-Elmer 457 grating infra-red spectrometer. The spectra were recorded with the samples as nujol mulls or thin films on sodium chloride plates, or as potassium bromide discs.

Proton NMR and carbon-13 NMR spectra were recorded on either a Bruker AM-250 or a Bruker AC-250 spectrometer at 250 MHz and 62.5 MHz respectively. All chemical shifts are reported using the δ scale in parts per million (ppm) with respect to tetramethylsilane (TMS) except when $D_2O$ was used as solvent. In this case 2,2-dimethyl-2-silapentane-5-sulphonate was used as the reference sample. Coupling constants (J) refer to vicinal proton-proton coupling ($3J_{H,H}$) in Hertz (Hz) unless otherwise stated. The following abbreviations are used to describe signal splitting: s, singlet; d, doublet; t, triplet; q, quartet; qui, quintet; and m, multiplet.

Phosphorus-31 NMR spectra were recorded on either a Bruker AM-250 or a Bruker AC-250 spectrometer at 101 MHz or a Bruker WP80SY spectrometer at 32.4 MHz. Chemical shifts (deltaP) are quoted in ppm downfield from 85% $H_3PO_4$ as external reference.

Chemical ionisation (CI), electron impact (EI) and electrospray (ES) mass spectra were recorded on either a Kratos MS25 or a Fisons Instruments Prospec 3000 mass spectrometer. Fast atom bombardment (FAB) mass spectra were recorded on a Kratos MS80RF mass spectrometer or a Fisons Instruments Prospec 3000 mass spectrometer in conjunction with a DS55 Data Station.

$R_F$ Values were obtained with either Merck Art. 5719 DC-Fertigplatten Kieselgel 60 $F_{254}$ silica gel plates or reversed-phase C-18 200 μm silica plates. Localisation of spots was effected by u.v. light or alkaline potassium permanganate spray.

Column chromatography was performed using Kieselgel 60, 230–400 mesh (Merck 385). H.p.l.c. was performed using a Spherisorb or Technosphere ODS column (4.6 mm×25 cm or 20 mm×25 cm) with a 0 to 100% water/acetonitrile gradient and 0.1% TFA as eluant. A flow rate of 2 ml min-1 was used and the eluant monitored at 254 nm.

Medium pressure liquid chromatography (m.p.l.c.) was performed using a DEAE A25 sephadex column (6 cm×30 cm) and linear gradients of triethylammonium bicarbonate buffer (TEAB). A flow rate of 10 ml min$^{-1}$ was used and the eluant was collected in 10–15 ml fractions and monitored at 254 nm.

TEAB (2M) was prepared by adding triethylamine (557 ml, 4 mol) to distilled water (1.2 L) in a glass vessel surrounded by ice. The mixture was stirred and $CO_2$ was bubbled through until the two phases mixed and a pH of 8.0 was achieved. The buffer was then diluted to a final volume of 2 L.

U.v. spectra were measured on a Philips PU8720 scanning spectrophotometer using 1 ml quartz cuvettes (1 cm pathlength). Molar absorbance coefficients (epsilon) are quoted in cm$^2$ mol$^{-1}$.

Carbon, hydrogen and nitrogen combustion analysis was performed on a Perkin Elmer 2400 elemental analyser to an accuracy of ±0.4%.

7.3.2 METHODS 7.3.2.1 SYNTHESIS OF HAPTENS

Routes to the phosphonochloridate (7.15).
Dimethyl 5-aminoisophthalate hydrochloride (7.23).

Thionyl chloride (1.8 g, 15 mmol) was added dropwise to stirred methanol (30 ml) with the temperature maintained at −10° C. When addition was complete, the reaction mixture was allowed to warm to room temperature and 5-aminoisophthalic acid (7.39) (1.0 g, 4.7 mmol) was added via a powder funnel. The mixture was heated under reflux for 45 min and then solvent removed in vacuo. All traces of HCl and thionyl chloride were removed by repeated washings with methanol (5×50 ml). After final evaporation of solvent this yielded the title compound which recrystallised (methanol/diethyl ether) as a white crystalline solid (needles) (1.0 g, 85%). M.p. 176°–178° C. (Ref. 216) m.p. 179°–182° C.); m/z (+FAB) 210 (100%, M+H+) 209 (90%, M) 178 (26%, M-MeO); numax (nujol mull, cm$^{-1}$) 1720 (ester); δH (250 MHz, $CD_3OD$), 4.00 (6H, s, 2×$CH_3$), 8.25 (2H, s, ArH), 8.65 (1H, s, ArH); δC (62.5 MHz, δ6-DMSO) 53.0, 124.0, 124.4, 131.6, 140.6, 165.5; $R_F$ 0.8 [ethyl acetate/petrol 40–60 (1:1)].

Diethyl (4-nitrophenyl)methylphosphonate (Ref. 179) (7.16).

METHOD 1 (Ref. 180,217)

Freshly distilled triethyl phosphite (7.20) (6.0 ml, 51 mmol) and benzyl bromide (7.19) (7.1 ml, 60 mmol) were heated under reflux for 10 h. The excess phosphite and volatiles were removed under reduced pressure to yield a pink oil (10.4 g) which was distilled by Kugelrohr to give diethyl (phenylmethyl)phosphonate (7.18) as a pale pink oil (12.2 g, 90%). B.p. 105°–108° C. @ 1 mm (lit. ref.179) b.p. 106°–108° C. @ 1 mm); m/z (+EI) 227 (M); $v_{max}$ (thin film, cm$^{-1}$) 1250 (b, P=O), 1025 (b, P—O-alkyl); δH (250 MHz, $CDCl_3$) 1.15 (6H, t, J 7.5 Hz, 2×$CH_3$), 3.15 (2H, d, $2J_{PH}$ 22.5 Hz, Ar—$CH_2$), 3.90 (4H, dq, $J_{HP}$ 8.5 Hz, J 7.5 Hz, 2×$OCH_2$), 7.15–7.40 (5H, bm, 5×Ar—H); δP (101 MHz, $CDCl_3$) 24.49 (s) The phosphonate (7.3) (5.0 g, 22 mmol) was then added dropwise with cooling to a stirring mixture of concentrated nitric and sulphuric acids [50 ml (1:1 v/v)] at 0° C. The mixture was allowed to warm to room temperature and stirred for a further 1 h. The reaction was poured onto ice and extracted into toluene (3×100 ml). The combined organic fractions were washed with water (3×50 ml) and saturated $NaHCO_3$ (3×50 ml) and dried over $MgSO_4$. Removal of toluene under reduced pressure yielded a pale green oil (5.3 g, 88%) which was found to be a mixture of the title compound and its ortho isomer in a molar ratio of ca. 85:15 respectively (determined by $^{31}P$ NMR). Analysis by TLC in a range of solvent systems failed to separate the two isomers. Repeated attempts to purify the mixture by silica gel chromatography were of limited success, only increasing the isomeric ratio to 90:10 (overall yield, 71%).

METHOD 2 (Ref. 183)

Freshly distilled diethyl phosphite (7.22) (6.0 ml, 51 mmol) was added dropwise to freshly prepared sodium powder (1.2 g, 51 mmol) in toluene (50 ml). The reaction was heated under reflux until all the sodium had dissolved (4–6 h). The toluene was allowed to cool to room temperature and p-nitrobenzyl bromide (7.21) (13.0 g, 60 mmol) was added and the mixture heated under reflux for 6 h. The toluene was removed under reduced pressure to give a colourless oil, purified by distillation to yield the title compound as a colourless oil (9.0 g, 65%). B.p. 150°–152° C. @ 0.1 mm (lit. ref. 217) b.p. 148°–153° C. @ 0.1 mm); m/z (+EI) 273 (M); $^{nu}{max}$ (thin film, cm$^{-1}$) 1510 (asymm, C—$NO_2$), 1350 (symm, C—$NO_2$), 1250 (P=O), 1025 (b, P—O-alkyl); δH (250 MHz, $CDCl_3$) 1.15 (6H, t, J 7.5 Hz, 2×$CH_3$), 3.15 (2H, d, $2J_{PH}$ 22.5 Hz, Ar—$CH_2$), 3.90 (4H, dq, $J_{HP}$ 8.5 Hz, J 7.5 Hz, 2×$CH_2$), 7.30 (2H, d, J 7.5 Hz, 2×Ar—H), 8.00 (2H, d, J 7.5 Hz, 2×Ar—H); δP (101 MHz, $CDCl_3$) 24.59 (s); $R_F$ 0.35 [ethyl acetate/petrol 40–60 (1:1)].

Ethyl (4-nitrophenyl)methylphosphonochloridate (7.15)

This method is a modification of that outlined by Doak and Freedman (Ref. 178). Diethyl (p-nitrophenyl) methylphosphonate (7.16) (1.0 g, 3.6 mmol) in DCM (10 ml) was added dropwise to a solution of $PCl_5$ (0.9 g, 4.32 mmol) in $CCl_4$ (20 ml) under an inert atmosphere. The reaction was stirred at 30° C. and the progress of the chlorination was followed by $^{31}P$ NMR which showed the reaction was complete after 24 h. Solvent and phosphoryl chloride were removed in vacuo to yield a pale yellow, moisture-sensitive oil (0.8 g, 90%) which was used without further purification. δH (250 MHz, $CDCl_3$) 1.40 (3H, t, J 7.5 Hz, $CH_3$), 3.60 (2H, d, $2J_{PH}$ 22.5 Hz, Ar—$CH_2$), 4.25–4.43 (2H, m, $J_{HP}$ 8.5 Hz, J 7.5 Hz,CH2), 7.5 (2H, d, J 7.5 Hz, Ar—H), 8.20 (2H, d, J 7.5 Hz, Ar—H); δP (101 MHz, $CDCl_3$) 35.94 (s).

Synthesis of the phosphonamides.
Ethyl N-[(3,5-dimethoxycarbonyl)phenyl]-P-(4-nitrophenylmethyl)phosphonamidate (7.24).

Two methods were used to prepare the title compound (7.24), the second was by far the more successful:
METHOD 1 (Ref. 178).

Ethyl (4-nitrophenyl)methylphosphonochloridate (7.15) (3.7 g, 14 mmol) was dissolved in CCl4 (20 ml) under an atmosphere of nitrogen. The solution was cooled to −10° C. and dimethyl 5-aminoisophthalate (7.23) (2.9 g, 14 mmol) and triethylamine (3.0 g, 30 mmol) were added as a suspension in anhydrous THF (250 ml), with cooling. The reaction was stirred at 30° C. and followed by $^{31}$P NMR. After 22 h, all of the. phosphonochloridate (7.15) had disappeared [$\delta_P$ (101 MHz, CDCl$_3$) 35.94 (s)]. The reaction mixture was concentrated under reduced pressure, filtered to remove triethylamine hydrochloride, and the filtrate evaporated in vacuo. The brown residue was dissolved in CHCl$_3$ (50 ml), washed with water (3×50 ml), 1M HCl (3×50 ml), NaHCO$_3$ (3×50 ml) and finally brine (2×50 ml). The organic phase was then dried (MgSO$_4$), filtered, and evaporated to dryness in vacuo to yield a dark brown oil (3.2 g). The residue was purified by silica gel chromatography using mixtures of ethyl acetate/petrol 40–60 (1:2) as eluant. Evaporation of the solvent in vacuo yielded a pale yellow solid (1.4 g) which was recrystallised from a mixture of DCM and petrol 40–60 to give the title compound as a white powder (0.6 g, 10%).
METHOD 2

The phosphonochloridate (7.15) (5.0 g, 19 mmol) was dissolved in CHCl$_3$ (25 ml) under an atmosphere of nitrogen. The solution was cooled to −10° C. and dimethyl 5-aminoisophthalate (7.23) (2.9 g, 47.5 mmol), triethylamine (3.0 g, 30 mmol) and 4-dimethylaminopyridine (DMAP) (0.2 g, 1.9 mmol) were added as a suspension in anhydrous THF (250 ml), with cooling. The reaction was stirred at room temperature and monitored by $^{31}$P NMR. The reaction was complete after 2 h. The reaction mixture was concentrated under reduced pressure and filtered to remove the amine hydrochloride (7.23). The remaining solvent was evaporated in vacuo. The brown residue was dissolved in DCM (100 ml), washed with water (3×50 ml), 1M HCl (3×50 ml), NaHCO$_3$ (3×50 ml), and brine (2×50 ml). The organic phase was then dried (MgSO$_4$), filtered, and evaporated to dryness in vacuo to yield a tan oil. The residue was purified by recrystallisation from DCM/petrol 40–60 to give the title compound as a white powder (5.6 g, 68%). M.p. 152.8°–153.1° C.; m/z (+FAB) 437 (85%, M+H$^+$), 436 (48%, M), 406 (38%, M+H$^+$-OMe), 405 (95%, M-OMe), 377 (100%, M-2OMe+2H$^+$); [Found: (M)+, 436.1038. C$_{19}$H$_{21}$N$_2$O$_8$P requires (M) 436.1036]; v$_{max}$ (KBr disc, cm$^{-1}$) 1720 (s, ester), 1520 (asymm., NO$_2$), 1350 (symm., NO$_2$), 1250 (P=O), 1120 (P—O-alkyl); δH (250 MHz, CDCl$_3$) 1.25 (3H, t, J 7.5 Hz, CH$_3$), 3.35 (2H, d, 2J$_{PH}$ 22.5 Hz, Ar—CH$_2$), 4.05–4.25 (2H, m, J$_{HP}$ 8.5 Hz, J 7.5 Hz, CH$_2$), 7.0 (1H, b, NH), 7.25 (2H, d, J 7.5 Hz, 2×Ar—H), 7.85 (2H, s, 2×Ar—H), 8.0 (2H, d, J 7.5 Hz, 2×Ar—H), 8.25 (1H, s, Ar—H); δC (62.5 MHz, CDCl$_3$) 16.0 (d, 3J$_{CP}$ 6.8 Hz), 34.2 (d, 1J$_{CP}$ 124.5 Hz), 52.6, 61.5 (d, 2J$_{CP}$ 7.04 Hz, OCH$_2$), 122.2, 123.5, 123.7, (d, 2J$_{CP}$ 6.2 Hz, ArCH), 130.7, (d, 3J$_{CP}$ 6.0 Hz), 131.9, 139.1 (d, 2J$_{CP}$ 12.6 Hz), 140.9, 146.9 165.9; δP (101 MHz, CDCl$_3$) 23.23 (s); Calcd. for C$_{19}$H$_{21}$N$_2$O$_8$P: C, 52.30; H. 4.84; N, 6.42; Found: C, 52.09; H, 4.85; N, 6.40; R$_F$ 0.35 [ethyl acetate/petrol 40–60 (1:1)].

Ethyl N-[(1 S)-(1,3-dimethoxycarbonyl)propyl]-P-(4-nitrophenylmethyl)-phosphonamidate (7.30) (FIG. 7A14)

Two methods were used to synthesise the title compound (7.30), the use of DMAP in the second procedure improved the yield for the reaction.

METHOD 1:

A mixture of dimethyl L-glutamate hydrochloride (7.28) (10.0 g, 50.7 mmol) and Et$_3$N (11.5 g, 110.4 mmol) was dissolved in anhydrous CHCl$_3$ (150 ml) and stirred vigorously for 30 min. This mixture was then added dropwise to a solution of the phosphonochloridate (7.15) (15.9 g, 68.4 mmol) in CHCl$_3$ (20 ml) at −10° C., under an inert atmosphere. Once the addition was complete the reaction mixture was warmed to room temperature and stirred for 8 h. The reaction was worked up as described in method 1 above for the phosphonamidate (7.24) to give a pale yellow solid (15 g). The residue was purified by silica gel chromatography using ethyl acetate/petrol 40–60 (1:2) as eluant. This yielded the title compound as a yellow powder (10.4g, 60%).
METHOD 2:

Compound 7.29 (2.0 g, 4.0 mmol) was reacted with phosphonochloridate (7.15) (1.1 g, 4.2 mmol) by method 2 described above for the synthesis of phosphonamidate (7.24) and gave the title compound as a pale yellow solid (83%). M.p. 157.7°–158.0° C.; m/z (+FAB) 425 (20%, M+Na$^+$), 403 (100%, M+H$^+$), 342 (28%, M-2OMe+2H$^+$); [Found: (M)+, 403.1272. C$_{16}$H$_{24}$N$_2$O$_8$ requires (M) 403.1270]; v$_{max}$ (KBr disc, cm$^{-1}$) 1740 (ester), 1510 (asymm., NO$_2$), 1350 (symm., NO$_2$), 1220 (P=O), 1125 (P—O-Alkyl); dH (250 MHz, CDCl$_3$) 1.20 (3H, t, J 7.5 Hz, CH$_3$), 1.80–2.05 (2H, m, 2Hβ), 2.23–2.38 (2H, m, 2Hδ), 2.90 (2H, d, 2J$_{PH}$22.5 Hz, Ar—CH$_2$), 3.65 (3H, s, OCH3), 3.75 (3H, s, OCH$_3$), 3.90–4.10 (3H, m, Hα, OCH$_2$CH$_3$), 7.55 (2H, d, J 7.5 Hz, 2×Ar—H), 8.15 (2H, d, J 7.5 Hz, 2×Ar—H); δC (62.5 MHz, CDCl$_3$) 16.60 (d, 3JCP 6.8 Hz, OCH$_2$CH$_3$), 29.54, 29.62, 36.3 (d, $^2$J$_{CP}$ 125 Hz), 53.2, 53.64, 53.55, 60.85 (d, 2JCP 7.0 Hz), 123.65, 130.59, 140.21 (d, $^2$J$_{CP}$ 8.8 Hz) 146.91, 170.23, 172.09; δP (101 MHz, CDCl$_3$) 26.80 (s); Calcd. for C$_{16}$H$_{23}$N$_2$O$_8$P: C, 47.75; H, 5.76; N, 6.97; Found: C, 48.02; H, 5.72; N, 6.78. R$_F$ 0.37 [DCM/methanol (95:5)]; h.p.l.c. r.t. 15 min.

Ethyl N-[(1S)-(1,3-dibenzyloxycarbonyl)propyl]-P-(4-nitrophenyl-methyl) phosphonamidate (7.31)

METHOD 1:

The p-toluenesulfonate salt of dibenzyl L-glutamic acid ((7.29) (10.0 g, 20.0 mmol) was dissolved in a solution of Et$_3$N (0.6 ml, 4.4 mmol) in DCM (20 ml) and stirred for 5 min at 0° C. This mixture was then reacted with the phosphonochloridate (7.15) (5.1 g, 22.0 mmol) by method 1 above, to yield the title compound 7.31 as a pale yellow solid (8.0 g, 74%).

METHOD 2:

Compound 7.28 (2.0 g, 10.3 mmol) was reacted with phosphonochloridate (7.15) (3.2 g, 12.0 mmol) by method 2 above, which gave the title compound 7.31 as a pale yellow solid (81%). M.p. 85.2°–85.9° C.; m/z (+ES) 577 (95%, M+Na+), 555 (37%, M+H+); [Found (M)+, 555.1902. C$_{28}$H$_{32}$N$_2$O$_8$P requires (M) 555.1896]; numax (KBr disc, cm$^{-1}$) 1740 (ester), 1735 (ester), 1510 (asymm., NO$_2$), 1350 (symm., NO2), 1220 (P=O), 1105 (P—O-alkyl); δH (250 MHz, CDCl$_3$) 1.20 (3H, t, J 7.5 Hz, CH$_3$), 1.70–2.0 (2H, bm, 2Hβ), 2.09–2.43 (2H, bm, 2Hg), 3.08 (2H, d, 2JPH 22.5 Hz, Ar—CH$_2$), 3.80–4.05 (3H, bm, Hα, OCH$_2$CH$_3$), 5.05 (2H, s, Ar—CH$_2$), 5.15 (2H, s, Ar—CH$_2$), 7.35 (12H, m, 12×Ar—H), 8.15 (2H, d, J 7.5 Hz, 2×Ar—H); δC (62.5 MHz, CDCl$_3$) 16.26 (d, 3JCP 6.8 Hz), 29.54, 29.63, 36.3 (d, $^1$J$_{CP}$ 125 Hz), 53.2, 60.85 (d, $^2$J$_{CP}$ 7.0 Hz), 60.81, 60.93, 123.60, 123.65, 128.25, 128.35, 128.44, 128.63, 128.67, 130.65 (d, $^2$J$_{CP}$ 6.8 Hz, ArCH), 135.0, 135.7, 140.25, 146.91, 172.28, 172.94; dP (101 MHz, CDCl$_3$) 26.70 (s); Calcd. for C$_{28}$H$_{31}$N$_2$O$_8$P: C, 60.63; H, 5.64; N, 5.04; Found: C, 60.35; H, 5.62; N, 5.02. R$_F$ 0.5 [DCM/methanol (95:5)]; h.p.l.c. r.t. 18.8 min.

Routes to the isophthalic acid series.
Ethyl N-[(3,5-dicarboxy)phenyl]-P-(4-nitrophenylmethyl)phosphonamidate (7.38).

Sodium hydroxide (0.5M, 4.0 ml, 2.0 mmol) was added to a solution of the phosphonamidate (7.24) (0.4 g, 0.9 mmol) in methanol (20 ml) and stirred at room temperature. After 24 h all of the phosphonamidate had disappeared (as shown by TLC) and the solvent was removed in vacuo to give a brown oil (0.3 g). The residue was purified by h.p.l.c., which gave 3 peaks. The fractions for each peak were combined and the solvent removed by lyophilisation.
The fractions were analysed as follows:
Fraction 1: (r.t. 2.14 min) was a white powder characterised as ethyl (4-nitrophenylmethyl)phosphinic acid (7.17). M.p. 155°–158° C. (lit.184 m.p. 156°–157° C.); m/z (+FAB) 246 (95%, M+H$^+$); numax (KBr disc, cm$^{-1}$) 1720 (ester), 1520 (asymm., NO$_2$), 1350 (symm., NO$_2$), 1250 (P=O), 1120 (P—O-alkyl); dH (250 MHz, CDCl$_3$) 1.25 (3H, t, J 7.5 Hz, CH$_3$), 3.35 (2H, d, 2JPH 22.5 Hz, Ar—CH$_2$), 4.05–4.17 (2H, dq, JHP 8.5 Hz, J 7.5 Hz, CH$_2$), 7.4 (2H, d, J 7.5 Hz, 2×Ar—H), 8.0 (2H, d, J 7.5 Hz, 2×Ar—H); dP (101 MHz, CDCl3) 23.83 (s).
Fraction 2: (r.t. 5.59 min) was a white solid characterised as 5-aminoisophthalic acid (7.39). δH (CD$_3$OD) 8.25 (2H, s, ArH), 8.65 (1H, s, ArH).
Fraction 3: (r.t. 4.31 min) was a pale yellow solid which recrystallised from ethyl acetate to give the title compound 7.38 as a pale yellow powder (120 mg, 28%). M.p. 226.2°–226.9° C.; m/z (+FAB) 431 (25%, M+Na$^+$), 409 (90%, M+H$^+$), 408 (95%, M); [Found: (M)+, 409.0801. C$_{17}$H$_{18}$N$_2$O$_8$P requires 409.0801]; vmax (nujol mull, cm$^{-1}$) 1690 (acid), 1510 (asymm., NO2), 1350 (symm., —NO$_2$), 1250 (b, P=O), 1105 (P—O-alkyl); δH (250 MHz, CD$_3$OD) 1.35 (3H, t, J 7.5 Hz, CH$_3$), 3.50 (2H, d, 2JPH 22.5 Hz, Ar—CH$_2$), 4.00–4.25 (2H, m, CH$_2$) 7.40 (2H, d, J 7.5 Hz, 2×Ar—H), 7.80 (2H, s, 2×Ar—H) 8.05 (2H, d, J 7.5 Hz, 2×Ar—H), 8.15 (1H, s, Ar—H); δC (62.5 MHz, CD$_3$OD) 16.67 (d, $^3J_{CP}$ 6.8 Hz), 34.79 (d, 1JCP 124.73 Hz), 61.55 (d, $^2J_{CP}$ 7.09 Hz), 122.15, 123.47, 123.53 (d, $^3J_{CP}$ 5.8 Hz), 130.63 (d, $^3J_{CP}$ 5.8 Hz, ArCH), 131.75, 139.00 (d, $^2J_{CP}$ 6.2 Hz), 140.94, 146.8, 168.23; (δP 101 MHz, CD$_3$OD) 28.37 (s); R$_F$ 0.35 [DCM/methanol (1:1)].

Ethyl N-[(3,5-dimethoxycarbonyl)phenyl]-P-(4-aminophenylmethyl)phosphonamidate (7.36)

The phosphonamidate (7.24) (1.8 g, 4.0 mmol) was added to a stirred suspension of Adam's catalyst (0.2 g, 10% w/w) in methanol (20 ml) and the reaction stirred under an atmosphere of H2 for 4 h. The catalyst was removed by filtration through Celite under an inert atmosphere and the filtrate was evaporated under reduced pressure to yield a white solid which recrystallised from petrol ether/ethyl acetate to give the title compound as white crystals (1.6 g, 100%). M.p. 66.6°–66.9° C.; m/z (+FAB) 407 (100%, M+H+), 406 (95%, M); [Found: 407.1376. C$_{19}$H24N$_2$O$_6$P requires 407.1372]; numax (nujol mull, cm$^{-1}$) 3250 (amine), 1710 (ester), 1250 (P=O), 1020 (P—O-alkyl); H (250 MHz, CD$_3$OD) 1.35 (3H, t, J 7.5 Hz, CH$_3$), 3.30 (2H, d, 2JPH 22.5 Hz, Ar—CH$_2$), 3.90 (6H, s, 2×OCH$_3$) 4.07–4.29 (2H, m, OCH$_2$CH$_3$) 6.90 (2H, d, J 7.5 Hz, 2×Ar—H), 7.20 (2H, d, J 7.5 Hz, 2×Ar—H), 7.85 (2H, s, 2×Ar—H), 8.15 (1H, s, Ar—H); δC (62.5 MHz, CD$_3$OD) 16.65 (d, 3JCP 6.3 Hz), 34.7 (d, 1JCP 125.78 Hz), 52.96, 62.62 (d, 2JCP 6.88 Hz), 114.53, 116.63, (d, 2JCP 5.8 Hz), 121.05, 123.93, 131.83 (d, 2JCP 6.0 Hz), 132.63, 143.63, 147.88, 167.46; δP (101 MHz, CD$_3$OD) 27.37 (s); Calcd. for C$_{19}$H$_{23}$N$_2$O$_6$P: C, 56.16; H, 5.70; N, 6.89; Found: C, 56.37; H, 5.62; N, 6.62. R$_F$ 0.37 [ethyl acetate/petrol 40–60 (1:2)].

Ethyl N-[(3,5-dicarboxy)phenyl]-P-(4-aminophenylmethyl)phosphonamidate, di-sodium salt (7.37).

The phosphonamidate (7.36) (0.5 g, 1.2 mmol) was dissolved in 20% aqueous MeOH (10 ml) and sodium hydroxide (0.1 g, 2.8 mmol) was added. The reaction was stirred for 2 d and then neutralised with ion-exchange resin (Amberlite 120-H). The reaction mixture was filtered through Celite and the solvent removed by lyophilisation to yield a pale yellow solid (0.4 g) which was dissolved in triethylammonium bicarbonate (TEAB) (0.05M, 10 ml) and chromatographed using a linear elution gradient (0.05M–0.5M, TEAB; 5 L) on a DEAE-sephadex column. The desired fractions were detected by u.v., combined, and evaporated to dryness under reduced pressure to yield a white solid (0.4 g). The bis-triethylammonium salt of the product, identified by 1 H NMR was, lyophilised and converted into its sodium salt by a modification of the method outlined by Langston: (Ref. 191). The TEA salt (100 mg) was dissolved in methanol (1 ml) and transferred to a centrifuge tube. Sodium iodide dissolved in acetone (1.0M, 5 ml) was added and the sodium salt of the phosphonamidate precipitated immediately. The solution was centrifuged (3000 rpm, 5.0 min) and the supernatant decanted to leave a pale yellow pellet, which was broken up into a powder. Fresh acetone was added and this process was repeated several times to yield the title compound 7.37 as a white powder (38 mg, 83%). M.p. 226.9227.8° C.; m/z (+FAB) 423 (95%, M+H$^+$), 401 (75%, M—Na$^+$+2H$^+$); numax (KBr disc, cm$^{-1}$) 1610 (carboxylate), 1250 (b, P=O), 1105 (P—O-alkyl); δH (250 MHz, CD$_3$OD) 1.25 (3H, t, J 7.5 Hz, CH$_3$), 3.35 (2H, d, 2JPH 22.5 Hz, Ar—CH$_2$), 4.03–4.27 (2H, m, CH$_2$), 6.4 (2H, d, J 7.5 Hz, Ar—H), 6.80 (2H, d, J 7.5 Hz, 2×Ar—H), 7.45 (s, 2H, 2×Ar—H), 7.80 (1H, s, Ar—H); δC (62.5 MHz, CD$_3$OD) 16.71 (d, 3JCP 6.3 Hz), 34.7 (d, 1JCP 123.46 Hz), 62.46 (d, 2JCP 6.98 Hz), 116.63 (d, 3JCP 5.8 Hz), 121.05, 123.75 (d, 3JCP 6.2 Hz), 123.93, 132.43 (d, 3JCP 6.0 Hz), 132.63, 142.93, 144.69, 168.86; δP (101 MHz, CD$_3$OD) 28.23 (s); R$_F$ 0.50 (reversed-phase C-18, 200 mm silica gel plates, 10% aqueous acetonitrile).

5-(2',5'-Dioxo-1'-pyrrolidinyl)oxy-5-oxopentanoyl chloride (7.42) (FIG. 7A11)

Triethylamine (9.1 ml, 65.1 mmol) was added dropwise to a stirred suspension of N-hydroxysuccinimide (7.14) (5.0 g, 43.4 mmol) and glutaric anhydride (7.43) (5.5 g, 47.8 mmol) in DCM (40 ml) and the solution stirred at room temperature for 24 h. The reaction mixture was concentrated under reduced pressure, diluted with ethyl acetate (50 ml), and washed with 1M HCl (3×50 ml) and water (3×50 ml). The organic layer was dried (MgSO$_4$) and evaporated to give a pink oil (8.3 g). $^1$H NMR confirmed the presence of 5-[(2',5'-dioxo-1'-pyrrolidinyl)oxy]pentanoic acid (7.44) which was used without further purification. δH (250 MHz, CD$_3$OD) 1.87 (2H, qui, J 7.3 Hz, CH$_2$), 2.35 (4H, t, 7.3 Hz, 2×CH$_2$), 3.5 (4H, s, 2×CH$_2$). The carboxylic acid (7.44) was dissolved in freshly distilled thionyl chloride (30 ml) and stirred for 8 h. Excess thionyl chloride was removed under reduced pressure, leaving a pink oil which as triturated with anhydrous ether. The ether fractions were combined and evaporated in vacuo to leave a white powder which recrystallised from ether/hexane to yield the title compound 7.42 as a white crystalline (plates) solid (1.8 g, 16%). M.p. 87° C.; m/z (+FAB) 265 (20%, M—Cl+m—NO$_2$BzOH), 212 (70%, M—Cl); numax (nujol mull. cm$^{-1}$) 1810 (acyl chloride), 1785 (imide), 1735 (ester); δH (250 MHz, CDCl$_3$) 2.15 (2H, qui, J 7.3 Hz, CH$_2$CH$_2$CH$_2$), 2.70 (2H, t, J 7.3 Hz, OCOCH$_2$), 2.80 (4H, s, 2×COCH$_2$), 3.10 (2H, t, J 7.3 Hz, CH$_2$COCl).

Ethyl N-[(3,5-dimethoxycarbonyl)phenyl]-P-{N-[5'-(2",5'-dioxo-1"pyrrolidinyl)oxy-1',5"-dioxopentyl]-4-aminophenylmethyl}phosphonamidate (7.49) (FIG. 7A13)

A solution of 5-(2',5'-dioxo-1'-pyrrolidinyl)oxy-5-oxopentanoyl chloride (7.42) (1.0 g, 4.0 mmol) in anhydrous DCM (20 ml) was added dropwise to a stirred mixture of the phosphonamidate (7.36) (1.6 g, 4.0 mmol) and triethylamine (0.7 ml, 4.8 mmol) in dry DCM (20 ml), with cooling. The reaction mixture was stirred for 8 h at room temperature and then concentrated under reduced pressure. Triethylamine hydrochloride was removed by filtration and the filtrate was evaporated to dryness in vacuo to yield a brown solid 30 which was purified by silica gel chromatography with DCM/petrol 60–80 (1:1) as eluant. This yielded the title compound 7.49 as a white solid (1.4 g, 58%). M.p. 107.5°–108.3° C.; m/z (+EI) 617 (100%, M); [Found: (M)+, 617.1775. $C_{28}H_{32}N3O_{11}P$ requires 617.1774]; numax (KBr disc, cm$^{-1}$), 1765 (imide), 1735-1710 (ester), 1680 (amide I), 1530 (amide II), 1250 (b, P=O), 1010 (P—O-alkyl); δH (250 MHz, $CD_3OD$) 1.35 (3H, t, J 7.5 Hz, $CH_3$), 2.05 (2H, qui, J 7.5 Hz, $CH_2CH_2CH_2$), 2.45 (2H, t, J 7.5 Hz, $OCOCH_2$), 2.75 (2H, t, J 7.5 Hz, $NHCOCH_2$), 2.85 (4H, s, 2×$CH_2$), 3.30 (2H, d, 2JPH 22.5 Hz, Ar—$CH_2$), 3.90 (6H, s, 2×$OCH_3$), 4.05–4.25 (2H, m, $CH_2$), 7.10 (2H, d, J 7.5 Hz, Ar—H), 7.4 (2H, d, J 7.5 Hz, Ar—H), 7.80 (2H, s, Ar—H), 8.15 (1H, s, Ar—H); δC (62.5 MHz, $CD_3OD$) 16.65 (d, 3JCP 6.6 Hz), 22.0, 26.3, 26.5, 30.91, 35.1 (d, 1JCP 125.78 Hz), 52.96, 62.62 (d, $^2J^{CP}$ 6.88 Hz), 118.24, 120.96, 123.65 (d, $^2J_{CP}$ 6.2 Hz), 123.99, 127.75 (d, $^3J_{CP}$ 6.2 Hz). 131.45 (d, $^2J_{CP}$ 6.2 Hz), 132.62, 143.54, 167.41, 171.91, 173.04, 173.71; δP (101 MHz, $CD_3OD$) 27.22 (s); Calcd. for $C_{28}H_{32}N_3O_{11}P$: C, 54.44; H, 5.23; N, 6.81; Found: C, 54.62: H, 5.46; N, 6.75; $R_F$ 0.35 (ethyl acetate); max (95% EtOH) 257 nm (ε 617), 321 mn (ε 185).

Ethyl N-[(3,5-dicarboxy)phenyl]-P-[N-(4'-carboxybutyroyl)-4-aminophenylmethyl]phosphonamidate, tri-lithium salt (7.6) (FIG. 7A13)

The procedure outlined is similar to the method of Jacobsen and Marlowe (Ref. 175). Lithium hydroxide (1M, 1.3 ml, 1.3 mmol) was added to a stirred solution of the phosphonamidate ester (7.49) (0.3 g, 0.4 mmol) dissolved in 10% aqueous dioxan (10 ml). The reaction was stirred at room temperature for 2 h and the solvent was evaporated under reduced pressure. The resultant white paste was lyophilised to give a white powder (0.3 g) which was dissolved in TEAB (0.05M, 10 ml) and purified by m.p.l.c. using the same procedure as outlined for phosphonamidate (7.37). The fractions containing the product were pooled and solvent removed under reduced pressure to give the product as its triethylammonium salt (0.3 g, 0.37 mmol). The residue was dissolved in water and 1.2 times the theoretical amount of 1M lithium hydroxide (0.3 ml) was added. The solution was lyophilised to yield the title compound 7.6 as a white powder (0.2 g, 77%). M.p. >280° C.; m/z (+EI) 511 (90%, M+H$^+$); numax (KBr disc, cm$^{-1}$) 1650 (amide I), 1620 (carboxylate), 1520 (amide II), 1245 (P=O), 1105 (P—O-alkyl); δH (250 MHz, $D_2O$) 1.35 (3H, t, J 7.5 Hz, $CH_3$), 2.05 (2H, qui, J 7.5 Hz, $CH_2CH_2$), 2.35 (2H, t, J 7.5 Hz, $OCOCH_2$), 2.75 (2H, t,J 7.5 Hz, $NHCOCH_2$), 3.35 (2H, d, 2JPH 22.5 Hz, Ar—$CH_2$), 4.09–4.34 (2H, m, $CH_2$) 6.47 (2H, d, J 7.5 Hz, 2×Ar—H) 6.80 (2H, d, J 7.5 Hz, 2×Ar—H), 7.45 (2H, s, 2×Ar—H) 7.80 (1H, s, Ar—H); δC (62.5 MHz, $D_2O$) 16.65 (d, 3JCP 6.6 Hz), 22.5, 26.9, 30.85, 35.1 (d, 1JCP 125.78 Hz), 62.58 (d, $^2J_{CP}$ 6.98 Hz), 117.24, 119.86, 123.55 (d, $^3J_{CP}$ 6.2 Hz), 123.89, 127.75 (d, $^2J_{CP}$ 7.01 Hz), 131.45 (d, $^3J_{CP}$ 6.8 Hz, ArCH), 134.79, 144.54, 167.41, 173.09, 174.37; δP (101 MHz, $D_2O$) 27.22 (s); $R_F$ 0.50 (reversed-phase C-18, 200 mm silica gel plates, 10% aqueous methanol); h.p.l.c. r.t. 4.8 min.

N-[(3,5-Dicarboxy)phenyl]-P-[N-(4'-carboxybutyroyl)-4-aminophenyl-methyl]phosphonamidic acid, tetra-sodium salt (7.7) (FIG. 7A13)

The phosphonamidate ester (7.49) (0.1 g, 0.2 mmol) was dissolved in a solution of trimethylsilyl bromide (0.1 ml, 0.64 mmol) in acetonitrile (2 ml). The reaction was stirred at 30° C. and followed by $^{31}P$ NMR which showed that after 3 d ca. 50% of the phosphonamidate ester had been dealkylated. More trimethylsilyl bromide (0.1 ml, 0.64 mmol) was added and after 3 d solvents and volatiles were removed in vacuo. The crude reaction mixture was repeatedly solvolysed with 0.05M TEAB (5×20 ml). The solvent was evaporated and the residue purified by m.p.l.c. using the procedure outlined earlier. This gave the product as its triethylammonium salt, which was converted into the sodium form by the technique described for (7.37). This yielded the title compound 7.7 as a pale yellow solid (36 mg, 42%). Because of the instability of the title compound on both h.p.l.c. and ion-exchange columns (DEAE-sephadex), subsequent production of this compound involved lyophilisation after solvolysis by $NaHCO_3$. M.p.>280° C.; m/z (+FAB) 575 (M+Na$^+$), 553 (80%, M+H$^+$), 531 (8%, M–Na$^+$+2H$^+$); numax (KBr disc, cm$^{-1}$) 1650 (amide I), 1580 (carboxylate), 1535 (amide II), 1200 (P=O); dH (250 MHz, $D_2O$) 2.18 (2H, qui, J 7.5 Hz, $CH_2CH_2CH_2$), 2.35 (2H, t, J 7.5 Hz, $OCOCH_2$), 2.75 (2H, t, J 7.5 Hz, $NHCOCH_2$), 3.35 (2H, d, 2JPH 22.5 Hz, Ar—$CH_2$), 6.50 (2H, d, J 7.5 Hz, 2×Ar—H) 6.80 (2H, d, 2×Ar—H), 7.45 (2H, s, 2×Ar—H), 7.80 (1H, s, Ar—H); δP (101 MHz, D2O) 27.74 (s); $R_F$ 0.35 (reversed-phase C-18, 200 mm silica gel plates, methanol); h.p.l.c. r.t. 4.3 min.

N-[(3,5-dicarboxy)phenyl]-P-(4-aminophenylmethyl) phosphonamidic acid, tri-sodium salt (7.50).

The triethylamnmonium salt of the phosphonamidate (7.37) (100 mg, 0. 2 mmol) was deesterified with trimethylsilyl bromide by the method outlined for phosphonamidate (7.49) to yield the title compound 7.5 as a white solid (37 mg, 44%) M.p. 265.3°–267.8° C.; m/z (+FAB) 417 (99%, M+H+); numax (KBr disc, cm–1) 1600 (carboxylate), 1250 (b, P=O); δH (250 MHz, $D_2O$) 6.2 (2H, d, J 7.5 Hz, Ar—H), 6.50 (2H, d, J 7.5 Hz, 2×Ar—H), 7.63 (s, 2H, 2×Ar—H), 7.80 (1H, s, Ar—H); δC (62.5 MHz, $CD_3OD$) 33.9 (d, 1JCP 123.46 Hz), 62.46 (d, 2JCP 6.98 Hz), 123.25, 123.79 (d, 3JCP 6.7 Hz), 124.25, 132.43 (d, 3JCP 6.5 Hz), 133.65, 143.64, 144.72, 168.86; δP (101 MHz, D2O) 23.23 (s); $R_F$ 0.60 (reversed-phase C-18, 200 mm silica gel plates, acetonitrile); h.p.l.c. r.t. 2.5 min.

Ethyl N-[(3,5-dicarboxy)phenyl]-P-{N-[5'-(2",5"-dioxo-1"pyrrolidinyl)-oxy-1',5'-dioxopentyl]-4-aminophenylmethy}phosphonamidate (Hapten 1, 7.2). (FIG. 7A9)

A solution of 5-(2',5'-dioxo-1'-pyrrolidinyl)oxy-5-oxopentanoyl chloride (7.42) (0.30 g, 1.2 mmol) in $CHCl_3$ (10 ml) was added dropwise to a stirred mixture of the triethylammonium salt of the phosphonamidate (7.37) (0.4 g, 0.68 mmol) and triethylamine (0.1 ml, 0.8 mmol) in anhydrous DMF (10 ml) with cooling. This mixture was allowed to stir at room temperature under an atmosphere of nitrogen for 6 h. The solvent was removed in vacuo and the residue dissolved in ethyl acetate (30 ml) and washed with water (5×50 ml), 1M citric acid (3×50 ml) and brine (2×50 ml). The combined organic fractions were dried over $MgSO_4$, filtered and the solvent removed in vacuo to give a brown oil which was purified by h.p.l.c. The title compound was isolated as a pale yellow solid (0.14 g, 34%)

M.p. 158.1°–160.3° C.; m/z (+FAB) 612 (10%, M+Na+), 590 (90%, M+H+), 589 (55%, M+), 432(45%); [Found (M)+, 589.1465. $C_{26}H_{28}N_3O_{11}P$ requires 589.1462]; numax (KBr disc, cm$^{-1}$) 1750 (imide), 1735 (ester), 1690 (acid), 1665 (amide I), 1540 (amide II), 1250 (P=O), 1105 (P—O-alkyl); δH (250 MHz, CD$_3$OD) 1.35 (3H, t, J 7.5 Hz, CH$_3$), 2.05 (2H, qui, CH$_2$CH$_2$CH$_2$), 2.45 (2H, t, OCOCH$_2$), 2.75 (2H, t, NHCOCH$_2$), 2.85 (s, 4H, CH$_2$), 3.30 (2H, d, 2JPH 22.5 Hz, Ar—CH$_2$), 4.05–4.25 (2H, m, CH$_2$) 7.10 (2H, d, J 7.5 Hz, Ar—H) 7.4 (2H, d, J 7.5 Hz, Ar—H), 7.90 (2H, s, Ar—H), 8.20 (1H, s, Ar—H); δC (62.5 MHz, CD3OD) 16.65 (d, 3JCP 6.6 Hz), 21.78, 26.24, 25.94, 30.87, 35.1 (d, 1JCP 125.78 Hz), 62.65 (d, 2JCP 6.88 Hz), 118.24, 120.96, 123.65, (d, 2JCP 5.8 Hz), 123.99, 127.75, 131.45 (d, 2JCP 6.2 Hz), 132.62, 143.54, 167.41, 171.91, 173.04, 173.71; δP (101 MHz, CD$_3$OD) 27.74 (s); R$_F$ 0.30 [methanol/DCM (1:1)]; h.p.l.c. r.t. 7.5 min.

N-[(3,5-Dicarboxy)phenyl]-P-{N-[5'-(2",5"-dioxo-1"-pyrrolidinyl)oxyl1',5'-dioxopentyl]-4-aminophenylmethyl}phosphona midic acid, the-sodium salt (Hapten 2, 7.4) (Ref. 195, 218) (FIG. 7A9)

Deprotection with bromotrimethylsilane. (Ref195,218).

The phosphonamide ester (7.2) (100 mg, 0.16 mmol) was dissolved in a solution of TMSBr (0.02 ml, 0.19 mmol) and acetonitrile (2 ml). The reaction was stirred at room temperature and followed by $^{31}$P NMR which showed that after 3 d, ca. 70% of the phosphonamidate ester had been dealkylated. A further equivalent of TMSBr (0.018 ml, 0.16 mmol) was added. and, after 3 d, solvents and volatiles were removed in vacuo and the residue repeatedly solvolysed with aqueous 0.5M NaHCO$_3$ (3×20 ml). The solvent was evaporated, the residue dissolved in water, neutralised to pH 6 with ion-exchange resin (DEAE Sephadex), and the solvent evaporated in vacuo to give a brown oil. This residue was purified by h.p.l.c. to give the title compound 7.4 as the free acid as a white solid. This was converted into the tri-sodium salt (24 mg, 24%) by the same procedure outlined for the phosphonamidate (7.37). M.p. 231.4°–233.6° C.; m/z (+FAB) 672 (25%, M+2Na$^+$—H$^+$), 650 (55%, M+Na$^+$), 628 (88%, M+H$^+$); numax (KBr disc, cm$^{-1}$) 1750 (imide), 1715 (ester), 1650 (amide I), 1590 (carboxylate), 1240 (P=O); δH (250 MHz, D2O) 1.97 (2H, qui, J 7.5 Hz, CH$_2$CH$_2$CH$_2$), 2.41 (2H, t, J 7.5 Hz, OCOCH$_2$), 2.74 (2H, t, J 7.5 Hz, NHCOCH$_2$), 2.85 (4H, s, 2×CH$_2$), 3.29 (2H, d, 2JPH 22.5 Hz, Ar—CH2), 6.5 (2H, d, J 7.5 Hz, 2×Ar—H) 6.75 (2H, d, J 7.5 Hz, 2×Ar—H), 7.43 (2H, s, 2×Ar—H), 7.76 (1H, s, Ar—H); δC (62.5 MHz, D$_2$O) 22.13, 24.35, 26.50, 30.91, 35.24 (d, 1JCP 125.78 Hz) 118.24, 120.96, 123.65 (d, 2JCP 6.2 Hz), 123.99, 126.96, 130.40 (d, 2JCP 6.2 Hz) 132.62, 143.54, 167.60, 171.91, 173.04, 173.71; dP (101 MHz, D2O) 23.04 (s); R$_F$ 0.60 (reversed-phase C-18, 200 mm thickness silica gel plates, methanol); h.p.l.c. r.t. 5.2 min.

Routes to the L-glutamic acid series of haptens.

Ethyl N-[(1S)-(1,3-dimethoxycarbonyl)propyl]-P-(4-aminophenylmethyl)-phosphonamidate (7.51) (FIG. 7A14)

Adam's catalyst (75 mg) was added to a stirred solution of the phosphonamidate (7.30) (750 mg, 1.8 mmol) in methanol (20 ml). The reaction mixture was then stirred under a hydrogen atmosphere. Once hydrogen uptake had ceased, the catalyst was removed by filtration through Celite under an inert atmosphere. The filtrate was evaporated in vacuo to yield a brown oil which was purified by flash column chromatography using ethyl acetate/petrol 40–60 (1:1) as eluant. This yielded the title compound 7.51 as a white powder (558 mg, 84%), which was stored at −20° C. under an inert atmosphere to prevent oxidation.

M.p. 72.8°–73.5° C.; m/z (+FAB) 395 (25%, M+Na$^+$), 373 (100%, M+H+); [Found (M)$^+$,−373.1527. $C_{16}H_{26}N_2O_6P$ requires 373.1529]; vmax (KBr disc, cm$^{-1}$) 3250 (amine), 1740 (ester), 1200 (P=O), 1150 (P—O-alkyl); δH (250 MHz, CDCl$_3$) 1.20 (3H, t, J 7.5 Hz, CH$_3$), 1.67–2.03 (2H, bm, 2H$^\beta$), 2.10–2.45 (2H, bm, 2H$^\gamma$), 3.07 (2H, d, $^2J_{PH}$ 22.5 Hz, Ar—CH$_2$), 3.81–4.11 (3H, bm, H$^\alpha$, OCH$_2$CH$_3$), 6.47 (2H, d, J 7.5 Hz, 2×Ar—H), 6.83 (2H, d, J 7.5 Hz, 2×Ar—H); δC (62.5 MHz, CDCl$_3$) 16.26 (d, 3JCP 6.8 Hz), 29.54, 29.63, 36.3 (d, 1JCP 125 Hz), 53.2, 53.64, 53.55, 60.85 (d, 2JCP 7.0 Hz), 120.43, 131.70, 120.01 (d, 2JCP 8.8 Hz) 147.85, 172.29, 173.14; δP (101 MHz, CDCl$_3$) 26.70 (s). Calcd. for $C_{16}H_{25}N_2O_6P$: C, 51.59; H, 6.77; N, 7.53; Found: C, 51.62; H, 6.92; N, 7.49; R$_F$ 0.30 [DCM/methanol (9:1)].

Ethyl N-[(1S)-(1,3-dicarboxy)propyl]-P-(4-aminophenylmethyl)phosphonamidate, di-sodium salt (7.52). (FIG. 7A14 and 7A15)

Several attempts were made to synthesise compound (7.52).

METHOD 1: Deesterification of phosphonamidate (7.51)

1. By alkaline hydrolysis. The phosphonamidate (7.51) (0.5 g, 1.2 mmol) was dissolved in a stirred solution of 1M lithium hydroxide (2.6 ml, 1.28 mmol) in aqueous methanol. The reaction mixture was stirred for 2 d and its progress followed by TLC. No change was observed. Therefore more 1M lithium hydroxide (2.56 ml, 2.56 mmol) was added and the reaction mixture was heated under reflux. No reaction occurred after a further 3 d. Therefore this reaction was abandoned. The reaction was repeated with increasing strengths of LiOH and NaOH in the procedure outlined above, but little transformation occurred.

2. Neutral hydrolysis. The phosphonamidate (7.51) (0.5 g, 1.2 mmol) and lithium chloride (0.12 g, 2.8 mmol) were heated under reflux in 2,6-dimethylpyridine for 1 h in a modification of the method described by Eschenmoser et al. (Ref. 207) TLC analysis showed little dealkylation had occurred. Therefore the reaction was continued for a further 48 h. No transformation was detected so this reaction was abandoned. This reaction was repeated with LiI in refluxing pyridine but with little success. Therefore the dimethyl L-glutamyl phosphonamidate (7.30) was replaced in the synthetic route by the dibenzyl ester (7.31).

Method 2: Reduction of phosphonamidate (7.31)

The phosphonamidate (7.31) (0.45 g, 1.2 mmol) was hydrogenated by the same procedure as for phosphonamidate (7.30). Once hydrogen uptake had ceased, the catalyst was removed by filtration and the filtrate was evaporate in vacuo to yield a pale brown solid. Analytical h.p.l.c. showed two major peaks which were characterised by 1H NMR. Peak 1: (r.t. 3.0 min) A pale yellow solid was found to be the title compound and was characterised as described below. Peak 2: (r.t. 3.9 min), a white solid which was characterised as ethyl (4-aminophenylmethyl)phosphinic acid. M/z (+EI) 216 (M+H$^+$); δH (250 MHz, CD$_3$OD) 1.13 (6H, t, J 7.5 Hz, CH$_3$), 3.17 (2H, d, 2JPH 22.5 Hz, Ar—CH$_2$), 3.90 (4H, dq, J 7.5 Hz, OCH$_2$), 6.93 (2H, d, J 7.5 Hz, Ar—H), 7.24 (2H, d, J 7.5 Hz, Ar—H). To reduce the risk of hydrolysis during the reaction a modification of a method used by Elliot et al. (177) for the debenzylation of phosphonopeptides was attempted. The phosphonamidate (7.30) (250 mg, 0.45 mmol) was added to a stirred suspension of Adam's catalyst (25 mg) and NaHCO$_3$ (75.6 mg, 0.90 mmol) in 10% aqueous ethanol (10 ml) under an atmosphere of hydrogen. After hydrogen uptake had ceased, the catalyst was removed by filtration under an inert atmosphere and concentrated under reduced pressure to give the title compound 7.52 as a white powder (101.3 mg, 58%). M.p. 187.2°–189.8° C.; m/z (+FAB) 411 (35%, M+Na$^+$), 389 (90%, M+H$^+$), 367

(M—Na$^+$+2H$^+$); vmax (KBr disc cm$^{-1}$) 1690 (carboxylate), 1250 (b, P=O) 1150 (P—O-alkyl); δH (250 MHz, CD$_3$OD) 1.19 (3H, t, J 7.5 Hz, CH$_3$), 1.79–2.12 (2H, bm, 2H$^β$), 2.07–2.38 (2H, bm, 2H$^γ$), 3.05 (2H, d, 2JPH 22.5 Hz, Ar—CH$_2$), 3.80–4.05 (3H, bm, H$^α$, OCH$_2$CH$_3$), 6.50 (2H, d, J 7.5 Hz, 2×Ar—H), 6.94 (2H, d, J 7.5 Hz, 2×Ar—H); δC (62.5 MHz, CD$_3$OD) 16.35 (d, $^3J_{CP}$ 7.0 Hz), 29.64, 29.69, 36.67 (d, 1JCP 125 Hz), 53.2 (C$^α$), 60.85 (d, 2JCP 7.0 Hz), 121.79, 131.62, 120.24 (d, 2JCP 7.2 Hz) 147.89, 168.25, 169.36; δP (101 MHz, CDCl$_3$) 27.20 (s); R$_F$ 0.30 (reversed-phase C-18, 200 mm thickness silica gel plates, methanol). Ethyl N-[(1S)-(1,3-dicarboxy)propyl]-P-{N-[5'-(2'',5''-dioxo-1''-pyrrolidinyl)oxy-1',5'-dioxopentyl]-4-aminophenylmethyl}phosphonamidate (Hapten 3, 7.3).

A solution of the acyl chloride (7.42) (130 mg, 0.5 mmol) in anhydrous DCM (5 ml) was added dropwise to a mixture of the phosphonamidate (7.52) (150 mg, 0.4 mmol) and N-ethylmorpholine (0.2 ml, 1.6 mmol) in anhydrous DMF (10 ml). The reaction was stirred at room temperature under an inert atmosphere and followed by TLC. After 8 h the phosphonamidate (7.52) had disappeared and the reaction was worked up as for Hapten 1 (7.2), to yield a brown solid which was purified by h.p.l.c. The title compound 7.3 (r.t. 6.8 min) was isolated as a pale yellow powder which was crystallised from isopropanol/ether as pale yellow crystals (100 mg, 45%). M.p. 162.7°164.3° C.; m/z (+FAB) 1109 (28%, 2M+H$^+$), 578 (8%, M+Na+) 555 (100%, M); [Found (M)$^+$, 555.1618. C$_{23}$H$_{30}$N$_3$O$_{11}$P requires 555.1618]; numax (KBr disc, cm$^{-1}$), 1740 (ester), 1695 (acid), 1675 (amide I), 1530 (amide II), 1235 (P=O), 1150 (P—O-alkyl); δH (250 MHz, CD$_3$OD) 1.20 (3H, t, J 7.5 Hz. CH3), 1.75–2.05 (2H, bm, 2H$^β$), 2.05 (2H, qui, J 7.5 Hz, CH$_2$CH$_2$Ch$_2$), 2.12–2.37 (2H, bm, 2Hg), 2.43 (2H, t, J 7.5 Hz, OCOCH2), 2.75 (2H, t, J 7.5 Hz, NHCOCH$_2$), 2.85 (s, 4H, 2×CH2), 3.05 (2H, d, 2JPH 22.5 Hz, Ar—CH2), 3.75–4.00 (3H, bm, H$^α$, OCH$_2$CH$_3$), 7.25 (2H, d, J 7.5 Hz, 2×Ar—H), 7.50 (2H, d, J 7.5 Hz, 2×Ar—H); δC (62.5 MHz, CDCl$_3$) 16.55 (d, 3JCP 7.0 Hz), 21.09, 25.35, 26.95, 29.64, 29.69, 30.19, 36.67 (d, 2JCP 125 Hz), 53.2, 60.85 (d, 2JCP 7.0 Hz), 120.24 (d, 2JCP 7.2 Hz), 121.79, 131.62, 143.89, 162.41. 163.45, 171.91, 173.04, 173.71; δP (101 MHz, CD$_3$OD) 27.20 (s); R$_F$ 0.20 [DCM/methanol (1:1)]; h.p.l.c. r.t. 6.8 min.

Ethyl N-[(1S)-(1,3-dicarboxy)propyl]-P-[(4'-carboxy)butyroyl-4-amino-phenylmethyl]phosphonamidate, tri-sodium salt (7.8) (FIG. 7A2)

The phosphonamidate ester (7.3) (250 mg, 0.5 mmol) was dissolved in 10% aqueous ethanol (10 ml) and 1M sodium hydroxide (1.5 ml, 1.5 mmol) was added and the reaction stirred at room temperature for 5 h. The solvent was evaporated under reduced pressure and the resulting yellow gum was lyophilised to give the title compound 7.8 as a pale yellow powder (180 mg, 68%). M.p. 256.8°–257.4° C.; m/z (+FAB) 569 (45%, M+2Na$^+$—H$^+$), 547 (100%, M+Na$^+$), 525 (38%, M+H$^+$); numax (KBr disc, cm$^{-1}$) 1675 (amide I), 1550 (amide II), 1590 (carboxylate), 1225 (P=O), 1105 (P—O-alkyl); δH (250 MHz, D$_2$O) 1.20 (3H, t, J 7.5 Hz, CH$_3$), 1.80–2.05 (2H, bm, 2H$^β$), 2.10 (2H, qui, J 7.5 Hz, CH$_2$CH$_2$CH$_2$), 2.22–2.37 (2H, bm, 2H$^γ$), 2.45 (2H, t, J 7.5 Hz, OCOCH$_2$), 2.75 (2H, t, J 7.5 Hz, NHCOCH$_2$), 3.05 (2H, d, 2JPH 22.5 Hz, Ar—CH$_2$), 3.75–4.00 (3H, bm, H$^α$, OCH$_2$CH$_3$), 6.80 (2H, d, J 7.5 Hz, 2×Ar—H), 7.20 (2H, d, J 7.5 Hz, 2×Ar—H); δC (62.5 MHz, D2O) 16.55 (d, 3JCP 7.0 Hz), 22.17, 25.83, 26.09, 29.64, 29.69, 36.67 (d, 1JCP 123.8 Hz), 53.2, 60.85 (d, 2JCP 7.0 Hz), 119.38 (d, 2JCP 7.2 Hz), 121.79, 131.62, 144.71, 160.41, 163.45, 173.27, 174.09; δP (101 MHz, D$_2$O) 23.24 (s); R$_F$ 0.50 (reversed-phase C-18, 200 mm silica gel plates, methanol).

N-[(1S)-(1,3-Dicarboxy)propyl]-P-{N-[5'-(2'',5''-dioxo-1''-pyrrolidinyl)oxy-1',5'-dioxopentyl]-4-aminophenylmethyl}phosphonamidic acid, tri-sodium salt (Hapten 4, 7.5) (FIG. 7A2)

The phosphonamidate (7.3) (100 mg, 0.18 mmol) was de-esterified using trimethylsilyl bromide by the procedure used for (7.4) (195). This yielded a crude brown solid which was purified by h.p.l.c. The fraction containing the product (r.t. 4.3 min) was dried by lyophilisation and resuspended in methanol (2 ml). The tri-sodium salt was then prepared as described previously to yield the title compound 7.5 as a pale brown solid (48 mg, 58%). M.p. 274.5°–278° C.; m/z (+FAB) 1187 (10%, 2M+H$^+$), 616 (90%, M+Na$^+$) 594 (38%, M+H$^+$); numax (KBr disc, cm$^{-1}$), 1730 (ester), 1695 (amide I), 1585 (carboxylate), 1530 (amide II), 1250 (P=O); δH (250 MHz, D2O) 1.75–2.15 (2H. bm, 2H$^β$) 2.05 (2H, qui, J 7.5 Hz. CH$_2$CH$_2$CH$_2$), 2.15–2.35 (2H, bm, 2H$^γ$) 2.45 (2H, t, J 7.5 Hz, OCOCH$_2$), 2.75 (2H, t, J 7.5 Hz, NHCOCH$_2$), 2.85 (4H, s, CH$_2$) 3.85–3.90 (1H, m, H$^α$, 7.25 (2H, d, J 7.5 Hz, 2×Ar—H), 7.50 (2H, d, J 7.5 Hz, 2×Ar—H). δC (62.5 MHz, D$_2$O) 22.09, 26.31, 26.53, 29.64, 30.69, 30.78, 36.67 (d, $^2J_{CP}$ 125 Hz), 54.56, 120.97, 131.57, 127.75 (d, $^2J_{CP}$ 8.9 Hz, ArC) 143.54, 160.37, 163,57, 170,97, 172.09, 173.97; δP (101 MHz, D$_2$O) 22.89 (s); R$_F$ 0.50 (reversed-phase C-18, 200 mm silica gel plates, 10% aqueous methanol); h.p.l.c. r.t. 4.3 min.

N-[(1S)-(1,3-Dicarboxy)propyl]-P-[(4'-carboxybutyroyl)-4-aminophenyl-methyl]phosphonamidic acid, tetra-sodium salt (7.9) (FIG. 7A2)

The phosphonamidate ester (7.5) (297 mg, 0.5-mmol) was dissolved in 10% aqueous ethanol (10 ml) and aqueous NaOH (1M, 1.5 ml, 1.5 mmol) added. The reaction was stirred at room temperature for 5 h then the solvent was lyophilised to give the title compound 7.9 as a pale yellow powder (180 mg, 68%). M.p.>285° C.; m/z (+FAB) 541 (100%, M+Na+), 519 (74%, M+H+); numax (KBr disc, cm$^{-1}$), 1695 (acid), 1678 (amide), 1205 (P=O); δH (250 MHz, D$_2$O) 1.76–2.03 (2H, bm, 2H$^β$), 2.07 (2H, qui, J 7.5 Hz, CH$_2$CH$_2$CH$_2$), 2.17–2.33 (2H, bm, 2Hg), 2.47 (2H, t, J 7.5 Hz, OCOCH$_2$), 2.75 (2H, t, J 7.5 Hz, NHCOCH2), 3.05 (2H, d, 2JPH 22.5 Hz, Ar—CH$_2$), 3.89 (1H, m, H$^α$), 6.80 (2H, d, J 7.5 Hz, 2×Ar—H), 7.20 (2H, d, J 7.5 Hz, 2×Ar—H); δC (62.5 MHz, D$_2$O) 22.19, 25.8, 26.11, 29.65, 29.69, 36.67 (d, $^1J_{CP}$ 123.8 Hz), 53.2, 119.38 (d, $^2J_{CP}$ 7.2 Hz), 121.79, 131.59, 144.69, 160.41, 163.39, 173.24, 174.08; δP (101 MHz, D$_2$O) 20.24 (s); R$_F$ 0.58 (reversed-phase C-18, 200 mm silica gel plates, methanol); h.p.l.c. r.t. 4.1 min.

7.3.2.2 SYNTHESIS OF SUBSTRATES

Synthesis of bis-aryl carbamate substrates (7.53–7.57) (FIG. 7B1)

Synthetic route via the reaction of an unprotected amine with a chloroformate

This procedure was a modification of that outlined by Kruse and Holden (Ref. 210). The substituted chloroformate (7.58) (20 mmol) was added to a stirred suspension of 5-aminoisophthalic acid (7.39) (40 mmol) in anhydrous DCM (150 ml) at room temperature and followed by TLC. A precipitate formed almost immediately following the addition of the chloroformate. Once the reaction was complete, the precipitate was collected by filtration to give a pale pink solid. TLC analysis showed that there were two components: the product and the hydrochloride of 5-aminoisophthalic acid. These two components proved to be virtually insoluble in all organic solvents and water. Therefore, an aqueous work-up was impossible and purification was achieved by h.p.l.c. Two peaks were obtained with a 10–50% acetonitrile/water gradient and 0.5% TFA as eluant. The first (r.t. 12.05 min) was characterised as 5-aminoisophthalic acid and the second (r.t. 15.00 min) was the carbamate product.

p-Nitrophenyl N-[(3,5-dicarboxy)phenyl]carbamate (7.53)

The title compound 7.53 was prepared by the route described above as a white solid (14.6 mmol, 73%). M.p.>300° C.; m/z (+ES) 369 (25%, M+Na$^+$), 347 (18%, M+H$^+$); vmax (nujol mull, cm$^{-1}$) 1700 (acid), 1680 (urethane); δH (250 MHz, d$^6$-DMSO) 7.55 (2H, d, J 7.5 Hz, 2×Ar—H), 8.15 (1H, t, 4J 1.5 Hz, Ar—H), 8.25 (2H, d, J 7.5 Hz, 2×Ar—H) 8.30 (2H, d, 2×Ar—H), 10.90 (1H, s, NH), 12.50–13.75 (2H, b, 2×COOH); δC (62.5 MHz, d$^6$-DMSO) 123.45, 125.16, 125.72, 132.47, 139.49, 145.22, 151.16, 155.77, 166.67; RF 0.2 [DCM/methanol (1:1); h.p.l.c. r.t. 15.6 min.

4-Bromophenyl N-[(3,5-dicarboxy)phenyl]carbamate (7.54)

The title compound 7.54 was synthesised by the procedure above to yield a white solid (9.9 mmol, 49%). M.p.>300° C.; m/z (+ES) 381 (10%, M), 379 (10%, M), 301 (20%, M-Br) 149 (50%), 91 (100%); numax (nujol mull, cm$^-$), 1700 (acid), 1680 (urethane); δH (250 MHz, d$^6$-DMSO) 7.27 (2H, d, J 7.5 Hz, Ar—H), 7.63 (2H, d, Ar—H), 8.18 (1H,t,4J 1.5 Hz, Ar—H), 8.35 (2H, d, Ar—H), 10.70 (1H, s, NH), 13.20–13.40 (2H, b, COOH); δC (62.5 MHz, d$^6$-DMSO) 118.36, 123.38, 124.77, 132.42, 132.78, 139.75, 150.09, 151.88, 166.83; R$_F$ 0.20 [DCM/methanol (1:1)]; h.p.l.c. r.t. 16.0 min.

Synthetic route via di-t-butyl 5-aminoisophthalate (7.59)

Di-t-butyl 5-aminoisophthalate (7.59) (FIG. 7B2)

The procedure used was a low pressure modification of the method outlined by McCloskey (Ref. 213) for esterifying hindered acids. A stirred suspension of 5-aminoisophthalic acid (7.39) (6.48 g, 33.6 mmol) in CHCl$_3$ (100 ml) was cooled to −10°C. The reaction mixture was then saturated with isobutylene gas and conc. sulfuric acid (2.5 ml) was added dropwise. The reaction vessel was stoppered and the reaction mixture was allowed to warm to room temperature. After 4 d the reaction was quenched by pouring onto a mixture of crushed ice and solid NaHCO$_3$. The organic layer was washed with water (3×200 ml), brine (2×100 ml), and dried (MgSO$_4$). After filtration, the solvent and volatiles were removed under reduced pressure to yield the title compound 7.59 as a pale pink solid (1.48 g, 15%). δH (250 Mhz, d$^6$-DMSO) 1.60 (18H, s, CH$_3$), 5.47 (2H, s, NH), 7.38 (2H, s, 2×Ar—H), 7.65 (1H, s, Ar—H).

General procedure for carbamate synthesis via di-t-butyl 5-amino isophthalate (7.59) (FIG. 7B2)

The procedure involved two steps: firstly the reaction of a chloroformate (7.58) with (7.59) in the presence of a tertiary amine and then subsequent TFA deprotection of the t-butyl esters.

STEP 1 The chloroformate (2.2 mmol), was added dropwise to a mixture of di-t-butyl 5-aminoisophthalate (2 mmol) and N-ethylmorpholine (2.2 mmol) in anhydrous DCM (20 ml) with cooling. The reaction was stirred at room temperature under an inert atmosphere and followed by TLC. After 2 h, the reaction was diluted with DCM (30 ml) and quenched by pouring onto water. The DCM layer was washed with water (3×50 ml), 1M HCl (2×50 ml), and brine (2×50 ml) then dried (MgSO$_4$). After filtration, the DCM was evaporated under reduced pressure to yield the di-t-butyl protected carbamates which were used without further purification.

STEP 2 (Ref. 211) The di-t-butyl protected carbamates were dissolved in 30% v/v TFA/DCM (10 ml) and stirred for 2 h at room temperature. All traces of TFA were removed by repeatedly resuspending the carbamate in DCM and evaporating under reduced pressure. The carbamates were isolated as white solids which were recrystallised from DCM/methanol.

4-Fluorophenyl N-[(3,5-dicarboxy)phenyl]carbamate (7.55).

The title compound 7.55 was synthesised in two steps as outlined above.

The intermediate 4-fluorophenyl N-[(3,5-di-t-butyloxycarbonyl)phenyl]carbamate was isolated as a white solid (1.0 mmol, 50%). δH (250 MHz, d$^6$-DMSO) 1.50 (18H, s, 6×CH$_3$), 7.05–7.17 (4H, m, 4×ArH), 7.50 (1H, s, NH), 8.35 (2H, s, 2×Ar—H) 8.25 (1H, s, Ar—H). The title compound 7.55 was isolated as a white solid (1.0 mmol, 50%). M.p. >300° C.; m/z (+ES) 319 (2%, M), 302 (2%, M—F), 207 (75%, M—FC$_6$H$_5$O) 190 (45%, FC$_6$H$_4$OH—F); numax (nujol mull, cm$^{-1}$), 1700 (acid), 1675 (urethane); δH (250 MHz, d$^6$-DMSO) 7.27 (2H, d, J 7.5 Hz, Ar—H), 7.63 (2H, d, 7.5 Hz, Ar—H), 8.18 (1H, s, Ar—H), 8.35 (2H, s, 2×Ar—H), 10.70 (1H, s, NH), 13.20–13.40 (2H, b, 2×COOH); δC (62.5 MHz, d$^6$-DMSO) 116.36 (d, $^2J_{CF}$ 23.8 Hz), 123.34, 124.25 (d, $^3J_{CF}$ 8.6 Hz), 132.40, 132.78, 139.84, 146.89, 152.26, 159.95 (d, $^1J_{CF}$245.29 Hz); R$_F$ 0.23 [DCM/methanol (1:1)]; h.p.l.c. r.t. 16.6 min.

4-Methoxyphenyl N-[(3,5-dicarboxy)phenyl]carbamate (7.56)

The title compound 7.56 was synthesised as outlined above but with the addition of h.p.l.c. purification of the crude reaction mixture after TFA deprotection of the intermediate p-methoxy N-[(di-tert-butyloxycarbonyl)phenyl] carbamate. This yielded the title compound 7.56 as a white solid (0.67 mmol, 33.5%). M.p.>300° C.; m/z (+ES) 332 (15%, M+H+), 288 (10%, M-CO$_2$+H$^+$) 85 (100%); [Found (M)+, 332.0770. C$_{16}$H$_{14}$NO$_7$ requires 332.0770]; numax (nujol mull, cm$^{-1}$), 1690 (acid), 1680 (urethane); δH (250 MHz, d$^6$-DMSO) 6.95 (2H, d, J 7.5 Hz, 2×Ar—H), 7.43 (2H, d, 2×Ar—H), 8.18 (1H, s, Ar—H), 8.35 (2H, s, 2×Ar—H), 10.65 (1H, s, NH), 13.20–13.40 (2H, b, 2×COOH) δC (62.5 MHz, d6-DMSO) 28.19, 114.86, 123.28, 132.30, 132.78, 140.04, 143.83, 152.63, 157.27, 164.50 166.84; R$_F$ 0.35 [DCM/methanol (1:1)); h.p.l.c. r.t. 16.0 min Synthetic route via dibenzyl 5-aminoisophthalate (7.59)

Dibenzyl 5-aminoisophthalate (Ref. 219) (7.60) was prepared in three steps: firstly, protection of the aniline nitrogen with di-tert-butyl dicarbonate, secondly alkylation with benzyl chloride and finally deprotection of the Boc protecting group with p-toluenesulfonic acid.

STEP 1 t-Butyl N-[(3,5-dicarboxy)phenyl]carbamate (7.61). Di-t-butyl dicarbonate (34.0 g, 0.16 mol) was added to a stirred mixture of 5-aminoisophthalic acid (7.39) (26.0 g, 0.14 mol) and sodium hydroxide (11.5 g, 0.29 mol) in water/DMF (156:195 ml). The reaction was stirred for 24 h and then evaporated to dryness under reduced pressure using a cold finger. The brown residue was dissolved in water (250 ml) and washed with ethyl acetate (3×200 ml). The aqueous phase was then neutralised with 1M citric acid (pH<3) which caused the title compound to precipitate immediately. The precipitate was collected by filtration, washed with water and ether and dried at 50° C. under reduced pressure to yield the title compound 7.60 as a white solid (37.7 g, 93.5%) which was used without further purification. M/z (+ES) 304 (100%, M+Na$^+$); δH (250 MHz, d$^6$-DMSO) 1.50 (18H, s, CH$_3$), 8.18 (1H, s, Ar—H), 8.35 (2H, s, 2×Ar—H), 9.75 (1H, s, NH); R$_F$ 0.55 [DCM/methanol (1:1)].

STEP 2 t-Butyl N-[(3,5-dibenzyloxycarbonyl)phenyl]carbamate (7.62)

Benzyl chloride (24.5 ml, 55 mmol) was added via a syringe to a stirred suspension of (7.61) (15.0 g, 53 mmol) and triethylamine (14.5 ml, 110 mmol) in dry acetone (60 ml) under an inert atmosphere. The reaction mixture was then-heated under reflux for 4 h and left to stir at room temperature for a further 48 h. During the reaction the suspension of (7.61) dissolved and the reaction mixture turned orange. TLC analysis showed the presence of many products. The reaction mixture was concentrated and filtered to remove triethylamine hydrochloride. The solvent was evaporated and the crude mixture was purified by silica gel chromatography with DCM/methanol (99:1) as eluant. This gave the title compound 7.62 as a white solid (5.1 g, 21%). M/z (+FAB) 461 (34%, M), 406 (36%, M—$C_4H_9$+$H^+$), 361 (60%, M-C5H9O2); $\delta$H (250 MHz, $CDCl_3$) 1.45 (9H, s, 3×CH3), 5.30 (4H, s, 2×Ar—$CH_2$), 6.80 (1H, s, NH), 7.25–7.40 (10H, m, 10×Ar—H), 8.20 (2H, s, 2×Ar—H), 8.30 (1H, s, Ar—H); $R_F$ 0.65 [DCM/methanol (95:5)].

STEP 3 Dibenzyl 5-aminoisophthalate, p-toluenesulfonate salt (7.60)

Carbamate (7.61) (3.75 g, 8 mmol) and p-toluenesulfonic acid monohydrate (1.5 g, 8 mmol) were dissolved in toluene (55 ml) and heated at 80° C. for 45 min. A white precipitate formed during the reaction. This was collected by filtration, washed with hexanes, and dried to give the title compound which recrystallised from toluene as a white crystalline solid (needles) (3.91 g, 96%). M.p. 200°–201° C.; m/z (+ES) 362 (100%, M+H+); $\delta$H (250 MHz, $d^6$-DMSO) 2.5 (3H, s, $CH_3$), 5.35 (4H, s, 2×Ar—$CH_2$), 7.05 (2H, d, J 7.5 Hz 2×Ar—H), 7.25–7.60 (12H, m, 12×Ar—H), 7.75 (2H, d, 2×Ar—H), 8.00 (1H, s, Ar—H); $\delta$C (62.5 MHz, $\delta$6-DMSO) 21.24, 67.08, 118.13, 121.94, 122.61, 125.95, 128.63, 128.74, 129.04, 131.52, 136.31, 138.40, 143.88, 145.65, 165.84; $R_F$ 0.15 [DCM/methanol (9:1).

General procedure for carbamate synthesis via dibenzyl 5-amino isophthalate (7.60).

The procedure has two stages involving reaction of the substituted chloroformate with (7.60) in the presence of a tertiary amine as previously described. The benzyl esterified carbamates were then dissolved in DCM/MeOH and reduced under a hydrogen atmosphere with palladium on carbon (10% w/w) as a catalyst. The products were isolated by filtration to remove the catalyst and evaporation of the solvent in vacuo.

Phenyl N-[(3,5-dicarboxy)phenyl]carbamate (7.57)

The title compound 7.57 was synthesised using the procedure outlined above as a white solid (overall yield, 91%). M.p.>300° C.; $\delta$H (250 MHz, $d^6$-DMSO) 7.30–7.45 (3H, m, 3×Ar—H), 7.50 (2H, d, J 6.5 Hz, 2×Ar—H), 7.05 (2H, d, J 6.5 Hz, 2×Ar—H), 8.10 (1H, s, Ar—H), 8.40 (2H, s, 2×Ar—H); $\delta$C (62.5 MHz, $d^6$-DMSO) 122.40, 123.32, 124.81, 126.10, 129.93, 132.40, 139.92, 150.79, 152.26, 166.87; $R_F$ 0.15 [DCM/methanol (1:1)]; h.p.l.c. r.t. 16.6 min.

Synthesis of the amide substrate analogue (7.66). (FIG. 7B4)

The title compound 7.66 was synthesised in two steps via its dimethyl ester (7.68).

N-[(3,5-dicarboxy)phenyl]-phenylethanamide (7.66)

STEP 1 Phenylacetylchloride (3.8 ml, 29 mmol) was added dropwise to a stirred suspension of dimethyl 5-aminoisophthalate (7.23) (4.4 g, 19 mmol) and N-ethylmorpholine (3.7 ml, 29 mmol) in DCM (25 ml). The reaction mixture was stirred at room temperature for 3 h and monitored by TLC. The reaction mixture was concentrated and filtered to remove amine hydrochloride. The filtrate was evaporated to dryness under reduced pressure, dissolved in DCM (60 ml) and washed with water (3×100 ml) and 1M HCl (3×50 ml). The solution was then dried ($MgSO_4$), filtered, and evaporated to yield a pale brown solid. This was washed with ether to yield N-(3,5-dimethoxycarbonylphenyl)-phenylethanamide (7.68) as a white solid (5.0 g, 79%). M.p.>300° C. (decomp.); $\delta$H (250 MHz, CDC13) 3.75 (2H, s, ArCH2), 3.88 (6H, s, 2×$OCH_3$), 7.25–7.41 (5H, m, 5×Ar—H), 7.59 (1H, s, NH), 8.28 (2H, s, 2×ArCH), 8.37 (1H, s, Ar—H); $R_F$ 0.6 [DCM/methanol (95:5)].

STEP 2 The dimethyl ester (7.68) (0.5 g, 1.5 mmol) was dissolved in a solution of sodium hydroxide (1M, 3.4 ml, 3.4 mmol) in MeOH/DCM (1:1) (10 ml) and stirred for 8 h. Solvent was then removed under reduced pressure and the residue redissolved in water and washed with DCM (3×50 ml). The aqueous layer was then acidified when the product precipitated immediately. The precipitate was collected by filtration, dried and recrystallised from methanol to yield the title compound 7.66 as a white powder (0.3 g, 66 M.p.>300° C.; m/z (+ES) 300 (42%, M+H+); [Found: (M)$^+$, 300.0878. $C_{16}H_{14}NO_5$ requires (M) 300.0872]; $\delta$H (250 MHz, d6-DMSO) 3.65 (2H, s, Ar$CH_2$). 7.25–7.41 (5H, m, Ar—H), 8.14 (1H, t, 4J 1.5 Hz, ArCH), 8.45 (2H, d, Ar—H), 10.59 (1H, s, NH), 13.28 (2H, s, $CO_2$H), $\delta$C (62.5 MHz, $d^6$-DMSO) 43.81, 123.95, 125.01, 127.11, 128.82, 129.60, 132.20, 136.08, 140.27, 166.90, 170.12; $R_F$ 0.6 [DCM:methanol (1:1)]; h.p.l.c.r.t. 13.6 min.

Synthesis of urea substrate analogue (7.65). (FIG. 7B4)
N-(3,5-Dimethoxycarbonylphenyl)-N'-(4-nitrophenyl)urea (7.67)

A solution of 4-nitrophenylisocyanate (2.17 g, 12.83 mmol) in anhydrous DCM (15 ml) was added dropwise to a stirred suspension of dimethyl 5-aminoisophthalate (7.23) (2.71 g, 12.83 mmol) in DCM (35 ml). The reaction mixture was stirred for 1 h under an inert atmosphere after which it was diluted with ethyl acetate (100 ml) to dissolve a yellow precipitate which had formed during the reaction. This gave a yellow solution which formed a white precipitate on addition of water (30 ml). The precipitate was collected by filtration, repeatedly washed with water, and dried under reduced pressure. This gave a white solid which was recrystallised from acetone/petrol 40–60 to give the title compound 7.67 as a white powder (2.53 g, 53%). M.p. 193°–195° C.; m/z (+EI) 748 (5%, 2M+H+), 374 (100%, M+H$^+$), 373 (32%, M), 342 (35%, M+H+-OMe); $\delta$H (250 MHz, $d^6$-DMSO) 3.85 (s, 6H, 2×$OCH_3$), 7.70 (2H, d, J 7.5 Hz, 2×Ar—H), 8.10 (1H, s, Ar—H), 8.25 (2H, d, J 7.5 Hz, 2×Ar—H) 8.40 (2H, s, Ar—H), 9.50 (1H, s, NH), 9.55 (1H, s, NH); $\delta$C (62.5 MHz, $CD_3OD$) 52.96. 118.28, 123.40, 123.65, 131.13, 140.65, 141.73, 146.43, 152.41, 165.74; $R_F$ 0.19 [DCM/methanol (95:5)].

N-(3,5-Dicarboxyphenyl)-N'-(4-nitrophenyl)urea (7.65)

The urea (7.67) (100 mg, 0.27 mmol) was added to a stirred solution of sodium hydroxide (1M, 5 ml). After 0.5 h the reaction was complete by TLC examination. The reaction mixture was neutralised to pH 2 with 1M HCl, causing the urea to precipitate. The precipitate was collected by filtration, washed, dried, and recrystallised from dioxan to give the title compound 7.65 as a yellow powder (82 mg, 91%).

M.p. 244° C. (decomp.); m/z (+ES) 433, (100%, M-4H$^+$ +4Na$^+$), 411 (25%, M—3H++3Na+), 390 (18%, M—H$^+$+ 2Na$^+$), 368 (55%, M+Na$^+$), 346 (5%, M+H+), 345 (3% M); numax (nujol mull, cm–1), 1700 (acid), 1650 (urea); $\delta$H (250 MHz, $\delta^6$-DMSO) 3.15–3.95 (b, 2H, 2×COOH), 7.70 (2H, d, J 7.5 Hz, 2×Ar—H), 8.10 (1H, s, Ar—H), 8.25 (2H, d, 2×Ar—H) 8.30 (2H, s, 2×Ar—H), 10.10 (1H, s, NH), 10.40 (1H, s, NH); $\delta$C (62.5 MHz, CD3OD) 117.50, 122.71, 123.65, 125.08, 132.07, 139.59, 141.06, 146.31, 152.21, 166.67; $R_F$ 0.25 [DCM/methanol (1:1)]; h.p.l.c. r.t. 15.8 min.

8. EXAMPLE-MONOCLONAL ANTIBODY GENERATION AND CHARACTERISATION

8.1 Hapten Density Determination

When embarking on an immunisation protocol which could feasibly last from 3 months to a year, it is important that the immunogen being used has been successfully adducted with the haptenic groups. There are a number of standard ways this can be achieved. Isotopic labelling of the hapten confers specific activity on the conjugate which can be measured quantitatively (Ref. 220,221). The need to resort to labelling may be circumvented if the hapten's u.v. spectrum is both significantly different from that of the carrier protein and will allow quantification (Ref. 222). However, the majority of haptens will not possess a suitable chromophoric group and isotopic labelling may not be an option, therefore other procedures have to be sought. Three techniques have been used for hapten density determination and the limitations of each are discussed in turn.

8.1.1 SDS-polyacrylamide gel electrophoresis (SDS-PAGE)

The most routine technique available for determining the weight of proteins is SDS-PAGE. The technique involves sodium dodecyl sulphate (SDS) binding to the protein and coating it with a net negative charge. The subsequent electrophoretic mobility of the protein is then due to its mass rather than its individual charge. Polyacrylamide gels consist of long chains of acrylamide molecules cross-linked with bisacrylamide molecules. Solutions of acrylamide and bisacrylamide are stable but polymerisation occurs when N,N,N',N'-tetramethylethylenediamine (TMED) and ammonium persulphate are added. The pore size of a gel is dependent upon the proportions of bisacrylamide and acrylamide. To allow resolution, the pore size has to restrict the mobility of the proteins. We have used gradient gels which have the advantage of being able to separate a wider range of molecular weights with high resolution. This is because, at a constant field voltage, the mobility of all the proteins decreases as retardation due to sieving occurs. SDS-gels were run with the KLH, OVA and BSA conjugates. Unfortunately, the KLH-conjugates were too large ($>4\times10^6$ Da) to permeate the gel, but excellent resolution was achieved with both the BSA and OVA samples. The SDS-PAGE technique only indicates if the protein has been adducted, not how many haptens are on the protein or what the hapten density is. Therefore other techniques were sought to allow determination of the precise hapten density of the conjugates.

8.1.2 Trinitrobenzenesulphonic acid (8.1) (TNBS) assay (Ref. 223,224)

This technique originates from a procedure developed by Sanger (Ref. 225) for the dinitrophenylation of proteins. The Sanger procedure was modified by Erlanger et al. (Ref. 226) to assess the hapten density of steroid protein conjugates. Habeeb (Ref. 223) further developed the Sanger technique by utilising TNBS (8.1) as a reagent for assessing the free amino groups of the conjugate. By conjugation of the chromophore with the free amine groups of lysine residues in the carriers, the degree of haptenic substitution can be determined. This test analysis is always run in conjunction with an unsubstituted carrier as a control and the difference between the OD405 nm of the conjugate and unmodified carrier protein is taken to be the extent of the hapten substitution. While there are no 'hard and fast' rules regarding the 'required' hapten density for a successful immunisation protocol, it has been shown that using high hapten densities yields higher serum titres (Ref. 227). Hapten numbers of between 10 and 30 per carrier molecule have been suggested for induction of a strong immune response (Ref. 228). The protocol used was a modification of the Habeeb (Ref. 223) procedure and incorporates a reduced reaction time to minimise photolytic side reactions (Ref. 224). Hapten densities on all three carriers (OVA, BSA and KLH) were determined by this technique. Typical results are shown in FIG. 8A2 and table 8.1. For the BSA conjugates in table 8.1, the percentage of free amino acid residues represented by the OD at 405 nm was calculated from the standard curve (FIG. 8A2) given that the total number of available lysines in BSA is assumed to be 60. Hapten substitutions for the KLH conjugate were calculated in a similar way. Assuming a molecular weight of $4\times10^6$ for KLH, there are $1.43\times10^3$ lysine residues per molecule, calculated from the percentage value for lysine in KLH (Protein database, Daresbury). This allows hapten-protein substitution ratios to be calculated in the same manner as for BSA. The results confirmed that the KLH and OVA conjugates contained between 10 and 70% hapten density. The TNBS technique is ideal for rapid, semi-quantitative determination of hapten integrity and can be applied to carriers of any size assuming they possess free amino groups. Unfortunately, if the hapten itself contains a free amino group then this method is invalid.

8.1.3 Matrix-assisted laser desorption mass spectrometry (LDMS) analysis (Ref. 230).

LDMS techniques have extended mass spectrometry to the realm of proteins and other biopolymers (Ref. 231,232). In matrix-assisted LDMS, the samples are prepared by adding the conjugate to a concentrated solution of matrix material. The matrix is a u.v. absorbing, low-mass acid (e.g. cinnamic acid). The sample is then dried and inserted into the spectrometer, where it is subjected to pulsed u.v. radiation from a laser source. This causes some of the matrix, along with the embedded conjugate, to be volatilised by the energy absorbed. The ions are accelerated by focusing electrodes to a flight tube which is field free. Therefore the mass analyser is based on 'time of flight' and the time taken to reach the analyser is proportional to mass. FIG. 8A3 shows an LDMS spectrum for the BSA-hapten 1 (7.2) conjugate. The spectra shows the molecular ion (m/z) of the conjugate as being 81 740, which is the mass of BSA (66 431) plus 15 309 Da for the hapten adducts. By deducting the mass of the carrier protein from the molecular ion value, the mass difference due to hapten conjugation is easily determined. This value is then converted to the number of haptenic molecules bound by division with the molecular weight of the hapten. For hapten 1 (7.2), this corresponds to a hapten number of 32.1 which is a hapten density of ca. 53.5% (Table 8.2). Because of the high molecular weight difference between the BSA-conjugate and the unconjugated carrier protein an internal BSA standard was added to the mixture to make the mass determination more accurate. The mass range of LDMS is from approximately 500 to 200 000 Da, therefore KLH conjugates (MW>$4\times10^6$ Da) are outside the maximum limitation of this procedure. With careful sample preparation accurate mass determinations for all the OVA and BSA conjugates were achieved. This technique for hapten determination gives the most direct, quantitative information of any procedure available for assessing hapten density. The only problem is set by the mass limitation of the machine, which means that high molecular weight carriers (KLH) cannot be measured.

8.2 Immunisations

There are two important features in an immunisation schedule: the preparation of the immunogen for injection and the timing between each immunisation. Both of these variables have been studied extensively and have been optimised to such an extent that standard protocols have existed for many years. (Ref. 21,233). Immunisations were performed with all the target haptens (7.2–7.5). A cycle of boosting was carried out until the serum titre exceeded 25000 (FIG. 8B). For all the haptens only 3 or 4 injections were required. Once a high serum titre was achieved, the mice were kept for up to a year. When required, they were boosted with antigen in incomplete Freund's adjuvant and the titre was checked. Two weeks later a final boost in PBS was administered 3–4 days prior to fusion.

8.3 Cell Fusion
8.3.1 Myeloma cell lines

Three cell lines have been employed: P3-NS1/Ag 4-1 (Ref. 234) a non-secreting variant of the MOPC-21 cell line, P3-Sp2/Ag14 (Ref. 235) another non-expressing variant of the MOPC-21 cell line and P3-NS0/1 (Ref. 236) a non-expressing variant of the NS1 cell line. For one week prior to fusion, the cells were grown in thioguanine supplemented medium to exclude HAT-resistant mutants (Chapter 5, Section 5.1.1). If an antibody is being used in an immunoassay, it is not always necessary to have 100% active protein. However, in the production of antibodies as catalysts, the protein preparation has to be homogenous from batch to batch otherwise catalytic activity-will vary and make interpretation of rate data very difficult. The P3-NS1/Ag4-1 (abbreviated NS-1) mouse plasmacytoma cell line was first described by Kohler et al. (Ref. 234). Although NS-1 continue to make kappa light chains, they are degraded intracellularly and are not secreted. However, immunoglobulins secreted by NS-1 fusion hybrids, while having spleen cell heavy chains, have light chains derived from both spleen and MOPC-21 cells. The pairing of the light and heavy chains is random and if the rates of production of spleen and MOPC-21 light chains is equal (there is no guarantee that this is the case), one would expect 25% of molecules to possess only the spleen cell light chains (and therefore have two functional combining sites), 50% to have one spleen cell light chain and one MOPC-21 light chain (one functional site) and 25% to have both light chains from MOPC-21 (no functional combining sites). Therefore the use of NS-1 as a fusion partner only predicts ca. 75% of the secreted immunoglobulin to have antibody activity. Clearly this value is not constant, therefore batch to batch variability in active protein may be expected and would cause a problem in assessing catalytic activity. In this work, the catalytic clone DF8-D5, an NS-1 derived monoclonal antibody, did exhibit variability in terms of binding to its hapten and catalytic performance from sample to sample and therefore the myeloma cell line was changed for subsequent fusions to SP2 or NS0. The NS0/1 and SP2/0-Ag/14 cell lines are both nonproducer variants of MOPC-21 which synthesise neither heavy or light chains but can produce antibody secreting hybridomas when fused with spleen cells. Spleens from each group of mice immunised with either of the four TSAs were fused with the myeloma cell lines as follows (Table 8.3):

8.4 Hybridoma Production

Multiple fusions have been carried out with the spleens from mice immunised with the KLH conjugate of all 4 haptens (7.2–7.5) and the results are shown in table 8.4. More than 15 fusions have been performed with varying degrees of success. One of the fusions using a spleen of a mouse that had been immunised with the KLH conjugate of (7.4) was completely refractory, whereas re-fusing with the spleen from a different mouse from the same group led to a yield of 24% positive clones, well above the expected average for that immunogen.

The fusions were a success with a total of 593 positive colonies (based on recognition of the relevant TSA in an ELISA screen) going forward for cloning and expansion. Of those positives, 58 stable cell lines (>150 stable sub-clones) have been established to the isophthalate haptens (7.2 and 7.4) and a high proportion of the remaining hybridoma wells have been put in cryogenic store after a primary cloning. Fusions have been carried out and 122 positive hybridoma colonies have been selected to the L-glutamate haptens (7.3 and 7.5).

8.5 Hybridoma Characterisation 8.5.1 Affinity determination

A rapid and accurate technique was required for the measurement of the binding affinities of the antibodies to their respective transition state analogues because cell line selection for expansion was on the basis of recognition of the TSA. Therefore, in the first instance, inhibition ELISA assays were developed for an approximation of the affinity constant (aK). Subsequently, a BIAcore method was incorporated to give an 'accurate' measure of the true affinity constants (Ka) and a comparison of both techniques is discussed.

8.5.2.1 aK Measurements using inhibition ELISA assays

The procedure used throughout this work was a modification of the method described by Nieto et al. (Ref. 171). An apparent affinity constant, aK, can be defined as the reciprocal concentration of free hapten required for 50% inhibition of antibody binding to immobilised ligand (Chapter 5, Section 5.1.4.1). By increasing the concentration of free hapten and measuring absorbance in the resulting ELISA, inhibition curves can be plotted from which the hapten concentration causing 50% binding inhibition can be determined and the aK calculated. The immobilised ligand was always a conjugate containing a carrier protein which had not been used in the immunisations. For example, FIG. 8C1 and table 8.5 show the inhibition ELISA results for a panel of monoclonals elicited to the KLH conjugate of (7.4). The immobilised immunogen is the BSA conjugate of (7.4), which prevents highlighting any cross-reactivity with the carrier protein. The competing TSA (7.7) is a modified form of (7.4) which prevents side-reactions with the carrier protein. These reactions would reduce the effective concentration of the free hapten in solution and make the assay inaccurate. All the apparent affinity measurements, determined by ELISA for the 55 cell lines elicited to the isophthalate haptens are reported in Appendix A, tables 1 and 2. In addition to being very labour intensive, the inhibition ELISA assay is prone to inaccuracies (Ref. 228). The major error is caused because the antibodies are bound to a solid-phase and therefore their natural avidity contributes to the interaction with the bound immunogen (Ref. 31). Avidity is the co-operative nature by which multi-valent antibody Fabs bind after the first Fab has bound. This means that it is more difficult for the free hapten to displace the antibody from the solid-phase, elevating the apparent affinity constant (aK). A BIAcore method offers not only a rapid and more versatile approach to measuring the true affinity constant (Ka) for the antigen-antibody interaction but is inherently more accurate because the hydrogel to which the immunogen is bound is not a true solid-phase and therefore antibody affinity should not be perturbed by avidity.

8.5.2.2 Measuring affinity constants (Ka) by BIAcore

The affinity constants (Ka) for all the cell lines elicited to the haptens (7.2 and 7.4) have been measured by this method and the results are presented in Appendix A, tables 1 and 2. The experiment involves binding a modified TSA (7.37 or 7.50), which does not contain the glutaryl spacer to the hydrogel. The TSAs are linked via their aniline amino group, by EDC/NHS chemistry to the carboxylated dextran. TSAs (7.37 and 7.50) without the glutaryl spacer were used so that any antibodies that have recognition for the spacer will either not bind to this molecule or will bind with reduced affinity. These clones could then be discarded. Optimal conditions for kinetic runs require the presence of low concentration of the antigen on the matrix so the reaction reaches equilibrium within reasonable time limits (usually <15 min). (Ref. 172). Accurate values of reaction are obtained if the rate is larger than 0.25 RU s$^{-1}$. To meet these conditions, the amount of TSA (7.37) immobilised was adjusted so that the antibody response at surface saturation would be between 300 and 1500 RU. FIG. 8C2 shows a typical immobilisation plot of the TSA (7.37).

Once the TSA (7.37) was immobilised, the antibodies were injected at 5 different concentrations and the binding curves were reported on sensorgrams. FIG. 8C3 shows a typical example for the monoclonal, CF6, elicited to the TSA (7.2). From the corresponding reaction rate (dRA/dt) vs. bound antibody (RA) plot for 5 concentrations of antibody CF6 between 50 nM and 500 nM, the BIAcore software determined the mean $k_a=5.66 \times 10^4 M^{-1} s^{-1}$ and $k_d=2.58 \times 10^{-4} s^{-1}$, which gave the association constant at equilibrium, $K^a$ as $2.19 \times 10^8 M^{-1}$. The complete affinity constants for the cell lines elicited to the hapten (7.2 and 7.4) are also listed in Appendix A, tables 1 and 2.

An important question when needing to accurately determine the affinity constants of a large number of monoclonals is how reproducible is the assay from run to run. With a view to answering this question, the experiment was repeated 4 times for a purified monoclonal, EA11-D7, and the results are shown in table 8.6. The assay showed good reproducibility with the $K_a$ values varying from the mean by no more than 25%. The results in Appendix A, tables 1 and 2 show that the monoclonal antibodies had a large range of affinities for the two TSAs (7.2 and 7.4), ranging from $10^5$ to $10^{11} M^{-1}$. It has been found that catalytic antibodies can have an affinity as low as $10^5$ for their TSA (Ref. 27). It was felt that any of the antibodies may be catalytic and so none of them were discarded. One of the antibodies, CF7, showed no binding to the TSA (7.37) in the BIAcore assay but had an affinity of $5.2 \times 10^6 M^{-1}$ in the ELISA. This was thought to be due to the antibody only recognising the linker group and therefore this cell line was abandoned. A limitation of the BIAcore assay was encountered when measuring the affinity of the antibody BG11. It dissociated so slowly within the time course of the assay (ca. 5 min), that an accurate measurement of the change in RUs could not be made and a kd couldn't be measured. The ELISA was able to determine the aK for this clone because the inhibitor concentration could be lowered to a concentration at which 0% inhibition occurred. It has been reported that there are significant differences in the values of the equilibrium association constants determined by different assays such as equilibrium dialysis and precipitation assays (Ref. 238). BIAcore is a new technique for Ka determinations and because of the large population of monoclonals available, the affinities of all the monoclonals elicited to haptens (7.2 and 7.4) were determined by both BIAcore and ELISA and a comparison between the two was made (Appendix A, tables 1 and 2). In common with observations from other groups, (Ref. 239) the results from both techniques were fairly compatible. The affinities are ranked very similarly, with the majority of measurements being within 25% of each other which was the inter-assay variability encountered with this procedure (Table 8.6). This suggests that either the avidity effect, described above, is minimal in the ELISA assay, or, that there is an inaccuracy in the BIAcore process that is artificially elevating the binding constant. This inaccuracy has been suggested to be caused by 're-binding' of the antibody during the dissociation phase (Ref. 240). The phenomena is caused because the hydrogel is 100 nm in depth and not a monolayer, consequently antibody that is dissociating from deep within the hydrogel can feasibly re-bind to antigen situated higher on the dextran surface. This has the effect of reducing the kd and hence elevating the observed $K_a$, To assess whether re-binding was contributing to the overall affinity of the antibodies a control experiment was run which involved immobilising the TSA (7.37) on the hydrogel and then injecting a TSA (7.2) specific monoclonal antibody onto the sensor chip and following the association phase. Instead of allowing the antibody to dissociate under the effect of buffer the antibody was washed off the chip with increasing concentrations of TSA (7.37). The free TSA (7.37) competes with the bound TSA (7.37) in the same way as in the inhibition ELISA preventing re-binding, which elevates the kd to its true value. It was found that re-binding was a minimal component of the affinity constant, contributing <15% of the kd and therefore was not thought to be the major cause of the similarity between aK values determined by ELISA and the $K_a$ values measured on the BIAcore. One further explanation is that avidity may be contributing to the affinity constant measurements on the BIAcore. In theory the hydrogel is a mobile surface which should preclude avidity but it may be possible at certain concentrations of antigen that binding can occur to multiple epitopes and hence avidity would contribute to the measured binding constant. This is difficult to prove experimentally but would probably involve sequentially lowering the amount of immobilised immunogen on the hydrogel and determining whether there was any correlation with the measured affinity constants.

8.5.2 Isotyping

During the immunisation schedule no attempt was made to measure the hapten specific isotype response of the Mab. It was hoped that the immunisation schedules were of a sufficient duration to generate affinity matured isotypes (IgG). Therefore it was quite important at an early stage after fusions to determine whether the antibodies were predominantly IgG or IgM. The enzyme-labelled secondary antibody in the ELISA screen is IgG specific. However, it has been both reported in the literature (Ref. 237) and found by experience in the lab that this enzyme-labelled antibody can cross-react with IgMs. Therefore, to ensure that none of the positive clones were IgM, isotyping was performed very early in the cell-line's life-time. Isotyping was performed by two procedures: ELISA and BIAcore. A typical example of an ELISA experiment is shown in FIG. 8C4. The labour intensive nature and length of assay (48 h) for the ELISA assay has meant that other techniques were sought to improve the isotyping determination. For this reason a BIAcore method was utilised. The experiment involved binding the TSAs (7.37 or 7.50) via their free aniline groups to the hydrogel as described above. The antibody to be isotyped was then washed over the sensor chip and bound to the TSA. Goat anti-mouse subclass specific antibodies were then injected sequentially onto the chip and whichever one bound to the antibody produced an increase in the RUs and subsequently indicated the isotype of the test monoclonal (FIG. 8C5). The isotypes of the 55 cell lines elicited to the isophthalate haptens have been measured and the majority are $IgG_1$, with a low percentage being $IgG_{2a}$ and one IgM (Appendix A, Tables 1 and 2). Of the murine IgG subclasses, $IgG_1$ and $IgG_{2a}$ are the most common, (Ref. 228), so the results are not surprising. The presence of the IgM monoclonal, BG11, confirms the findings of others described earlier.

8.5.3 Production and purification of anti-TSA antibodies

The monoclonals were routinely purified from hybridoma supernatants by a two-stage procedure which involved ammonium-sulphate precipitation followed by affinity chromatography on a protein-G column. The antibodies were shown to be pure by SDS-PAGE using Coomassie staining under reducing conditions. The need for rigorous purity of the monoclonal antibody preparations which were to be screened for catalysis has meant that in addition to growing the antibodies in media supplemented with FCS, they were also grown in protein-free media without FCS. While the yield of antibody from protein-free media is much lower than with media supplemented with FCS, it does not contain any bovine serum immunoglobulin, which is a source of contaminating protein, that arguably may contribute to any catalysis observed. The monoclonals were isolated from protein-free supernatants by affinity purification. It was noted throughout that the monoclonals generated by both FCS and protein-free methods behaved identically in both affinity determination and catalysis assays, suggesting that bovine IgG does not contribute at all to the characteristics of the protein preparation. The purification procedure involves washing the antibody off the column at low pH (Ref. 166). Because of the instability of antibodies at low pH, they were immediately neutralised to pH 7, with TRIS buffer [(tris(hydroxy-methyl)aminomethane] (pH 9.0). The antibody catalysis studies were performed in either MES [2-(N-morpholino)ethanesulfonic acid] or PBS. Therefore, following purification, the antibody preparations were exhaustively dialysed into either of these buffers. The protein concentration was then measured at OD280 nm and the solutions were filter sterilised, aliquoted into Eppendorf™ tubes and stored at −20° C. No azide was added to sterilise the antibody preparations because it was felt that this may interfere with the catalytic assays.

8.6 Materials and Methods
8.6.1 Materials
Antibodies and Cell Lines

HRP-conjugated goat and rabbit anti-mouse immunoglobulin Mabs were obtained from Sigma. Anti-mouse immunoglobulin isotype Mabs were purchased from Serotec, Oxford and Sigma.

Tissue Culture Materials

RPMI-1640, Dulbeccos Modified Eagle Medium (DMEM), HAT (hypoxanthine, aminopterine and thymidine) selection media, protein-free media, antibiotics (benzyl penicillin, streptomycin sulphate and gentamicin), and L-glutamine were obtained from Gibco BRL. Most of the tissue culture flasks and 96-Well microtitre plates were procured from Nunclon (Denmark). Foetal calf serum (FCS) was purchased from Globepharm Ltd. Erythrosine B dye for cell counting was obtained from Gurr Stains, BDH Chemicals Ltd.

Centrifuges

A Beckman microfuge II was used for small sample volumes (<1.5 ml) that required spins of below 11 000 g. For sample volumes of up to 50 ml, a Sorvall Instruments Technospin-R centrifuge was used. For large volumes (>200 ml) requiring spins of below 11 000 g a refrigerated MSE 3000 centrifuge was used.

Sterilisation

All glassware was autoclaved for 20 min at 151 psi and 121° C. or at 23 psi and 126° C. in an autoclave. All media was filtered through Sartorius 0.2 μm cellulose nitrate filters using a Sartorius in-line pressure filter holder and pressure tank. Other solutions and purified antibody preparations were usually filtered through 0.2 μm disposable filters (Sartorius).

Spectrophotometry and ELISA plate reading

Optical density (OD) measurements were performed using a dual beam Kontron-Instruments u.v./visible spectrophotometer with a paired set of 1.0 ml quartz cuvettes. An anthos htII ELISA plate reader coupled to a Compaq 386 work station, using Softmax software was used for assessing ELISA data.

Microscopy

An Olympus Model CKP (Olympus Optical Co. Ltd.) inverted microscope was used for viewing a haemocytometer (Improved Neubauer, Weber Scientific International) for cell counting and for observation of tissue culture flasks.

SDS-PAGE

SDS gels were run in a Bio-Rad Mini Protean II cell, with a Bio-Rad model 1000/500 power supply.

LDMS measurements

All matrix-assisted laser desorption mass spectroscopy (LDMS) determinations were performed on a Finnigan MAT LDMS machine with an IBM 486 workstation.

Photography

Gels and ELISA plates were photographed using Polaroid 4×5 Instant Film in a Polaroid model 545 film holder camera. BIAcore measurements All BIAcore association and dissociation constants were determined on a Pharmacia BIAcore machine coupled to a Compaq 386 workstation. All kinetic evaluation was performed with BIAcore Kinev software supported by Microsoft Excel.

RPMI and DMEM

All culture solutions were made up in 2 L batches, stored at 37° C. and used within 14 days of preparation. 500 ml volumes of the culture media were supplemented with 10% of heat inactivated FCS, 2% penicillin-streptomycin and 2% L-glutamine.

Phosphate Buffered Saline

A sodium/potassium phosphate buffered saline solution was routinely made up as follows: 140 mM NaCl, 2.7 mM KCl, 8.1 mM $Na_2HPO_4$, 1.5 mM $KH_2PO_4$. This was converted to PBS-Tween (PBS-Tw) by adding 0.05% v/v Tween-20 (polyoxyethylenesorbitan monolaureate). Block for ELISA plates, to prevent non specific binding, was prepared by adding 5% w/v of non-fat milk powder to 100 ml of PBS.

TMB solution

Because of the instability of the reagents in this preparation, this solution was prepared fresh when required. A 1 mg tablet of 3,3′,5,5′-tetramethylbenzidine (TMB) was dissolved in 10 ml of 0.1M citrate/phosphate buffer (pH 6.0). To this solution was added 100 ml of 30% H2O2. 100 μl was added to each microtitre well. Sodium Phosphate Buffer, 0.02M Sodium phosphate buffer (pH 7.0) was routinely prepared by the mixing of 20 ml of 0.2M $Na_2HPO_4$ (pH 9.0) and 30 ml of 0.2M NaH2PO4 (pH 5.0) with the pH being adjusted by the addition of 1M NaOH and the volume being diluted to 500 ml.

8.6.2 Methods 8.6.2.1 Hapten conjugation to the carrier protein

Three carrier proteins have been utilised in this study and the procedures for the conjugate preparations are outlined below. The method for hapten conjugation to BSA and OVA are virtually identical with only the amount of hapten added changing to account for the difference in MW of the two proteins.

Bovine serum albumin (BSA) & Chick ovalbumin (OVA) -hapten conjugates.

BSA (20 mg, 0.3 $\mu$mol) was dissolved in phosphate buffered saline (PBS) (10 ml). The haptens (0.1 mmol) dissolved in either DMF or water (0.1 ml) were then added dropwise with cooling. The solution was left stirring overnight at room temperature. The conjugate was then dialysed extensively against 1% PBS solution at 4° C. This required dialysis for 24–48 h, with changing the 2 L of dialysis solution 3–4 times every 24 h. The conjugate was stored either lyophilised or in aliquots at −20° C.

Keyhole limpet haemocyanin (KLH)—hapten conjugates

KLH (MW ca. $4\times10^6$) (20 mg, 5 nmol) was dissolved in water to yield a stock dilution of 0.5 mg ml$^{-1}$. The haptens (2.5 $\mu$mol) were added very slowly with cooling to minimise precipitation and the solution was stirred at room temperature for 4 h. The conjugate was then dialysed and stored as outlined above.

8.6.2.2 Determination of hapten density

METHOD 1: Sodium dodecyl sulfate polyacrylamide gel electrophoresis (SDS-PAGE) (Ref. 241,242)

The method used is a modification of the standard SDS-PAGE method outlined in Harlow and Lane (Ref. 243). In order to measure the change in weight caused by hapten conjugation, the conjugates were all compared with standard solutions of the carrier proteins. In order to maximise resolution, a precast gradient gel was used. The conjugates and standard protein solutions (BSA and OVA) were diluted to 1 mg ml$^{-1}$ in PBS and 20 $\mu$l of this solution was added to an equal volume of sample buffer (1% SDS, 8M urea, 50 mM Tris HCl pH 6.8, 1 mg ml$^{-1}$ bromophenol blue, 20 ml ml$^{-1}$ beta-mercaptoethanol) in an Eppendorf tube. The tube was covered with a pierced lid and placed in a steam bath for 2 min. After cooling, 20 $\mu$l of this mixture was added to the top of the gradient gel. The gel was then placed in a Bio-Rad Mini Protean II cell and reservoir buffer (25 mM Tris, 192 mM glycine, 0.1% SDS) was added. The gel was run at 100 volts (V) until the dye front reached the bottom of the plate after which the bands were localised with Coomassie blue in 40% methanol and destained overnight with several changes of destain (30% isopropanol, 10% glacial acetic acid in water) (Ref. 243).

METHOD 2: 2,4,6-Trinitrobenzenesulphonic acid (TNBS) method (Ref. 224)

It was essential to ensure that the protein conjugate to be analysed has been fully dialysed to remove any non-covalently bound hapten from the carrier protein. Each assay was performed with its own internal calibration curve to account for inter assay variation. The reproducibility of the assay was demonstrated by little variation between the standard curves.

Construction of calibration curves and assay

Calibration curves for the three carrier proteins utilised were measured by adding 50–250 $\mu$l of a (10 $\mu$gml$^{-1}$) protein solution, in triplicate, to wells of a microtitre plate. The volume was made up to 200 $\mu$l with distilled water. For the assay, 200 $\mu$l and 100 $\mu$l of a ca. 1 mg ml$^{-1}$ solution of the conjugates, in duplicate, was also added to the microtitre plate. To all the sample wells 50 $\mu$t of a TNBS (1 mgml$^{-1}$) in 0.1M borate buffer (pH 9.2) solution was added. The plate was then shaken for 2 h at 37° C. The absorbance was read at 405 nm in an ELISA plate reader. The OD405 nm values obtained were plotted vs. $\mu$g of sample protein.

METHOD 3: Laser-desorption mass spectrometry (LDMS) (Ref. 231,232)

Sample preparation is vital to the success of this technique. There must be no ionic contamination in the conjugate preparation, therefore the samples, which were prepared in PBS, were either exhaustively redialysed into distilled deionised water, or repeatedly centrifuged through a centricon filter and resuspended in distilled water. Once the conjugate had been de-salted it was diluted to a concentration of between 10 and 100 pmol ml$^{-1}$ in water. Approximately 0.4 $\mu$l of the conjugate solution was then mixed with an excess of the appropriate matrix, in this case 1.0 $\mu$l of a 50 mM cinnamic acid solution, in an Eppendorf tube. −1 $\mu$l of this mixture was placed on a Finnigan sample cassette and allowed to stand at room temperature. Once the sample had dried, the cassette was placed in the spectrometer and the mass spectrum was measured. The spectra of the BSA conjugates were measured with an internal standard of an analytical grade BSA solution of between 10 and 100 pmol $\mu$l$^{-1}$.

8.6.2.3 Immunisation, Preparing the Immunogen

50 $\mu$l of a 1.5 mgml$^{-1}$ antigen solution was pipetted into a 1.5 $\mu$l eppendorf tube and then diluted to 150 $\mu$l with distilled H$_2$O. 150 $\mu$l of Freund's adjuvant was then added, the lid sealed and the contents mixed on a vortex mixer until a white emulsion persisted. The emulsion was then drawn into a glass syringe through a No. 26 gauge (blue) needle. Complete Freund's adjuvant was used for the first injection, incomplete Freund's (without M. tuberculosis) for subsequent booster doses to reduce both the chance of hypersensitivity to the bacteria and to minimise the chance of granulomas (Ref. 244). 150–200 $\mu$l of immunogen emulsion (in complete Freund's) were injected, via the intraperitoneal route (i.p.), into groups of female 6–8 week old BALB/c mice. Booster doses were given at 3 to 4 week intervals (using incomplete Freund's) and the pre-term boost was given in aqueous solution. The final boost was dosed both i.p and intravenous (i.v.) to increase the concentration of B-cells specific for the antigens in the spleen (Ref. 166). The number of booster doses was determined by serum titre measurements taken 4–5 days after each dose.

8.6.2.4 Enzyme linked immunosorbent assay

Conjugate addition

The antigen i.e. TSA-carrier protein conjugate was diluted to a concentration of 1–2 $\mu$gml-1 in 50 mM carbonate/bicarbonate buffer (pH 9.0). Using an pipette, 100 $\mu$l of antigen solution was added to each well of a 96 well microtitre plate (Costar 3690) and the plate was then covered (Cling Film) and stored at 4° C. overnight. At no time were the wells allowed to dry out. The plates were then washed 3× with PBS and blocked by addition of 150 $\mu$l of a 0.5% w/v milk powder in PBS solution per well, after which the plates were allowed to stand at room temperature for 2 h.

Primary and secondary antibody addition

The solution or supernatant containing the primary antibody was added at 100 $\mu$l per well. Suitable positive and negative controls were used in each assay. To minimise edge effects, the outer wells were only used if absolutely necessary. The plates were then covered (Cling Film) and incubated at either room temperature for 2 h or at 4° C. overnight. After washing the plates, 3× PBS, the enzyme labelled secondary antibody was added. This was either a goat or rabbit anti-mouse, IgG specific, HRP conjugated antibody (Sigma), diluted to 1:2000 in PBS. The labelled antibody was added at 100 µl per well and the plates were covered and left to stand at room temperature for a further 2 h after which they were washed exhaustively, 5× PBS and 3× distilled $H_2O$, and then dried.

Substrate addition

Throughout this study 3,3',5,5'-tetramethylbenzidine has been used as the developing reagent. Because of its short shelf life, the reagent was prepared fresh before each assay. 100 µl was aliquoted into each well and the colour allowed to develop for 20 min at room temperature. The reaction was then stopped with 3M $H_2SO_4$ (100 µl/well). The ODs were measured using either an Anthos htII ELISA plate reader or a Molecular Devices Thermomax microplate reader at 450 nm.

8.6.2.5 Antibody titration

Antibody serum titres are important for assessing the immunisation status of the mouse and deciding when to fuse. They were first measured after the second boost with immunogen and then at regular intervals throughout the immunisation schedule. Serum from the hyperimmunised mouse was serially diluted with PBS in a 96 well microtitre plate. The ELISA assay was then carried out using the standard procedure above. The results were plotted as % OD versus dilution to yield a titration curve. Antibody titre is defined as the dilution which yields 50% of the maximal OD. Whilst there is no strict relationship between serum titre and the yield of positive hybridomas, a good serum titre gives you confidence that the mouse is producing antibodies to your immunogen and therefore to proceed with the fusion.

8.6.2.6 Competition ELISAs

A number of competition assays exist, but the one utilised for aK determinations throughout this study was a modification of a standard antibody capture assay (Ref. 166). Hapten-conjugate was bound to PVC microtitre wells at different concentrations (2.000–0.001 µgml$^{-1}$). A range of concentrations of the test antibody (titrated to give ODs of about 1.0) were incubated at 37° C. for 30 min, in Eppendorf tubes, with known concentrations of free hapten (diluted in PBS). The antibody-free hapten mixture was then added to the microtitre plates and the remainder of the assay was identical to the ELISA protocol already described. As the free hapten concentration rises, the degree of competition for the bound hapten-conjugate increases and the OD measured after substrate development falls. A displacement curve canbe constructed by plotting absorbance against log [hapten] and the aK can be measured directly from the sigmoidal plot (Ref. 171).

8.6.2.7 Biacore methods

All the BIAcore experiments involved two stages: immobilisation of the ligand, then an assay and regeneration phase which were repeated until the experiment was completed.

Immobilisation of the ligand

The test ligand consisted of the hapten modified by omission of the five carbon chain spacer (7.37). It was covalently linked through a free aniline moiety to the CM5 sensor chip following NHS/EDC activation of the hydrogel as discussed earlier (Chapter 5, Section 5.1.4.2). The hydrogel was activated by 35 µl of a 0.05M NHS/0.2M EDC solution in water at a flow rate of 5 µl min$^{-1}$. The ligand was dissolved in DMSO and diluted to 100 µg ml$^{-1}$ in acetate buffer (pH 4) and injected onto the sensor chip at a flow rate of 5 µl min$^{-1}$ for 7 min. Then, the remaining sites were deactivated by injection of 25 µl of 1M ethanolamine hydrochloride (pH 8.5) at a flow rate of 5 µl min$^{-1}$. The immobilisation yield was then determined by the difference in resonance units (RU) between the baseline level and the level after immobilisation.

Affinity determination assay ($K_a$)

The test antibodies were prepared in a range of dilutions, usually from 50–1000 ngml$^{-1}$, in HBS (hepes buffered saline). They were then injected individually onto the BIAcore at a flow rate of 5 µl min$^{-1}$ for 5 min, to allow measurement of the association phase (Chapter 5, FIG. 5D). After which, pure buffer (HBS) was injected at the same rate for a further 5 min to allow measurement of the dissociation phase. The sensor chip was then regenerated as outlined below, before testing of the next antibody concentration.

Regeneration of the sensor chip

Regeneration of the sensor chip involved the removal of all non-covalently linked species from the hydrogel. This included any antibody that was either still bound to the immobilised ligand or had adsorbed to the hydrogel surface by electrostatic attraction. This was achieved by lowering the pH of the sample buffer by injection of 6 µl of 50 mM HCl at the standard flow rate.

8.6.2.8 Cell culture

All work was carried out in a flow hood (Gelaire BSB4) using sterile techniques.

Maintenance of Cell lines

All the cell lines used throughout the studies were cultured routinely in either supplemented RPMI-1640 or DMEM in 80 cm$^2$ tissue culture flasks. The cells were maintained at 37° C. in a humidified $CO_2$ atmosphere and a cell concentration of $0.2\times10^6$–$0.8\times10^6$ cells per ml, to ensure the cell population was in a logarithmic growth phase. The cells were harvested by centrifugation at 400 g for 10 mins.

Test for Cell Viability

Erythrosine B was used routinely to measure the viability of cells in culture. It was prepared by mixing 0.4 g of Erytfirosine B, 0.81 g of NaCl, 0.6 g of $K_2HPO_4$ and 0.05 g of methyl p-hydroxybenzoate in hot distilled water (95 ml). The dye was then cooled and filtered through a filter paper 3M Whatman and the pH adjusted to 7.2 with 1M NaOH. For cell viability and concentration determinations 50 µl of Erythrosine B was mixed with 200 µl of cell suspension. The number of viable (unstained) and non-viable (stained) cells were counted using a haemocytometer and a microscope. Percentage viability=number of viable cells/total number of cells×100.

Cell fusion

Standard protocols were used for the fusion experiments based on adaptations of the Galfré and Milstein procedure (Ref. 245). The method outlined below is for a fusion using the NSO/1 myeloma cell line in DMEM medium.

Several days before the fusion, the NSO/1 cells are recovered from cryogenic store and are grown in DMEM/10% FCS such that they are growing in the log phase (approximately $4$–$6\times10^6$ ml$^{-1}$). Four days before the fusion, the mice are given their final boost as outlined above. On the day of the fusion the mice were anaesthetised and a heart-bleed was collected. The mice were then killed by cervical dislocation. Immediately, the spleen was removed aseptically. The blood sample was spun for 5 min at 1300 rpm in a microfuge and the supernatant collected for ELISA titration studies. The spleen was rapidly perfused with 2×10 ml of DMEM medium in syringes fitted with gauge No. 26 needles. The cells were then spun down at 2000 rpm for 3 min and washed by resuspension in 40 ml of DMEM and spun down at 2000 rpm for a further 3 min. The cells were then counted using the erythrosine dye exclusion method. Typically $3$–$10\times10^7$ cells were obtained per spleen and a splenocyte:myeloma cell ratio of 5 to 1 was utilised. The appropriate number of NS0/1 cells were centrifuged in a separate universal container and washed once in 40 ml of DMEM. They were then added to the splenocytes and centrifuged together, the supernatant was poured off to yield a dry pellet. The pellet was resuspended with gentle tapping and 1 ml of warm 25% PEG 1600 was added dropwise over 1 min. The fusion mixture was then stirred gently with the tip of a Pasteur pipette for a further minute. Over the next 2 min, 2 ml of DMEM was added without FCS. Over the next 4 min, 8 ml of DMEM was added. Finally 10 ml of DMEM was added dropwise. The cells were then spun down at 2000 rpm for 3 min, the supernatant was-aspirated and the cells were resuspended in complete DMEM with 10% NSO preconditioned media and plated out at 50 μl per well in 96 well microtitre plates, to a constant cell density of 4×10$^4$ cells per well. 50 μl of complete DMEM with a 1:50 dilution of 50× stock of HAT solution was added to each well 24 h later. The plates were left undisturbed at 37° C. for a further 4 days after which a further 100 μl of HAT medium was added. After 5 days the plates were scored for growth. When hybridoma colonies were well established (by day 14), 50 μl of supernatant was tested by ELISA for recognition of the immunogen. Positive wells were picked and expanded into 24 well plates and rapidly cloned to stabilise the cell line.

Cloning by limiting dilution

A higher success rate was achieved when complete DMEM was supplemented with 10–15% NS0 preconditioned media for plating out the cloned cell line. Only cells that looked healthy under the microscope were cloned and this was performed as early as feasible in the cell line's lifetime, to minimise the chance of antibody secretion being terminated. The cells in 24 well plates were counted using a haemocytometer and diluted in complete DMEM with 10% preconditioned NS0 medium. The cells were plated out at 200 μl per well using a multi-channel pipette (Costar), such that the cell density of a microtitre plate was either 16, 8, 4, 2, or 1 per well. Clones were usually visible under the microscope after one week. Wells were checked for monoclonality and the supernatants of these wells were screened, by ELISA, against the hapten.

Cryogenic storage of cell lines

After cloning, once a cell line was considered to be stable, the cells were grown in the logarithmic phase and subcultured whenever necessary. It was vitally important to freeze down the cells at any opportunity to minimise the risk of contamination and to have a stock of 'secreting' cells if the cell line should suddenly become unstable. Prior to freezing the cells were checked for viability and only cells that were >90% viable were frozen since high viability and logarithmic growth are essential for good recovery from the thawing process. 1.5–2.0×10$^7$ cells were harvested by centrifugation and these were resuspended in 3 ml of a 90% v/v FCS, 10% v/v DMSO solution at 4° C. 1 ml aliquots of this suspension were then pipetted into 1.8 ml screw top cryo tubes (NUNC) and placed in a −78° C. freezer overnight before being stored under liquid nitrogen (−196° C.).

Thawing cell lines

Frozen cell lines were recovered by agitating the cryo tube in a water bath at 37° C. As the contents thawed, the cells were rapidly diluted with 20 ml of prewarmed complete DMEM. The cells were harvested and resuspended in 10 ml of complete media in a 25 ml tissue culture flask. Recovery was determined after approximately 3 days of growth.

8.6.2.9 Isotyping

Two techniques have been used throughout this work: a triple sandwich ELISA procedure and BIAcore determination.

Triple sandwich ELISA

This is an ELISA which uses class specific goat antimouse antibodies to recognise a test antibody that has been bound to the solid phase and then uses a third enzyme-labelled anti-goat immunoglobulin antibody to elucidate which class specific antibody has been bound. This method was adapted from the standard ELISA antibody capture assay described above. Microtitre plates were coated with antigen and blocked with 1% BSA/PBS as already described. The antibody containing sample, either culture supernatant, test bleed sera or purified antibody, was serially diluted (in duplicate) in 1% BSA/PBS across the plate to give 50 μl per well. The plates were covered and incubated overnight at room temperature. After washing with distilled water and tapping dry, class specific goat anti-mouse antibodies (anti-IgG$_1$, -IgG$_{2a}$, -IgG$_{2b}$, -IgG$_3$) diluted 1 in 1000 in 1% BSA/PBS was then added at 50 μl per well and the plate was covered and incubated at 37° C. for an hour. Following the washing step, rabbit anti-goat immunoglobulin HRP conjugated monoclonal antibody, diluted 1 in 1000 in 1% BSA/PBS was then pipetted at 50 μl per well and the plate incubated for two hours at 37° C. The plate was then washed and developed with TMB substrate in the usual way.

Isotyping with BIAcore

The hapten was immobilised on a CM5 sensor chip as described above. The test antibody was diluted to 50 μg ml$^{-1}$ in (HBS) and injected at a flow rate of 5 μl min$^{-1}$ for 2 min to allow equilibration of the sample antibody and the bound analyte. Then class specific rabbit anti-mouse immunoglobulin antibodies (anti-Ig$_{G1}$, -IgG$_{2a}$, -IgG$_{2b}$, -IgG$_3$) were injected sequentially onto the sensor chip at 50 μg ml$^{-1}$ in HBS at 200 s intervals. After equilibration of the final class specific antibody, the sensor chip was regenerated with 50 mM HCl (6 μl).

8.6.2.10 Purification of hybridoma supernatants

The risk of non-specific enzyme contamination is a constant problem in the field of catalytic antibodies, therefore the rigorous purification of cell supernatants is vital if the resulting antibody solution is to go forward for catalytic assessment. Two strategies have been used for the production of homogenous antibody preparations. Firstly, cell supernatants supplemented with FCS have been purified in a two step process involving an initial ammonium sulfate precipitation stage followed by affinity chromatography (Ref. 243). Secondly, because of the risk of bovine serum IgG contamination of the antibody preparations, the strongest growing cell lines were cultured in completely protein free media and purification was by affinity cliromatography.

Ammonium sulfate precipitation (cutting).

The cell supernatants from all the culture flasks were combined and added to a container and centrifuged at 3000 rpm for 5 min. The supernatant was added to an appropriate beaker charged with a magnetic stirrer bar. An equal volume of cold saturated ammonium sulfate was carefully added to the stirring supernatant. The rate of addition of the ammonium sulfate was controlled so that the local concentration at the site of addition did not exceed the total salt concentration thus minimising the risk of precipitating other serum proteins. The mixture was then allowed to stand at 4° C. for an hour until precipitation had occurred. The solution was then centrifuged and the supernatant decanted to leave a dry plug. The plug was resuspended in the minimum volume of PBS, sealed in dialysis tubing and dialysed exhaustively against 0.02M Na$_2$HPO$_4$ (pH 7.0).

Affinity chromatography on a Protein G column

This method of purification was used for both the antibody preparations that had been cut with ammonium sulfate and for the cell supernatants grown in protein free media.

The protein G column (protein G bound to a Sepharose matrix) was washed with two column lengths of 0.02M $Na_2HPO_4$ buffer (pH 7.0). The protein solution was added to the top of the column via a syringe and Luerlock needle and washed through the column with the buffer until the effluent remained clear. The antibody was eluted from the column by addition of Tris glycine buffer adjusted to ca. pH 2.6 with 0.1M HCl. 1.2 ml fractions were collected in Eppendorf tubes and the pH was adjusted to 7.0 by addition of 20 µl of 1M Tris Glycine buffer (pH 9.0). The absorbance of the fractions was measured on a u.v. spectrophotometer at 280 mm. The fractions containing protein were combined and filter sterilised by passage through a Sartørius 0.2 µm filter and stored at 4° C. If repeated handling of antibody solutions was anticipated, they were aliquoted into Eppendorf tubes (1 ml) and stored at −20° C.

8.6.2.11 Measuring antibody purity

To determine the purity of the antibody preparation it was run on an SDS gel under reducing conditions. The protocol used was identical to the technique outlined for assessing hapten density (Chapter 8, Section 8.6.2.2) except that the gel was freshly prepared before each assay.

8.6.2.12 Isolation of Fab fragments by papain digest

The major sites of papain cleavage are found on the amino terminal side of the disulfide bonds that hold the two heavy chains together. Therefore, digestion with papain releases two antigen domains and an Fc fragment. The papain used was immobilised on Sephadex beads (Sigma) to allow ease of purification. The antibody for digestion was concentrated to 15 mg ml$^{-1}$ by centrifugation using a filter (Centricon). This solution was dialysed into 100 mM sodium acetate (pH 5.5). To 5 ml of this solution in an Eppendorf tube was added 0.25 ml of 1M cysteine solution and 0.25 ml of 25 mM ethylenediaminetetraacetic acid (EDTA). Papain (140 µg) was added, the tube was sealed and the mixture was stirred and placed in a water bath at 37° C. overnight. The mixture was then centrifuged at 3000 rpm for 3 min to allow separation of the immobilised papain. The supernatant was decanted and the Fab fragments were purified on a protein G column as described earlier. The theoretical yield from papain digest should have been 10 mg of Fab, i.e. 66% of the total weight of the sample. However, because of problems associated with incomplete digestion of the sample antibody and inconsistencies in enzyme batches, this method of Fab production is notoriously inefficient; for the Fabs produced for DF8-D5 and EA11-D7, the maximum yield obtained was ca. 5 mg (50%).

9. EXAMPLE—CATALYTIC EVALUATION OF TSA SPECIFIC MONOCLONAL ANTIBODIES

9.1 Developing an Early Screen for Catalysis

From the outset, while selecting clones for expansion was carried out on the basis of recognition of the respective TSAs, efforts were made to devise a more selective method of deciding which cell lines to develop for study. Therefore, attempts were made to develop either a direct screen for catalysis or a way of correlating the affinity of the antibodies for the transition state analogue to their catalytic activity. Previous workers have focused on looking for catalysis of an 'activated' form of their ideal substrate: typically a 4-nitrophenyl ester (Ref. 206) or carbonate (Ref. 246). The benefits of this particular strategy are three-fold. Firstly, the kinetic barrier to hydrolysis of the substrate is quite low, with the consequent effect that the degree of transition state stabilisation required by a potential catalyst is minimal. Secondly, both 4-nitrophenolate and 4-nitrophenol have u.v. spectra with absorbance maxima, (or lambdamax) at ca. 405 nm and 320 nm respectively, which are ideal for studying catalysis by proteins which absorb at ca. 280 nm. Thirdly, the molar extinction coefficient (ε) values for the phenol and phenolate are very large, which means that a small change in concentration of these molecules results in a marked optical density (OD) change. Any failure to detect catalytic clones by this methodology is usually attributed to a high background rate of reaction. This is caused either by spontaneous breakdown or by contaminant enzyme-mediated hydrolysis of the substrate which can mask any catalysis achieved by the abzyme. To improve the chances of highlighting catalytic clones, Professor Bernard Green (Ref. 247) at the Weizmann Institute has developed a 'catELISA' analysis, a new screening methodology based on the standard ELISA protocol (Chapter 8) but which highlights catalytic clones in culture supernatants (FIG. 9A1). The procedure relies on a polyclonal antibody preparation being able to recognise the product generated from hydrolysis of the substrate by antibodies in hybridoma supernatants. Green reports excellent selectivity in recognition for the product relative to substrate for his polyclonal preparation.

However, it has been found by other workers that trying to generate a 'selective' polyclonal preparation to an antigen for catELISA can lead to recognition of both substrate and product. (Ref. 248).

9.1.1 Detecting catalysis by an in vitro cytotoxicity study

Anticancer agents were routinely screened using an in vitro cytotoxicity study: the sulforhodamine B (SRB) assay developed by Skehan et al. (Ref. 249). The technique provides a rapid, sensitive, and inexpensive method for measuring the cellular protein content of adherent and suspension cell cultures in 96-well microtitre plates. SRB is an anionic dye containing two sulfonic acid groups which, under the conditions of the assay. are deprotonated. This allows the dye to bind electrostatically to the positively charged amino-acids of cellular proteins, causing them to be stained. By raising the pH by addition of high pH Tris buffer [tris(hydroxymethyl)aminomethane)], the basic amino-acids are deprotonated and the electrostatic interactions between the dye and protein are destroyed causing the dye to be extracted from the protein into solution when the OD is then measured. This OD was found to be directly proportional to cell density to the upper limit of u.v. detection (OD ca. 2.0) (Ref. 249).

9.1.1.1 Screening hybridoma supernatants

This SRB assay was seen as an ideal means for screening the hybridoma supernatants from cell fusions. A rapid 'throughput' of positive hybridomas could be screened with only small volumes of supernatant being required and catalysis would be assessed directly against the target prodrug (9.1) (FIG. 9A2). As outlined earlier (Chapter 4, Section 4.2), by the process of eliciting antibodies that are capable of hydrolysing carbamates via the 'disfavoured' mechanism, antibodies of relatively poor catalytic power might be able to activate the prodrug, which is thought to have a Hammett σ value of between 0 and −0.5 (though this has not been measured experimentally). This means that the cytotoxicity screen is potentially a very sensitive assay for detecting catalytic clones.

To optimise the chance of success, both the L-glutamic acid (9.1) and the isophthalic acid prodrug (9.2) were used as substrates in the cytotoxicity screen. The major thrust of work has centred around antibody generation and characterisation from the isophthalic acid haptens (7.2 and 7.4) and it was felt that the antibodies generated to these haptens would be as likely to be active against (9.1) as against (9.2).

Two variables had to be considered before the assay could be undertaken: firstly the concentration of prodrug (9.1 and 9.2) to be employed and secondly the controls to be included to ensure that any cytotoxicity observed was the result of abzyme activity and not of a contaminating enzyme.

The answer to the first problem was dictated by the $IC_{50}$s of the two prodrugs (9.1 and 9.2) and the drug (9.3) (data not shown). During the assay, which was arbitrarily chosen as of 1 h duration (although this was altered as required) the LoVo cells were incubated in the presence of the prodrug and antibody. Therefore, the prodrug concentration must be sufficiently low so as not to be cytotoxic under the assay conditions and hence raise background levels. However, it must be feasible for an abzyme to generate a detectable amount of cytotoxicity. These two components have to be balanced. In the first instance, the hybridoma supernatants (20 μl, of unknown antibody concentration) were incubated with a 10 μM prodrug (9.1) concentration. By interpolation from dose-response plots of prodrug cytotoxicity, this concentration was expected to give little cytotoxicity asssociated with the prodrug (9.1) during the 1 h incubation. However, an antibody has to turn over only 20% of the total prodrug in the well to generate 2 μM of active phenol drug (9.3), which would knock out ca. 50% of the LoVo cells. The isophthalate prodrug (9.2) proved to be more problematic in dose selection because of the reduced ratio between its own IC50 and that of the actual N-mustard drug (9.3). During preliminary screening with 10 μM prodrug (9.2), a significant amount of background cytotoxicity was observed which would have masked any activity exhibited by the antibodies. The question of controls was approached as follows. Control wells involved cells being incubated with either spent or fresh media, PBS, or with a completely unrelated antibody, MOPC (a mineral oil plasmacytoma protein) to ensure that any catalysis observed was not the result of non-specific enzyme contaminants or serum bovine IgG protein. In the event, throughout the experiments the most reliable controls were internal: i.e. the non-active antibodies that were being screened in the assay. In total, more than 100 hybridoma supernatants that were known to be positive binders for their respective TSAs were put through the SRB assay and preliminary results did not look hopeful (FIG. 9A3).

All supernatants were assayed in duplicate on either 2 or 4 different 96-well microtitre plates. The mean OD readings at 540 nm were measured and compared with the mean control values. If the supernatant generates free drug (9.3), the cell viability will decrease, SRB staining will be lowered and hence the OD will fall relative to control values. The results are reported as a percentage difference of the mean OD relative to controls. Therefore if the OD of the test wells fall relative to controls the result is negative. FIG. 9A3 shows the results of an SRB assay in which the supernatants from antibodies elicited to haptens (7.2–7.5) were screened. The data presented are a completely arbitrary fraction of the population of >150 supernatants tested. The main information gained from the experiments was that the hybridoma supernatants rather than cause a fall in cell viability, if anything, promoted cell growth. The reasons for this are not immediately obvious, but could simply be caused by the presence of factors in the supernatant which aid the growth of the LoVo cells. This is observed between cells of the same lineage. NSO cell growth is accelerated if it is cultured in media in which NSO cells have been grown [preconditioned media (Chapter 8, Section 8.5.2.7)]. Also macrophages are used as feeder layers to release growth factors into hybridoma supernatants to promote fusion efficiency (Ref. 233). The only reason to doubt this idea is that the cells were only exposed to the supernatants for 1 hour, after which the wells were washed and fresh media added. Therefore the factors would have had to have been taken up rapidly to cause the observed cell growth.

Hybridoma supernatants are largely of indeterminate constitution, with the antibody level being generally unmeasurable. Different batches have different properties with different cell lines secreting antibody at different rates. The problems associated with trying to detect catalysis in supernatants by this in vitro assay are numerous.

9.1.1.2 Screening purified monoclonal antibody preparations

The assay was identical to the one outlined above with the replacement of hybridoma supernatant by purified monoclonal antibody (Mab) of a known concentration. The SRB assay has been performed using the 35 cell lines raised to the phosphonamidate ester hapten (7.2) and the 23 cell lines raised to the phosphonamidic acid hapten (7.4) and the results were more encouraging than when screening the supernatants (FIGS. 9A4, and 9A5 and 9A6, and 9A7). Although there was some inter-assay variability in terms of the per cent difference from the mean, the clones that caused a marked drop in OD were consistently positive. The variance can arise from a number of sources. Firstly, the cell density at the time of plating out (on day 1 of the assay) is critical. Clearly, if cell density fluctuates from assay to assay then so will OD. This is only a problem when the cell density at the start of the assay is so low that the sensitivity of the assay is brought into question (Ref. 249). This causes non-linearity in the relationship described earlier between cell density and OD, and the difference between controls and test wells becomes non-comparable. As work progressed, the cell density of the LoVo cells decreased. Therefore the difference between controls and test wells also fell. This in no way invalidates the data, because controls were determined in the course of every assay. It simply means that the mean OD differences from control values varied (±15%) from assay to assay. Antibodies elicited to both haptens (7.2 and 7.4) had the capacity to activate the prodrug (9.1). Most of the monoclonals showed a mean OD difference of between 0 and 10% below background. In the preliminary screens, this was probably the limits of accuracy of the assay and therefore these antibodies are the internal controls alluded to earlier in the discussion. While the external control (MOPC) had no effect on cell viability, it was additionally reassuring that antibodies generated by identical procedures to the positive clones in the assay were good negative controls. A handful of monoclonals for both haptens (7.2 and 7.4) showed intermediate activity, between 30 and 50% of control values, but the highest activity in the preliminary screens was a mean OD of ca. 70% below control values. This was achieved by two monoclonals, BH3-B8 and EA11-D7, both of which were raised to the phosphonamidate ester (7.2).

After highlighting 'potentially' catalytic clones they were 'grown up' in sufficient amounts to perform multiple assays, it was important to see if the clones followed any concentration vs. effect relationships (a good sign of a catalyst) and whether the effect could be blocked by the hapten to which they were raised. Primarily the work focused on three clones elicited to the phosphonamidate ester (7.2): BH3-B8, EA11-D7 and DF8-D5. EA11-D7 and BH3-B8 were selected because they performed the most consistently throughout repeated cytotoxicity studies. DF8-D5 was expanded because of its performance in a u.v. screen to be described later. The concentration effect SRB employed the same procedure as outlined earlier. The prodrug (9.1) concentration was maintained at 10 μM and the incubation time of 1 h allowed excellent differentiation between background and test samples. The controls included the use of MOPC at identical concentrations to the test monoclonals. The results showed good linearity up to the maximum antibody concentrations assayed (FIG. 9AB). This linearity was quite encouraging and the relative activity EA11-D7 greater than or equal to BH3-B8>DF8-D5 of the clones in the concentration studies correlates with their relative activities in the preliminary screens (FIG. 9A4, 9A5). The next stage involved ensuring that the turnover of prodrug was occurring in the antibody binding site and could therefore be blocked by the phosphonamidic ester TSA (7.6). Also the Fab of EA11-D7, the most active clone, was prepared by papain digest (Ref. 21) by the method outlined in Chapter 8 (Section 8.6.2.12) and its activity relative to the parent monoclonal IgG was assessed (FIG. 9A). The standard SRB assay was performed with increasing concentration of test protein, normalised for two binding sites on the parent antibody. The prodrug (9.1) concentration was 10 μM and a stoichiometric concentration of TSA (7.6) (relative to protein concentration) was included to theoretically reduce to base-line the activity of the EA11 clone [$K_d$ for hapten (7.6) is <4 nM] (Ref. 247).

These data confirm that the antibody EA11-D7 and its Fab catalyse the hydrolysis of the prodrug (9.1) and that the catalysis is inhibited by TSA (7.6). At this stage, u.v. studies to determine the kcat and Km values for this Mab were undertaken.

9.2 Kinetic Evaluation of EA11-D7

The catalytic activity of the protein G purified antibody was determined by measuring the disappearance of the prodrug (9.1) at 260 nm and 37° C. at pH 7 in PBS. This wavelength is selected as it gives the maximum difference in the molar extinction coefficient ($\epsilon$) between the prodrug (9.1) ($\epsilon$=16 000 $M^{-1}$ $cm^{-1}$) and the phenol product (9.3) ($\epsilon$=4400$M^{-1}$ $cm^{-1}$) (FIG. 9B1).

The catalysis by EA11-D7 was observed for concentrations of prodrug (9.1) between 10 and 500 μM and the EA11-D7 concentration was 0.64 μM (dialysed into PBS; the maximum concentration available after purification). The reaction was found to obey Michaelis-Menten kinetics (FIG. 9B2).

The initial rate data for EA11-D7 mediated hydrolysis of (9.1) (corrected for background) was fitted to a non-linear regression program (Enzfitter) and the kinetic parameters were measured as Km 235 μM, $k_{cat}$ 1.8 $min^{-1}$ and $V_{max}$=1.2 μM $min^{-1}$. Unfortunately no direct comparison between background rate and antibody catalysed rate can be made because the prodrug does not hydrolyse spontaneously via cleavage of the carbamate bond. The background hydrolysis involves loss of chlorine from the N-mustard (9.1) and by u.v. spectrophotometry it is difficult to dissect this rate from the carbamate hydrolysis rate. This suggests the need for an h.p.l.c. assay which would allow the decomposition products to be monitored individually and enable a true enhancement ratio to be determined.

Product inhibition has been associated with some examples of catalytic antibody catalysis (Ref. 250–253). It is the phenomenon by which the catalytic rate of the protein is reduced during the course of the experiment due to a build up of product which competes with substrate for binding to the antibody. This is characterised by curvature in the reaction progression profile. Though no definitive studies have been performed concerning the inhibitory effect of the N-mustard (9.3) on the catalytic rate, the reaction has been followed for 15–30 minutes and the initial linear response showed no curvature. With a turnover number of 1.8 $min^{-1}$, under saturating substrate conditions (500 μM) multiple turnovers are occurring (at least 16) during the course of the assay and product inhibition does not seem significantly to affect the reaction rate under these conditions. It should be noted that any catalyst selected for use in the ADAPT (Chapter 1) system would be working under dynamic conditions. The products would be able to diffuse away into the blood stream or tissue etc. and therefore product inhibition (of a competitive nature) even if it were detected in vitro would not be a serious problem in vivo if the catalytic rate was sufficiently high. EA11-D7 compares rather favourably to literature precedence of antibodies activating prodrugs. Schultz (Ref. 118) has generated an antibody which hydrolyses a 5'-D-valyl prodrug (9.4) of 5-fluorodeoxyuridine (9.5) (FIG. 9B3). The kinetic parameters for this monoclonal, 49.AG.659.12, were $K_m$ 218 μM and $k_{cat}$ 0.03 $min^{-1}$. This means EA11-D7 turns over its N-mustard substrate (9.1) 60 times faster. While Schultz has looked at the in vitro effect of his antibody mediated activation of the prodrug (9.4) on Escherichia coli, he has not presented any attempt to correlate activity against a human cell line.

By contrast, in our hands EA11-D7 has been shown to be active in an assay against a human tumour cell line. The conclusion from this study is that the antibody (EA11-D7) the hapten design and screening process have combined to yield a catalyst which is believed to be the best catalytic antibody in its field.

9.3 Correlating Antibody Affinity for the TSA to Activity

Although by using the SRB assay we had selected active clones from the fifty or more that bound tightly to their TSA, this test was still only applicable to purified antibodies. None of the supernatants had caused a reproducible fall in cell viability under the conditions of the assay. The experiment to test the supernatants of positive clones such as EA11-D7 and BH3-B8 was repeated, but no fall in cell viability was observed. Therefore, the only option left to reduce the number of clones to be screened was on the basis of affinity. Having generated a large population of monoclonals with affinity for either the phosphonamidate ester (7.2) or the phosphonamidic acid (7.4) and having ascertained that the sensitivity of the SRB assay was such that catalysis could be detected and quantified, attempts were made to correlate the affinity ($K_a/M^{-1}$) of the monoclonals for their TSA with activity in the SRB assay (FIG. 9C1). Theoretically, as affinity for the transition state increases then so should catalytic power (Ref. 10,255). However, as shown in FIG. 9C1, there is no correlation between affinity and activity. This is a problem encountered when ranking antibodies in terms of affinity for the TSA. It is undesirable to risk throwing away any binders with affinities greater than $10^5$ without having first gone through the procedure of growing them up, purifying etc., and then screening for catalysis.

There is a real need for a more precise way of selecting catalytic antibodies from a large population of monoclonals which simply bind strongly to the transition state. Tawfik (Ref. 256) has suggested that a better way of screening for catalysts is on the basis of affinity to a 'short transition state analogue'. Such molecules are truncated analogues of the immunising haptens and ideally possess all the elements of the transition state and should bind strongly to the catalytic monoclonals. In addition, the shortened analogue should contain only a few features of the products to minimise product inhibition. Tawfik elicited antibodies to the hapten (9.6) and screened the clones that recognised the hapten for recognition of 4-nitrophenyl methylphosphonate (9.7) (FIG. 9C2). Tawfik found that many of the antibodies which recognised the short transition state analogue (9.7) with comparable affinity to the parent hapten were also catalytic (>50%). The apparent generality of this procedure and the routine nature of measuring binding affinities on a BIAcore machine made this technique an interesting option. All the antibodies (35 cell lines) generated to the phosphonamidate ester (7.2) were incorporated in this study which sought to correlate the affinity of antibodies for the attenuated transition state analogue (9.8) to their activity shown in the SRB assay (FIG. 9C3).

The inhibition BIAcore assay was a modification of a method described by Altschuh et al. (Ref. 257). The phosphonamidate (7.37) was bound to the CM5 sensor chip by the procedure mentioned in Chapter 8 (Section 8.5.2.2). The experiment involved injecting known concentrations (50 μg ml−1) of antibody onto the chip and following the association phase. During this binding phase a known concentration of the inhibitor (9.8) was also injected. The inhibitor competes with the solid phase antigen (7.37) for the antibody and hence washes the antibody off the sensor chip in an exaggerated dissociation phase. This dissociation rate (kd) increased in the presence of inhibitor to a plateau rate ($k_{max}$), which is antibody dependent, and the concentration of inhibitor that caused 50% of kmax, $I_{50}$, was measured for each antibody. This gave the 'relative' affinities of each clone for the attenuated transition state analogue. The lower the $I_{50}$ for the inhibitor, the higher is the 'relative' affinity of the antibody for the inhibitor (FIG. 9C4).

The $I_{50}$ values, determined graphically, were then correlated with catalytic activity as determined in the SRB screen and the linearity of the relationship examined (FIG. 9C5). This experiment has been performed only once and therefore significance of the correlation (r=0.8) has to be treated with care. However, it is clear that the correlation is far superior to that observed between affinity for the transition state and activity (r=0.13). This result supports Tawfik's (Ref. 256) original findings, suggesting that a good strategy when designing haptens for eliciting catalytic antibodies is to synthesise an attenuated transition state mimic and then all the clones that are positive for the TSA can be screened against this compound and the strongest binders, judging from this work and that of Tawfik, have a good chance of being catalytic. The most satisfying feature of the correlation is how the three most active clones in the SRB assay have the highest relative affinities for the attenuated transition state analogue (9.8), which offers weight to the idea that the correlation is a good marker for screening for catalysis.

9.4 A Preliminary U.V.-Based Screen

While developing the cytotoxicity screen for detecting catalytic clones, a standard spectrophotometric assay was also being used for monitoring catalysis. Antibodies were tested for their ability to hydrolyse either the isophthalic acid carbamate (9.9) or the L-glutamic acid carbamate (9.10) (FIG. 9D).

These two substrates were chosen for a number of reasons. Firstly, it was hoped that antibodies to all four haptens (Chapter 7, Section 7.1) would be tested in this screen. Therefore, to optimise the chance of highlighting a catalytic clone, the substrates were designed to incorporate structural features common to both series of haptens. Secondly, the 4-nitrophenyl group was included for reasons alluded to above. The high molar extinction coefficient and $\lambda_{max}$ value associated with either 4-nitrophenolate (>pH 7) or 4-nitrophenol (<pH7) mean that they are ideal entities to follow spectrophotometrically during a biocatalytic process (Ref. 121).

Unfortunately, only purified antibody preparations were suitable for screening for catalysis with these 4-nitrophenylcarbamate substrates because their background rate of decomposition is quite high which increases the risk of masking catalysis by low antibody concentrations. To lower the background hydrolysis rate of these activated carbamates, all assays were run at 15° C. and at pH 6.5.

All the clones elicited to the haptens of the isophthalate series have been screened in this assay. In total more than 50 purified antibody preparations have been tested. The assay involves measuring the initial linear appearance of 4-nitrophenol at 320 nm. The antibodies (with concentrations determined by absorbance at 280 nm and assuming the molecular weight of IgG to be 150 000) (Ref. 166) were preincubated in a final reaction volume of 0.5 ml at 15° C. with 50 mM MES [2-(N-morpholino)-ethanesulfonic acid)] at pH 6.5 and ionic strength 1.0 (KCl). The reaction was initiated by addition of the carbamate (20 μl) to a final concentration of either 20 μM, 200 μM or 2 mM. It was anticipated that most catalysts would show reactivity at one or more of these concentrations. As the carbamates were very poorly soluble in water, they were dissolved in DMSO to give a 25× stock solution prior to addition. Therefore, the final organic solvent concentration was 4%. The pH of the reaction mixture was measured at the end of each assay to ensure that the buffer capacity had not been exceeded. The background rate ($k_{uncat}$) was measured by initial rates and found to be independent of buffer concentration. This finding is in total agreement with other findings regarding the hydrolysis of aryl carbamates (Ref. 14,17).

After screening the whole antibody population by this u.v. method, only one clone showed any rate enhancement that was measurable using the conditions previously outlined. DF8-D5, already identified as an active clone in the cytotoxicity assay, showed an enhancement of the hydrolysis rate of the isophthalate carbamate (9.9) but not of the glutamate carbamate (9.10). A result from the u.v. assay was that neither EA11-D7 nor BH3-B8 showed any detectable rate of hydrolysis for either of the activated carbamates. The explanation may be due to the difference in mechanism between the catalysed rate and the spontaneous rate (Chapter 4, Section 4.2). Although the 2 clones hydrolyse the prodrug (9.1), with a detectable rate (EA11-D7: $k_{cat}$ 0.02 s$^{-1}$, $K_m$ 235 μM), because the background rate is more dependent on leaving group ability (ρ=2.8) (Ref. 14,17) than the catalytic rate, for activated substrates such as (9.9 and 9.10) the spontaneous decomposition may well mask any catalysis that occurs.

Having isolated a potentially catalytic clone, the next stage of analysis was the determination of the mechanism employed by DF8-D5. Both to validate hapten design and to show that we had specifically enhanced a 'disfavoured' mechanism for carbamate hydrolysis, it was important to ascertain whether the antibody was a catalyst for the $B_{AC}2$ process or whether by chance we had isolated an antibody capable of hydrolysing the carbamate substrate by an E1cB mechanism.

9.5 The DF8-D5 Mediated Hydrolysis of Aryl Carbamates

With the wealth of kinetic data regarding carbamate hydrolysis available it was clear that structure-activity relationships, such as Hammett correlations, distinguish clearly between the E1cB and $B_{AC}2$ processes. Therefore in the original hapten design, the linker was located in the same position as modified substituents would appear in the substrates in expectation that variable substitution would not influence $K_m$ greatly (FIG. 9E1). As previously described (Section 2.5.3.2), Ian Wilson (Ref. 78) has found that the region around the linker can be poorly recognised by catalytic antibodies, offering the option of substrate modulation at this point. It was hoped that we could establish a structure-activity relationship for DF8-D5 to a series of 4-substituted phenylcarbamates. The only previous report of such a structure-activity relationship determination was by Benkovic and Lerner (Ref. 258) who had elicited antibody NPN43C9 to the phosphonamidate hapten (9.11) for ester and amide hydrolysis (FIG. 9E2 and Table 9.1) (Ref. 206). They found that the $K_m$ of the substrates varied greatly. This was due to the modulation site on the substrates being an important recognition site for the antibody NPN34C9.

The first stage in measuring the structure activity relationship was to ensure that the bis-aryl carbamates (9.9 and 9.12–9.15) undergo hydrolysis by the classical E1cB mechanism outlined by Williams (Ref. 13) and Hegarty (FIG. 9E3) (Ref. 17). For this purpose a u.v. assay was set up to monitor either the formation of the substituted phenol or the loss of the carbamate during alkaline hydrolysis.

9.5.1 Alkaline hydrolysis of substituted phenyl N-(3,5-dicarboxyphenyl)-carbamates (9.9 and 9.12–9.15)

Repetitive scanning of u.v. spectra during the base-catalysed hydrolysis of the substituted phenyl N-(3,5-dicarboxyphenyl)carbamates showed tight isosbestic wavelengths indicating a 1:1 reaction (Ref. 259). Both Christenson (Ref. 146) and Williams (Ref. 13) observed that phenyl N-phenylcarbamate produced N-phenylcarbamate rapidly while during a longer period this was further hydrolysed to aniline. Thus the reaction being followed during the hydrolysis of (9.9 and 9.12–9.15) is the formation of the N-(3,5-dicarboxyphenyl)carbamate anion (9.16) and a substituted phenol. Liberation of the substituted phenol from substituted phenyl N-(3,5-dicarboxyphenyl)carbamates (9.9 and 9.12–9.15) showed pseudo-first-order rate constants proportional to hydroxide ion concentration. A typical case was observed for the hydrolysis of 4-bromophenyl N-(3,5-dicarboxyphenyl)carbamate (9.12) (Table 9.2 and FIG. 9E4).

While these results cannot be exactly mapped on those of Williams (Ref. 13) and Christenson (Ref. 146) who determined rates at 25° C., the data are sufficiently similar to give confidence that the 4-substituted-phenyl N-(3,5-dicarboxyphenyl)carbamates (9.9 and 9.12–9.15) are hydrolysing by the same base-catalysed process as the substituted phenyl N-phenylcarbamates. It is to be noted that throughout the pH range examined, the two carboxyl groups of the isophthalate will be fully ionised and can be expected to raise the $pK_a$ of the carbamate NH group.

The other carbamates obeyed pseudo-first-order kinetics for at least three half-lives and bimolecular rate constants (kOH) were derived from apparent first order rate constants using the corresponding hydroxide ion concentration (calculated from the observed pH by use of the autoprotolysis constant for water at 15° C.) (Table 9.3).

In agreement with previous reports, buffer concentration did not significantly effect the hydrolysis rates (Ref. 13,17, 18,146). Furthermore, the base-catalysed rate constants followed a good Hammett relationship, with the high ρ value indicative of an E1cB mechanism with a strong dependence on leaving group ability, ρ=2.68 (cf. with ref. 13 ρ=2.86)

(FIG. 9E5). The Brønsted relationship for the alkaline hydrolysis of the 4-substituted-phenyl N-(3,5-dicarboxyphenyl)carbamates is also in accordance with previous literature examples, with the $β_{lg}$ value (−1.21) being close to that-previously reported (−1.35) (FIG. 9E6) (Ref. 17).

9.5.2 DF8-D5 Kinetics

Having ascertained that the aryl carbamates are hydrolysed via an E1cB mechanism, the kinetic parameters for these carbamates (9.9 and 9.12–9.15) were determined for the reaction catalysed by DF8-D5. The experiments were run at 15° C. to allow the inclusion of the 4-nitrophenyl N-(3,5-dicarboxyphenyl)carbamate (9.9). It was considered important to incorporate the nitro compound into the series because it has the potential of utilising either σ or σ⁻ in a Hammett correlation and therefore would be important in diagnosing by which mechanism the antibody DF8-D5 is working. The first experiment was to establish that DF8-D5 mediated catalysis by increasing the concentration of the protein under constant substrate concentration (9.9) (100 μM) (FIG. 9E7). The results were positive.

The structure activity experiments were performed by monitoring either the formation of the substituted phenol or the loss of carbamate in 0.5 ml reaction volumes at pH 6.5 (50 mM MES) ionic strength 1.0 at 15° C. (FIG. 9E8 and Table 9.4). The kinetic parameters were measured by the same technique used for EA11-D7. The linear change in OD was monitored over a range of carbamate concentrations (20–500 μM) and the results were fitted to a linear regression analysis program for interpretation. A typical Michaelis-Menten curve of carbamate concentration vs. initial rates was obtained for 4-methoxyphenyl N-(3,5-dicarboxyphenyl)carbamate (9.14) (FIG. 9E9). For case of measurement of the kinetic parameters, the initial rates data was fitted to a Lineweaver-Burke plot, a typical example is shown for the DF8-D5 catalysed hydrolysis of carbamate (9.13) (FIG. 9E10). To ensure that catalysis was occurring in the abzyme active-site, inhibition studies were undertaken with two of the carbamates: the 4-nitrophenyl (9.9) and the 4-fluoro-phenyl (9.13) carbamates. The TSA (7.6) was used as the inhibitor. The results in FIG. 9E11 show that the TSA is a competitive inhibitor for the abzyme. The Lineweaver-Burke analysis shows that the Vmax value is identical for the uninhibited reaction and when TSA is present, suggesting that the inhibitor is binding in the same site as the substrate in a competitive manner. The Ki values were measured by taking the ratio of the slopes with and without inhibitor and fitting to equation (9.1)

$$\text{Ratio of gradient} = (1+[TSA]/Ki) \quad (9.1)$$

Many previous studies have shown that catalytic antibodies are highly specific for their substrates (Ref. 11). It was demonstrated that DF8-D5 does not hydrolyse the L-glutamic acid carbamate (9.10) to a level which is detectable by u.v. assays. However, the cytotoxicity assay is sufficiently sensitive to detect DF8-D5 mediated turnover of the prodrug (9.1). The explanation for the lack of activity against the activated L-glutamate carbamate (9.9) while showing catalysis of the prodrug is because the L-glutamate carbamates are poor substrates for DF8-D5. The abzyme was elicited to the isophthalate hapten (7.2) and consequently appears to have a binding site which preferentially binds such substrates. The isophthalate haptens seemed a rational choice in our attempt to induce antibodies that would have low product inhibition during hydrolysis of glutamate N-mustards.

Neither the amide (9.16) nor the urea (9.17) were substrates for DF8-D5. This result is not surprising in view of the inherently greater stability of these compounds (FIG. 9E12).

There is no literature example of antibody hydrolysis of ureas which, by virtue of two heteroatoms adjacent to the carbonyl group, are very resistant to hydroxide attack. Only recently has a paper appeared on the antibody catalysed hydrolysis of an unactivated amide (Ref. 261). Such resistance to abzyme mediated catalysis was attributed to incorrect transition state representation (Ref. 262) or a too simple representation of amide hydrolysis: which requires protonation of the leaving nitrogen unless stabilisation of a nitrogen anion by a 4-nitrophenyl group is available (Ref. 206). However, Martin et al (Ref. 261) have elicited an amidase to a simple dialkyl phosphinate, which generates nothing more than transition state stabilisation in the combining site. All the clones were screened against the amide (9.17) but none was catalytic. The substituted carbamates (9.9 and 9.12–9.15) were hoped to be substrates for DF8-D5. Only the work of Gibbs et al. (Ref. 258) had shown that such structure-activity relationships were applicable to abzymes. In fact, four of the five carbamates tested were substrates for DF8-D5 (Table 9.5).

Preliminary studies on phenyl N-(3,5-dicarboxyphenyl) carbamate (9.15) have shown no catalysis by DF8-D5. This could either be the result of a poor batch of catalyst (which does occur) or of a positive requirement for a 4-substituent in the phenyl ring. It has been suggested that a substituent in the 4-position may be required to orient the substrate into the correct position for attack by an active-site nucleophile (Ref. 258).

However, further study is required with this substrate before a definitive answer is obtained. The $K_m$s of all the substrates are within a factor of three of each other, which seems to support our original analysis that placing the spacer in the position where substrate modulation was intended would produce little variation in recognition of such groups by the antibody. What is a little surprising is that the carbamate with the 4-$NO_2$ group has the highest $K_m$ of the substrates. With the hapten containing a 4-amido function it was expected that a 4-$NO_2$ group would be the best mimic of this and therefore have the lowest $K_m$. This result may indicate antibody recognition of the πelectrons in the benzene ring, undepleted by the most electron withdrawing group.

9.5.2.1 Kinetic mechanism for DF8-D5

Having measured all the kinetic parameters for the four aryl carbamates shown in Table 9.5, we then plotted the kcat values on a Hammett correlation graph in an identical manner to that outlined by Gibbs et al. (Ref 258). An excellent correlation was measured (r=0.933) (FIG. 9E13). The difference in the slopes of the hydroxide ($\rho$=2.682) and DF8-D5 ($\rho$=0.526) catalysed hydrolysis of the carbamates implies that the charge build-up in the two transition states is very different. As discussed earlier, the E1cB process proceeds through an anionic transition state with much phenolate character, hence stabilisation of this charge significantly influences the hydrolysis rate, resulting in high $\rho$ values (Ref. 13) in the range 2.8–3.4. Conversely the $B_{AC}2$ transition state is far less dependent on stabilisation of negative charge in the transition state and therefore the $\rho$ values are much lower ca. 1.0–1.2 (Ref 150,151,263). The choice of the appropriate σ value for the p-$NO_2$ group is important. In reactions where a p-nitro group can act conjugatively to delocalise charge in the transition state then the σvalue, 1.23, is employed (as in the E1cB mechanism). However, for reactions where inductive effects predominate ($B_{AC}2$) then the σ value of 0.78 is employed. In our results the p-nitro group fits well when the σ_ value of 0.78 is used and gives a Hammett slope of $\rho$=0.53. (It is to be noted that the use of σ⁻ would give an even lower value for $\rho$) This clearly indicates that DF8-D5 is hydrolysing the carbamates via the $B_{AC}2$ mechanism.

In summary we have generated the most active antibody elicited for cleavage of a prodrug yet known and demonstrated that it operates with a change in mechanism over the spontaneous process for hydrolysis of the more active substrates.

9.6 Materials and Methods
9.6.1 Materials
N-mustard compounds

The L-glutamate prodrug (9.1) was prepared as described in WO 94/02450.

The m-isophthalic acid prodrug (9.2) was prepared as follows (see FIG. 9F1). 4-[bis(2-chloroethyl)-amino]phenol hydrochloride (Biochem. Pharmacol. 17 893 (1968) (0.5 g, 2 mM) was suspended in chloroform 10 mL and this was shaken twice with 5% sodium bicarbonate 5 mL. The chloroform layer was separated, dried over magnesium sulphate and added to 1.9M phosgene in toluene (6 mL) and quinoline (0.25 mL). The mixture was allowed to stir at ambient temperature for 2 hours, washed with water, brine, dried and evaporated to an oil. This oil was redissolved in chloroform 20mL and to this solution was added 5-amino isophthalic acid dibenzyl ester (tosyl salt) (1.06 g) and triethylamine (0.3 mL). The mixture was stirred at ambient temperature for 18 hours. After evaporation to dryness the residue was redissolved in ethyl acetate washed with dilute hydrochloric acid, water, dried and evaporated to dryness. Trituration with ether/ethyl acetate gave a solid (2), 300 mg, melting point=134°–7° C. The dibenzyl ester 300 mg was dissolved in tetrahydrofuran (20 mL) and stirred under an atmosphere of hydrogen for 1 hour. After filtration of the catalyst through diatomaceous silica (Celite) the filtrate was evaporated to yield compound 9.2 as a solid (150 mg) melting point=221°–3° C. (dec.).

The 5-amino-isophthalic acid dibenzyl ester (tosyl salt) as prepared as follows (FIG. 9F2). Di-tert-butyl (13.0 g, 59.6 mmol) was added to a solution of 5-aminoisophthalic acid (10 g, 55.2 mmol) in aqueous DMF (60:75 mL, respectively) containing NaOH (4.42 g, 110.5 mmol) and the mixture was stirred at room temperature for 48 h. Solvent was removed by rotary evaporation at 50° C. and the solid residue was partitioned between ethyl acetate and water. The aqueous layer was separated, washed with ethyl acetate (2×100 mL) then treated with 1M citric acid solution (100 mL). The precipitate was filtered and dried at the pump (12.2 g). The crude BOC derivative was used for the next stage without further purification.

A mixture of BOC-aminoisophthalic acid (5 g, 17.8 mmol), acetone (30 mL), benzyl chloride (9.0 g, 71.1 mmol) and triethylamine (3.6 g, 35.6 mmol) was refluxed for 6 h. After cooling to room temperature dichloromethane (150 mL) was added and the mixture was washed with saturated sodium bicarbonate solution (3×100 mL), 1M citric acid solution (3×100 mL) and water (3×100 mL). Solvent was removed by rotary evaporation at 40° C. and the resulting thick oil was triturated with hexane to give a white solid which was filtered and dried at the pump (7.4 g). Recrystallisation from ethyl acetate/hexane gave white platelets of the dibenzyl ester (6.4 g) melting point=153°–5° C.

The BOC group was removed by refluxing the dibenzyl ester (5.0 g, 10.8 mmol) and p-toluene sulphonic acid (2.1 g, 11.04 mmol) in benzene (75 mL) for 1 h. The resulting precipitate was filtered and dried at the pump to give the tosyl salt of dibenzyl aminoisophthalic acid (5.6 g), melting point=193°–5° C.

The m-isophthalic acid prodrug (9.3) was prepared as described in Biochem. Pharmacol. 17 (1968) 893.

Buffers and solutions

All buffers and sodium hydroxide solutions were prepared fresh before every set of assays.

2-(N-Morpholino)ethanesulphonic acid (MFS)

MES (19.253 g) was dissolved in one litre of freshly distilled water, to give a 100 mM stock solution which was filter sterilised and stored as a stock solution at 4 oC. To prepare a 50 mM solution for kinetic studies, 25 ml of this stock solution was adjusted to pH 6.5 with 0.1M sodium hydroxide (ca. 14 ml) and then the solution was diluted to 50 ml final volume with distilled water.

9.6.2 METHODS 9.6.2.1 Sulforhodamine B (SRB) assay (Ref. 249)

All procedures were performed in a fume hood using standard aseptic techniques to minimise the chance of contamination. Day 1: 100 μl of LoVo cells (in DMEM with 10% FCS, 5% penicillin/streptomycin and 1% glutamine) at ca. $2.5 \times 10_4$ cells ml$^{-1}$ were aliquoted into 96-well microtitre plates, using a multi-channel pipette. N.B. Some wells were left without cells as blanks for comparison of OD measurements. The cells were incubated overnight at 37° C. with a 5% $CO_2$ atmosphere. Day 2: 20 μl of an antibody solution or cell supernatant were added to each test well. Compounds (9.1), (9.2) and (9.3) were dissolved in DMSO to a stock concentration 100× that used in the assay. The compounds were then diluted 1:50 in complete DMEM and pipetted (at 100 μl per well), into the appropriate wells. Fresh media (100 μl) was added to the control and blank wells. The plates were then incubated for 1 h at 37° C. (5% $CO_2$). The media was then removed using a multi-channel pipette, 200 μl of complete DMEM was added, and the plates incubated for a further 4 d as outlined above. Day 6: Cold (4° C.) 50% TCA (50 ml) was added to each well. The plates were incubated at 4° C. for 1 h. The supernatant was removed and the plates were repeatedly (5×) rinsed with water. The excess water was removed by shaking. SRB dye (0.1 ml, 0.4% SRB in 1% acetic acid) was then added and the plates were incubated at 37° C. for 30 min. The SRB was removed and the plates were washed quickly with acetic acid until the blank wells showed no pink staining. The plates were then allowed to dry at room temperature (1–2 h). Tris solution (100 μl, 10 mM) was then added to each well and the plates were covered and shaken for 30 minutes on a gyratory shaker. ODs were then measured on a microtitre plate reader at 540 nm.

9.6.2.2. Kinetic parameter measurement of EA11-D7

The reaction was performed in a 1.0 ml cuvette thermostatically maintained at 37° C. The antibody (0.05 ml of a stock concentration) was preincubated with PBS (430 μl) and the reaction was initiated by the addition of the prodrug (9.1) dissolved in DMSO (20 μl to a final concentration of 20–500 μM). The linear initial OD changes were measured and analysed with a linear regression analysis program (Enzfitter) for determination of the kinetic parameters.

9.6.2.3 Alkaline hydrolysis of the substituted phenyl N-(3,5-dicarboxyphenyl)carbamates.

The hydrolysis of the esters was initially followed at constant pH by repetitively scanning the u.v. spectrum during reaction with a Philips PU8720 spectrophotometer equipped with a thermostatted cuvette rack and a Hewlett Packard plotter. Kinetic observations were made at constant wavelength on the same machine. In a typical experiment, the ester (in acetonitrile or DMSO; 50 μl) was added via a pipette to buffer (1.95 ml, 1.0M ionic strength) in a quartz cuvette in the thermostatted cell compartment (15° C.) of the spectrophotometer. The solution was mixed to homogeneity with a plastic stirrer and the change of optical density with time recorded.

Pseudo first order rate constants were measured, if possible, by following the hydrolysis to beyond 5 half lives. If the hydrolysis rate was very slow, then the reaction was extrapolated to infinity. After the reaction was complete, the pH was measured to ensure that the buffering capacity had not been exceeded.

9.6.2.4 U.V. catalysis screen

In a typical experiment, the antibody [50 μl of a stock solution (antibody concentrations varied from 66.0 nM to 4.8 μM; assuming a molecular weight of 150,000 for IgG)] Ref. 21 was preincubated with buffer (430 μl, 50 μM MES, pH 6.5, ionic strength 1.0) in 0.5 μl quartz cuvettes at 15°±0.1° C. in a thermostatted cuvette rack. The reactions were initiated by addition of 20 μl of 4-nitrophenyl N-(3,5-dicarboxyphenyl)carbamate (9.9) (substrate concentrations at either 20 μM, 200 μM, 2 mM) and the OD change was monitored by fixed wavelength measurement on a Philips PU8720 u.v./vis instrument.

9.6.2.5 DF8-D5 Kinetic parameter determination

In a typical experiment, DF8-D5 [50 μl of a stock solution (1.64 μM–4.8 μM)] were pre-incubated as outlined above. The reactions were initiated by addition of the carbamates (9.9 and 9.12–9.15) to a final volume of 0.5 ml. The linear OD changes were followed using the same equipment as above. The linear slopes were then treated with a linear-regression analysis for determination of the kinetic parameters. Inhibitor studies were performed on two of the carbamates (9.9 and 9.13). The procedure was similar to that outlined above with the exception that the antibody-buffer solution was pre-incubated with TSA (10–100 nM) (7.6). The linear OD changes were measured in the same way outlined above and treated to analysis by the computer program.

10. REFERENCES (1) Salmon, S. E.; Dartorelli, A. C. In Basic and Clinical Pharmacology; B. G.Katzung, Eds.; Prentice-Hall International (UK) Ltd.: London, 1989; pp 683–715.

(2) Bowman, W. C.; Rand, M. J. Textbook of Pharmacology,; 2nd ed.; Blackwell Scientific Publications: Oxford, 1988.

(3) Bagshawe, K. D.; Springer, C. J.; Searle, F.; Antoniw, P.; Sharma, S. K.; Melton, R. G.; Sherwood, R. F. Br. J. Cancer 1988, 58, 700–703.

(4) Springer, C. J.; Antoniw, P.; Bagshawe, K. D.; Searle, F.; Bisset, G. M. F.; Jarman, M. J. Med. Chem. 1990, 33, 677–681.

(5) Springer, C. J.; Antoniw, P.; Bagshawe, K. D.; Wilman, D. E. V. Anti-Cancer Drug Design 1991, 6, 467–479.

(6) Bagshawe, K. D. Br. J. Cancer 1987, 56, 531–532.

(7) Bagshawe, K. D. Br. J. Cancer 1989, 60, 275–281.

(8) Bagshawe, K. D. Biochemical Society Transactions 1990, 18, 750–752.

(9) Winter, G.; Milstein, C. Nature 1991, 349, 293–299.

(10) Jencks, W. P. In Catalysis in Chemistry and Enzymology: McGraw Hill: New York, 1969; pp 3–6.

(11) Tramontano, A.; Janda, K. D.; Lerner, R. A. Proc. Nati. Acad. Sci. USA 1986, 83, 6736–6740.

(12) Pollack, S. J.; Jacobs, J. W.; Schultz, P. G. Science 1986, 234, 1570–1573.

(13) Williams, A. J.C.S. Perkin Trans. II 1972, 808–812.
(14) Williams, A.; Douglas, K. T. J.C.S. Perkin Trans. II 1972. 1455–1459.
(15) Williams, A.; Douglas, K. T. J.C.S. Perkin Trans. II 1972. 2112–2115.
(16) Williams, A. J.C.S. Perkin Trans. II 1973, 1244–1247.
(17) Hegarty, A. F.; Frost, L. N. J.C.S Chem. Commun. 1972, 500–501.
(18) Hegarty, A. F.; Frost, L. N. J.C.S. Perkin Trans. II 1973–, 1719–1728.
(19) Hegarty, A. F.; Frost, L. N.; Coy, J. H. J. Org. Chem. 1974, 39, 1089–1093.
(20) Stryer, L. Biochemistry; 3rd ed.; Freeman, W. H.: New York, 1988.
(21) Harlow, E.; Lane, D. P. Antibodies. A Laboratory Manual; Cold Spring Harbor Laboratory: Cold Spring Harbor, N.Y., 1988.
(22) Burton, D. R. TIBS 1990, 15, 64–69.
(23) Kabat, E. A.; Wu, T. T.; Perry, H. M.; Gottesman, K. S.; Foeller, C. Sequences of Proteins of Immunological Interest; 5th ed.; U.S. Department of Health and Human Services, Public Health Service, NIH: 1991.
(24) Burton, D. R. Acc. Chem. Res. 1993, 26, 405–411.
(25) Goodman, J. W. In Basic and Clinical Immunology; 7th ed.; D. P. Stites and A. I. Terr, Eds.; Appleton & Lange: Connecticut, 1991; pp 34–44.
(26) Landsteiner, K.; van den Scheer, J. J. Exp. Med. 1936, 63, 225–229.
(27) Padlan, E. A.; Davies, D. R.; Rudikoff, S.; Potter, M. Immunochem. 1976, 13, 945–949.
(28) Blake, C. C. F.; Koenig, D. F.; Mair, G. A.; North, A. C. T.; Philips, D. C.; Sarma, V. R. Nature 1965, 206, 757–761.
(29) Ramanadhan, M.; Sieker, L. C.; Jensen, L. H. The Immune Response to Structurally Defined Proteins. The Lysozyme Model New York, 1989.
(30) Berek, C.; Milstein, C. Immunol. Rev. 1988, 105, 5–26.
(31) Roitt, I. M. Essential Immunology; 7th ed.; Blackwell Scientific Publications: Oxford, 1991.
(32) Kohler, G.; Milstein, C. Nature 1975, 256, 495–497.
(33) Davies, D. R.; Chacko, S. Acc. Chem. Res. 1993, 26, 421–427.
(34) Neuberger, M. S.; Williams, G. T.; Mitchell, E. B.; Jouhal, S. S.; Flanagan, J. G.; Rabbitts, T. H. Nature 1985, 314, 268–270.
(35) Broggemann, M.; Winter, G.; Waldmann, H.; Neuberger, M. S. J. Exp. Med. 1989, 170, 2153–2157.
(36) Verhoeyen, M.; Milstein, C.; Winter, G. Science 1988, 239, 1534–1536.
(37) Queen, C.; Schneider, W. P.; Selick, H. E.; Payne, P. W.; Landolfi, N. F.; Duncan, J. F.; Avdalovic, N. M.; Levitt, M.; Junghans, R. P.; Waldmann, T. A. Proc. Natl. Acad. Sci. U.S.A. 1989, 86, 10029–10033.
(38) Ward, E. S.; Gussow, D.; Griffiths, A. D.; Jones, P. T.; Winter, G. Nature 1989, 341, 544–546.
(39) Williams, W. V.; Moss, D. A.; Kieber-Emmons, T.; Cohen, J. A.; Myers, J. N.; Weiner, D. B.; Greene, M. I. Proc. Natl. Acad. Sci. USA 1989, 86, 5537–5541.
(40) Burbaum, J. J.; Raines, R. T.; Albery, J.; Knowles, J. R. Biochemistry 1989, 28, 9293–9305.
(41) Pauling, L. Nature 1948, 161, 707–709.
(42) Evans, M. G.; Polanyi, M. Trans. Faraday Soc. 1935, 31, 875–894.
(43) Eyring, H. Chem. Rev. 1935, 17, 65–77.
(44) Fersht, A. In Enzyme Structure and Mechanism; 2nd ed.; W. H. Freeman: New York, 1985; pp 47–50.
(45) Albery, J.; Knowles, J. R. Biochemistry 1976, 15, 5631–5640.
(46) Albery, J.; Knowles, J. R. Angew. Chem. Int. Ed. Engl. 1977, 16, 285–293.
(47) Jencks, W. P. In Catalysis in Chemistry and Enzymology; McGraw-Hill: New York, 1969; pp 288–289.
(48) Bartlett, P. A.; Marlowe, C. K. Biochemistry 1983, 22, 4618–4624.
(49) Blackburn, G. M.; Kingsbury, G.; Jayaweera, S.; Burton, D. R. In Catalytic Antibodies Ciba Foundation Symposium 159; D. J. Chadwick and J. Marsh, Eds.; Wiley, J.: Chichester, 1991; pp 211–226.
(50) Heaton, P. A. PhD Thesis, Sheffield, 1994.
(51) Landsteiner, K. The Specificity of Serological Reactions; C. C. Thomas: 1936.
(52) Raso, V.; Stollar, B. D. Biochemistry 1975, 14, 584–591.
(53) Raso, V.; Stollar, B. D. Biochemistry 1975, 14, 591–599.
(54) Lerner, R. A.; Benkovic, S. J.; Schultz, P. G. Science 1991, 252, 659–667.
(55) Kraut, J. A. Annu. Rev. Biochem. 1977, 46, 331–358.
(56) Fink, A. L. In Enzyme Mechanisms; M. I. Page and A. Williams, Ed.^Eds.; Royal Society of Chemistry: London, 1987; pp 159–177.
(57) Carter, P.; Wells, J. A. Nature 1988, 332, 564–568.
(58) Grossberg, A. L.; Pressman, D. J. Am. Chem. Soc. 1960, 82, 5478–5482.
(59) Davies, D. R.; Padlan, E. A. Annu. Rev. Biochem. 1990, 59, 439–473.
(60) Pressman, D.; Siegel, M. J. Am. Chem. Soc. 1953, 75, 686–693.
(61) Shokat, K. M.; Leumann, C. J.; Sugasawara, R.; Schultz, P. G. Nature 1989, 338, 269–271.
(62) Janda, K. D.; Weinhouse, M. I.; Schloeder, D. M.; Lerner, R. A. J. Am. Chem. Soc. 1990, 112, 1274–1275.
(63) Janda, K. D.; Weinhouse, M. I.; Danon, T.; Pacelli, K. A.; Schloeder, D. M. J. Am. Chem. Soc. 1991, 113, 5427–5434.
(64) Benkovic, S. J. Annu. Rev. Biochem. 1992, 51, 29–54.
(65) Schultz, P. G. Angew. Chem. Int. Ed. Engl. 1989, 28, 1283–1295.
(66) Janda, K. D. Biotechnol. Prog. 1990, 6, 178–181.
(67) Page, M. I.; Jencks, W. P. Proc. Natl. Acad. Sci. U.S.A. 1971, 68, 1678–1683.
(68) Hilvert, D. In Catalytic Antibodies Ciba Foundation Symposium 159; D. J. Chadwick and J. Marsh, Ed.^Eds.; Wiley, J.: Chichester, 1991; pp 174–187.
(69) Hilvert, D.; Hill, K. W. Methods Enzymol. 1991, 203, 352–369.
(70) Weiss, U.; Edwards, J. M. The Biosynthesis of Aromatic Amino Acids; Wiley: New York, 1980, pp 134–184.
(71) Addadi, L.; Jaffi, E. K.; Knowles, J. R. Biochemistry 1983, 22, 4494–4501.
(72) Bartlett, P. A.; Johnson, C. R. J. Am. Chem. Soc. 1985, 107, 7792–7793.
(73) Jackson, D. Y.; Jacobs, J. W.; Sugasawara, R.; Reich, S. H.; Bartlett, P. A.; Schultz, P. G. J. Am. Chem. Soc. 1988, 110, 4841–4842.
(74) Hilvert, D.; Nared, K. D. J. Am. Chem. Soc. 1988, 110, 5593–5594.
(75) Scanlon, T. S.; Schultz, P. G. Phil. Trans. R. Soc. Lond. 1991, 332, 157–164.
(76) Bowdish, K.; Tang, Y.; Hicks, J. B.; Hilvert, D. The Journal of Biological Chemistry 1991, 18, 11901–11908.
(77) Tang, Y.; Hicks, J. B.; Hilvert, D. Proc. Natl. Acad. Sci. U.S.A. 1991, 88, 8784–8786.
(78) Haynes, M. R.; Stura, E. A.; Hilvert, D.; Wilson, I. A. Proteins: Structure, Function, and Genetics 1994, 18, 198–200.

(79) Haynes, M. R.; Stura, E. A.; Hilvert, D.; Wilson, I. A. Science 1994, 263, 646–652.
(80) Sauer, J. Angew. Chem. Int. Ed. Engl. 1966, 5, 211–220.
(81) Raasch, M. S. J. Org. Chem. 1980, 45, 856–867.
(82) Hilvert, D.; Hill, K. W.; Nared, K. D.; Auditor, M. M. J. Am. Chem. Soc. 1989, 111, 9261–9262.
(83) Schultz, P. G. Acc. Chem. Res. 1989, 22, 287–294.
(84) Jackson, D. Y.; Prudent, J. R.; Baldwin, E. P.; Schultz, P. G. Proc. Natl. Acad. Sci. 30 U.S.A. 1991, 88, 58–62.
(85) Pollack, S. J.; Nakayama, G. R.; Schultz, P. G. Science 1988, 242, 1038–1040.
(86) Pollack, S. J.; Schultz, P. G. J. Am. Chem. Soc. 1989, 111, 1929–1931.
(87) Nakayama, G. R.; Schultz, P. G. In Catalytic Antibodies Ciba Foundation Symposium 159; D. J. Chadwick and J. Marsh, Ed.^Eds.; Wiley, J.: Chichester, 1991; pp 72–90.
(88) Goetze, A. M.; Richards, J. H. Biochemistry 1977, 16, 228–232.
(89) Cheseboro, B.; Metzger, H. Biochemistry 1972, 11, 766–771.
(90) Segal, D. M.; Padlan, E. A.; Cohen, G. H.; Rudikoff, S.; Potter, M.; Davies, D. R. Proc. Natl. Acad. Sci. U.S.A. 1974, 71, 4298–4302.
(91) Kaiser, E. T.; Lawrence, D. S. Science 1984, 226, 505–511.
(92) Schultz, P. G.; Lerner, R. A. Acc. Chem. Res. 1993, 26, 391–395.
(93) Kitazume, T.; Lin, J. T.; Yamamoto, T.; Yamazaki, T. J. Am. Chem. Soc. 1991, 113, 8573–8575.
(94) Cravatt, B. F.; Ashley, J. A.; Janda, K. D.; Boger, D. L.; Lerner, R. A. J. Am. Chem. Soc. 1994, 116, 6013–6014.
(95) Janda, K. D.; Shevlin, C. G.; Lerner, R. A. Science 1993, 259. 490–493.
(96) Baldwin, J. E. J.C.S Chem. Commun. 1976, 734–736.
(97) Janda, K. D. Biochemical Society Transactions 1993, 21, 1090–1095.
(98) March, J. In Advanced Organic Chemistry; 4th Ed. ed.; John Wiley & Sons Inc.: New York, 1992; pp 839–850.
(99) Danishefsky, S.; Hershenson, F. M. J. Org. Chem. 1979, 44, 1180–1181.
(100) Gouverneur, V. E.; Houk, K. N.; de Pascual-Teresa, B.; Beno. B.; Janda, K. D.; Lerner, R. A. Science 1993, 262, 204–208.
(101) Seebach, D. Angew. Chem. Int. Ed. Engl. 1990, 29, 1320–1367.
(102) Katsuki, T.; Sharpless, K. B. J. Am. Chem. Soc. 1980, 102, 5974–5976.
(103) Wang, L.; Sharpless, K. B. J. Am. Chem. Soc. 1992, 114, 7568–7570.
(104) Xu, D.; Crispino, G. A.; Sharpless, K. B. J. Am. Chem. Soc. 1992, 114, 7570–7571.
(105) Noyori, R.; Kitamura, M. Modern synthetic methods; Springer-Verlag: Berlin, 1989; Vol. 5, pp 115–145.
(106) Zassinovitch, G.; Mestroni, G. Chem. Rev. 1992, 92, 1051–1069.
(107) Pollack, S. J.; Hsiun, P.; Schultz, P. G. J. Am. Chem. Soc. 1989, 111, 5961–5962.
(108) Janda, K. D.; Benkovic, S. J.; Lerner, R. A. Science 1989, 244. 437–440.
(109) Wirsching, P.; Ashley, J. A.; Benkovic, S. J.; Janda, K. D.; Lerner, R. A. Science 1991, 252, 680–685.
(110) Jacobsen, J. R.; Prudent, J. R.; Kochersperger, L.; Yonkovich, S.; Schultz, P. G. Science 1992, 256, 365–367.
(111) Braisted, A. C.; Schultz, P. G. J. Am. Chem. Soc. 1990, 112, 7430–7431.
(112) Janda, K. D.; Ashley, J. A.; Jones, T. M.; McLeod, D. A.; Schloeder, D. M.; Weinhouse, M. I. J. Am. Chem. Soc. 1990, 112, 8886–8888.
(113) Shevlin, C. G.; Hilton, S.; Janda, K. D. Bioorg. & Med. Chem. Let. 1994, 4, 297–302.
(114) Blackburn, G. M.; Wentworth, P. Chem. Ind. 1994, 338–342.
(115) Lerner, R. A. Hospital Practice 1993, 28, 53–59.
(116) Miyashita, H.; Karaki, Y.; Kikuchi, M.; Fujii, I. Proc. Natl. Acad. Sci. U.S.A. 1993, 90, 5337–5340.
(117) Kenten, J. H.; Von Borstel, R.; Casadei, J. M.; Kamireddy, B.; Martin, M. T.; Massey, R. J.; Napper, A. D.; Simpson, D. M.; Smith, R. G.; Titmas, R. C.; Williams R. O. "Prodrugs activated by targeted catalytic proteins," IGEN, INC. [U.S./U.S.], 1993. (118) Campbell, D. A.; Gong, B.; Kochersperger, L. M.; Yonkovich, S.; Gallop, M. A.; Schultz, P. G. J. Am. Chem. Soc. 1994, 116, 2165–2166.
(119) Schultz, P. G. Personal Communication 1993.
(120) Blackburn, G. M. Personal Communication 1994.
(121) Tramontano, A.; Janda, K. D.; Lerner, R. A. Science 1986, 234, 1566–1570.
(122) Tramontano, A.; Ammann, A. A.; Lerner, R. A. J. Am. Chem. Soc. 1988, 110, 2282–2286.
(123) Zhou, G. W.; Guo, J.; Huang, W.; Fletterick, R. J.; Scanlan, T. S. Science 1994, 265, 1059–1064.
(124) Knowles, J. R. Nature 1991, 350, 121–124.
(t25) Devereux, S.; Linch, D. C. Br. J. Cancer 1989, 59, 2–5.
(126) Marty, M.; Pouillat, P.; Scholl, S. New Engl. J. Med. 1990, 322, 816–821.
(127) Erlich, P. In Collected Studies on Immunity; Wiley: New York, 1906; Vol. 2; p 442.
(128) Matho, G.; Loc, T. B.; Bernard, J. C. R. Seances Acad. Sci 1958, 246, 1626–1628.
(129) Thorpe, P. E.; Ross, W. C. J.; Cumber, A. J. Nature 1978, 271, 752–755.
(130) Buchegger, F.; Vacca, A.; Carrel, S.; Schreyer, M.; Mach, J. P. Int. J. Cancer 1988, 41, 127–134.
(131) Kanellos, J.; Pietersz, G. A.; McKenzie, I. F. C. J. Natl. Cancer Inst. 1985, 75, 319–332.
(132) Senter, P. D.; Saulnier, M. G.; Schreiber, G. J.; Hirschberg, D. L.; Brown, J. P.; Hellstrom, I.; Hellstrom, K. E. Proc. Natl. Acad. Sci. U.S.A. 1988, 85, 4842–4846.
(133) Sherwood, R. F.; Melton, R. G.; Alwan, S. M.; Hughes, P. Eur. J. Biochem. 1985, 148, 447–453.
(134) Senter, P. D.; Schreiber, G. J.; Hirschberg, D. L.; Ashe, S. A.; Hellstrom, K. E.; Hellstrom, I. Cancer Research 1989, 49, 5789–5792.
(135) Frei, E.; Teicher, B. A.; Holden, S. A.; Cathcart, K. N. S.; Wang, Y. Y. Cancer Research 1988, 48, 6417–6423.
(136) Blackburn, G. M. In Nucleic acids in Chemistry and Biology; Oxford University Press: Oxford, 1990.
(137) Springer, C. J.; Bagshawe, K. D.; Sharma, S. K.; Searle, F.; Boden, J. A.; Antoniw, P.; Burke, P. J.; Rogers, G. T.; Sherwood, R. F.; Melton, R. G. European Journal of Cancer 1991,27, 1361–1366.
(138) Springer, C. J.; Niculescu-Duvaz, I.; Pedley, R. B. J. Med. Chem. 1994, 37, 2361–2370.
(139) Blakey, D.; Boyle, T. Personal Communication 1991.
(140) Guthrie, R. D.; Jencks, W. P. Ace. Chem. Res. 1989, 22, 343–349.
(141) Bender, M. L. J. Am. Chem. Soc. 1951, 73, 1626–1629.
(142) Fedor, L. R.; Bruice, T. C. J. Am. Chem. Soc. 1964, 86, 5697–5698.
(143) Adams, P.; Baron, F. A. Chem. Rev. 1965, 567–602.
(144) Lynn, K. R. J. Phys. Chem. 1965, 69, 687–689.

(145) Dittert, L. W. PhD Thesis, Wisconsin, 1961.
(146) Christenson, I. Acta. Chem. Scand. 1964, 18, 904–922.
(147) Bender, M. L,.; Homer, R. B. J. Org. Chem. 1965, 30, 3975–3978.
(148) Maskill, H. In The Physical Basis of Organic Chemistry; Oxford University Press: Oxford, 1985; pp 415–442.
(149) Hammett, L. P. Physical Organic Chemistry; 2nd ed.; McGraw-Hill: New York, 1970.
(150) Bruice, T. C.; Mayahi, M. F. J. Am. Chem. Soc. 1960, 82, 3067.
(151) Kirsch, J. F.; Clewell, W.; Simon, A. J. Org. Chem. 1968, 33, 127–132.
(152) Pratt, R. F.; Bruice, T. C. J. Am. Chem. Soc. 1970, 92, 5956–5964.
(153) Danishefsky, S. Science 1993, 259, 469–470.
(154) Jencks, W. P. In Catalysis in Chemistry and Enzymology; McGraw-Hill, Ed. New York, 1969; pp 523–537.
(155) Bartlett, P. A.; Lamden, L. A. Bioorg. Chem. 1986, 14, 356–377. (156) McLeod, D. A.; Brinkworth, R. I.; Ashley, J. A.; Janda, K. D.; Wirsching, P. Bioorg. & Med. Chem. Let. 1991, 1, 653–658.
(157) Suga, H.; Ersoy, O.; Tsumuraya, T.; Lee, J.; Sinskey, A. J.; Masamune, S. J. Am. Chem. Soc. 1994, 116, 487–494.
(158) Gallacher, G.; Jackson, C. S.; Topham, C. M.; Searcey, M.; Turner, B. C.; Badman, G. T.; Brocklehurst, K. Biochem. Soc. Trans. 1990, 18, 600–601.
(159) Gallacher, G.; Jackson, C. S.; Searcey, M.; Badman, G. T.; Goel, R.; Topham, C. M., Mellor, G. W.; Brocklehurst, K. Biochem. J. 1991, 279, 871–881.
(160) Gallacher, G.; Searcey, M.; Jackson, C. S.; Brocklehurst, K. Biochem. J. 1992, 284, 675–680.
(161) Gallacher, G.; Jackson, C. S.; Searcey, M.; Goel, R.; Mellor, G. W.; Smith, C. Z.; Brocklehurst, K. Eur. J. Biochem. 1993, 214, 197–207.
(162) Gallacher, G. Biochemical Society Transactions 1993, 21, 1087–1090.
(163) Paul, S.; Volle, D. J.; Beach, C. M.; Johnson, D. R.; Powell, M. J.; Massey, R. J. Science 1989, 244, 1158–1162.
(164) Kohler, G.; Milstein, C. Eur. J. Immunol. 1976, 6, 511–519.
(165) Littlefield, J. W. Science 1964, 145, 709–710.
(166) Harlow, E.; Lane, D. In Antibodies. A Laboratory manual; Cold Spring Harbor Laboratory: 1988; pp 139–243.
(167) Engvall, E.; Perlmann, P. Immunochem. 1971, 8, 871–878.
(168) Lefkovitz, I.; Waldmann, H. Limiting Dilution Analysis of Cells in the Immune System; Cambridge University Press: Cambridge, 1979.
(169) Eisen, H. N. Meth. Med. Res. 1964, 10, 106–109.
(170) Velick, S. F.; Parker, C. W.; Eisen, H. N. Proc. Natl. Acad. Sci. U.S.A. 1960, 46, 1470–1482.
(171) Nieto, A.; Gaya, A.; Jansa, M.; Moreno, C.; Vives, J. Mol. Immunol. 1984, 21, 537–543.
(172) Karisson, R.; Michaelsson, A.; Mattson, L. J. Immun. Meth. 1991, 145, 229–240.
(173) Leech, D. Chem. Soc. Rev. 1994, 94, 205–213.
(174) Christianson, D. W.; Lipscomb, W. N. J. Am. Chem. Soc. 1986, 108, 545–546.
(175) Jacobsen, N. E.; Bartlett, P. A. J. Am. Chem. Soc. 1981, 101, 654–657.
(176) Kam, C.-M.; Nishino, N.; Powers, J. C. Biochemistry 1979, 18, 3032–3038.
(177) Elliot, R. L.; Marks, N.; Berg, M. J.; Portoghese, P. S. J. Med. Chem. 1985, 28 1208–1216.
(178) Doak, G. O.; Freedman, L. D. J. Am. Chem. Soc. 1954, 76, 1621–1623.
(179) Kosolapoff, G. M. J. Am. Chem. Soc. 1945, 67, 2259–2261.
(180) Kosolapoff, G. M. J. Am. Chem. Soc. 1949, 71, 1876.
(181) Arbusov, A. E. J. Russ. Phys. Chem. Soc. 1906, 38, 687.
(182) Lugovkin; Arbuzov, A. E. Dokl. Akad. Nauk SSSR 1948, 59, 1301.
(183) Michaelis, A.; Becker, T. Chem. Ber. 1897, 30, 1003–1009.
(184) Okamoto, Y.; Iwamoto, S. T.; Takamuku, S. Bull. Chem. Soc. Jpn. 1987, 60, 277–282.
(185) Yamauchi, K.; Kinoshita, M.; Imoto, M. Bull. Chem. Soc. Jpn. 1972, 45, 2528–2531.
(186) Hersman, M. F.; Audrieth, L. F. J. Org. Chem. 1958, 23, 1889–1893.
(187) Hofle, G.; Steglich, W. Synthesis 1972, 619–621.
(188) Hofle, G.; Steglich, W.; Vorbruggen, H. Angew. Chem. Int. Ed. Engl. 1978, 17, 569–583.
(189) Litvinenko, L. M.; Kirichenko, A. I. Dokl. Akad. Nauk SSSR 1967, 176, 97.
(190) Laws, A. P.; Stone, J. R.; Page, M. I. J.C.S-Chem. Commun. 1994, 1223–1224.
(191) Langston, S. P. PhD Thesis, Sheffield, 1991.
(192) Kosolapoff, G. M. J. Am. Chem. Soc. 1947, 69, 2112–2113.
(193) Engel, R. Chem. Rev. 1977, 77, 349–367.
(194) Rabinowitz, R. J. Org. Chem. 1963, 28, 2975–2978.
(195) McKenna, C. E.; Higa, M. T.; Cheung, N. H.; McKenna, M.-C. Tetrahedron Lett. 1977, 155–158.
(196) Blackburn, G. M.; Ingleson, D. J.C.S Chem. Commun. 1978, 870–871.
(197) Kim, C. U.; Luh, B. Y.; Martin, J. C. J. Org. Chem. 1991, 56, 2642–2647. (198) Degenhardt, C. R.; Burdsall, D. C. J. Org. Chem. 1986, 51, 3488–3490.
(199) Rundinkas, A. J.; Hullor, T. L.; Salvador, R. N. J. Org. Chem. 1972, 42, 2771–2776.
(200) Olah, G. A.; Narang, S. C. Tetrahedron 1982, 38, 2225–2277.
(201) Parratt, M. J. PhD Thesis, Sheffield, 1983.
(202) Olah, G. A.; Narang, S. C.; Gupta, B. G. B.; Malhotra, R. Angew. Chem. Int. Ed. Engl. 1979, 18, 612–614.
(203) Jung, M. E.; Lyster, M. A. J. Am. Chem. Soc. 1977, 99. 968–969.
(204) Taylor, S. PhD Thesis, Sheffield, 1993.
(205) Olah, G. A.; Narang, S. C.; Balaram Gupta, B. G.; Malhotra, R. J. Org. Chem. 1979, 44, 1247–1251.
(206) Janda, K. D.; Schloeder, D.; Benkovic, S. J.; Lerner, R. A. Science 1988, 241, 1188–1191.
(207) Elsinger, F.; Schreiber, J.; Escheiunoser, A. Helv. Chim. Act. 1960, 43, 113–118.
(208) Van Vranken, D. L.; Panomitros, 1).; Schultz, P. G. Tetrahedron Lett. 1994, 35, 3873–3876.
(209) Hansen, J.; Mork, N.; Bundgaard, H. International Journal of Pharmaceutics 1992, 81. 253–261.
(210) Kruse, C. H.; Holden, K. G. J. Org. Chem. 1985, 50, 2792–2794.
(211) Bryan, D. B.; Hall, R. F.; Holden, K. G.; Huffman, W. F.; Gleason, J. G. J. Am. Chem. Soc. 1977, 99, 2353–2355.
(212) Anderson, G. W.; Callahan, F. M. J. Am. Chem. Soc. 1960, 82, 3359–3363.
(213) McCloskey, A. L,.; Fonken, G. S.; Kluiber, R. W.; Johnson, W. S. Organic Syntheses Collective Volumes 1963, IV, 261–263.

(214) Vogel, A. I. Textbook of Organic Chemistry; Longman Scientific and Technical: London, 1989.
(215) Casey, M.; Leonard, J.; Lygo, B.; Proctor, G. Advanced Practical Organic Chemistry; Chapman and Hall: New York, 1990.
(216) In Beilstein; 1931, Vol. 14, p 556.
(217) Kagan, F.; Birkenmeyer, R. D.; Strube, R. E. J. Am. Chem. Soc. 1959, 81, 3026–3031.
(218) McKenna, C. E.; Schmidhauser, J. J.C.S Chem. Commun. 1979, 739.
(219) Dowell, R. I. Personal Communication 1994.
(220) Lindner, H. R.; Perel, E.; Friedlander, A.; Zeitlin, A. Steroids 1972, 19, 357–375.
(221) Abraham, G. E.; Swerdloff, R.; Tulchinsky, D.; Odell, W. D. J. Clin. Endocrinol. Metab 1971, 32, 619.
(222) Erlanger, B. F.; Borek, F.; Beiser, S. M.; Lieberman, S. J. Biol. Chem. 1959, 234, 1090–1094.
(223) Habeeb, A. F. S. A. Analytical Biochem. 1966, 14, 328–336.
(224) Snyder, S. L.; Sobocinski, P. Z. Analytical Biochem. 1975, 64, 284–288.
(225) Sanger, F. Biochem. J. 1949, 45, 563–574.
(226) Erlanger, B. F.; Borek, F.; Beiser, S. M.; Lieberman, S. J. Biol. Chem. 1957, 228, 713–727.
(227) Klaus, G. G. B.; Cross, A. M. Cell. Immunol. 1974, 14, 226.
(228) Goding, J. W. Monoclonal Antibodies: Principles and Practice; Academic Press Inc.: London, 1986.
(229) Bauminger, S.; Kohen, F.; Lindner, H. R. J. Steroid. Biochem. 1974, 5, 739–747.
(230) Geisow, M. J. TIBTECH 1992, 10, 432–438.
(231) Beavis, R. C.; Chait, B. T. Proc. Natl. Acad. Sci. U.S.A. 1990, 87, 6873–6877.
(232) Mock, K. K.; Davey, M.; Stevenson, M. P.; Cottrell, J. S. Biochem. Soc. Trans. 1991, 19, 948–953.
(233) Galfro, G.; Milstein, C. Methods Enzymol. 1981, 73, 3–46.
(234) Kohler, G.; Howe, S. C.; Milstein, C. Eur. J. Immunol. 1976, 6, 292–295.
(235) Kohler, G.; Milstein, C. Eur. J. Immunol. 1976, 6, 511–519.
(236) Galfro, G.; Milstein, C. Methods Enzymol. 1981, 73, 3–46.
(237) Kingsbury, G. A. PhD Thesis, Sheffield, 1992.
(238) Stanley, C.; Lew, A. M.; Steward, M. W. J. Immun. Meth. 1983, 64, 119–132.
(239) Johne, B.; Gadnell, M.; Hansen, K. J. Immun. Meth. 1993. 160. 191–198.
(240) Copley, C. G. Personal Communication 1994.
(241) Raymond, S.; Weintraub, L. Science 1959, 130, 711.
(242) Ornstein, L. Annals of the New York Academy of Sciences 1963, 121, 321–349.
(243) Harlow, E.; Lane, D. In Antibodies. A Laboratory Manual; Cold Spring Harbor Laboratory: 1988; pp 635–657.
(244) Freund, I. Adv. Tuberc. Res 1956, 7, 1307–1310.
(245) Galfro, G.; Milstein, C. Methods Enzymol. 1981, 73, 1–46.
(246) Scanlan, T. S.; Prudent, J. R.; Schultz, P. G. J. Am. Chem. Soc. 1991, 113, 9397–9398.
(247) Tawfik, D. S.; Green, B. S.; Chap, R.; Sela, M.; Eshhar, Z. Proc. Natl. Acad. Sci. U.S.A. 1993, 90, 373–377.
(248) Garner, C.; Tagg, L.; Russell, D. Personal Communication 1994.
(249) Skehan, P.; Storeng, R.; Scudiero, D.; Monks, A.; McMahon, J.; Vistica, D.; Warren, J. T.; Bokesch, H.; Kennet, S.; Boyd, M. R. J. Natl. Cancer Inst. 1990, 82, 1107–1112.
(250) Benkovic, S. J.; Adams, J. A.; Borders, J., C. L.; Janda, K. D.; Lerner, R. A. Science 1990, 250, 1135–1139.
(251) Martin, M. T.; Schantz, A. R.; Schultz, P. G.; Rees, A. R. In Catalytic Antibodies Ciba Foundation Symposium 159; D. J. Chadwick and J. Marsh, Eds.; Wiley, J.: Chichester, 1991; pp 188–200.
(252) Martin, M. T.; Napper, A. D.; Schultz, P. G.; Rees, A. R. Biochemistry 1991, 30, 9757–9761.
(253) Janda, K. D.; Ashley, J. A.; Jones, T. M.; McLeod, D. A.; Schloeder, D. M.; Weinhouse, M. I.; Lerner, R. A.; Gibbs, R. A.; Benkovic, P. A.; Hilhorst, R.; Benkovic, S. J. J. Am. Chem. Soc. 1991, 113, 291–297.
(254) Boyle, T. Personal Communication 1993.
(255) Jacobs, J. W. Bio./Technology 1991, 9, 258–262.
(256) Tawfik, D. S.; Zemel, R. R.; Arad-Yellin, R.; Green, B. S.; Eshar, Z. Biochemistry 1990, 29, 9916–9921.
(257) Altschuh, D.; Dubs, M.-C.; Weiss, E.; Zeder-Lutz, G.; Van Regenmortal, M., H., V. Biochemistry 1992, 31, 6298–6304.
(258) Gibbs, R. A.; Benkovic, P. A.; Janda, K. D.; Lerner, R. A.; Benkovic, S. J. J. Am. Chem. Soc. 1992, 114, 3528–3534.
(259) Schofer, H. L.; Kling, O. Angew. Chem. 1956, 68, 667–671.
(260) Fersht, A. In Enzyme Structure and Mechanism; W. H. Freeman: New York, 1985; pp 155–174.
(261) Martin, M. T.; Angeles, T. S.; Sugasawara, R.; Aman, N. I.; Napper, A. D.; Darlsey, M. J.; Sanchez, R. I.; Booth, P.; Titmas, R. C. J. Am. Chem. Soc. 1994, 116, 6508–6512.
(262) Blackburn, G. M.; Deng, S.-X. Biochem. Soc. Trans. 1993, 21, 1102–1107.
(263) Bruice, T. C.; Mayahi, M. F. J. Am. Chem. Soc. 1960, 82, 3067–3071.

FORMULAE

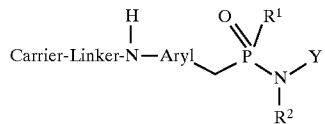

Formula I

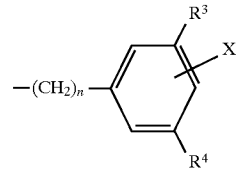

Formula II

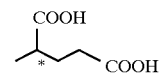

Formula III

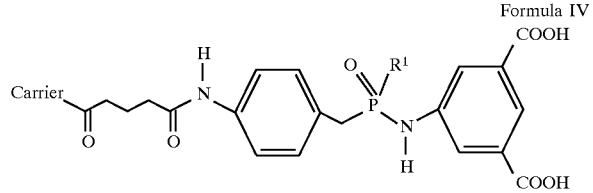

Formula IV

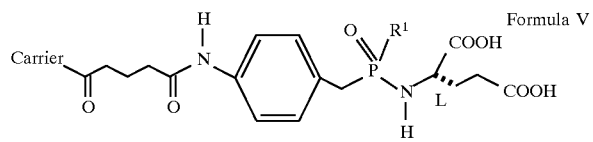

Formula V

FORMULAE

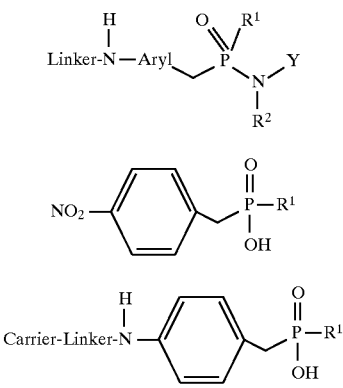

Formula VI

Formula VII

Formula VIII

Appendix
Characteristics of the 35 monoclonal antibodies elicited to the TSA (7.2)

|    | Cell line | Isotype | $K_a$ $M^{-1}$(BIAcore) | aK (ELISA) |
|----|-----------|---------|-------------------------|------------|
| 1  | BG11      | IgM     | —                       | 2.3E + 10  |
| 2  | BG3       | IgG1    | 1.3E + 09               | 1.4E + 08  |
| 3  | FB1       | IgG1    | 1.1E + 09               | 1.3E + 08  |
| 4  | AA10      | IgG1    | 1.0E + 08               | 3.6E + 07  |
| 5  | BH3-B8    | IgG1    | 1.1E + 07               | 5.6E + 06  |
| 6  | FA1       | IgG1    | 1.7E + 07               | 1.5E + 06  |
| 7  | D5        | IgG1    | 6.7E + 08               | 3.9E + 08  |
| 8  | FA1       | IgG1    | 1.9E + 09               | 4.8E + 07  |
| 9  | DF8-DS    | IgG1    | 1.5E + 08               | 1.3E + 08  |
| 10 | BD6       | IgG3    | 4.5E + 06               | 4.4E + 07  |
| 11 | FD12      | IgG1    | 9.3E + 05               | 9.5E + 06  |
| 12 | AF7       | IgG1    | 3.2E + 10               | 4.1E + 10  |
| 13 | CF6       | IgG1    | 2.2E + 08               | 3.8E + 08  |
| 14 | CF7       | IgG2a   | —                       | 5.2E + 06  |
| 15 | FG12      | IgG1    | 2.7E + 09               | 2.8E + 09  |
| 16 | BB6       | IgG1    | 1.8E + 06               | 1.9E + 05  |
| 17 | AF10      | IgG1    | 1.6E + 06               | 4.7E + 06  |
| 18 | EA11      | IgG1    | 8.8E + 07               | 4.3E + 07  |
| 19 | FD5       | IgG1    | 2.7E + 08               | 5.8E + 08  |
| 20 | AD3       | IgG1    | 6.7E + 05               | 4.3E + 05  |
| 21 | FD9       | IgG2a   | 2.9E + 04               | 4.8E + 05  |
| 22 | CC9       | IgG1    | 3.8E + 07               | 6.6E + 08  |
| 23 | AG12      | IgG1    | 2.9E + 06               | 3.6E + 05  |
| 24 | CB8       | IgG1    | 3.9E + 05               | 4.8E + 06  |
| 25 | DA9       | IgG1    | 4.7E + 07               | 7.4E + 07  |
| 26 | CF7       | IgG1    | 2.6E + 05               | 3.3E + 05  |
| 27 | FG9       | IgG1    | 3.9E + 08               | 9.8E + 08  |
| 28 | BF8       | IgG2a   | 3.5E + 06               | 5.2E + 07  |
| 29 | FG12      | IgG1    | 2.5E + 07               | 9.6E + 07  |
| 30 | BB6       | IgG1    | 2.8E + 05               | 5.2E + 05  |
| 31 | AB8       | IgG1    | 3.2E + 08               | 7.4E + 08  |
| 32 | EA11-D7   | IgG1    | 2.4E + 08               | 9.8E + 09  |
| 33 | FD12      | IgG1    | 8.3E + 06               | 5.6E + 06  |
| 34 | BG6       | IgG1    | 5.4E + 07               | 7.4E + 07  |
| 35 | DB5       | IgG1    | 3.3E + 07               | 4.8E + 08  |

Appendix
Characterisation of the monoclonal antibodies elicited to the TSA (7.4)

|   | Cell line  | Isotype | $K_a$ $M^{-1}$(BIAcore) | aK (ELISA) |
|---|------------|---------|-------------------------|------------|
| 1 | CC11-4B4   | IgG1    | 2.0E + 07               | 1.3E + 07  |
| 2 | AG10-16G4  | IgG1    | 1.8E + 06               | 5.8E + 06  |
| 3 | AB9-16H6   | IgG1    | 1.1E + 06               | 1.2E + 06  |
| 4 | DG10-8G7   | IgG1    | 1.1E + 08               | 1.0E + 08  |
| 5 | CA12-16H5  | IgG1    | 3.8E + 08               | 7.8E + 08  |
| 6 | DB10-4A4   | IgG1    | 1.0E + 05               | 1.5E + 06  |
| 7 | DG10-4C1   | IgG2a   | 2.7E + 06               | 2.9E + 06  |
| 8 | AC7-4A10   | IgG1    | 1.9E + 09               | 6.4E + 09  |

Appendix
Characterisation of the monoclonal antibodies elicited to the TSA (7.4)

|    | Cell line  | Isotype | $K_a$ $M^{-1}$(BIAcore) | aK (ELISA) |
|----|------------|---------|-------------------------|------------|
| 9  | FD4-4F6    | IgG1    | 1.5E + 08               | 1.3E + 08  |
| 10 | AC7-2A6    | IgG1    | 2.2E + 06               | 3.1E + 06  |
| 11 | DB10-2A3   | IgG1    | 9.3E + 05               | 4.2E + 06  |
| 12 | FD4-4E1    | IgG1    | 3.2E + 10               | 4.1E + 10  |
| 13 | CC9-8B11   | IgG2a   | 4.2E + 07               | 4.6E + 07  |
| 14 | AB9-16D12  | IgG1    | 3.6E + 05               | 2.9E + 05  |
| 15 | AG10-8G8   | IgG2a   | 2.7E + 09               | 5.8E + 09  |
| 16 | CC9-16F10  | IgG1    | 1.8E + 06               | 4.5E + 06  |
| 17 | AE6-2H6    | IgG1    | 1.6E + 06               | 4.7E + 06  |
| 18 | BC12-16H5  | IgG2a   | 3.8E + 05               | 4.9E + 05  |
| 19 | DG10-8G7   | IgG1    | 2.7E + 08               | 3.8E + 08  |
| 20 | CA12-16H5  | IgG1    | 6.7E + 05               | 4.8E + 05  |
| 21 | FD4-1E1    | IgG2a   | 2.9E + 04               | 2.9E + 05  |
| 22 | CG12-12E5  | IgG1    | 3.8E + 07               | 7.5E + 07  |
| 23 | BH9-8A1    | IgG1    | 2.9E + 06               | 9.3E + 06  |

TABLE 2.1

|                        | Heavy                      | Light          |
|------------------------|----------------------------|----------------|
| V gene segments        | 100                        | 100            |
| D gene segments        | 30                         | —              |
| J gene segments        | 6                          | 5              |
| Junctional diversity   | +++                        | +              |
| Somatic hypermutation  | +                          | +              |
| Combinatorial joining  | V × D × J = 18,000         | V × J = 500    |
|                        | 18,000                     | 500            |
| Combinatorial association | 9 × 10$^6$              |                |

TABLE 2.2

| Catalyst          | Rate Acceleration | $\Delta G$/ kcal mol$^{-1}$ | $\Delta H$/ kcal mol$^{-1}$ | $\Delta S$/ cal mol$^{-1}$ K$^{-1}$ |
|-------------------|-------------------|-----------------------------|-----------------------------|-------------------------------------|
| Spontaneous       | 1                 | 24.2                        | 20.5                        | -12.9                               |
| Chorismate Mutase | 3 × 10$^6$        | 15.9                        | 15.9                        | 0                                   |
| Antibody 1F7      | 250               | 21.3                        | 15.0                        | -22                                 |
| 11F1-2B11         | 10,000            | 18.7                        | 18.3                        | -1.2                                |

TABLE 2.3

|                     | Activation energy (kcal/mol) | |
|---------------------|------------------------------|-----------------|
| Transition structure | RHF/3-21G                   | 6-31G*/3-21G    |
| Ortho, endo         | 27.3                         | 40.80           |
| Ortho, exo          | 28.84                        | 42.70           |
| Meta, endo          | 29.82                        | 42.88           |
| Meta, exo           | 30.95                        | 43.94           |

TABLE 2.4

|        | Abs. config. of hapten | $k_{cat}$/ min$^{-1}$ | $K_m$/ μM | overall conversion/ % | optical yield/ % ee |
|--------|------------------------|------------------------|-----------|-----------------------|---------------------|
| (2.49) | 2R, 3R (+)             | 0.88                   | 390 ± 70  | 23.0                  | 99.0                |
| (2.50) | 2S, 3S (-)             | 0.91                   | 400 ± 70  | 23.5                  | 98.5                |
| (2.51) | 2R, 3S (+)             | 0.94                   | 410 ± 90  | 23.0                  | 98.5                |
| (2.52) | 2S, 3R (-)             | 0.86                   | 380 ± 50  | 23.0                  | 98.0                |

TABLE 3.2

| Tissue | Prodrug | Drug |
|---|---|---|
| Tumour | <0.05 | 0.86 |
| Liver | 22.0 | 7.5 |
| Kidney | 2.9 | 2.8 |
| Lung | 0.2 | 2.5 |
| Gut | 12.3 | 1.3 |

TABLE 3.3

| Active Drug | | $t_{1/2}^a$/min | $IC_{50}^b$/$\mu M$ |
|---|---|---|---|
| 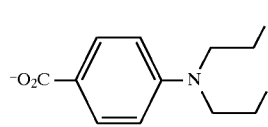 | (3.5) | 324 | >700 |
| 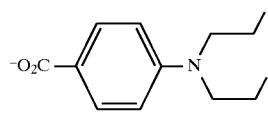 | (3.16) | 58 | 220 ± 10.0 |
| 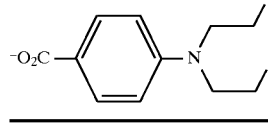 | (3.17) | 21 | 165 ± 19.0 |

TABLE 4.1

| Catalyst | $pK_{BH}$# | $k_b/M^{-1}s^{-1}$ |
|---|---|---|
| Hydroxide ion | 15.7 | $3.0 \times 10^3$ |
| $Na_2HPO_4$ | 7.21 | $1.4 \times 10^{-3}$ |
| Imidazole | 7.03 | $1.2 \times 10^{-4}$ |
| Water | −1.74 | $>4 \times 10^{-7}$ |

$pK_{BH}$ of a base = $pK_a$ of the corresponding conjugate acid

TABLE 4.2

| R | $pK_a1$ | $k_2/s^{-1}$ |
|---|---|---|
| Ph | 12.5 | 1.54 |
| p-ClC$_6$H$_4$ | 12.3 | 8.30 |
| m-BrC$_6$H$_4$ | 12.0 | 28.2 |
| m-NO$_2$C$_6$H$_4$ | 11.7 | 177 |

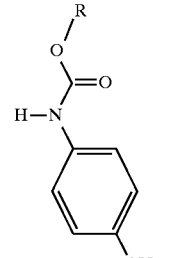
(4.15)

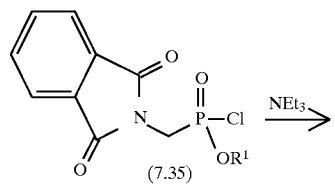
(7.35)

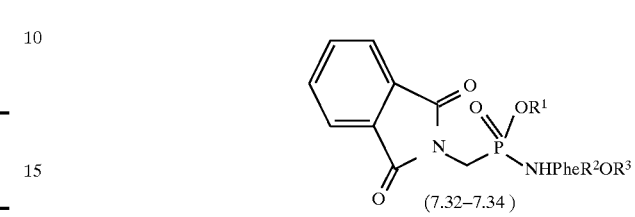
(7.32–7.34)

TABLE 7.1

| Compound | $R^1$ | $R^2$ | $R^3$ | Yield % |
|---|---|---|---|---|
| (7.32) | Bn | Leu | Bn | 47 |
| (7.33) | Et | Met | Me | 49 |
| (7.34) | Et | Leu | Me | 75 |

TABLE 7.2

| Compound | | Without DMAP | | With DMAP | |
|---|---|---|---|---|---|
| Reactant | Product | Yield % | Reaction time/h | Yield % | Reaction time$^\diamond$/h |
| (7.23) | (7.24) | 21 | 48 | 68 | 2 |
| (7.23) | (7.30) | 60 | 8 | 83 | 0.25 |
| (7.29) | (7.31) | 74 | 5 | 81 | 0.25 |

TABLE 8.1

| Conjugate | Hapten Density/% | Hapten No. |
|---|---|---|
| BSA-Hapten 1 (7.2) | 48.5 | 29.1 |
| BSA-Hapten 2 (7.4) | 27.9 | 16.7 |
| BSA-Hapten 3 (7.3) | 38.5 | 23.1 |
| BSA-Hapten 4 (7.5) | 28.9 | 17.34 |

TABLE 8.2

| Conjugate | m/z | Hapten No. | Density % |
|---|---|---|---|
| BSA-Hapten 1 | 81740 | 32.1 | 53.5 |
| BSA-Hapten 2 | 76647 | 23.4 | 39.0 |
| BSA-Hapten 3 | 79637 | 27.7 | 46.0 |
| BSA-Hapten 4 | 77450 | 24.7 | 41.2 |
| OVA-Hapten 3 | 48290 | 8.2 | 41.0 |
| OVA-Hapten 4 | 47387 | 6.6 | 33.0 |

TABLE 8.3

| TSA | Myeloma Cell Line |
|---|---|
| Hapten 1 (7.2) | P3-NS1/Ag 4-1 |
| Hapten 2 (7.4) | NSO/1 |
| Hapten 3 (7.3) | P32Sp2/Ag14 |
| Hapten 4 (7.5) | P3-Sp2/Ag14 |

TABLE 8.4

|  | Isophthalic acid series | | L-glutamic acid series | |
| --- | --- | --- | --- | --- |
|  | Hapten 1 (7.2) | Hapten 2 (7.4) | Hapten 3 (7.3) | Hapten 4 (7.5) |
| pre-term serum titres | >76000 | >50000 | >100000 | >80000 |
| no. of colonies screened | 1040 | 5023 | 462 | 547 |
| no. of positive[a] colonies | 193 | 278 | 36 | 86 |
| % positive Colonies | 18.6% | 5.5% | 7.7% | 15.7% |
| no. of cell lines | 35 | 23 | — | — |

TABLE 8.5

| Mab | $aK/M^{-1a}$ |
| --- | --- |
| AC7-4A10 | $2.2 \times 10^9$ |
| DG10-8G7 | $1.0 \times 10^8$ |
| CC11-4B4 | $1.3 \times 10^7$ |
| AB9-16H6 | $1.2 \times 10^6$ |

TABLE 8.6

|  | mean values obtained | | | |
| --- | --- | --- | --- | --- |
| data | RU TSA (7.37) immobilised | $k_a/M^{-1}s^{-1}$ | $k_d/s^{-1}$ | $K_a/M^{-1}$ |
| 1 | 104 | $6.04 \times 10^{-3}$ | $3.00 \times 10^{-5}$ | $2.01 \times 10^{-8}$ |
| 2 | 174 | $7.03 \times 10^{-3}$ | $3.34 \times 10^{-5}$ | $2.10 \times 10^{-8}$ |
| 3 | 154 | $4.56 \times 10^{-3}$ | $1.62 \times 10^{-5}$ | $2.81 \times 10^{-8}$ |
| 4 | 163 | $7.03 \times 10^{-3}$ | $2.51 \times 10^{-5}$ | $2.80 \times 10^{-8}$ |
| mean |  | $6.17 \times 10^{-3}$ | $2.54 \times 10^{-5}$ | $2.43 \times 10^{-8}$ |

TABLE 9.1

| X | $k_{cat}/s^{-1}$ | $K_m/mM$ | $k_{cat}/Km/ mM^{-1}s^{-1}$ | $k_{uncat}/s^{-1}$ | $K_d$ or $K_i$ $\mu M$ |
| --- | --- | --- | --- | --- | --- |
| NO$_2$ | ca. 25 | 0.053 | ca. 470 | $9.3 \times 10^{-4}$ | 1.0 |
| CH$_3$CO | ca. 0.87 | ca. 3.0 | ca. 0.282 | $5.1 \times 10^{-4}$ | — |
| CHO | $1.0 \pm 0.1$ | 0.25 | 4.1 | $2.6 \times 10^{-4}$ | $90 \pm 10$ |
| Cl | $1.7 \pm 0.2$ | 0.72 | 0.049 | $2.4 \times 10^{-4}$ | $180 \pm 40$ |
| Me | $0.15 \pm 0.03$ | ca. 3.0 | 1.01 | $0.93 \times 10^{-4}$ | — |

TABLE 9.2

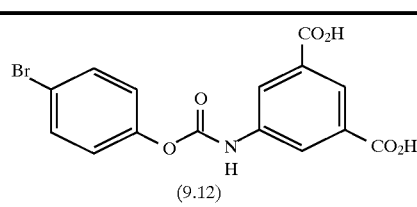

(9.12)

| pH[a] | $k_{obs}/s^{-1b}$ |
| --- | --- |
| 8.0 | $2.99 \pm 0.3 \times 10^{-4}$ |
| 9.0 | $3.15 \pm 0.2 \times 10^{-3}$ |
| 9.5 | $1.01 \pm 0.1 \times 10^{-2}$ |
| 10.0 | $3.09 \pm 0.2 \times 10^{-2}$ |
| 11.0 | $2.99 \pm 0.2 \times 10^{-1}$ |

TABLE 9.3

| Substituent | $\lambda/ nm^b$ | $k_{OH}/ M^{-1}s^{-1}$ | pH | $pK_a$ |
| --- | --- | --- | --- | --- |
| 4-OMe | 278 | $2.2 \pm 0.2 \times 10^0$ | 9.0 | 10.21 |
| 4-H | 278 | $1.58 \pm 0.3 \times 10^1$ | 9.0 | 10.00 |
| 4-F | 280 | $9.49 \pm 0.3 \times 10^1$ | 9.0 | 9.95 |
| 4-Br | 280 | $3.16 \pm 0.2 \times 10^2$ | c | 9.34 |
| 4-NO$_2$ | 318 | $3.16 \pm 0.4 \times 10^4$ | 6.5 | 7.15 |

TABLE 9.4

| Carbamate | $\lambda_{max}^a/ nm$ | Phenol $\lambda_{max}^b/ nm$ | $\lambda_{obs}^c/ nm$ |
| --- | --- | --- | --- |
| p-NO$_2$ | 280 ($\epsilon$ 6,532) | 325 ($\epsilon$ 8,124) | 340 |
| p-Br | 240 ($\epsilon$ 3,225) | 280 ($\epsilon$ 1,628) | 280 |
| p-F | 300 ($\epsilon$ 1,807) | 278 ($\epsilon$ 2,192) | 300 |
| p-H | 280 ($\epsilon$ 1,438) | 280 ($\epsilon$ 1,438) | — |
| p-MeO | 240 ($\epsilon$ 14,713) | 280 ($\epsilon$ 1,466) | 240 |

TABLE 9.5

| X |  | $k_{cat}/ min^{-1}$ | $K_m^a/ \mu M$ | $k_{cat}/K_m/ M^{-1} min^{-1}$ | $k_{uncat}^b/ min^{-1}$ | $k_{cat}/k_{un}$ | $K_i/ nM$ |
| --- | --- | --- | --- | --- | --- | --- | --- |
| NO$_2$ | (9.9) | 18 | 120 | 0.15 E6 | 6.0 E-2 | 300 | 25 |
| Br | (9.12) | 6 | 80 | 0.075 E6 | 6.0 E-4 | 1 E5 | — |
| F | (9.13) | 7.2 | 41 | 0.17 E6 | 1.8 E-5 | 4 E5 | 40 |
| MeO | (9.14) | 4.9 | 58 | 0.08 E6 | 4.2 E-7 | 1.2 E6 | — |

We claim:

1. A catalytic antibody capable of catalysing activation of a carbamate (—O—CO—NH—) containing prodrug suitable for Antibody Directed Abzyme Prodrug Therapy (ADAPT) by catalysing breakdown of the prodrug at the carbamate position by a non-spontaneous reaction mechanism.

2. A catalytic antibody according to claim 1 wherein the non-spontaneous reaction has a $B_{Ac}2$ mechanism and the prodrug is a nitrogen mustard aryl carbamate.

3. A catalytic antibody according to any one of claims 1–2 which produces a reduced immune response in humans compared with mouse antibodies.

4. A catalytic antibody according to claim 1 which was raised to an immunogen of Formula I

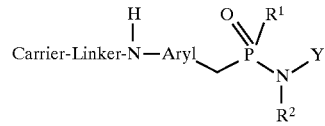

wherein Carrier represents a carrier protein; Linker represents a linking moiety; Aryl represents a group selected from naphthyl and phenyl; $R^1$ is selected from OH, $C_{1-4}$alkoxy, and —$C_{1-4}$alkylene—OH; $R^2$ is selected from H and $C_{1-4}$alkyl; Y represents a group of Formula II

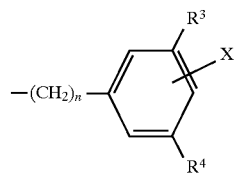

wherein: n is 0 to 4; $R^3$ and $R^4$ are independently selected from —COOH, —SO$_3$H and —PO$_3$H$_2$; X is selected from H, nitro, halogen, carboxy, —SO$_3$H, —PO$_3$H$_2$, —SO$_2$NHCO—C$_{1-4}$alkyl, tetrazol-5-yl; or Y represents a group of Formula III

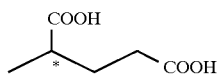

wherein the asterisked chiral centre can be L or D configuration.

5. A catalytic antibody according to claim 4 in which Linker represents —CO—(CH$_2$)$_3$—CO—; Aryl represents phenyl; $R^1$ represents —O-ethyl; $R^2$ represents H; and when Y represents a group of Formula II, n=0, $R^3$ and $R^4$ represent —COOH.

6. A catalytic antibody according to claim 1 which was raised to an immunogen of Formula IV

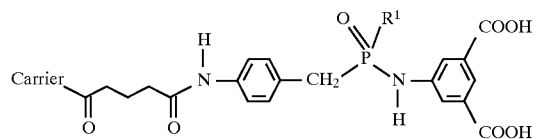

in which $R^1$ is selected from —OH or —O-ethyl.

7. A catalytic antibody according to claim 1 which was raised to an immunogen of Formula IV

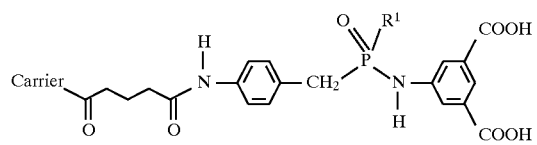

in which $R^1$ is —O-ethyl.

8. A catalytic antibody according to claim 1 which was raised to an immunogen of Formula V

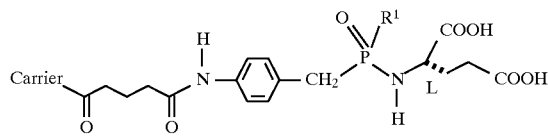

wherein $R^1$ represents —OH or —O-ethyl.

9. A catalytic antibody according to claim 1 which was raised to an immunogen of Formula V

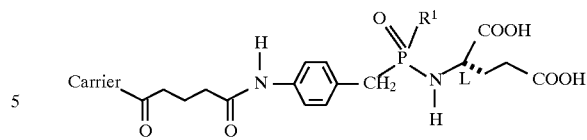

wherein $R^1$ is —O-ethyl.

10. Catalytic antibody BH3-B8-F9 as obtainable from hybridoma accession no. 96042611 as deposited at the European Collection of Animal Cell Cultures (ECACC).

11. Catalytic antibody DF8-D5 as obtainable from hybridoma accession no. 96042612 as deposited at the European Collection of Animal Cell Cultures (ECACC).

12. A method for screening potential catalytic antibodies raised to an immunogen as defined in any one of claims 4–9 for catalytic activity, said method comprising contacting said antibodies with a short transition state analogue of Formula VII

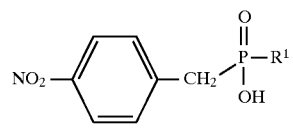

wherein $R^1$ is selected from OH, C$_{1-4}$alkoxy, and -C$_{1-4}$alkylene—OH.

13. The method according to claim 12 wherein said analog is attached to a solid phase through the —NO$_2$ group.

14. A catalytic antibody according to any one of claims 4–9 wherein the non-spontaneous reaction has a B$_{Ac}$2 mechanism and the prodrug is a nitrogen mustard aryl carbamate.

15. An Antibody Directed Abzyme Prodrug Therapy (ADAPT) system comprising a catalytic antibody as defined in any one of claims 1–2.

16. An Antibody Directed Abzyme Prodrug Therapy (ADAPT) system comprising a catalytic antibody as defined in claim 3.

17. An Antibody Directed Abzyme Prodrug Therapy (ADAPT) system comprising a catalytic antibody as defined in claim 4.

18. An Antibody Directed Abzyme Prodrug Therapy (ADAPT) system comprising a catalytic antibody as defined in claim 5.

19. An Antibody Directed Abzyme Prodrug Therapy (ADAPT) system comprising a catalytic antibody as defined in claim 6.

20. An Antibody Directed Abzyme Prodrug Therapy (ADAPT) system comprising a catalytic antibody as defined in claim 7.

21. An Antibody Directed Abzyme Prodrug Therapy (ADAPT) system comprising a catalytic antibody as defined in claim 8.

22. An Antibody Directed Abzyme Prodrug Therapy (ADAPT) system comprising a catalytic antibody as defined in claim 9.

23. An Antibody Directed Abzyme Prodrug Therapy (ADAPT) system comprising a catalytic antibody as defined in any one of claims 10–11.

* * * * *